(12) United States Patent
Nair et al.

(10) Patent No.: US 9,493,396 B2
(45) Date of Patent: Nov. 15, 2016

(54) SUBSTITUTED NAPHTHALENE COMPOUNDS AS CALCIUM SENSING RECEPTOR MODULATORS

(71) Applicant: LUPIN ATLANTIS HOLDINGS SA, Zug (CH)

(72) Inventors: Prathap Sreedharan Nair, Maharashtra (IN); Ganesh Bhausaheb Gudade, Maharashtra (IN); Mahadeo Bhaskar Tryambake, Maharashtra (IN); Chetan Sanjay Pawar, Maharashtra (IN); Sanjeev Anant Kulkarni, Maharashtra (IN); Venkata P. Palle, Maharashtra (IN); Rajender Kumar Kamboj, Maharashtra (IN)

(73) Assignee: LUPIN ATLANTIS HOLDINGS SA, Zug (CH)

( * ) Notice: Subject to any disclaimer, the term of this patent is extended or adjusted under 35 U.S.C. 154(b) by 0 days.

(21) Appl. No.: 14/915,014

(22) PCT Filed: Aug. 26, 2014

(86) PCT No.: PCT/IB2014/064067
§ 371 (c)(1),
(2) Date: Feb. 26, 2016

(87) PCT Pub. No.: WO2015/028938
PCT Pub. Date: Mar. 5, 2015

(65) Prior Publication Data
US 2016/0214924 A1 Jul. 28, 2016

(30) Foreign Application Priority Data

Aug. 28, 2013 (IN) .......................... 2814/MUM/2013
Aug. 28, 2013 (IN) .......................... 2815/MUM/2013
Mar. 27, 2014 (IN) .......................... 1091/MUM/2014

(51) Int. Cl.
| | |
|---|---|
| *C07D 231/12* | (2006.01) |
| *A61K 31/137* | (2006.01) |
| *A61K 31/195* | (2006.01) |
| *A61K 31/415* | (2006.01) |
| *A61P 13/12* | (2006.01) |
| *A61P 5/18* | (2006.01) |
| *C07C 211/30* | (2006.01) |
| *C07C 217/48* | (2006.01) |
| *C07C 217/58* | (2006.01) |
| *C07C 227/18* | (2006.01) |
| *C07C 229/34* | (2006.01) |
| *C07C 229/38* | (2006.01) |
| *C07C 317/32* | (2006.01) |
| *C07D 207/06* | (2006.01) |
| *C07D 295/135* | (2006.01) |
| *C07C 209/22* | (2006.01) |
| *C07C 213/08* | (2006.01) |
| *C07C 315/04* | (2006.01) |
| *C07D 305/08* | (2006.01) |
| *C07C 227/10* | (2006.01) |
| *C07C 237/20* | (2006.01) |

(52) U.S. Cl.
CPC .......... *C07C 211/30* (2013.01); *A61K 31/137* (2013.01); *A61K 31/195* (2013.01); *A61K 31/415* (2013.01); *C07C 209/22* (2013.01); *C07C 213/08* (2013.01); *C07C 217/58* (2013.01); *C07C 227/10* (2013.01); *C07C 227/18* (2013.01); *C07C 229/34* (2013.01); *C07C 229/38* (2013.01); *C07C 237/20* (2013.01); *C07C 315/04* (2013.01); *C07C 317/32* (2013.01); *C07D 231/12* (2013.01); *C07D 295/135* (2013.01); *C07D 305/08* (2013.01)

(58) Field of Classification Search
USPC ...................................... 514/231.2
See application file for complete search history.

(56) References Cited

U.S. PATENT DOCUMENTS

| | | |
|---|---|---|
| 7,084,167 B2 | 8/2006 | Ruat et al. |
| 7,157,498 B2 | 1/2007 | Dauban et al. |
| 7,285,572 B2 | 10/2007 | Shinagawa et al. |
| 7,585,886 B2 | 9/2009 | Hachiya et al. |
| 8,153,658 B2 | 4/2012 | Hachiya et al. |
| 9,174,932 B2 | 11/2015 | Sugiki et al. |
| 2003/0199497 A1 | 10/2003 | Ruat et al. |
| 2010/0125061 A1 | 5/2010 | Firooznia et al. |
| 2011/0028452 A1 | 2/2011 | Didiuk et al. |
| 2014/0080770 A1 | 3/2014 | Miyazaki et al. |
| 2014/0120233 A1 | 5/2014 | Kato et al. |
| 2014/0154161 A1 | 6/2014 | Campbell |

FOREIGN PATENT DOCUMENTS

| | | |
|---|---|---|
| EP | 2341044 A1 | 7/2011 |
| WO | 01/90069 A1 | 11/2001 |

(Continued)

OTHER PUBLICATIONS

Masashi Imanishi et al.: "Discovery of a Novel Series of Biphenyl Benzoic Acid Derivatives as Potent and Selective Human β3-Adrenergic Receptor Agonists with Good Oral Bioavailability. Part I", Journal of Medicinal Chemistry, vol. 51, Issue 6, Mar. 27, 2008, pp. 1925-19944.

(Continued)

*Primary Examiner* — Kristin Vajda
(74) *Attorney, Agent, or Firm* — Merchant & Gould P.C.

(57) ABSTRACT

The invention relates to naphthalene compounds of Formula (I) and their pharmaceutically acceptable salts, wherein the substituents are as described herein, and their use in medicine for the treatment of diseases, disorders associated with the modulation of calcium sensing receptor modulators (Ca SR). The invention also relates to pharmaceutical compositions containing such compounds in treating diseases disorders associated with calcium sensing receptor modulators (Ca SR) channel modulators.

18 Claims, No Drawings

(56) References Cited

FOREIGN PATENT DOCUMENTS

| WO | 02/12181 | A1 | 2/2002 |
|---|---|---|---|
| WO | 2004/069793 | A2 | 8/2004 |
| WO | 2004/106280 | A1 | 12/2004 |
| WO | 2006/123725 | A1 | 11/2006 |
| WO | 2008/059854 | A1 | 5/2008 |
| WO | 2009/065406 | A2 | 5/2009 |
| WO | 2010/038895 | A1 | 4/2010 |
| WO | 2010/042642 | A1 | 4/2010 |
| WO | 2010/136036 | A2 | 12/2010 |
| WO | 2010/136037 | A1 | 12/2010 |
| WO | 2010/150837 | A1 | 12/2010 |
| WO | 2012/069402 | A1 | 5/2012 |
| WO | 2012/069419 | A1 | 5/2012 |
| WO | 2012/069421 | A1 | 5/2012 |
| WO | 2012/120476 | A1 | 9/2012 |
| WO | 2012/127385 | A1 | 9/2012 |
| WO | 2012/127388 | A1 | 9/2012 |
| WO | 2013/002329 | A1 | 1/2013 |
| WO | 2013/124828 | A1 | 8/2013 |
| WO | 2013/136288 | A1 | 9/2013 |
| WO | 2014/033604 | A1 | 3/2014 |

OTHER PUBLICATIONS

Song Ye et al.: "Diastereoselective Synthesis of 4-Hydroxytetralones via a Cascade Stetter-Aldol Reaction Catalyzed by N-Heterocyclic Carbenes", the Journal of Organic Chemistry, vol. 75, Issue 1, Jan. 1, 2010, pp. 273-276.
Christopher D. Gabbutt et al: "Synthesis and Photochromic Properties of Methoxy Substituted 2,2-Diaryl-2H-Naphtho[1,2-b]Pyrans", Heterocycles, vol. 63, No. 4, Jan. 16, 2004, pp. 567-582.
Hari Pati et al.: "An Efficient Method for the Synthesis of Substituted 4- Acetoxynaphthalene-2-Carboxylate Esters, Ethyl 4-Acetoxybenzofuran-6-Carboxylate, and Ethyl 4-Acetoxybenzothiophene-6-Carboxylate", Heterocyclic Communications, vol. 9, No. 6, Dec. 2003, pp. 587-592.
Juan Mangas-Sanchez et al.: "Chemoenzymatic Synthesis of Rivastigmine Based on Lipase-Catalyzed Processes", the Journal of Organic Chemistry, vol. 74, Issue 15, Aug. 7, 2009, pp. 5304-5310.
Edward C. Lawson et al.: "Nonpeptide Urotensin-II Receptor Antagonists: A New Ligand Class Based on Piperazino-Phthalimide and Piperazino-Isoindolinone Subunits", the Journal of Medicinal Chemistry, vol. 52, Issue 23, Dec. 10, 2009, pp. 7432-7445.
Albane Kessler et al.: "N1-Benzoyl-N2-[1-(1-naphthyl)ethyl]-trans-1,2-diaminocyclohexanes: Development of 4-Chlorophenylcarboxamide (Calhex 231) as a New Calcium Sensing Receptor Ligand Demonstrating Potent Calcilytic Activity", the Journal of Medicinal Chemistry, vol. 49, Issue 17, Aug. 24, 2006, pp. 5119-5128.
International Search Report and Written Opinion from International Patent Application No. PCT/IB2014/064067, mailed Dec. 4, 2014.
Paul E. Harrington et al.: "The Discovery of an Orally Efficacious Positive Allosteric Modulator of the Calcium Sensing Receptor Containing a Dibenzylamine Core", Bioorganic & Medicinal Chemistry Letters, vol. 20, No. 18, Sep. 2010, pp. 5544-5547, XP55151208, ISSN: 0960-894X.
Anders A. Jensen et al.: "Allosteric Modulation of the Calcium-Sensing Receptor", Current Neuropharmacology, Bentham Science Publishers, Hilversum, NL, vol. 5, No. 3, Sep. 2007, pp. 180-186, XP002590070, ISSN: 1570-159X.
Lionel Kiefer et al.: "Novel Calcium Sensing Receptor Ligands: a Patent Survey", Expert Opinion on Therapeutic Patents, Jan. 2011, pp. 681-698, XP055062103.

SUBSTITUTED NAPHTHALENE COMPOUNDS AS CALCIUM SENSING RECEPTOR MODULATORS

RELATED APPLICATIONS

This application is a National Stage Application of International Patent Application No. PCT/IB2014/064067, filed 26 Aug. 2014, which claims the benefit of Indian Provisional Patent Application No. 2814/MUM/2013, filed Aug. 28, 2013, Indian Provisional Patent Application No. 2815/MUM/2013, filed Aug. 28, 2013, and Indian Provisional Patent Application No. 1091/MUM/2014, filed Mar. 27, 2014 and which applications are incorporated herein by reference. To the extent appropriate, a claim of priority is made to each of the above disclosed applications.

FIELD OF THE INVENTION

The present invention relates to substituted naphthalene compound of Formula (I), pharmaceutically acceptable salts thereof and pharmaceutical compositions for treating the diseases, disorders, syndromes or conditions associated with the modulation of calcium sensing receptors (CaSR). The invention also relates to methods of treating the diseases disorders, syndromes or conditions associated with the modulation of calcium sensing receptors (CaSR). The invention also relates to process for the preparation of the compounds of the invention.

BACKGROUND OF THE INVENTION $Ca^{2+}$ has been known to be an intracellular second messenger, with the molecular identification of an extracellular calcium sensing receptor (CaSR), it has further opened the possibility that $Ca^{2+}$ might also function as a messenger outside the cells. Information about the local changes in extracellular concentration of $Ca^{2+}$ is conveyed to the interior of many types of cells through this unique receptor.

Calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily. Structurally, CaSR has an exceptionally large amino-terminal extracellular (ECD) domain (about 600 amino acids), a feature that is shared by all of the members of the family C GPCRs.

In mammals, the expression of CaSR is quite ubiquitous and its presence in the parathyroid gland plays an important role in the secretion of parathyroid hormone (PTH). The reduction in serum calcium leads to the secretion of PTH. Consequently, PTH secretion leads to conservation of serum $Ca^{2+}$ by increasing kidney retention and intestinal absorption of $Ca^{2+}$. This happens indirectly through the PTH-induced synthesis of the active vitamin D metabolite, 2,5-dihydroxyvitamin D. In addition, the pulsatile action of PTH has anabolic effects on bone development and its sustained levels can lead to catabolic effects, in which the bones breakdown releasing $Ca^{2+}$ as in the case of osteoporosis. All these systems converge in maintenance of baseline serum $Ca^{2+}$ and it involves a tight regulation between serum PTH and extracellular calcium which is mediated by the remarkable CaSR.

In conditions such as primary and secondary hyperparathyroidism, there is excessive secretion of parathyroid hormone due to hyperplasia of the glands. The most common cause of primary hyperparathyroidism (PHPT) is parathyroid adenoma resulting from clonal mutations (~97%) and associated hypercalcemia. In the case of secondary hyperparathyroidism (SHPT), it is most commonly seen in patients with chronic renal failure. The kidneys fail to convert enough vitamin D to its active form and also does not adequately excrete phosphorous. Excess phosphorous further depletes serum calcium forming calcium phosphate (kidney stones) leading to hypocalcaemia.

Small molecules that are positive allosteric modulators called calcimimetics modulate and improve the receptors sensitivity to the already existing milieu of extracellular ionic calcium. This would eventually translate in lowering plasma PTH levels thereby improving conditions of hyperparathyroidism, calcium homeostasis and bone metabolism. WO 2013/124828, WO 2013/002329, WO 2013/136288, US 2014/0080770, US 2014/01554161, WO 2012/127388, WO 2012/120476, WO 2012/127385, WO 2012/069421, WO 2012/069419, WO 2012/069402, US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 applications disclose the compounds related to calcium sensing receptors (CaSR) for the treatment of various diseases mediated by CaSR. And also *J. Med. Chem.* (2006), 49, 5119-5128 discloses the compounds related to calcium sensing receptors (CaSR).

SUMMARY OF THE INVENTION

In accordance with one aspect, the invention provides compounds having the structure of Formula (I),

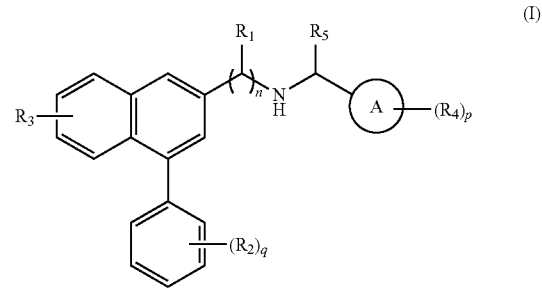

ring A is phenyl or naphthyl;

$R_1$ is hydrogen or substituted or unsubstituted $(C_1$-$C_6)$ alkyl;

$R_2$, which may be same or different at each occurrence, is independently selected from halogen, cyano, substituted or unsubstituted $(C_1$-$C_6)$alkyl, substituted or unsubstituted $(C_1$-$C_6)$haloalkyl, substituted or unsubstituted $(C_1$-$C_6)$hydroxyalkyl, —X—C(O)—Z, —OR$_9$, —NR$_7$R$_8$, —NR$_7$C(O)R$_6$, —S(O)$_{0-2}$R$_6$, —S(O)$_2$NR$_7$R$_8$, —NR$_7$S(O)$_2$R$_6$, substituted or unsubstituted $(C_3$-$C_{12})$cycloalkyl, substituted or unsubstituted phenyl, substituted or unsubstituted 5- to 6-membered heteroaryl, substituted or unsubstituted 5- to 6-membered heterocyclyl and ring D;

ring D is

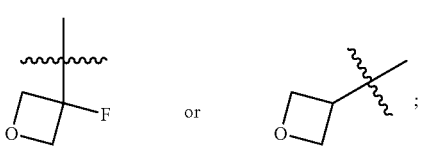

X is selected from a bond, —(CR$_a$R$_b$)$_m$—, —NR$_{12}$—, —O(CR$_a$R$_b$)$_m$—, —(CR$_a$R$_b$)$_m$O—, —C(O)NR$_{12}$—, —(CR$_a$R$_b$)$_m$O—(CR$_a$R$_b$)$_m$— and —C(O)NR$_{12}$(CR$_a$R$_b$)$_m$—;

R$_a$ and R$_b$ which may be same or different at each occurrence, are independently selected from hydrogen, halogen, hydroxy, substituted or unsubstituted (C$_1$-C$_6$)alkyl, substituted or unsubstituted (C$_1$-C$_6$)haloalkyl and substituted or unsubstituted (C$_3$-C$_6$)cycloalkyl; or R$_a$ and R$_b$, together with the carbon atom to which they are attached, form a substituted or unsubstituted 3 to 6 membered saturated carbocyclic ring;

Z is —OR$_{10}$ or —NR$_7$R$_8$;

R$_3$ is selected from hydrogen, halogen, substituted or unsubstituted (C$_1$-C$_6$)alkyl, substituted or unsubstituted (C$_1$-C$_6$)haloalkyl, —OR$_9$, and substituted or unsubstituted (C$_3$-C$_{12}$)cycloalkyl;

R$_4$, which may be same or different at each occurrence, is independently selected from halogen, substituted or unsubstituted (C$_1$-C$_6$)alkyl, substituted or unsubstituted (C$_1$-C$_6$)haloalkyl, substituted or unsubstituted (C$_1$-C$_6$)alkoxyalkyl, —SF$_5$ and —OR$_9$;

R$_5$ is substituted or unsubstituted (C$_1$-C$_6$)alkyl;

R$_6$ is selected from substituted or unsubstituted (C$_1$-C$_6$) alkyl, substituted or unsubstituted (C$_3$-C$_{12}$)cycloalkyl and substituted or unsubstituted (C$_6$-C$_{14}$)aryl;

R$_7$ and R$_8$, which may be same or different at each occurrence, are independently selected from hydrogen, substituted or unsubstituted (C$_1$-C$_6$)alkyl, —(CR$_a$R$_b$)$_{1-2}$R$_{11}$, —(CR$_c$R$_d$)$_m$—OH and substituted or unsubstituted (C$_3$-C$_{12}$)cycloalkyl;

R$_c$ and R$_d$ which may be same or different at each occurrence, are independently hydrogen or substituted or unsubstituted (C$_1$-C$_6$)alkyl;

R$_9$ is independently selected from hydrogen, substituted or unsubstituted (C$_1$-C$_6$)alkyl, substituted or unsubstituted (C$_1$-C$_6$)haloalkyl, substituted or unsubstituted (C$_1$-C$_6$)alkoxyalkyl and substituted or unsubstituted (C$_3$-C$_{12}$)cycloalkyl;

R$_{10}$ is selected from hydrogen, substituted or unsubstituted (C$_1$-C$_6$)alkyl and —(CR$_a$R$_b$)$_{1-2}$phenyl;

R$_{11}$ is substituted or unsubstituted phenyl, wherein the substituents are selected from halogen, (C$_1$-C$_6$)alkyl and —OR$_9$;

R$_{12}$ is hydrogen or substituted or unsubstituted (C$_1$-C$_6$)alkyl;

'm' is an integer ranging from 1 to 3, both inclusive;
'n' is an integer ranging from 1 to 3, both inclusive;
'p' is an integer ranging from 0 to 3, both inclusive; and
'q' is an integer ranging from 1 to 3, both inclusive;
or a pharmaceutically acceptable salt thereof.

According to one embodiment, there are provided compounds having the structure of Formula (II):

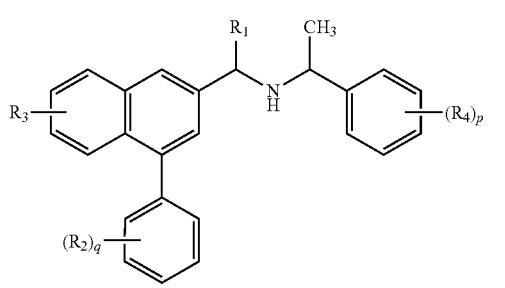

wherein,

R$_1$ is hydrogen or substituted or unsubstituted (C$_1$-C$_6$) alkyl;

R$_2$, which may be same or different at each occurrence, is independently selected from halogen, substituted or unsubstituted (C$_1$-C$_6$)alkyl, substituted or unsubstituted (C$_1$-C$_6$) haloalkyl, —X—C(O)—Z, —OR$_9$ and —S(O)$_{0-2}$R$_6$;

X is selected from a bond, —(CR$_a$R$_b$)$_m$—, —O(CR$_a$R$_b$)$_m$— and —(CR$_a$R$_b$)$_m$O—;

R$_a$ and R$_b$ which may be same or different at each occurrence, are independently selected from hydrogen, halogen, hydroxy and substituted or unsubstituted (C$_1$-C$_6$)alkyl;

Z is —OR$_{10}$ or —NR$_7$R$_8$;

R$_3$ is selected from hydrogen, halogen and substituted or unsubstituted (C$_1$-C$_6$)alkyl;

R$_4$, which may be same or different at each occurrence, is independently selected from halogen, substituted or unsubstituted (C$_1$-C$_6$)alkyl, substituted or unsubstituted (C$_1$-C$_6$) haloalkyl, substituted or unsubstituted (C$_1$-C$_6$)alkoxyalkyl and —OR$_9$;

R$_6$ is substituted or unsubstituted (C$_1$-C$_6$)alkyl or substituted or unsubstituted (C$_3$-C$_{12}$)cycloalkyl;

R$_7$ and R$_8$ which may be same or different at each occurrence, are independently selected from hydrogen, substituted or unsubstituted (C$_1$-C$_6$)alkyl, —(CR$_a$R$_b$)$_{1-2}$R$_{11}$ and substituted or unsubstituted (C$_3$-C$_{12}$)cycloalkyl;

R$_9$ is selected from hydrogen, substituted or unsubstituted (C$_1$-C$_6$)alkyl, substituted or unsubstituted (C$_1$-C$_6$)haloalkyl, substituted or unsubstituted (C$_1$-C$_6$)alkoxyalkyl and substituted or unsubstituted (C$_3$-C$_{12}$)cycloalkyl;

R$_{10}$ is hydrogen or substituted or unsubstituted (C$_1$-C$_6$) alkyl;

R$_{11}$ is substituted or unsubstituted phenyl, wherein the substituents are selected from halogen, (C$_1$-C$_6$)alkyl and (C$_1$-C$_6$)alkoxy;

'm' is an integer ranging from 1 to 3, both inclusive;
'p' is an integer ranging from 0 to 2, both inclusive; and
'q' is an integer ranging from 1 to 3, both inclusive;
or a pharmaceutically acceptable salt thereof.

According to another embodiment, there are provided compounds having the structure of Formula (III)

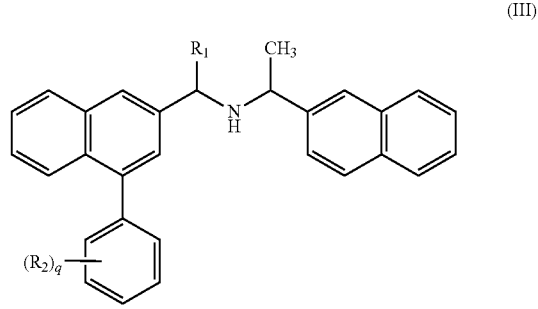

R$_1$ is hydrogen or substituted or unsubstituted (C$_1$-C$_6$) alkyl;

R$_2$, which may be same or different at each occurrence, is independently selected from halogen, substituted or unsubstituted (C$_1$-C$_6$)alkyl, substituted or unsubstituted (C$_1$-C$_6$) haloalkyl and —X—C(O)—Z;

X is selected from a bond, —(CR$_a$R$_b$)$_m$—, —O(CR$_a$R$_b$)$_m$— and —(CR$_a$R$_b$)$_m$O—;

R$_a$ and R$_b$ which may be same or different at each occurrence, are independently selected from hydrogen, halogen, hydroxy and substituted or unsubstituted (C$_1$-C$_6$)alkyl;

Z is —OR₁₀ or —NR₇R₈;

R₇ and R₈, which may be same or different at each occurrence, are independently selected from hydrogen, substituted or unsubstituted (C₁-C₆)alkyl and substituted or unsubstituted (C₃-C₁₂)cycloalkyl;

R₁₀ is hydrogen or substituted or unsubstituted (C₁-C₆)alkyl;

'm' is an integer ranging from 1 to 3, both inclusive; and
'q' is an integer ranging from 1 to 3, both inclusive;
or a pharmaceutically acceptable salt thereof.

According to another embodiment, there are provided compounds having the structure of Formula (IV):

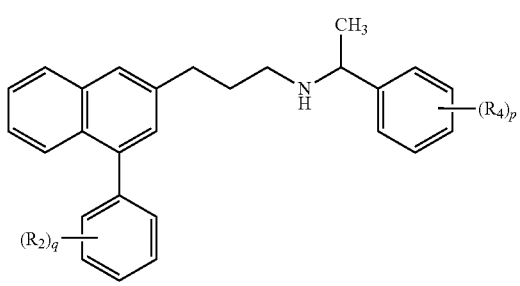

(IV)

R₂, which may be same or different at each occurrence, is independently selected from halogen, substituted or unsubstituted (C₁-C₆)alkyl and substituted or unsubstituted (C₁-C₆)haloalkyl;

R₄, which may be same or different at each occurrence, is independently selected from halogen, substituted or unsubstituted (C₁-C₆)alkyl, substituted or unsubstituted (C₁-C₆)haloalkyl, and —OR₉;

R₉ is hydrogen or substituted or unsubstituted (C₁-C₆)alkyl;

'p' is an integer ranging from 0 to 2, both inclusive; and
'q' is an integer ranging from 1 to 3, both inclusive;
or a pharmaceutically acceptable salt thereof.

According to another embodiment, there are provided compounds having the structure of Formula (V):

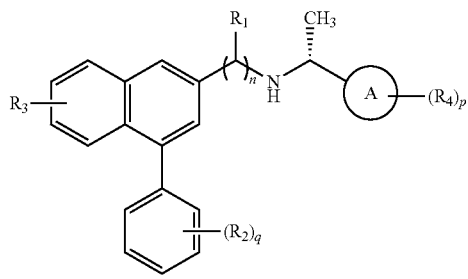

(V)

ring A is phenyl or naphthyl;

R₁ is hydrogen or substituted or unsubstituted (C₁-C₆)alkyl;

R₂, which may be same or different at each occurrence, is independently selected from halogen, cyano, substituted or unsubstituted (C₁-C₆)alkyl, substituted or unsubstituted (C₁-C₆)haloalkyl, substituted or unsubstituted (C₁-C₆)hydroxyalkyl, —X—C(O)—Z, —OR₉, —NR₇R₈, —NR₇C(O)R₆, —S(O)₀₋₂R₆, —S(O)₂NR₇R₈, —NR₇S(O)₂R₆, substituted or unsubstituted (C₃-C₁₂)cycloalkyl, substituted or unsubstituted phenyl, substituted or unsubstituted 5- to 6-membered heteroaryl, substituted or unsubstituted 5- to 6-membered heterocyclyl and ring D;

ring D is

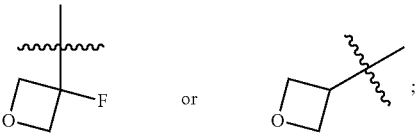 [SMILES: *C1(F)COC1 ; *C1COC1]

X is selected from a bond, —(CR_aR_b)_m—, —NR₁₂—, —O(CR_aR_b)_m—, —(CR_aR_b)_mO—, —C(O)NR₁₂—, —(CR_aR_b)_mO—(CR_aR_b)_m— and —C(O)NR₁₂(CR_aR_b)_m—;

R_a and R_b which may be same or different at each occurrence, are independently selected from hydrogen, halogen, hydroxy, substituted or unsubstituted (C₁-C₆)alkyl, substituted or unsubstituted (C₁-C₆)haloalkyl and substituted or unsubstituted (C₃-C₆)cycloalkyl; or R_a and R_b, together with the carbon atom to which they are attached, form a substituted or unsubstituted 3 to 6 membered saturated carbocyclic ring;

Z is —OR₁₀ or —NR₇R₈;

R₃ is selected from hydrogen, halogen, substituted or unsubstituted (C₁-C₆)alkyl, substituted or unsubstituted (C₁-C₆)haloalkyl, —OR₉, and substituted or unsubstituted (C₃-C₁₂)cycloalkyl;

R₄, which may be same or different at each occurrence, is independently selected from halogen, substituted or unsubstituted (C₁-C₆)alkyl, substituted or unsubstituted (C₁-C₆)haloalkyl, substituted or unsubstituted (C₁-C₆)alkoxyalkyl, —SF₅ and —OR₉;

R₆ is selected from substituted or unsubstituted (C₁-C₆)alkyl, substituted or unsubstituted (C₃-C₁₂)cycloalkyl and substituted or unsubstituted (C₆-C₁₄)aryl;

R₇ and R₈, which may be same or different at each occurrence, are independently selected from hydrogen, substituted or unsubstituted (C₁-C₆)alkyl, —(CR_aR_b)₁₋₂R₁₁, —(CR_cR_d)_m—OH and substituted or unsubstituted (C₃-C₁₂)cycloalkyl;

R_c and R_d which may be same or different at each occurrence, are independently hydrogen or substituted or unsubstituted (C₁-C₆)alkyl;

R₉ is independently selected from hydrogen, substituted or unsubstituted (C₁-C₆)alkyl, substituted or unsubstituted (C₁-C₆)haloalkyl, substituted or unsubstituted (C₁-C₆)alkoxyalkyl and substituted or unsubstituted (C₃-C₁₂)cycloalkyl;

R₁₀ is selected from hydrogen, substituted or unsubstituted (C₁-C₆)alkyl and —(CR_aR_b)₁₋₂phenyl;

R₁₁ is substituted or unsubstituted phenyl, wherein the substituents are selected from halogen, (C₁-C₆)alkyl and —OR₉;

R₁₂ is hydrogen or substituted or unsubstituted (C₁-C₆)alkyl;

'm' is an integer ranging from 1 to 3, both inclusive;
'n' is an integer ranging from 1 to 3, both inclusive;
'p' is an integer ranging from 0 to 3, both inclusive; and
'q' is an integer ranging from 1 to 3, both inclusive;
or a pharmaceutically acceptable salt thereof.

According to another embodiment, there are provided compounds having the structure of Formula (V):

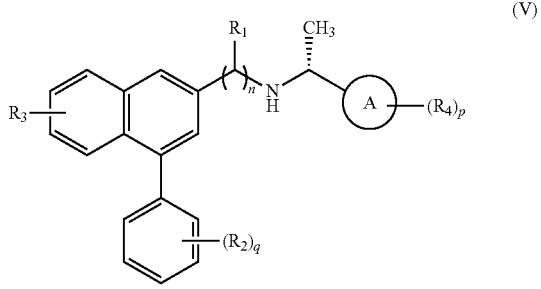

(V)

wherein, ring A is phenyl or naphthyl;

$R_1$ is hydrogen or substituted or unsubstituted $(C_1-C_6)$alkyl;

$R_2$, which may be same or different at each occurrence, is independently selected from halogen, substituted or unsubstituted $(C_1-C_6)$alkyl, substituted or unsubstituted $(C_1-C_6)$haloalkyl, —X—C(O)—Z, —$OR_9$ and —$S(O)_{0-2}$-alkyl;

X is selected from a bond, —$(CR_aR_b)_m$— and —$O(CR_aR_b)_m$—;

$R_a$ and $R_b$ which may be same or different at each occurrence, are independently selected from hydrogen, halogen and substituted or unsubstituted $(C_1-C_6)$alkyl;

Z is —$OR_{10}$ or —$NR_7R_8$;

$R_3$ is hydrogen or halogen;

$R_4$, which may be same or different at each occurrence, is independently selected from halogen, substituted or unsubstituted $(C_1-C_6)$alkyl, substituted or unsubstituted $(C_1-C_6)$haloalkyl and —$OR_9$;

$R_7$ and $R_8$ are independently selected from hydrogen, substituted or unsubstituted $(C_1-C_6)$alkyl and $(CR_aR_b)_{1-2}R_{11}$;

$R_9$ is selected from hydrogen, substituted or unsubstituted $(C_1-C_6)$alkyl and substituted or unsubstituted $(C_1-C_6)$haloalkyl;

$R_{10}$ is hydrogen or substituted or unsubstituted $(C_1-C_6)$alkyl;

$R_{11}$ is substituted or unsubstituted phenyl, wherein the substituents are selected from halogen, $(C_1-C_6)$alkyl and $(C_1-C_6)$alkoxy;

'm' is an integer ranging from 1 to 3, both inclusive;

'n' is an integer ranging from 1 to 3, both inclusive;

'p' is an integer ranging from 0 to 2, both inclusive; and

'q' is an integer ranging from 1 to 3;

or a pharmaceutically acceptable salt thereof.

It should be understood that the Formula (I), Formula (II), Formula (III), Formula (IV) and/or Formula (V) structurally encompasses all tautomers, stereoisomers, enantiomers and diastereomers, including isotopes wherever applicable and pharmaceutically acceptable salts that may be contemplated from the chemical structures generally described herein.

The details of one or more embodiments of the invention set forth in the below are illustrative in nature only and not intended to limit to the scope of the invention. Other features, objects and advantages of the inventions will be apparent from the description and claims.

According to one embodiment, there are provided compounds of Formula (I) and/or Formula (V) in which ring A is phenyl or naphthyl; $R_4$ is independently selected from halogen, substituted or unsubstituted $(C_1-C_6)$alkyl and substituted or unsubstituted $(C_1-C_6)$haloalkyl and —$OR_9$ where $R_9$ is $(C_1-C_6)$alkyl or $(C_1-C_6)$haloalkyl; and 'p' is 0, 1 to 2.

According to another embodiment, there are provided compounds of Formula (I), Formula (II), Formula (III) and/or Formula (V) in which $R_1$ is hydrogen or substituted or unsubstituted $(C_1-C_6)$alkyl.

In another embodiment there are provided compounds of Formula (I), Formula (II), Formula (III) and/or Formula (V) in which $R_1$ is methyl or ethyl.

According to another embodiment, there are provided compounds of Formula (I) in which $R_2$ is independently selected from halogen, substituted or unsubstituted $(C_1-C_6)$alkyl, substituted or unsubstituted $(C_1-C_6)$haloalkyl, substituted or unsubstituted $(C_1-C_6)$hydroxyalkyl, X—C(O)—Z, —O—$(C_1-C_6)$alkyl, —O—$(C_1-C_6)$haloalkyl, —NHC(O)alkyl, —$S(O)_{0-2}$alkyl, substituted or unsubstituted phenyl, substituted or unsubstituted 5- to 6-membered heteroaryl, substituted or unsubstituted 5- to 6-membered heterocyclyl,

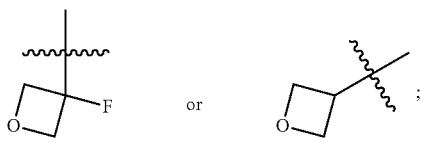

wherein X is selected from a bond, —$(CR_aR_b)_m$— and —$O(CR_aR_b)_m$— where $R_a$ and $R_b$ are independently hydrogen, halogen, or substituted or unsubstituted $(C_1-C_6)$alkyl; Z is —$OR_{10}$ where $R_{10}$ is hydrogen or $(C_1-C_6)$alkyl; 'm' is selected from 1, 2 or 3 and 'q' is selected from 1, 2 or 3.

According to another embodiment, there are provided compounds of Formula (I) and/or Formula (V) in which $R_1$ is $(C_1-C_3)$alkyl;

$R_2$ which may be same or different at each occurrence, is independently selected from halogen, $(C_1-C_4)$alkyl, $(C_1-C_4)$haloalkyl, —X—C(O)—Z, —O—$(C_1-C_4)$alkyl or —O—$(C_1-C_4)$haloalkyl;

X is selected from a bond or —$(CR_aR_b)_m$ where $R_a$ and $R_b$ are independently hydrogen or substituted or unsubstituted $(C_1-C_6)$alkyl;

Z is —OH;

$R_3$ is hydrogen;

$R_4$, which may be same or different at each occurrence, is independently selected from halogen and —$OR_9$;

$R_9$ is $(C_1-C_4)$alkyl, haloalkyl;

$R_5$ is $(C_1-C_3)$alkyl;

'm' is an integer selected from 1 or 2;

'n' is 1;

'p' is 0, 1 or 2; and

'q' is an integer ranging from 1 to 3, both inclusive;

or a pharmaceutically acceptable salt thereof.

According to another embodiment, there are provided compounds of Formulae (I) to (V) wherein the compound is in the free base form.

According to another embodiment, there are provided compounds of Formulae (I) to (V) wherein the compound is a pharmaceutically acceptable salt.

According to another embodiment, there are provided compounds of Formulae (I) to (V) wherein pharmaceutically acceptable salt is hydrochloride salt.

According to another embodiment, the provided compounds of Formulae (I) to (V) structurally encompass stereoisomers including enantiomers and diastereomers.

Below are the representative compounds, which are illustrative in nature only and are not intended to limit to the scope of the invention:

(R)-1-(Naphthalen-1-yl)-N-((4-(4-(trifluoromethyl)phenyl) naphthalen-2-yl) methyl)ethanamine hydrochloride;
(R)-1-(4-Fluoro-3-methoxyphenyl)-N-((4-(4-(trifluoromethyl)phenyl)naphthalen-2-yl)methyl) ethanamine hydrochloride;
(R)-1-(Naphthalen-1-yl)-N-((4-(3-(trifluoromethyl) phenyl) naphthalen-2-yl) methyl)ethanamine hydrochloride;
(R)-1-(4-Fluoro-3-methoxyphenyl)-N-((4-(3-(trifluoromethyl)phenyl) naphthalen-2-yl) methyl)ethanamine hydrochloride;
(R)—N-(1-(3-Methoxyphenyl)ethyl)-3-(4-(4-(trifluoromethyl) phenyl) naphthalen-2-yl)propan-1-amine hydrochloride;
(1R)-1-(3-Methoxyphenyl)-N-(1-(4-(4-(trifluoromethyl) phenyl)naphthalen-2-yl) ethyl)ethanamine hydrochloride;
1-(4-(3-Fluoro-4-methoxyphenyl) naphthalen-2-yl)-N—((R)-1-(3-methoxyphenyl) ethyl) ethanamine hydrochloride;
(1R)-1-(3-Chlorophenyl)-N-(1-(4-(3-fluoro-4-methoxyphenyl) naphthalen-2-yl) ethyl) ethanamine hydrochloride;
(1R)-1-(Naphthalen-1-yl)-N-(1-(4-(4-(trifluoromethyl) phenyl) naphthalen-2-yl) ethyl) ethanamine hydrochloride;
(1R)-1-(3-Chlorophenyl)-N-(1-(4-(4-(trifluoromethyl) phenyl) naphthalen-2-yl) ethyl) ethanamine hydrochloride;
(1R)-1-(4-Fluoro-3-methoxyphenyl)-N-(1-(4-(4-(trifluoromethyl)phenyl) naphthalen-2-yl) ethyl ethanamine hydrochloride;
(1R)-1-(3-Ethoxyphenyl)-N-(1-(4-(4-(trifluoromethyl)phenyl)naphthalen-2-yl)ethyl)ethanamine hydrochloride;
(1R)-1-(3-Fluorophenyl)-N-(1-(4-(4-(trifluoromethyl) phenyl) naphthalen-2-yl)ethyl)ethanamine hydrochloride;
(1R)-1-(3-Chlorophenyl)-N-(1-(4-(3-(trifluoromethyl) phenyl) naphthalen-2-yl) ethyl)ethanamine hydrochloride;
1-(4-(4-Fluorophenyl) naphthalen-2-yl)-N—((R)-1-(3-methoxyphenyl)ethyl) ethanamine hydrochloride;
(1R)-1-(3-Chlorophenyl)-N-(1-(4-(4-fluorophenyl) naphthalen-2-yl)ethyl) ethanamine hydrochloride;
(1R)-1-(3-Methoxyphenyl)-N-(1-(4-(4-(methylsulfonyl) phenyl)naphthalen-2-yl) ethyl)ethanamine hydrochloride;
N—((R)-1-(3-Methoxyphenyl)ethyl)-1-(4-(4-(trifluoromethyl)phenyl) naphthalen-2-yl)propan-1-amine hydrochloride;
(1R)-1-(3-Methoxyphenyl)-N-(1-(4-(4-(trifluoromethoxy) phenyl) naphthalen-2-yl)ethyl) ethanamine hydrochloride;
(1R)-1-(3-Chlorophenyl)-N-(1-(4-(4-(trifluoromethoxy) phenyl) naphthalen-2-yl)ethyl)ethanamine hydrochloride;
1-(4-(4-(Difluoromethoxy) phenyl) naphthalen-2-yl)-N—((R)-1-(3-methoxyphenyl) ethyl) ethanamine hydrochloride;
(1R)-1-(3-Chlorophenyl)-N-(1-(4-(4-(difluoromethoxy) phenyl) naphthalen-2-yl)ethyl)ethanamine hydrochloride;
(1R)-1-(3-chlorophenyl)-N-(1-(4-(4-(3-fluorooxetan-3-yl) phenyl)naphthalen-2-yl)ethyl)ethanamine hydrochloride;
(R)-Methyl-2-methyl-5-(3-(((1-(naphthalen-1-yl)ethyl) amino)methyl)naphthalen-1-yl)benzoate;
(R)-Methyl 5-(3-(((1-(3-methoxyphenyl)ethyl) amino) methyl) naphthalen-1-yl)-2-methylbenzoate;
(R)-Methyl 5-(3-(((1-(3-ethoxyphenyl)ethyl)amino) methyl) naphthalen-1-yl)-2-methylbenzoate;
(R)-Methyl 2-methyl-5-(3-(((1-(3-propoxyphenyl) ethyl) amino)methyl) naphthalen-1-yl)benzoate;
(R)-Methyl 5-(3-(((1-(4-fluoro-3-methoxyphenyl) ethyl) amino)methyl)naphthalen-1-yl)-2-methylbenzoate;
(R)-methyl 5-(3-(((1-(3-chlorophenyl)ethyl)amino) methyl) naphthalen-1-yl)-2-methylbenzoate;
(R)-Methyl 5-(3-(((1-(3-(2,2-difluoroethoxy)phenyl)ethyl) amino)methyl)naphthalen-1-yl)-2-methylbenzoate;
(R)-Methyl 2-fluoro-5-(3-(((1-(4-fluoro-3-methoxyphenyl) ethyl)amino)methyl)naphthalen-1-yl)benzoate;
(R)-Methyl 2-fluoro-5-(3-(((1-(3-methoxyphenyl)ethyl) amino)methyl)naphthalen-1-yl)benzoate;
(R)-Methyl 5-(3-(((1-(3-ethoxyphenyl)ethyl)amino) methyl) naphthalen-1-yl)-2-fluorobenzoate;
(R)-Methyl 2-fluoro-5-(3-(((1-(3-(2-methoxyethoxy) phenyl)ethyl)amino)methyl) naphthalen-1-yl)benzoate;
(R)-Methyl 2-chloro-5-(3-(((1-(3-methoxyphenyl) ethyl) amino)methyl) naphthalen-1-yl)benzoate;
(R)-Methyl 2-chloro-5-(3-(((1-(3-ethoxyphenyl) ethyl)amino)methyl) naphthalen-1-yl)benzoate;
(R)-Methyl 3-(3-(((1-(3-methoxyphenyl)ethyl)amino) methyl)naphthalen-1-yl)-2-methylbenzoate
(R)-Methyl 3-(3-(((1-(3-ethoxyphenyl)ethyl)amino)methyl) naphthalen-1-yl)-2-methylbenzoate;
(R)-Methyl 2-fluoro-3-(3-(((1-(3-methoxyphenyl) ethyl)amino)methyl) naphthalen-1-yl)benzoate;
(R)-Methyl 2-methoxy-5-(3-(((1-(3-methoxyphenyl) ethyl) amino) methyl) naphthalen-1-yl)benzoate;
(R)-Methyl 2-isopropyl-5-(3-(((1-(3-methoxyphenyl)ethyl) amino)methyl)naphthalen-1-yl)benzoate;
(R)-Ethyl 4-(3-(((1-(naphthalen-1-yl)ethyl)amino) methyl) naphthalen-1-yl)benzoate;
(R)-Ethyl 4-(3-(((1-(4-fluoro-3-methoxyphenyl) ethyl)amino)methyl) naphthalen-1-yl)benzoate;
(R)-Methyl 3-(3-(((1-(3-methoxyphenyl)ethyl)amino) methyl)naphthalen-1-yl) benzoate;
(R)-methyl 2-fluoro-5-(3-(((1-(3-methoxyphenyl) ethyl) amino)methyl) naphthalen-1-yl)benzoate hydrochloride;
(R)-Methyl 3-(2-fluoro-5-(3-(((1-(3-methoxyphenyl) ethyl) amino)methyl) naphthalen-1-yl)phenyl) propanoate;
(R)-Methyl 2-(4-(3-(((1-(3-methoxyphenyl)ethyl)amino) methyl)naphthalen-1-yl) phenyl)-2-methylpropanoate;
(R)-2-(3-(3-(((1-(3-Methoxyphenyl)ethyl)amino)methyl) naphthalen-1-yl)phenyl)-2-methylpropanoic acid;
Isopropyl-5-(3-(1-(((R)-1-(3-methoxyphenyl)ethyl)amino) ethyl)naphthalen-1-yl)-2-methyl benzoate;
Isopropyl 5-(3-(1-(((R)-1-(4-fluoro-3-methoxyphenyl) ethyl)amino)ethyl)naphthalen-1-yl)-2-methylbenzoate;
Isopropyl 3-(3-(1-(((R)-1-(3-methoxyphenyl)ethyl)amino) ethyl)naphthalen-1-yl)-2-methylbenzoate;
Isopropyl 5-(3-(1-(((R)-1-(3-chlorophenyl)ethyl)amino) ethyl)naphthalen-1-yl)-2-methylbenzoate;
Isopropyl 3-fluoro-5-(3-(1-(((R)-1-(3-methoxyphenyl)ethyl) amino)ethyl)naphthalen-1-yl)benzoate;
Isopropyl 4-(3-(1-(((R)-1-(3-methoxyphenyl)ethyl)amino) ethyl)naphthalen-1-yl)benzoate;
Isopropyl 3-fluoro-4-(3-(1-(((R)-1-(3-methoxyphenyl)ethyl) amino)ethyl)naphthalen-1-yl)benzoate;
Isopropyl 2-chloro-4-(3-(1-(((R)-1-(3-methoxyphenyl) ethyl) amino)ethyl)naphthalen-1-yl)benzoate;
Isopropyl 3-(2-fluoro-5-(3-(1-(((R)-1-(3-methoxyphenyl) ethyl) amino)ethyl)naphthalen-1-yl)phenyl)propanoate;
Isopropyl 2-fluoro-5-(3-(1-(((R)-1-(3-methoxyphenyl)ethyl) amino)ethyl)naphthalen-1-yl)benzoate;
Isopropyl 4-(3-(1-(((R)-1-(3-methoxyphenyl)ethyl)amino) ethyl) naphthalen-1-yl)-2-(trifluoromethyl)benzoate;
Isopropyl 3-(3-(1-(((R)-1-(3-methoxyphenyl)ethyl)amino) ethyl) naphthalen-1-yl)-5-methylbenzoate;
Isopropyl 5-(3-(1-(((R)-1-(3-ethoxyphenyl)ethyl)amino) ethyl) naphthalen-1-yl)-2-fluorobenzoate;
Isopropyl 5-(3-(1-(((R)-1-(3-chlorophenyl)ethyl)amino) ethyl) naphthalen-1-yl)-2-fluorobenzoate;

Isopropyl 5-(3-(1-(((R)-1-(3-methoxyphenyl)ethyl)amino) ethyl) naphthalen-1-yl)-2-(trifluoromethyl)benzoate;
Isopropyl 3-(2-fluoro-3-(3-(1-(((R)-1-(3-methoxyphenyl) ethyl) amino)ethyl) naphthalen-1-yl)phenyl)propanoate;
Isopropyl 4-(3-(1-(((R)-1-(3-methoxyphenyl)ethyl)amino) ethyl) naphthalen-1-yl)-2-methylbenzoate;
Isopropyl 3-(2-methoxy-5-(3-(1-(((R)-1-(3-methoxyphenyl) ethyl) amino)ethyl) naphthalen-1-yl)phenyl)propanoate;
Isopropyl 2-fluoro-4-(3-(1-(((R)-1-(3-methoxyphenyl)ethyl) amino) naphthalen-1-yl)benzoate;
Isopropyl 3-methoxy-5-(3-(1-(((R)-1-(3-methoxyphenyl) ethyl)amino) ethyl) naphthalen-1-yl)benzoate;
Isopropyl 2-chloro-5-(3-(1-(((R)-1-(3-methoxyphenyl) ethyl) amino)ethyl) naphthalen-1-yl)benzoate;
Isopropyl 3-(3-fluoro-5-(3-(1-(((R)-1-(3-methoxyphenyl) ethyl) amino)ethyl) naphthalen-1-yl)phenyl)propanoate;
Isopropyl 2-(3-fluoro-5-(3-(1-(((R)-1-(3-methoxyphenyl) ethyl) amino)ethyl)naphthalen-1-yl)phenoxy)-2-methylpropanoate;
2,2-Difluoro-N—((R)-1-(3-methoxyphenyl)ethyl)-2-(4-(3-(1-(((R)-1-(3-methoxyphenyl) ethyl)amino)ethyl)naphthalen-1-yl)phenyl)acetamide;
Isopropyl 3-(2-fluoro-4-(3-(1-(((R)-1-(3-methoxyphenyl) ethyl) amino)ethyl) naphthalen-1-yl)phenyl)propanoate;
Isopropyl 3-(5-(3-(1-(((R)-1-(3-methoxyphenyl)ethyl) amino) ethyl) naphthalen-1-yl)-2-methylphenyl)propanoate;
Isopropyl 2-(4-(3-(1-(((R)-1-(3-methoxyphenyl)ethyl) amino)ethyl) naphthalen-1-yl)phenyl)-2-methylpropanoate;
Isopropyl 2-(3-(3-(1-(((R)-1-(3-methoxyphenyl)ethyl) amino) ethyl) naphthalen-1-yl)phenyl)-2-methylpropanoate;
Isopropyl 3-(2-fluoro-5-(3-(1-(((R)-1-(3-methoxyphenyl) ethyl)amino) propyl) naphthalen-1-yl)phenyl)propanoate;
Isopropyl 3-(5-(3-(1-(((R)-1-(3-chlorophenyl)ethyl)amino) propyl) naphthalen-1-yl)-2-fluorophenyl) propanoate;
Isopropyl 3-(5-(3-(1-(((R)-1-(3-ethoxyphenyl)ethyl)amino) propyl)naphthalen-1-yl)-2-fluorophenyl) propanoate;
Isopropyl 3-(5-(3-(1-(((R)-1-(3-ethoxyphenyl)ethyl)amino) ethyl) naphthalen-1-yl)-2-fluorophenyl) propanoate;
Isopropyl 5-(3-(1-(((R)-1-(3-ethoxyphenyl)ethyl)amino) ethyl) naphthalen-1-yl)-2-methylbenzoate;
Isopropyl 3-(5-(3-(1-(((R)-1-(3-chlorophenyl)ethyl)amino) ethyl) naphthalen-1-yl)-2-fluorophenyl) propanoate;
Isopropyl 3-(5-(3-(1-(((R)-1-(3-methoxyphenyl) ethyl) amino) ethyl)naphthalen-1-yl)-2-(trifluoromethyl)phenyl)propanoate;
Isopropyl 3-(5-(3-(1-(((R)-1-(3-chlorophenyl)ethyl)amino) ethyl) naphthalen-1-yl)-2-(trifluoro methyl)phenyl)propanoate;
Isopropyl 3-(3-fluoro-5-(7-fluoro-3-(1-(((R)-1-(3-methoxyphenyl) ethyl)amino)ethyl)naphthalen-1-yl)phenyl)propanoate;
Isopropyl 3-(3-fluoro-5-(3-(1-(((R)-1-(3-methoxyphenyl) ethyl) amino)propyl) naphthalen-1-yl)phenyl)propanoate;
Isopropyl 3-(3-(3-(1-(((R)-1-(3-ethoxyphenyl)ethyl)amino) ethyl)naphthalen-1-yl)-5-fluorophenyl)propanoate;
Isopropyl 5-(3-(1-(((R)-1-(3-methoxyphenyl)ethyl)amino) propyl)naphthalen-1-yl)-2-methylbenzoate;
(R)-2-Methyl-5-(3-(((1-(naphthalen-1-yl)ethyl)amino) methyl)naphthalen-1-yl)benzoic acid;
(R)-5-(3-(((1-(3-Methoxyphenyl)ethyl)amino)methyl)naphthalen-1-yl)-2-methylbenzoic acid hydrochloride;
(R)-5-(3-(((1-(3-Ethoxyphenyl)ethyl) amino)methyl)naphthalen-1-yl)-2-methylbenzoic acid hydrochloride;
(R)-2-Methyl-5-(3-(((1-(3-propoxyphenyl)ethyl) amino) methyl)naphthalen-1-yl)benzoic acid hydrochloride;
(R)-5-(3-(((1-(4-Fluoro-3-methoxyphenyl)ethyl) amino) methyl)naphthalen-1-yl)-2-methylbenzoic acid hydrochloride;
(R)-5-(3-(((1-(3-Chlorophenyl)ethyl)amino)methyl)naphthalen-1-yl)-2-methylbenzoic acid hydrochloride;
(R)-5-(3-(((1-(3-(2,2-Difluoroethoxy)phenyl)ethyl)amino) methyl)naphthalen-1-yl)-2-methylbenzoic acid hydrochloride;
(R)-2-Fluoro-5-(3-(((1-(4-fluoro-3-methoxyphenyl) ethyl) amino)methyl)naphthalen-1-yl)benzoic acid hydrochloride;
(R)-2-Fluoro-5-(3-(((1-(3-methoxyphenyl)ethyl) amino) methyl)naphthalen-1-yl)benzoic acid hydrochloride;
(R)-5-(3-(((1-(3-Ethoxyphenyl)ethyl) amino) methyl)naphthalen-1-yl)-2-fluorobenzoic acid hydrochloride;
(R)-2-Chloro-5-(3-(((1-(3-methoxyphenyl)ethyl) amino) methyl)naphthalen-1-yl)benzoic acid hydrochloride;
(R)-2-Chloro-5-(3-(((1-(3-ethoxyphenyl)ethyl)amino) methyl)naphthalen-1-yl)benzoic acid hydrochloride;
(R)-3-3-(((1-(3-Methoxyphenyl)ethyl) amino)methyl) naphthalen-1-yl)-2-methylbenzoic acid hydrochloride;
(R)-3-(3-(((1-(3-Ethoxyphenyl)ethyl) amino)methyl)naphthalen-1-yl)-2-methylbenzoic acid hydrochloride;
(R)-2-Fluoro-3-(3-(((1-(3-methoxyphenyl)ethyl) amino) methyl)naphthalen-1-yl)benzoic acid hydrochloride;
(R)-2-Methoxy-5-(3-(((1-(3-methoxyphenyl)ethyl) amino) methyl)naphthalen-1-yl)benzoic acid hydrochloride;
(R)-2-Isopropyl-5-(3-(((1-(3-methoxyphenyl)ethyl) amino) methyl)naphthalen-1-yl)benzoic acid hydrochloride;
(R)-4-(3-(((1-(Naphthalen-1-yl)ethyl)amino) methyl)naphthalen-1-yl)benzoic acid hydrochloride;
(R)-4-(3-(((1-(4-Fluoro-3-methoxyphenyl)ethyl) amino) methyl)naphthalen-1-yl)benzoic acid hydrochloride;
(R)-3-(3-(((1-(3-Methoxyphenyl)ethyl) amino)methyl) naphthalen-1-yl)benzoic acid hydrochloride;
(R)-3-(3-(((1-(3-Methoxyphenyl)ethyl) amino)methyl) naphthalen-1-yl)-2,6-dimethylbenzoic acid hydrochloride;
(R)-3-(2-Fluoro-5-(3-(((1-(3-methoxyphenyl)ethyl) amino) methyl)naphthalen-1-yl)phenyl)propanoic acid hydrochloride;
(R)-2-(4-(3-(((1-(3-Methoxyphenyl)ethyl) amino)methyl) naphthalen-1-yl)phenyl)-2-methylpropanoic acid hydrochloride;
(R)-2-(3-(3-(((1-(3-Methoxyphenyl)ethyl) amino)methyl) naphthalen-1-yl)phenyl)-2-methylpropanoic acid hydrochloride;
(R)-2-Fluoro-5-(3-(((1-(3-(2-methoxyethoxy)phenyl) ethyl) amino)methyl) naphthalen-1-yl) benzoic acid hydrochloride;
5-(3-(1-(((R)-1-(3-methoxyphenyl)ethyl)amino)ethyl)naphthalen-1-yl)-2-methylbenzoic acid hydrochloride;
5-(3-(1-(((R)-1-(4-Fluoro-3-methoxyphenyl)ethyl) amino) ethyl)naphthalen-1-yl)-2-methylbenzoic acid hydrochloride;
3-(3-(1-(((R)-1-(3-Methoxyphenyl)ethyl) amino)ethyl) naphthalen-1-yl)-2-methylbenzoic acid hydrochloride;
5-(3-(1-(((R)-1-(3-Chlorophenyl)ethyl)amino) ethyl)naphthalen-1-yl)-2-methylbenzoic acid hydrochloride;
3-Fluoro-5-(3-(1-(((R)-1-(3-methoxyphenyl)ethyl) amino) ethyl)naphthalen-1-yl)benzoic acid hydrochloride;
4-(3-(1-(((R)-1-(3-Methoxyphenyl)ethyl) amino)ethyl) naphthalen-1-yl)benzoic acid hydrochloride;
3-Fluoro-4-(3-(1-(((R)-1-(3-methoxyphenyl)ethyl) amino) ethyl)naphthalen-1-yl)benzoic acid hydrochloride;

2-Chloro-4-(3-(1-(((R)-1-(3-methoxyphenyl)ethyl) amino) ethyl)naphthalen-1-yl)benzoic acid hydrochloride;

3-(2-Fluoro-5-(3-(1-(((R)-1-(3-methoxyphenyl) ethyl) amino)ethyl)naphthalen-1-yl)phenyl)propanoic acid hydrochloride;

2-Fluoro-5-(3-(1-(((R)-1-(3-methoxyphenyl)ethyl) amino) ethyl)naphthalen-1-yl)benzoic acid hydrochloride;

4-(3-(1-(((R)-1-(3-Methoxyphenyl)ethyl) amino)ethyl) naphthalen-1-yl)-2-(trifluoromethyl) benzoic acid hydrochloride;

3-(3-(1-(((R)-1-(3-Methoxyphenyl)ethyl) amino)ethyl) naphthalen-1-yl)-5-methylbenzoic acid hydrochloride;

5-(3-(1-(((R)-1-(3-Ethoxyphenyl)ethyl) amino)ethyl)naphthalen-1-yl)-2-fluorobenzoic acid hydrochloride;

5-(3-(1-(((R)-1-(3-Chlorophenyl)ethyl)amino)ethyl)naphthalen-1-yl)-2-fluorobenzoic acid hydrochloride;

5-(3-(1-(((R)-1-(3-Methoxyphenyl)ethyl) amino)ethyl) naphthalen-1-yl)-2-(trifluoromethyl) benzoic acid hydrochloride;

3-(2-Fluoro-3-(3-(1-(((R)-1-(3-methoxyphenyl)ethyl) amino)ethyl)naphthalen-1-yl)phenyl)propanoic acid hydrochloride;

4-(3-(1-(((R)-1-(3-Methoxyphenyl)ethyl) amino)ethyl) naphthalen-1-yl)-2-methylbenzoic acid hydrochloride;

3-(2-Methoxy-5-(3-(1-(((R)-1-(3-methoxyphenyl) ethyl) amino)ethyl) naphthalen-1-yl)phenyl) propanoic acid hydrochloride;

2-Fluoro-4-(3-(1-(((R)-1-(3-methoxyphenyl)ethyl) amino) ethyl)naphthalen-1-yl)benzoic acid hydrochloride;

2-Chloro-5-(3-(1-(((R)-1-(3-methoxyphenyl)ethyl) amino) ethyl)naphthalen-1-yl)benzoic acid hydrochloride;

3-(3-Fluoro-5-(3-(1-(((R)-1-(3-methoxyphenyl)ethyl) amino)ethyl)naphthalen-1-yl)phenyl)propanoic acid hydrochloride;

2,2-Difluoro-2-(4-(3-(1-(((R)-1-(3-methoxyphenyl) ethyl) amino)ethyl) naphthalen-1-yl)phenyl) acetic acid hydrochloride;

3-(2-Fluoro-4-(3-(1-(((R)-1-(3-methoxyphenyl) ethyl) amino)ethyl) naphthalen-1-yl)phenyl) propanoic acid hydrochloride;

3-(5-(3-(1-(((R)-1-(3-Methoxyphenyl)ethyl) amino)ethyl) naphthalen-1-yl)-2-methylphenyl) propanoic acid hydrochloride;

2-(4-(3-(1-(((R)-1-(3-Methoxyphenyl)ethyl) amino)ethyl) naphthalen-1-yl)phenyl)-2-methylpropanoic acid hydrochloride;

2-(3-(3-(1-(((R)-1-(3-Methoxyphenyl)ethyl) amino)ethyl) naphthalen-1-yl)phenyl)-2-methylpropanoic acid hydrochloride;

3-(2-Fluoro-5-(3-(1-(((R)-1-(3-methoxyphenyl)ethyl) amino)propyl)naphthalen-1-yl)phenyl)propanoic acid hydrochloride;

3-(5-(3-(1-(((R)-1-(3-Ethoxyphenyl)ethyl) amino)propyl) naphthalen-1-yl)-2-fluorophenyl) propanoic acid hydrochloride;

3-(5-(3-(1-(((R)-1-(3-Ethoxyphenyl)ethyl) amino) ethyl) naphthalen-1-yl)-2-fluorophenyl) propanoic acid hydrochloride;

5-(3-(1-(((R)-1-(3-Ethoxyphenyl)ethyl) amino) ethyl)naphthalen-1-yl)-2-methylbenzoic acid hydrochloride;

3-(5-(3-(1-(((R)-1-(3-Chlorophenyl)ethyl)amino)ethyl) naphthalen-1-yl)-2-fluorophenyl)propanoic acid hydrochloride;

3-(5-(3-(1-(((R)-1-(3-Methoxyphenyl)ethyl) amino)ethyl) naphthalen-1-yl)-2-(trifluoromethyl) phenyl)propanoic acid hydrochloride;

3-(5-(3-(1-(((R)-1-(3-Chlorophenyl)ethyl) amino)ethyl) naphthalen-1-yl)-2-(trifluoromethyl) phenyl)propanoic acid hydrochloride;

3-(3-Fluoro-5-(7-fluoro-3-(1-(((R)-1-(3-methoxyphenyl) ethyl) amino)ethyl)naphthalen-1-yl)phenyl)propanoic acid hydrochloride;

3-(3-Fluoro-5-(3-(1-(((R)-1-(3-methoxyphenyl) ethyl) amino)propyl)naphthalen-1-yl)phenyl)propanoic acid hydrochloride;

5-(3-(1-(((R)-1-(3-Methoxyphenyl)ethyl) amino)propyl) naphthalen-1-yl)-2-methylbenzoic acid hydrochloride;

3-Methoxy-5-(3-(1-(((R)-1-(3-methoxyphenyl)ethyl) amino)ethyl)naphthalen-1-yl)benzoic acid hydrochloride;

2-(3-Fluoro-5-(3-(1-(((R)-1-(3-methoxyphenyl)ethyl) amino)ethyl)naphthalen-1-yl)phenoxy)-2-methylpropanoic acid hydrochloride;

3-(5-(3-(1-(((R)-1-(3-Chlorophenyl)ethyl)amino)propyl) naphthalen-1-yl)-2-fluorophenyl)propanoic acid hydrochloride;

Isopropyl 3-(3-(3-(1-(((R)-1-(3-chlorophenyl) ethyl) amino) ethyl) naphthalen-1-yl)-5-fluorophenyl) propanoate hydrochloride;

Isopropyl 3-(5-(3-(1-(((R)-1-(3-ethoxyphenyl)ethyl) amino) ethyl)naphthalen-1-yl)-2-methylphenyl) propanoate hydrochloride (R)-Methyl 5-(3-(((1-(3-methoxyphenyl)ethyl) amino) methyl) naphthalen-1-yl)-2-methylbenzoate hydrochloride;

3-(3-(3-(1-(((R)-1-(3-Chlorophenyl)ethyl)amino)ethyl) naphthalen-1-yl)-5-fluorophenyl)propanoic acid hydrochloride;

3-(5-(3-(1-(((R)-1-(3-Ethoxyphenyl)ethyl) amino)ethyl) naphthalen-1-yl)-2-methylphenyl) propanoic acid hydrochloride;

3-(3-(3-(1-(((R)-1-(3-Ethoxyphenyl)ethyl) amino)ethyl) naphthalen-1-yl)-5-fluorophenyl) propanoic acid hydrochloride;

(1R)-1-(3-Chlorophenyl)-N-(1-(4-(4-(methylsulfonyl) phenyl)naphthalen-2-yl)ethyl)ethanamine hydrochloride;

(1R)-1-(3-Chlorophenyl)-N-(1-(4-(4-(pyrrolidin-1-yl) phenyl)naphthalen-2-yl)ethyl)ethanamine hydrochloride;

1-(4-(3-Fluoro-5-morpholinophenyl)naphthalen-2-yl)-N—((R)-1-(3-methoxyphenyl)ethyl)ethanamine hydrochloride;

(1R)-1-(3-methoxy phenyl)-N-(1-(7-fluoro-4-(4-(trifluoromethyl) phenyl)naphthalen-2-yl) ethyl)ethanamine 1-(3-Fluoro-5-methoxyphenyl)-N-(1-(4-(4-(trifluoromethyl) phenyl) naphthalen-2-yl)ethyl)ethanamine hydrochloride;

1-(4-(3',5-Difluoro-[1,1'-biphenyl]-3-yl)naphthalen-2-yl)-N—((R)-1-(3-methoxy phenyl)ethyl) ethanamine hydrochloride;

1-(4-(3-Fluoro-5-(1-methyl-1H-pyrazol-4-yl)phenyl)naphthalen-2-yl)-N—((R)-1-(3-methoxy phenyl)ethyl)ethanamine hydrochloride;

Isopropyl-5-(3-(1-(((R)-1-(3-fluoro-5-methoxyphenyl) ethyl)amino) ethyl) naphthalen-1-yl)-2-methylbenzoate;

Isopropyl-3-(3-fluoro-5-(3-(1-(((R)-1-(3-fluoro-5-methoxyphenyl)ethyl)amino) ethyl) naphthalen-1-yl)phenyl)propanoate;

5-(3-(1-(((R)-1-(3-Fluoro-5-methoxyphenyl)ethyl)amino) ethyl)naphthalen-1-yl)-2-methyl benzoic acid hydrochloride; and 3-(3-Fluoro-5-(3-(1-(((R)-1-(3-fluoro-5-methoxyphenyl) ethyl)amino) ethyl)naphthalen-1-yl) phenyl)propanoic acid hydrochloride or a free base thereof or a pharmaceutically acceptable salt thereof.

In another aspect of the invention, there is provided a compound of Formulae (I) to (V) or a pharmaceutically acceptable salt thereof for use as a medicament.

In another aspect of the invention, there is provided a compound of Formulae (I) to (V) or a pharmaceutically acceptable salt thereof, for use in treating the diseases, disorders, syndromes or conditions associated with calcium sensing receptor (CaSR) modulators.

In another aspect, the invention provides a pharmaceutical composition comprising at least one compound of Formulae (I) to (V) or a pharmaceutically acceptable salt thereof and at least one pharmaceutically acceptable excipient.

In another aspect, the invention provides a pharmaceutical composition comprising a compound of Formulae (I) to (V), or a pharmaceutically acceptable salt thereof, for use in treating, the diseases disorders, syndromes or conditions associated with calcium sensing receptor (CaSR) modulators in a subject, in need thereof by administering to the subject, one or more compounds described herein in a therapeutically effective amount to cause modulation of such receptor.

In another aspect, the invention provides a pharmaceutical composition comprising a compound of Formulae (I) to (V), or a pharmaceutically acceptable salt thereof, or a pharmaceutically acceptable stereoisomer, thereof together with a pharmaceutically acceptable excipient.

In another aspect of the invention, there is provided use of a compound of Formulae (I) to (V), or a pharmaceutically acceptable salt thereof, for the manufacture of a medicament for treating, the diseases, disorders, syndromes or conditions associated with calcium sensing receptor (CaSR) modulators.

In another aspect, there are provided process for the preparation of compounds of Formula (Ic) and Formula (Id):

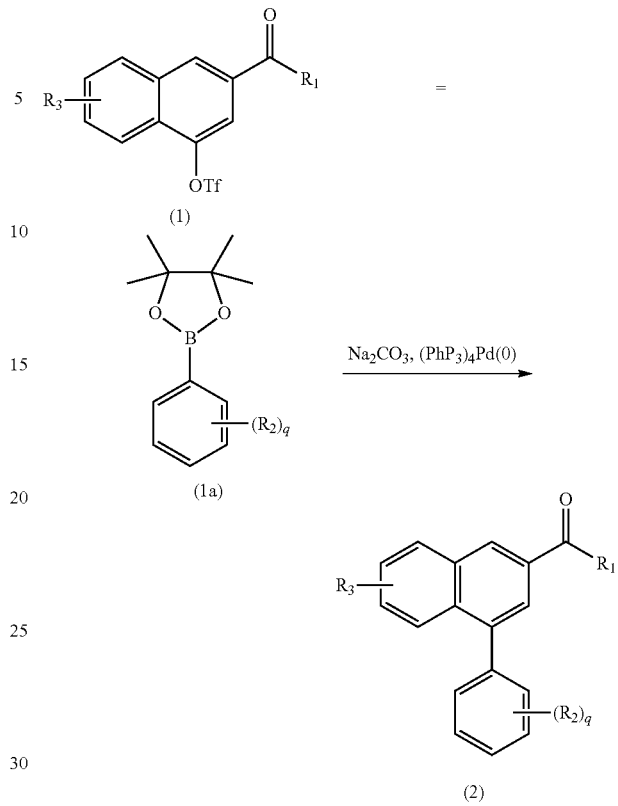

wherein ring A, $R_1$, $R_2$, $R_3$, $R_4$, X, 'p' and 'q' are as described herein above;
the process comprising the steps of:
(a) reacting compound of Formula (1) with compound of Formula (1a) in presence of base and palladium complex to give compound of Formula (2)

(b) coupling of a compound of Formula (2) with compound of Formula (12) using suitable amide coupling reagents followed by reduction using suitable reducing agent to give compound of Formula (Ic).

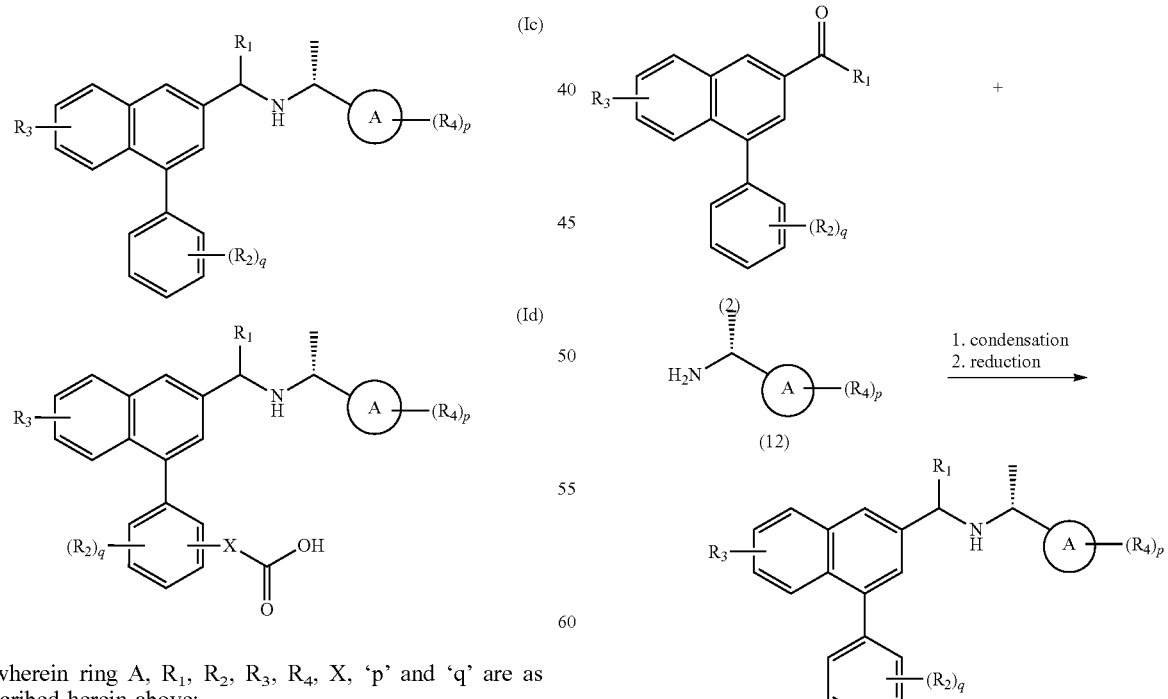

(c) hydrolyzing a compound of Formula (Ic) (when any of $R_2$ is X—(CO)—Z represents to an ester) to give corresponding acid compound of Formula (Id) where 'q' is 0, 1 or 2

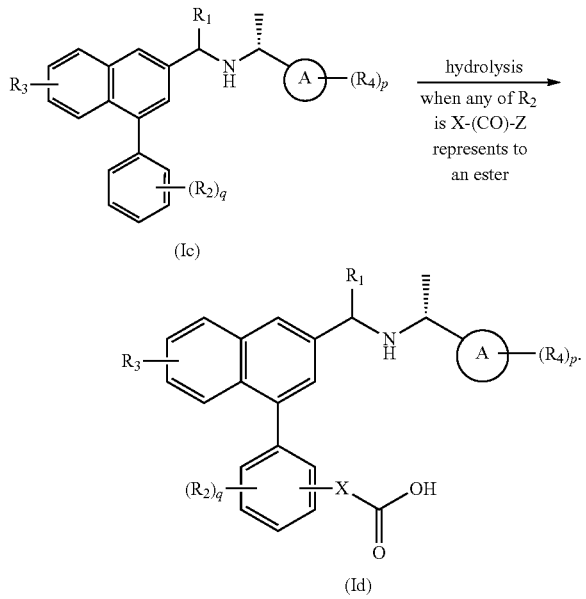

(Ic)

(Id)

DETAILED DESCRIPTION OF THE INVENTION

Definitions and Abbreviations:

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, for example $(C_1-C_6)$alkyl or $(C_1-C_4)$alkyl, representative groups include e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched.

The term "alkenyl" refers to a hydrocarbon radical containing from 2 to 10 carbon atoms and including at least one carbon-carbon double bond. Non-limiting Examples of alkenyl groups include, for example $(C_2-C_6)$alkenyl, $(C_2-C_4)$alkenyl, ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched.

The term "alkynyl" refers to a hydrocarbon radical containing 2 to 10 carbon atoms and including at least one carbon-carbon triple bond. Non-limiting Examples of alky-nyl groups include, for example $(C_2-C_6)$alkynyl, $(C_2-C_4)$alkynyl, ethynyl, propynyl, butynyl and the like. Unless set forth or recited to the contrary, all alkynyl groups described or claimed herein may be straight chain or branched.

The term "alkoxy" refers to an alkyl group attached via an oxygen linkage. Non-limiting Examples of such groups include, for example $(C_1-C_6)$alkoxy,$(C_1-C_4)$alkoxy, methoxy, ethoxy and propoxy and the like. Unless set forth or recited to the contrary, all alkoxy groups described or claimed herein may be straight chain or branched.

The term "alkoxyalkyl" refers to an alkoxy group as defined above directly bonded to an alkyl group as defined above, for example $(C_1-C_6)$alkoxy-$(C_1-C_6)$alkyl,$(C_1-C_4)$ alkoxy-$(C_1-C_4)$alkyl, —$CH_2$—O—$CH_3$, —$CH_2$—O—$CH_2CH_3$, —$CH_2CH_2$—O—$CH_3$ and the like.

The term "haloalkyl" refers to an alkyl group as defined above that is substituted by one or more halogen atoms as defined above. For example $(C_1-C_6)$haloalkyl or $(C_1-C_4)$ haloalkyl. Suitably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Suitably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched.

The term "cycloalkyl" refers to a non-aromatic mono or multicyclic ring system having 3 to 12 carbon atoms, such as $(C_3-C_{10})$cycloalkyl, $(C_3-C_6)$cycloalkyl, cyclopropyl, cyclobutyl, cyclopentyl, cyclohexyl and the like. Examples of multicycliccycloalkyl groups include, but are not limited to, perhydronaphththyl, adamantyl and norbornyl groups, bridged cyclic groups or spirobicyclic groups, e.g., spiro(4,4)non-2-yl and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like.

The term "arylalkyl" refers to an aryl group as defined above directly bonded to an alkyl group as defined above, e.g., —$CH_2C_6H_5$ and —$C_2H_4C_6H_5$.

"3 to 6 membered saturated carbocyclic ring" refers to a carbocyclic ring which is a monocyclic and non-aromatic carbocyclic ring as defined herein.

A "carbocyclic ring" or "carbocycle" as used herein refers to a 3- to 6 membered saturated or partially unsaturated, monocyclic, fused bicyclic or spirocyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, etc.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(S) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(S), and one or two carbon atoms(S) in the heterocyclic ring or heterocyclyl may be interrupted with —$CF_2$—, —C(O)—, —S(O)—, $S(O)_2$, —C(=N—($C_1$-$C_6$)alkyl)-, or —C(=N—($C_3$-$C_{12}$) cycloalkyl, etc. In addition heterocyclic ring may also be fused with aromatic ring. Non-limiting Examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinylsulfoxide, thiamorpholinylsulfoneindoline, benzodioxole, tetrahydroquinoline, tetrahydrobenzopyran and the like. The heterocyclic ring may be attached by any atom of the heterocyclic ring that results in the creation of a stable structure.

The term "heteroaryl" unless otherwise specified, refers to a substituted or unsubstituted 5- to 14-membered aromatic heterocyclic ring with one or more heteroatom(S) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like.

The term "heterocyclylalkyl" refers to a heterocyclic ring radical directly bonded to an ($C_1$-$C_6$)alkyl group. The heterocyclylalkyl radical may be attached to the main structure at any carbon atom in the alkyl group that results in the creation of a stable structure.

The term "heteroarylalkyl" refers to a heteroaryl ring radical directly bonded to an ($C_1$-$C_6$)alkyl group. The heteroarylalkyl radical may be attached to the main structure at any carbon atom in the alkyl group that results in the creation of a stable structure.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), ($C_1$-$C_6$)alkyl, ($C_1$-$C_6$)haloalkyl, ($C_2$-$C_6$)alkenyl, ($C_2$-$C_6$)alkynyl, aryl, aryl($C_1$-$C_6$)alkyl, ($C_3$-$C_{12}$)cycloalkyl, heteroaryl, heterocyclic ring, heterocyclyl($C_1$-$C_6$)alkyl, heteroaryl($C_1$-$C_6$)alkyl, —C(O)$OR^x$, —C(O)$R^x$, —C(S)$R^x$, —C(O)$NR^xR^y$, —$NR^xC(O)NR^yR^z$, —$NR^xR^y$, —$NR^xC(O)R^y$, —$S(O)_2NR^xR^y$, —$OR^x$, —OC(O)$R^x$, —OC(O)$NR^xR^y$, $R^xC(O)R^y$, —$SR^x$, and —$S(O)_2R^x$; wherein each occurrence of $R^x$, $R^y$ and $R^z$ are independently selected from hydrogen, halogen, ($C_1$-$C_4$)alkyl, ($C_1$-$C_4$)haloalkyl, ($C_3$-$C_{12}$)cycloalkyl and aryl.

For example one representative group of moieties which may be a "substituent" is selected from hydroxy, halogen, cyano, nitro, oxo (=O), thio (=S), ($C_1$-$C_4$)alkyl, ($C_1$-$C_4$)haloalkyl, ($C_3$-$C_7$)cycloalkyl, —C(O)$OR^x$, —C(O)$R^x$, —C(O)$NR^xR^y$, —$NR^xR^y$, —$NR^xC(O)R^y$, —$S(O)_2NR^xR^y$, —$OR^x$, —OC(O)$R^x$, —$SR^x$ and —$S(O)_2R^x$; wherein each occurrence of $R^x$ and $R^y$ are independently selected from hydrogen, halogen, ($C_1$-$C_4$)alkyl, ($C_1$-$C_4$)haloalkyl and ($C_3$-$C_6$)cycloalkyl.

It is to be understood that the aforementioned "substituted" groups cannot be further substituted. For Example, when the substituent on "substituted alkyl" is "aryl" or "alkenyl", the aryl or alkenyl cannot be substituted aryl or substituted alkenyl respectively.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are non-superimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the a disease disorder or condition or at least one of its clinical or subclinical symptoms or (d) relieving the disease, i.e., causing regression of the state, disorder or condition or at least one of its clinical or subclinical symptoms.

The term "modulate" or "modulating" or "modulation" or "modulator" refers to an increase in the amount, quality, or effect of a particular activity or function of the receptor. By way of illustration and not limitation, it includes agonists, partial agonists and allosteric modulators of calcium sensing receptor (CaSR) of the present invention. Such modulation may be contingent on the occurrence of a specific event, such as activation of a signal transduction pathway.

The term "allosteric modulators of calcium-sensing receptor", refers to the ability of a compound that binds to calcium sensing receptors and induces a conformational change that reduces the threshold for calcium sensing receptor activation by the endogenous ligand $Ca^{2+}$ depending on the concentration of the compound exposed to the calcium-sensing receptor.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for Example by reacting sufficiently basic compound such as an amine with a suitable acid affording a physiologically acceptable anion.

With respect to the overall compounds described by the Formulae (I) to (V) herein, the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Screening of compounds of invention for calcium sensing receptor (CaSR) modulation activity can be achieved by using various in vitro and in vivo protocols mentioned herein below or methods known in the art.

Pharmaceutical Compositions

The invention relates to pharmaceutical compositions containing the compounds of the Formulae (I) to (V), or pharmaceutically acceptable salts thereof disclosed herein. In particular, pharmaceutical compositions containing a therapeutically effective amount of at least one compound of Formula (I) described herein and at least one pharmaceutically acceptable excipient (such as a carrier or diluent). Preferably, the contemplated pharmaceutical compositions include the compound(s) described herein in an amount sufficient to modulate calcium sensing receptor (CaSR) mediated diseases described herein when administered to a subject.

The subjects contemplated include, for Example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For Example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be in conventional forms, for Example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For Example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For Example, the daily dosage of the CaSR modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In another aspect, the invention provides compounds and pharmaceutical compositions thereof that are useful in treating the of diseases, disorders, syndromes or conditions modulated by calcium sensing receptor (CaSR). The invention further provides method of treating diseases, disorders, syndromes or conditions modulated by CaSR in a subject in need thereof by administering to the subject a therapeutically effective amount of a compound or a pharmaceutical composition of the invention.

In another aspect of the invention, the methods provided are also useful for diagnosis of conditions that can be treated by modulating CaSR for determining if a patient will be responsible to therapeutic agents.

In another aspect, the invention provides a method for the treatment of diseases, disorders or conditions through modulating CaSR. In this method, a subject in need of such treatment is administered a therapeutically effective amount of a compound of Formulae (I) to (V), or a pharmaceutically acceptable salt thereof described herein.

The compound and pharmaceutical composition of the present invention is useful to a subject in need of the treatment having a disease, disorder, syndrome or condition characterized by one or more of the following: (a) abnormal calcium ion homeostasis, (b) an abnormal level of a messenger whose production or secretion is affected by the calcium sensing receptor (CaSR) activity or (c) an abnormal level of activity of a messenger whose function is affected by the calcium sensing receptor activity. In one aspect, the patient has a disease, disorder, syndrome or condition characterized by an abnormal level of one or more calcium sensing receptor-regulated components and the compound is active on a CaSR of a cell including parathyroid cell, bone cells (pre-osteoclast, osteoclast, pre-osteoblast, osteoblast), juxtaglomerular kidney cell, kidney messengial cell, glomerular kidney cell, proximal tubule kidney cell, distal tubule kidney cell, cell of the thick ascending limb of Henle's loop and/or collecting duct, parafollicular cell in the thyroid (C-cell), intestinal cell, platelet, vascular smooth muscle cell, gastrointestinal tract cell, pituitary cell or hypothalamic cell. The messenger of the calcium sensing receptor is Calcium.

The compounds of Formulae (I) to (V), or a pharmaceutically acceptable salts thereof, being modulators of CaSR, is potentially useful in treating the severity, morbidity/mortality or complications of diseases, disorders, syndromes or conditions include but are not limited to primary hyperparathyroidism, secondary hyperparathyroidism, tertiary hyperparathyroidism, chronic renal failure (with or without dialysis), chronic kidney disease (with or without dialysis) adenoma, parathyroid hyperplasia, parathyroid carcinoma, vascular & valvular calcification, abnormal calcium homeostasis such as hypercalcemia, abnormal phosphorous homeostasis such as hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

Primary hyperparathyroidism, is a disorder of one or more of the parathyroid glands, resulting from a hyper function of the parathyroid glands themselves (acquired sporadically or familial) resulting in PTH over secretion which could be due to single or double adenoma, hyperplasia, multi-gland disease or rarely, carcinoma of the parathyroid glands. As a result, the blood calcium rises to a level that is higher than normal (called hypercalcemia). This elevated calcium level can cause many short-term and long-term complications.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, magnesium deficiency and renal hypercalciuria. Tertiary hyperparathyroidism may occur after a long period of secondary hyperparathyroidism and hypercalcemia.

In one aspect, the compound and composition of the present invention can be used in treating the vascular or valvular calcification in a subject. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits. In one aspect, the compounds of the invention may also be used to treat atherosclerotic calcification and medial calcification and other conditions characterized by vascular calcification. In one aspect, vascular calcification may be associated with chronic renal insufficiency or end-stage renal disease or excess calcium or PTH itself. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

Abnormal calcium homeostasis such as hyperparathyroidism related diseases can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hyperparathyroidism.

Abnormal phosphorous homeostasis such as hypophosphatemia can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hypophosphatemia.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intra-glomerular pressure; (v) synthesis and maintenance of the glomerular basement membrane (GMB); (vi) production and secretion of vascular endothelial growth factor (VEGF) required for the glomerular endothelial cell (GEN) integrity. Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for Example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgesic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins.

In one aspect, the compounds of the invention can be used for treating abnormal intestinal motilities disorders such as diarrhea. The methods of the invention comprise administering to the subject a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with gastrointestinal or abdominal surgery, chemotherapy, radiation treatment, inflammation or toxic traumatic injury. In another aspect, diarrhea can be secretary, means that there is an increase in the active secretion, or there is an inhibition of absorption. There is little to no structural damage. The most common cause of this type of diarrhea is cholera. In another aspect, diarrhea can be due to acceleration of intestinal transit (rapid transit diarrhea). Such condition may occur because the rapid flow-through impairs the ability of the gut to absorb water.

The compound and composition of the present invention can be used, in particular, to participate in an augmenting gastrin or gastric acid secretion to directly or indirectly benefit certain medical conditions such as but not limited to atrophic gastritis or to improve absorption of pharmacological compounds, drugs or supplements from gastro-intestinal tract by augmenting gastric acidity.

It is to be understood that the invention encompasses any of the compounds of Formulae (I) to (V), or pharmaceutically acceptable salts thereof for use in the treatment of any of the conditions disclosed herein.

It is to be understood that the invention encompasses the use of any of the compounds of Formulae (I) to (V), or pharmaceutically acceptable salts thereof for the manufacture of a medicament for the treatment of any of the conditions disclosed herein.

All of the patent, patent application and non-patent publications referred to in this specification are incorporated herein by reference in their entireties.

General Methods of Preparation

The compounds described herein may be prepared by techniques known in the art. In addition, the compounds described herein may be prepared by following the reaction sequence as depicted in Scheme-1 to Scheme-5. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for Example, temperature and/or duration of the reaction, which may be used as known in the art, are also within the scope of the present invention. All the isomers of the compounds in described in these schemes, unless otherwise specified, are also encompassed within the scope of this invention.

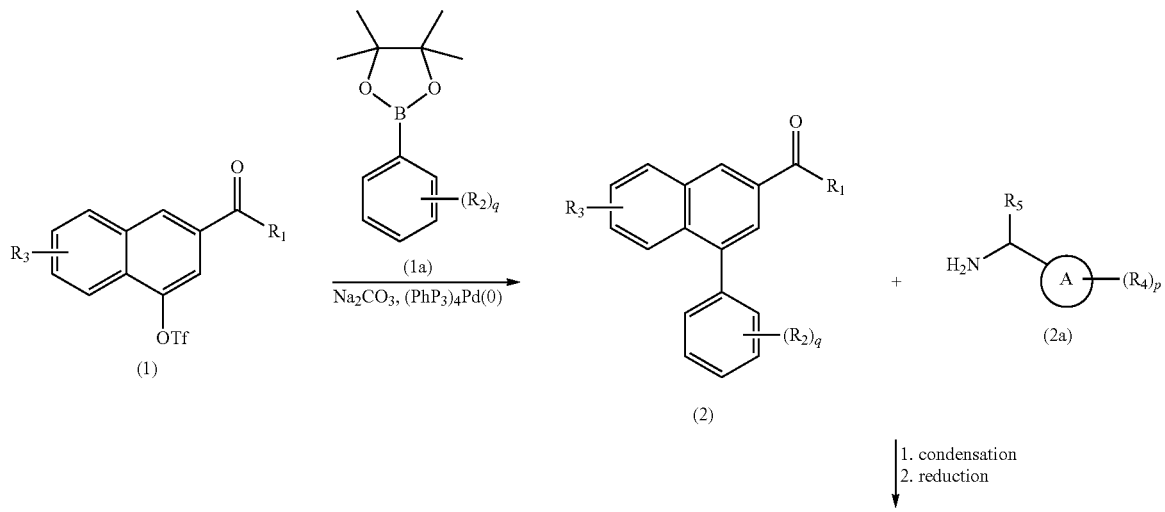

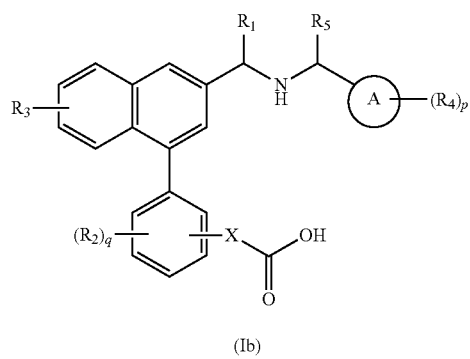

(Ib)

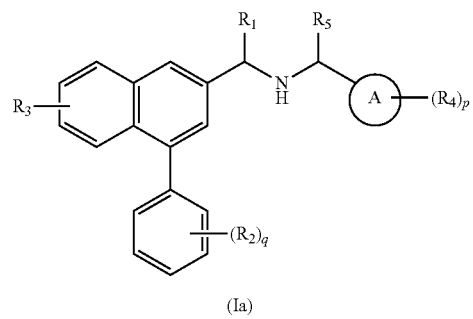

(Ia)

A compound of Formula (Ia), where ring A, $R_1$, $R_2$, $R_3$, $R_4$, $R_5$, 'p' and 'q' are defined herein above, can be prepared as depicted in Scheme-1. Thus, the C—C bond formation of compound of Formula (1) can be carried by reacting with tetrakis (triphenylphosphine) palladium(0) and a compound of Formula (1a) using a base to afford a compound of Formula (2). This compound of Formula (2) is converted to compound of Formula (Ia) in two sequential steps. Thus, in first step, coupling of primary amine of Formula (2a) with compound of formula (2) using titanium(IV) isopropoxide followed by reduction of resultant imine compound using suitable reducing agent such as sodium cyanoborohydride, sodium triacetoxyborohydride or sodiumborohydride to afford compound of Formula (Ia). If the compound of Formula (2) is a methyl ester it can be transformed to isopropyl ester in presence of titamium(IV) isopropoxide, this is explained on the basis of transesterification of methyl ester with titanium(IV) isopropoxide. If the compound of Formula (Ia) is an ester, it further undergoes ester hydrolysis in presence of a base to give compound of Formula (Ib). The compounds of Formula (2a) are commercially available or can be prepared as depicted in Scheme-2a or Scheme-2b [*J. Med. Chem.*, 2009, 52(23), 7432-7445; *JOC*, 2009, 74(15), 5304-5310; EP2341044A1].

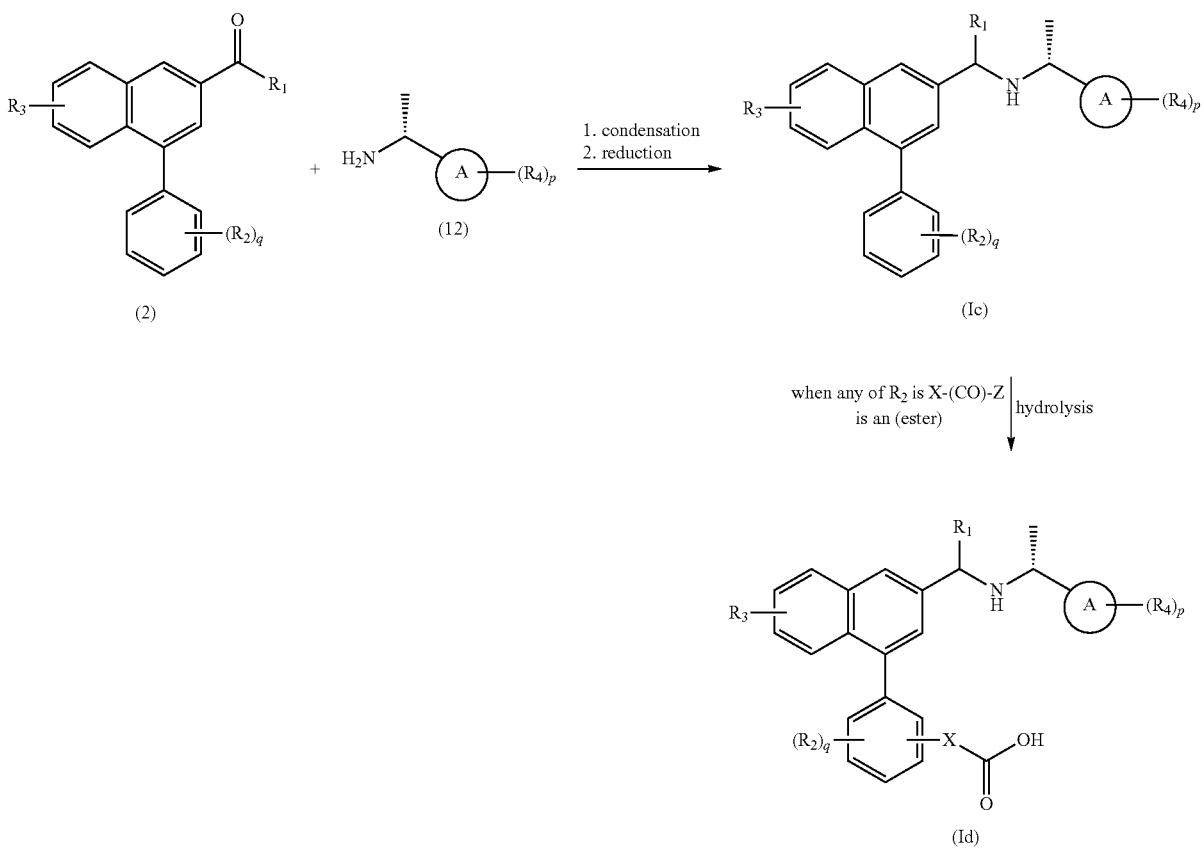

Similarly, compound of Formula (Ic) and (Id), where ring A, R₁, R₂, R₃, R₄, X, Z, 'p' and 'q' are as defined herein above, can be prepared as depicted in Scheme-2. The compound of Formula (2) is coupled with primary amine of Formula (12) followed by reduction of resultant imine compound using suitable reducing agent such as sodium cyanoborohydride, sodium triacetoxyborohydride or sodiumborohydride to afford compound of Formula (Ic). If the compound of Formula (Ic) is an ester, it further undergoes ester hydrolysis in presence of a base to give compound of Formula (Id) where 'q' is 0, 1 or 2. The compounds of Formula (12) are commercially available or can be prepared as depicted in Scheme-2a or Scheme-2b [*J. Med. Chem.*, 2009, 52(23), 7432-7445; *JOC*, 2009, 74(15), 5304-5310; EP2341044A1]

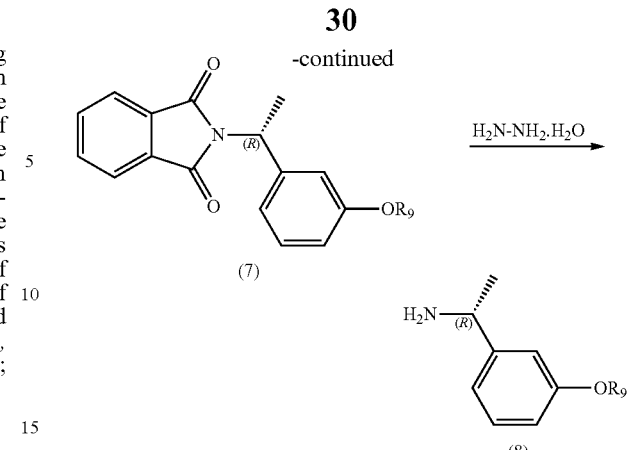

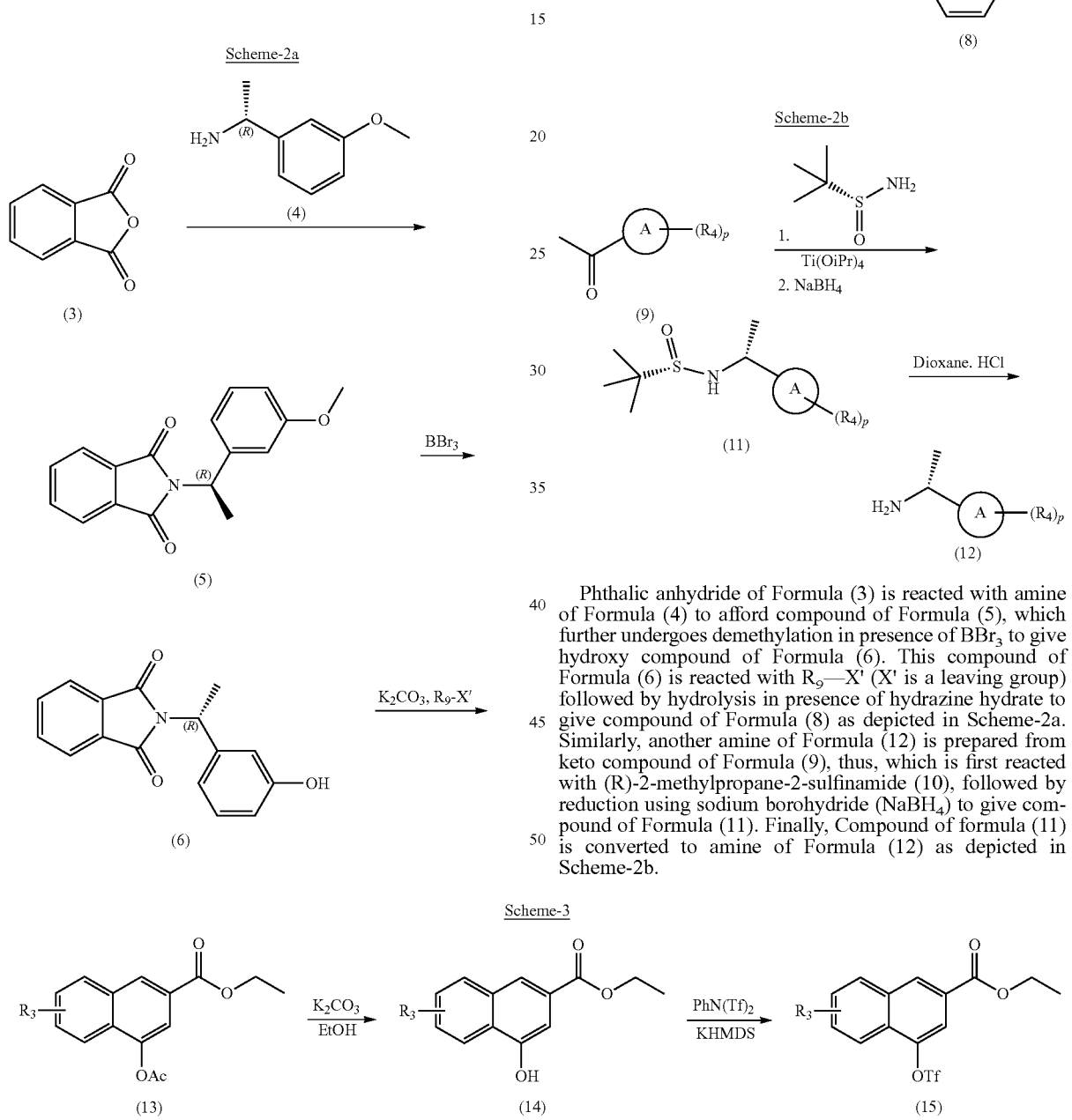

Phthalic anhydride of Formula (3) is reacted with amine of Formula (4) to afford compound of Formula (5), which further undergoes demethylation in presence of BBr₃ to give hydroxy compound of Formula (6). This compound of Formula (6) is reacted with R₉—X' (X' is a leaving group) followed by hydrolysis in presence of hydrazine hydrate to give compound of Formula (8) as depicted in Scheme-2a. Similarly, another amine of Formula (12) is prepared from keto compound of Formula (9), thus, which is first reacted with (R)-2-methylpropane-2-sulfinamide (10), followed by reduction using sodium borohydride (NaBH₄) to give compound of Formula (11). Finally, Compound of formula (11) is converted to amine of Formula (12) as depicted in Scheme-2b.

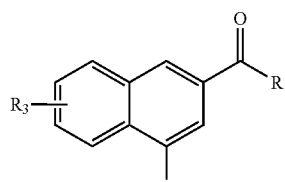 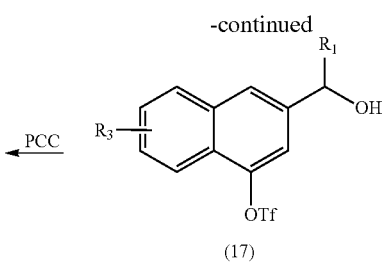 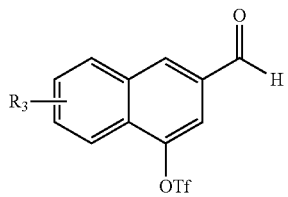

Compound of Formula (14) is prepared by reacting compound of Formula (13) with a base such as K₂CO₃ in a suitable solvent {(*Heterocycles*, 2004, 63(3), 576-582; *Heterocyclic communications*, 2003, 9(6), 587-592); (US2010/125061 A1)} further it undergoes protection with N-Phenylbis(trifluoromethanesulphonamide) in presence of base Potassium bis(trimethylsilyl)amide (KHMDS) to obtain a compound of Formula (15). The aldehyde of Formula (16) is prepared in two steps, thus, the reduction of ester group of Formula (15) using Diisobutylaluminium hydride (DIBAL) in first step and oxidation of resultant alcohol using pyridinium chlorochromate (PCC) in second step. This aldehyde of Formula (16) is reacted with alkylmagnesium bromide to give alcohol of Formula (17) followed by oxidation of resultant alcohol using PCC to afford the ketone of Formula (1) as shown in scheme-3.

-continued

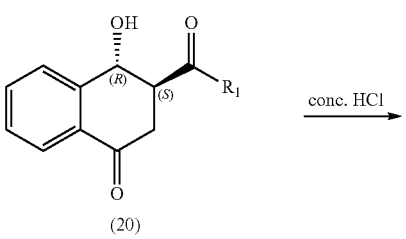

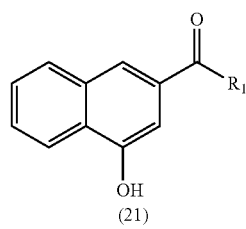

Compound of Formula (21) can be prepared in two steps as described in Song Ye et. al J. Org. Chem. 2010, 75, 273-276. Reacting o-phthalaldehyde (18) with methyl-vinylketone (19) and a base such as Cs₂CO₃ in presence of a thiazolium salt in a solvent such as DMF to give a diastereomer, which upon aromatization affords compound (21) as shown in scheme-4.

Scheme-4

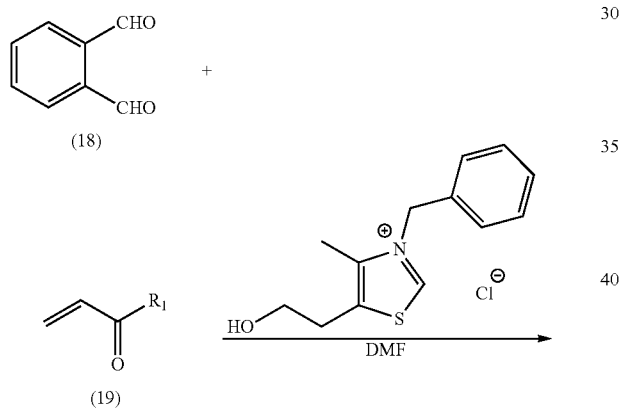

Scheme 5

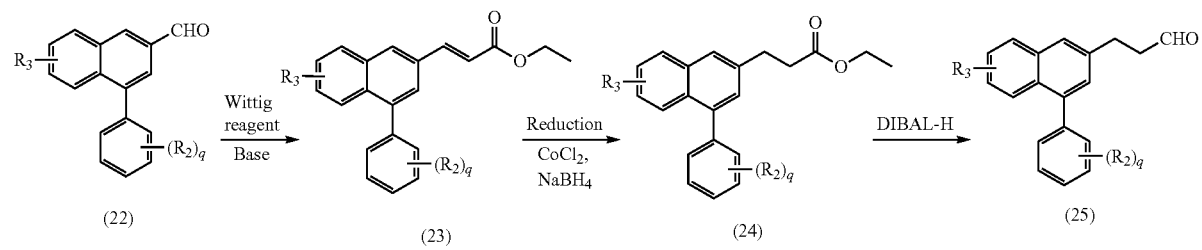

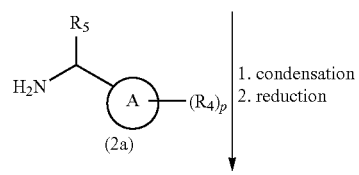

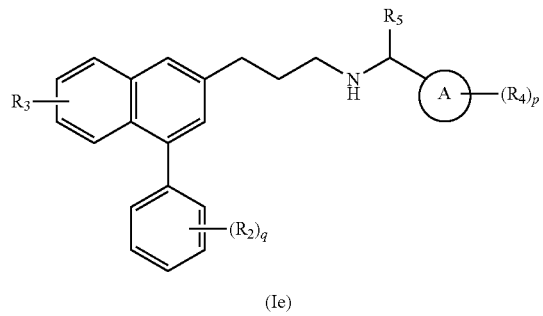

(Ie)

A compound of Formula (Ie) where ring A, $R_2$, $R_3$, $R_4$, $R_5$, 'p' and 'q' are as defined herein above, can be prepared as depicted in Scheme-5. Compound of Formula (23) is prepared by reacting compound of Formula (22) with a base such as sodium hydride and Wittig reagent such as triethyl phosphonoacetate in a suitable solvent such as tetrahydrofuran. The compound of Formula (22) can be prepared as depicted in Scheme-1. The compound of Formula (23) is reacted with transition metal chloride such as $CoCl_2$ and suitable reducing agent such as sodium borohydride in a solvent such to obtain a compound of Formula (24) which further converted to compound of Formula (25) using suitable reducing agent such as DIBAL-H. Finally the compound of Formula (25) is coupled with primary amine of Formula (2a) followed by reduction of resultant imine compound using suitable reducing agent such as sodium cyanoborohydride, sodium triacetoxyborohydride or sodiumborohydride to afford compound of Formula (Ie) as shown in scheme-5.

Experimental

The invention is further illustrated by the following Examples which are provided merely to be exemplary of the invention and do not limit the scope of the invention. The Examples set forth below demonstrate the synthetic procedures for the preparation of the representative compounds. It is to be understood by the skilled person in the art that one of the major or minor diastereomers mentioned herein is R, R isomer and the other is R,S isomer. Certain modifications and equivalents will be apparent to those skilled in the art and are intended to be included within the scope of the invention. It is to be understood that the examples of hydrochloride salts were prepared by using the similar hydrochloride salt procedure by adding HCl in suitable solvent to a corresponding free base as mentioned herein or any other procedure known in the art. The aforementioned patents and patent applications are incorporated herein by reference.

INTERMEDIATES

Intermediate-1: 3-(Hydroxymethyl) naphthalen-1-yl trifluoromethanesulfonate

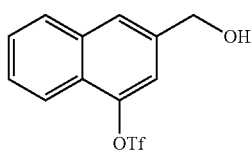 [SMILES: O=S(=O)(Oc1cc(CO)cc2ccccc12)C(F)(F)F]

A solution of ethyl 4-{[(trifluoromethyl)sulfonyl]oxy}-2-naphthoate (0.250 g, 0.718 mmol) in dichloromethane (10 ml) was cooled to −78° C. A solution of 1M DIBAL-H (1.436 ml, 1.436 mmol) in THF was added drop-wise at −78° C. and the solution was stirred for 1 h at −78° C. The reaction mixture was allowed to warm to 25° C. and then stirred for 2 h. The progress of reaction was monitored by TLC. The reaction mixture was quenched with methanol (2 mL), resulting solid material was filtered through celite. The filtrate was dried over anhydrous $Na_2SO_4$ and concentrated under reduced pressure to get title compound (0.2 g, 0.653 mmol, 91% yield) as yellowish oil. $^1$H NMR (400 MHz, DMSO-d) δ 8.12-8.07 (m, 1H), 8.03-8.00 (m, 1H), 7.94 (dd, J=8.2, 1.4 Hz, 1H), 7.77-7.67 (m, 2H), 7.63 (d, J=1.4 Hz, 1H), 5.60 (s, 1H), 4.72 (s, 2H); MS (ES+) m/z=288.8 (M+1, 100%).

Intermediate-2: 3-Formylnaphthalen-1-yl trifluoromethanesulfonate

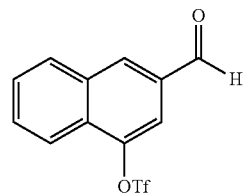 [SMILES: O=Cc1cc(OS(=O)(=O)C(F)(F)F)c2ccccc2c1]

To a stirred solution of Intermediate-1 (100 mg, 0.327 mmol) in dichloromethane (5 ml), pyridiniumchlorochromate (77 mg, 0.359 mmol) was added lot-wise over 15 min at 25° C. and The reaction mixture was stirred for 2 h. After completion of reaction, the reaction mixture was diluted with ethyl acetate (10 ml) and quenched with ice water (10 ml). The resulting emulsion was filtered through celite bed. Layers were separated and the organic layer was washed with brine (15 ml). The organic layer was dried over anhydrous sodium sulfate, filtered and the solvent was evaporated in vacuo to get a crude compound. The crude compound was purified by column chromatography over silica gel (100-200 mesh) with isocratic elution of 10% ethyl acetate in hexane to afford title compound (65 mg, 65.4%) as an off white solid. $^1$H NMR (400 MHz, DMSO-$d_6$) δ 10.17 (s, 1H), 8.87-8.71 (m, 1H), 8.37 (dd, J=8.2, 1.2 Hz, 1H), 8.09-8.04 (m, 1H), 7.98 (ddd, J=8.4, 6.9, 1.2 Hz, 1H), 7.94 (d, J=1.3 Hz, 1H), 7.87 (ddd, J=8.2, 6.9, 1.2 Hz, 1H). MS (ES+) m/z=304.8 (M+1, 100%).

Intermediate-3: 3-(1-Hydroxyethyl)naphthalen-1-yl trifluoromethanesulfonate

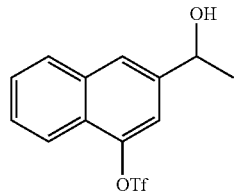 [SMILES: CC(O)c1cc(OS(=O)(=O)C(F)(F)F)c2ccccc2c1]

To a solution of Intermediate-2 (3 g, 9.86 mmol) in diethyl ether (20 ml) at 0° C. was added methylmagnesium bromide (4.93 ml, 14.79 mmol) drop-wise. After stirring for 5 min at 0° C. saturated aqueous NH$_4$Cl (10 mL) solution was added, and the resulting mixture extracted with diethyl ether (10 mL×3). The combined organic layers were washed with brine, dried over MgSO$_4$, filtered and concentrated in vacuo. Flash chromatography (ethyl acetate/hexane=1:10) afforded title compound (3.1 g, 9.68 mmol, 98% yield) as a colorless oil. $^1$H NMR (400 MHz, DMSO-d$_6$) δ 8.10 (d, J=8.0 Hz, 1H), 8.03 (s, 1H), 7.93 (d, J=8.1 Hz, 1H), 7.78-7.62 (m, 3H), 5.57 (d, J=4.3 Hz, 1H), 4.95 (p, J=5.8 Hz, 1H), 1.41 (d, J=6.4 Hz, 3H); MS (ES+) m/z=302.9 (M+1, 100%).

Intermediate-4: 3-Acetylnaphthalen-1-yl trifluoromethanesulfonate

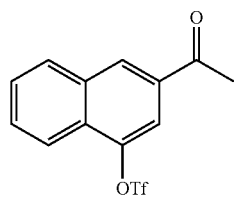 [SMILES: CC(=O)c1cc(OS(=O)(=O)C(F)(F)F)c2ccccc2c1]

Intermediate-3 (1.4 g, 4.37 mmol) was dissolved in dichloromethane (30 ml). Then pyridinium chlorochromate (1.036 g, 4.81 mmol) was added lot wise over 15 min. the reaction mixture was stirred for 2 h at 25° C. After completion of reaction, reaction mixture was quenched by ice water (50 ml) and extracted by using ethyl acetate (50 ml), washed with brine (50 ml). Organic layer was dried over anhydrous sodium sulphate and evaporated to get crude product which was purified by using 10% ethyl acetate in hexane to give title compound (0.9 g, 65%) as an off white solid. $^1$H NMR (400 MHz, DMSO-d$_6$) δ 8.95-8.88 (m, 1H), 8.35 (dd, J=8.2, 1.2 Hz, 1H), 8.04 (dd, J=8.5, 1.2 Hz, 1H), 8.00-7.92 (m, 2H), 7.85 (ddd, J=8.1, 6.9, 1.2 Hz, 1H), 2.75 (s, 3H); (ES+) m/z=319 (M+1, 100%).

3-Acetylnaphthalen-1-yl trifluoromethanesulfonate was also prepared in two steps as given below.

Step-1: 1-(4-Hydroxynaphthalen-2-yl)ethanone

To a stirred solution of 3-benzyl-5-(2-hydroxyethyl)-4-methylthiazol-3-ium chloride (4.02 g, 14.91 mmol) and o-phthalaldehyde (10 g, 74.6 mmol) was added DMF (375 ml) and but-3-en-2-one (5.23 g, 74.6 mmol), then stirred for 10 min at 25° C. Cesium carbonate (4.86 g, 14.91 mmol) was added to reaction mixture and stirred the reaction mixture at 25° C. for 3 h. TLC showed completion of reaction. Reaction mixture was diluted with ethyl acetate (500 ml), washed successively with water (400 ml) and brine (250 ml). Organic layer was dried over anhydrous Na$_2$SO$_4$, and concentrated in vacuo to get 20 g of (3S,4R)-3-Acetyl-4-hydroxy-3,4-dihydronaphthalen-1(2H)-one.

To 1 L rounded-bottom flask charged with (3S,4R)-3-acetyl-4-hydroxy-3,4-dihydronaphthalen-1(2H)-one (15 g, 73.4 mmol), 450 ml of CH$_3$OH and 33.5 ml of concentrated HCl (aq). The mixture was refluxed under a nitrogen atmosphere for 16 h. The solvent was removed under reduced pressure. The residue was diluted with ethyl acetate (200 ml), washed successively with water (100 ml) and brine (250 ml), dried over Na$_2$SO$_4$, and filtered. Organic layer was concentrated in vacuo to get 14 g of crude compound. This residue was purified by chromatography on SiO$_2$ (1:1, hexanes:ethylacetate) to afford a 1-(4-hydroxynaphthalen-2-yl)ethanone (3.2 g, 17.19 mmol, 23.40% yield) as a pale yellow solid. $^1$H NMR (400 MHz, DMSO-d$_6$) δ 10.48 (s, 1H), 8.19-8.14 (m, 2H), 8.06-8.02 (m, 1H), 7.62-7.58 (m, 2H), 7.33 (d, J=1.5 Hz, 1H), 2.66 (s, 3H); (ES+) m/z=187.3 (M+1, 50%).

Step-2

To a solution of step-1 Intermediate (8.4 g, 45.1 mmol) was dissolved in dichloromethane (80 ml) and cool to 0° C. Then triethylamine (18.86 ml, 135 mmol) was added drop wise and reaction mixture stirred for 15 min at 0° C. After drop wise addition of triflic anhydride (9.91 ml, 58.6 mmol) at 0° C., reaction mixture was stirred at 25° C. for 3 h. TLC showed completion of reaction. Reaction mixture was quenched by using ice water (15 mL) and extracted with ethyl acetate (2×150 mL), dried over anhydrous sodium sulphate and filtered. Organic layer was concentrated in vacuo to afford 11.5 g of crude compound. This residue was purified by column chromatography with isocratic elution of 10% ethyl acetate in hexane to get 3-acetylnaphthalen-1-yl trifluoromethanesulfonate (9.6 g, 66.9% yield) as a pale yellow solid. $^1$H NMR (400 MHz, DMSO-d$_6$) δ 8.95-8.88 (m, 1H), 8.35 (dd, J=8.2, 1.2 Hz, 1H), 8.04 (dd, J=8.5, 1.2 Hz, 1H), 8.00-7.92 (m, 2H), 7.85 (ddd, J=8.1, 6.9, 1.2 Hz, 1H), 2.75 (s, 3H); (ES+) m/z=319; (M+1, 100%).

Intermediate-5: 3-Acetyl-7-fluoronaphthalen-1-yl trifluoromethanesulfonate

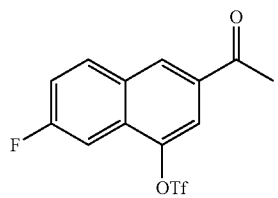 [SMILES: CC(=O)c1cc(OS(=O)(=O)C(F)(F)F)c2cc(F)ccc2c1]

The title compound was prepared by following the similar procedure as described in Intermediate-4. $^1$H NMR (400 MHz, DMSO-d$_6$) δ 10.17 (s, OH), 8.99-8.93 (m, 1H), 8.47 (dd, J=9.1, 5.6 Hz, 1H), 8.08-8.01 (m, 1H), 7.88-7.65 (m, 2H), 2.74 (s, 3H); (ES+) m/z=337.02 (M+1, 100%).

Intermediate-6: 3-Acetyl-6-fluoronaphthalen-1-yl trifluoromethanesulfonate

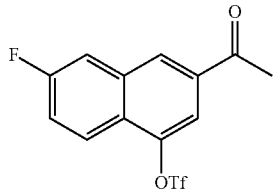 [SMILES: CC(=O)c1cc(OS(=O)(=O)C(F)(F)F)c2ccc(F)cc2c1]

The title compound was prepared by following the similar procedure as described in Intermediate-4. MS (ES+) m/z=337.26 (M+1).

Intermediate-7 3-(1-Hydroxypropyl)naphthalen-1-yl trifluoromethanesulfonate

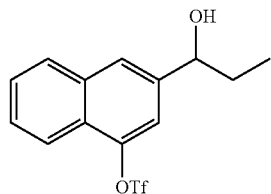 [SMILES: CCC(O)c1cc(OS(=O)(=O)C(F)(F)F)c2ccccc2c1]

To a solution of Intermediate-2 (1 g, 3.29 mmol) in diethyl ether (20 ml) at 0° C. was added ethyl magnesium bromide (3.29 ml, 3.29 mmol) drop-wise. After stirring for 5 min at 0° C. saturated aqueous $NH_4Cl$ (10 mL) solution was added and the resulting mixture extracted with diethyl ether (50 mL×3). The combined organic layers were washed with brine, dried over $MgSO_4$, filtered and concentrated in vacuo. Flash chromatography (ethyl acetate/hexane=1:10) afforded title compound (0.7 g, 2.094 mmol, 63.7% yield) as a yellowish oil. $^1H$ NMR (400 MHz, DMSO-$d_6$) δ 8.14-8.07 (m, 1H), 8.00 (d, J=1.3 Hz, 1H), 7.93 (dd, J=8.5, 1.3 Hz, 1H), 7.76-7.65 (m, 2H), 7.63 (d, J=1.3 Hz, 1H), 5.54 (d, J=4.4 Hz, 1H), 4.71 (dd, J=8.1, 5.2 Hz, 1H), 1.77-1.63 (m, 2H), 0.85 (t, J=7.3 Hz, 3H); MS (ES+) m/z=317 (M+1, 100%)

Intermediate-8: 3-Propionylnaphthalen-1-yl trifluoromethanesulfonate

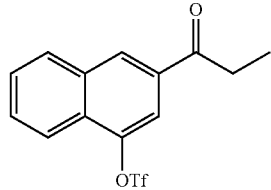 [SMILES: CCC(=O)c1cc(OS(=O)(=O)C(F)(F)F)c2ccccc2c1]

Intermediate-7 (0.9 g, 2.69 mmol) was taken in dichloromethane (30 ml). Then, pyridinium chlorochromate (0.638 g, 2.96 mmol) was added lot wise over 15 min. the reaction mixture was stirred for 2 h at room temperature. After completion of reaction, reaction mixture was quenched with ice water (25 ml) and extracted by using ethyl acetate (25 ml) and washed with brine (25 ml). Organic layer was dried over anhydrous sodium sulphate and evaporated to get a crude product, which was purified by using 10% ethyl acetate in hexane to give title compound (0.7 g, 78%) as an off white solid. $^1H$ NMR (400 MHz, DMSO-$d_6$) δ 8.93-8.90 (m, 1H), 8.37-8.32 (m, 1H), 8.04 (dd, J=8.3, 1.1 Hz, 1H), 8.00 (d, J=1.4 Hz, 1H), 7.94 (ddd, J=8.4, 6.9, 1.2 Hz, 1H), 7.84 (ddd, J=8.2, 6.9, 1.2 Hz, 1H), 3.24 (q, J=7.1 Hz, 2H), 1.16 (t, J=7.1 Hz, 3H); MS (ES+) m/z=331.1 (M+1, 100%).

3-propionylnaphthalen-1-yl trifluoromethanesulfonate was also prepared in two steps as given below.

Step-1: 1-(4-hydroxynaphthalen-2-yl)propan-1-one 1-(4-Hydroxynaphthalen-2-yl)propan-1-one was prepared in two steps as described in Song Ye et. al, *J. Org. Chem.* 2010, 75, 273-276. $^1H$ NMR (400 MHz, DMSO-$d_6$) δ 10.46 (s, 1H), 8.19-8.12 (m, 2H), 8.07-7.99 (m, 1H), 7.63-7.54 (m, 2H), 7.35 (d, J=1.5 Hz, 1H), 3.13 (q, J=7.2 Hz, 2H), 1.13 (t, J=7.2 Hz, 3H); MS (ES+) m/z=333.1 (100%).

Step 2

To a solution of step-1 Intermediate (160 mg, 0.799 mmol) was dissolved in dichloromethane (5 ml) and cool to 0° C. Then triethylamine (0.334 ml, 2.397 mmol) was added drop wise and reaction mixture was stirred for 15 min at 0° C. After drop wise addition of triflic anhydride (0.175 ml, 1.039 mmol) at 0° C., reaction mixture was stirred at 25° C. for 3 h. TLC showed completion of reaction. Reaction mixture was quenched by using ice water (5 mL) and extracted with ethyl acetate (2×10 mL), dried over anhydrous sodium sulphate and filtered. Organic layer was concentrated in vacuo to afford 0.3 g of crude compound. This residue was purified by column chromatography with isocratic elution of 10% ethyl acetate in hexane to get 3-propionylnaphthalen-1-yl trifluoromethanesulfonate (0.18 g, 67.8% yield) as a pale yellow solid. $^1H$ NMR (400 MHz, DMSO-$d_6$) δ 8.94-8.88 (m, 3H), 8.34 (d, J=8.2 Hz, 3H), 8.10-7.90 (m, 9H), 7.84 (ddd, J=8.1, 6.9, 1.2 Hz, 3H), 3.35 (s, 4H), 3.24 (q, J=7.1 Hz, 6H), 1.16 (t, J=7.1 Hz, 10H); MS (ES+) m/z=332.94 (M+1, 100%).

Intermediate-9: 4-(4-(Trifluoromethyl)phenyl)-2-naphthaldehyde

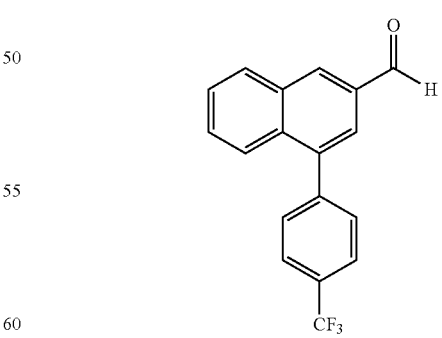

To an oven-dried round-bottomed flask was added Intermediate-2 (1 g, 3.29 mmol), (4-(Trifluoromethyl)phenyl) boronic acid (0.687 g, 3.62 mmol) and anhydrous dioxane (10 ml) under $N_2$ atmosphere. A degassed aqueous solution of sodium carbonate (4.93 ml, 9.86 mmol) was then added via syringe to the vigorously stirred reaction mixture, followed by tetrakis(triphenylphosphine)palladium(0) (0.190 g, 0.164 mmol). The reaction mixture was stirred at 90° C. for 4 h. TLC showed completion of reaction. The reaction mixture was diluted with water (25 ml) and ethyl acetate (25 ml). The phases were separated and the aqueous phase was extracted with ethyl acetate (2×15 ml). The combined organic extract was washed with water (2×25 ml), brine (50 ml) and dried over anhydrous sodium sulphate, filtered and concentrated in vacuo to get 1.3 g of the crude residue. This residue was purified by column chromatography over silica gel (100-200 mesh) with an isocratic elution of 15% ethyl acetate in pet ether to afford 4-(4-(Trifluoromethyl)phenyl)-2-naphthaldehyde (0.8 g, 2.66 mmol, 81% yield) as an off white solid. $^1$H NMR (400 MHz, DMSO-$d_6$) δ 10.22 (s, 1H), 8.42 (s, 1H), 8.14-8.10 (m, 1H), 7.91 (d, J=1.6 Hz, 1H), 7.89-7.86 (m, 1H), 7.80 (d, J=1.6 Hz, 2H), 7.66-7.62 (m, 4H); MS (ES+) m/z=300.9 (M$^+$, 100%).

Intermediate-10: (E)-Ethyl 3-(4-(4-(trifluoromethyl)phenyl)naphthalen-2-yl)acrylate

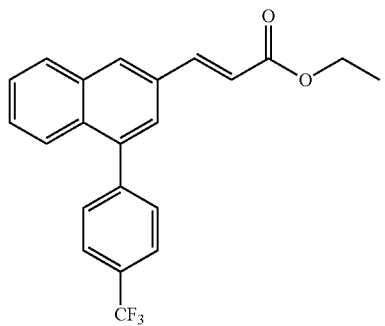 [SMILES: CCOC(=O)/C=C/c1cc(-c2ccc(C(F)(F)F)cc2)c2ccccc2c1]

To a solution of triethylphosphonoacetate (1.600 ml, 7.99 mmol), sodium hydride (0.320 g, 7.99 mmol) in THF (15 ml), 4-(4-(trifluoromethyl)phenyl)-2-naphthaldehyde (Intermediate-9) (1 g, 3.33 mmol) was added at 0° C. The reaction mixture was then stirred under nitrogen at 25° C. for 4 h. TLC showed completion of reaction. The reaction mixture was diluted with water (25 ml) and dichloromethane (25 ml). The phases were separated and the aqueous phase was extracted with dichloromethane (2×15 ml). The combined organic extract was washed with water (2×25 ml), brine (50 ml) and dried over anhydrous sodium sulphate, filtered and concentrated in vacuo to get 0.17 g of the crude residue. This residue was purified by column chromatography over silica gel (100-200 mesh) with an isocratic elution of 20% ethyl acetate in petroleum ether to afford (E)-Ethyl 3-(4-(4-(trifluoromethyl)phenyl)naphthalen-2-yl)acrylate (0.98 g, 2.65 mmol, 79% yield) as an off white solid $^1$H NMR (400 MHz, DMSO-$d_6$) δ 8.00 (s, 1H), 7.96 (d, J=8.4 Hz, 1H), 7.89 (d, J=16 Hz, 1H), 7.80-7.77 (m, 3H), 7.64-7.61 (m, 3H), 7.57-7.48 (m, 2H), 6.58 (d, J=16 Hz, 1H), 4.30 (q, J=7.2 & 14 Hz, 2H), 1.38 (t, J=7.2 Hz, 3H); MS (ES+) m/z=371.0 (M+1, 100%).

Intermediate-11: Ethyl 3-(4-(4-(trifluoromethyl)phenyl)naphthalen-2-yl)propanoate

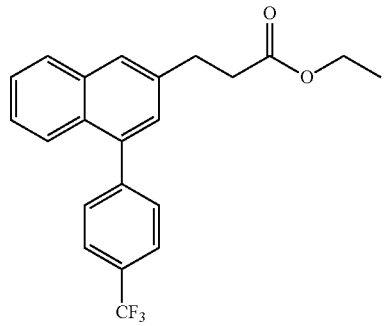 [SMILES: CCOC(=O)CCc1cc(-c2ccc(C(F)(F)F)cc2)c2ccccc2c1]

Cobalt (II) chloride hexahydrate (32.1 mg, 0.135 mmol) and Intermediate-10 (500 mg, 1.350 mmol) was dissolved in methanol (5 ml) under argon atmosphere. Reaction mixture was stirred at 25° C. for 10 min. sodium borohydride (77 mg, 2.025 mmol) was added in portions when the colour faded from black-brown to pink. After consumption of the starting material (30 minutes), reaction mixture was diluted with water (20 ml) and extracted with ethyl acetate (20 ml×3). The organic phases were combined, washed with brine (25 ml), dried over MgSO$_4$, and concentrated under vacuum to get 0.6 g of crude compound. This residue was purified by flash chromatography with isocratic elution of 15% ethyl acetate in petroleum ether to give ethyl 3-(4-(4-(trifluoromethyl)phenyl)naphthalen-2-yl)propanoate (0.5 g, 99%) as an off white solid. $^1$H NMR (400 MHz, Chloroform-d) δ 7.91-7.85 (m, 1H), 7.81-7.75 (m, 3H), 7.75-7.71 (m, 1H), 7.65-7.60 (m, 2H), 7.51 (ddd, J=8.2, 6.8, 1.3 Hz, 1H), 7.43 (ddd, J=8.3, 6.8, 1.4 Hz, 1H), 7.31 (d, J=1.8 Hz, 1H), 4.16 (q, J=7.1 Hz, 2H), 3.18 (t, J=7.8 Hz, 2H), 2.77 (dd, J=8.2, 7.2 Hz, 2H), 1.25 (t, J=7.2 Hz, 3H); MS (ES+) m/z=373.12 (M+1, 100%).

Intermediate-12: 3-(4-(4-(Trifluoromethyl)phenyl)naphthalen-2-yl)propanal

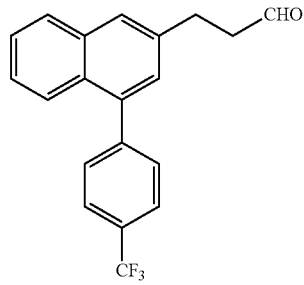 [SMILES: O=CCCc1cc(-c2ccc(C(F)(F)F)cc2)c2ccccc2c1]

A solution of Intermediate-11 (500 mg, 1.343 mmol) in dichloromethane (10 mL) was cool to −78° C. then the solution of diisobutylaluminum hydride (2.69 mL, 2.69 mmol) in THF was added drop wise. The reaction mixture was stirred for 1 h at same temperature and then at 25° C. for 2 h. TLC showed completion of reaction. Reaction mixture quenched by using methanol (2 mL) then solid material was observed which was filtered through celite, the filtrate was dried over Na$_2$SO$_4$ and concentrated under reduced pressure to give title compound (0.42 g, 95%) as an off white solid. $^1$H NMR (400 MHz, Chloroform-d) δ 9.90 (t, J=1.3 Hz, 1H), 7.92-7.83 (m, 1H), 7.82-7.74 (m, 3H), 7.74-7.69 (m, 1H), 7.62 (dp, J=7.5, 0.8 Hz, 2H), 7.52 (ddd, J=8.2, 6.8, 1.2 Hz, 1H), 7.43 (ddd, J=8.3, 6.8, 1.4 Hz, 1H), 7.29 (d, J=1.8 Hz, 1H), 3.19 (t, J=7.5 Hz, 2H), 2.98-2.90 (m, 2H), MS (ES+) m/z=329.12 (M+1, 100%).

Intermediate-13: 4-(3-(Trifluoromethyl)phenyl)-2-naphthaldehyde

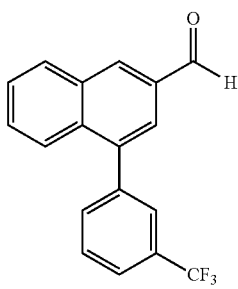 [SMILES: O=Cc1cc(-c2cccc(C(F)(F)F)c2)c2ccccc2c1]

Title compound was prepared by following the similar procedure as described in Intermediate-9 by taking aldehyde Intermediate-2 and (3-(trifluoromethyl)phenyl)boronic acid. $^1$H NMR (400 MHz, DMSO-d$_6$) δ 10.23 (s, 1H), 8.42 (s, 1H), 8.14-8.10 (m, 1H), 7.92 (d, J=1.6 Hz, 1H), 7.87-7.84 (m, 1H), 7.78-7.74 (m, 2H), 7.70-7.63 (m, 4H); MS (ES+) m/z=300.9 (M$^+$, 100%).

Intermediate-14: 1-(4-(3-Fluoro-4-methoxyphenyl)naphthalen-2-yl)ethanone

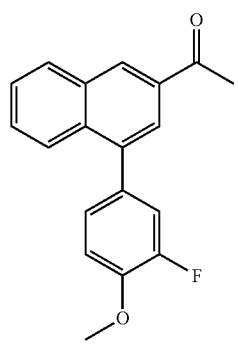 [SMILES: COc1ccc(-c2cc(C(C)=O)cc3ccccc23)cc1F]

Title compound was prepared by following the similar procedure as described in Intermediate-9 by taking ketone Intermediate-4 and (3-fluoro-4-methoxyphenyl)boronic acid. $^1$H NMR (400 MHz, Chloroform-d) δ 8.53-8.46 (m, 1H), 8.10-8.02 (m, 1H), 8.00-7.89 (m, 2H), 7.65-7.54 (m, 2H), 7.27-7.21 (m, 2H), 7.12 (t, J=8.4 Hz, 1H), 4.00 (s, 3H), 2.77 (s, 3H), MS (ES+) m/z=313.03.

Intermediate-15: 1-(4-(4-(Trifluoromethoxy)phenyl)naphthalen-2-yl)ethanone

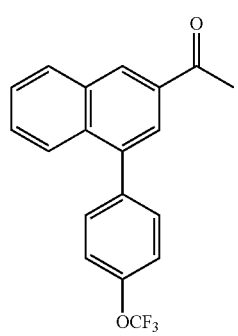 [SMILES: CC(=O)c1cc(-c2ccc(OC(F)(F)F)cc2)c2ccccc2c1]

Title compound was prepared by following the similar procedure as described in Intermediate-9 by taking ketone Intermediate-4 and (4-(trifluoromethoxy)phenyl)boronic acid. $^1$H NMR (400 MHz, Chloroform-d) δ 8.55-8.50 (m, 1H), 8.11-8.04 (m, 1H), 7.98 (d, J=1.8 Hz, 1H), 7.92-7.84 (m, 1H), 7.65-7.58 (m, 2H), 7.57-7.49 (m, 2H), 7.43-7.34 (m, 2H), 2.78 (s, 3H); MS (ES+) m/z=331.11 (M+1, 100%).

Intermediate-16: 1-(4-(4-(Trifluoromethyl)phenyl)naphthalen-2-yl)ethanone

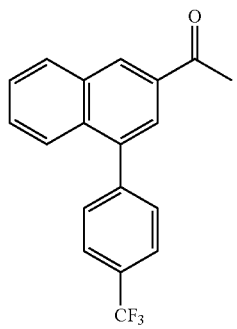 [SMILES: CC(=O)c1cc(-c2ccc(C(F)(F)F)cc2)c2ccccc2c1]

Title compound was prepared by following the similar procedure as described in Intermediate-9 by taking ketone Intermediate-4 and (4-(trifluoromethyl)phenyl)boronic acid. $^1$H NMR (400 MHz, DMSO-d$_6$) δ 8.79-8.77 (m, 1H), 8.30-8.25 (m, 1H), 7.96-7.93 (m, 1H), 7.93-7.90 (m, 2H), 7.82-7.74 (m, 3H), 7.73-7.66 (m, 2H), 2.75 (s, 3H); MS (ES+) m/z=315.05.

Intermediate-17: 1-(4-(4-(Difluoromethoxy)phenyl)naphthalen-2-yl)ethanone

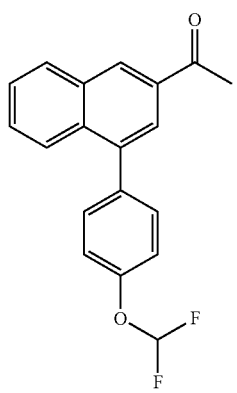 [SMILES: CC(=O)c1cc(-c2ccc(OC(F)F)cc2)c2ccccc2c1]

Title compound was prepared by following the similar procedure as described in Intermediate-9 by taking ketone Intermediate-4 and 2-(4-(difluoromethoxy)phenyl)-4,4,5,5-tetramethyl-1,3,2-dioxaborolane. $^1$H NMR (400 MHz, Chloroform-d) δ 8.53-8.47 (m, 1H), 8.12-8.03 (m, 1H), 7.98 (d, J=1.8 Hz, 1H), 7.95-7.83 (m, 1H), 7.66-7.55 (m, 2H), 7.55-7.46 (m, 2H), 7.35-7.24 (m, 3H), 6.64 (t, J=73.8 Hz, 1H), 2.78 (s, 3H); MS (ES+) m/z=294.98 (M+1, 100%).

Intermediate-18: 1-(4-(3-(Trifluoromethyl)phenyl) naphthalen-2-yl)ethanone

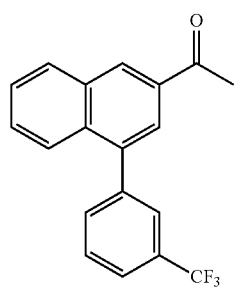 [SMILES: CC(=O)c1cc(-c2cccc(C(F)(F)F)c2)c2ccccc2c1]

Title compound was prepared by following the similar procedure as described in Intermediate-9 by taking ketone Intermediate-4 and (3-(trifluoromethyl)phenyl)boronic acid. $^1$H NMR (400 MHz, Chloroform-d) δ 8.56-8.52 (m, 1H), 8.13-8.04 (m, 1H), 8.00 (d, J=1.8 Hz, 1H), 7.83 (dddd, J=6.7, 5.9, 3.0, 2.2 Hz, 1H), 7.78 (tt, J=1.8, 0.7 Hz, 1H), 7.77-7.73 (m, 1H), 7.71 (dt, J=7.7, 1.7 Hz, 1H), 7.68-7.65 (m, 1H), 7.64-7.60 (m, 2H), 2.79 (s, 3H); MS (ES+) m/z=315.08.

Intermediate-19: 1-(4-(4-(Methylsulfonyl)phenyl) naphthalen-2-yl)ethanone

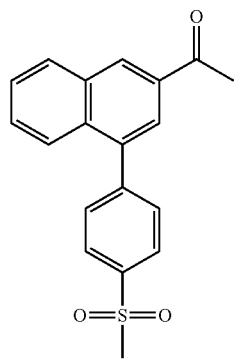 [SMILES: CC(=O)c1cc(-c2ccc(S(C)(=O)=O)cc2)c2ccccc2c1]

Title compound was prepared by following the similar procedure as described in Intermediate-9 by taking ketone Intermediate-4 and (4-(methylsulfonyl)phenyl)boronic acid. $^1$H NMR (400 MHz, DMSO-d$_6$) δ 8.79 (dd, J=1.7, 0.8 Hz, 1H), 8.32-8.23 (m, 1H), 8.15-8.07 (m, 2H), 7.92 (d, J=1.7 Hz, 1H), 7.81 (dd, J=9.1, 2.8 Hz, 3H), 7.70 (dtd, J=6.8, 5.3, 4.8, 3.4 Hz, 2H), 3.34 (s, 7H), 2.76 (s, 3H); MS (ES+) m/z=325 (M+1, 100%).

Intermediate-20: 1-(4-(4-(Pyrrolidin-1-yl)phenyl) naphthalen-2-yl)ethanone

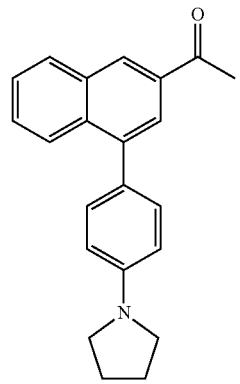 [SMILES: CC(=O)c1cc(-c2ccc(N3CCCC3)cc2)c2ccccc2c1]

Title compound was prepared by following the similar procedure as described in Intermediate-9 by taking ketone Intermediate-4 and 1-(4-(4,4,5,5-tetramethyl-1,3,2-dioxaborolan-2-yl) phenyl)pyrrolidine. $^1$H NMR (400 MHz, DMSO-d$_6$) δ 8.65-8.60 (m, 2H), 8.20 (dt, J=6.4, 3.4 Hz, 2H), 8.02-7.93 (m, 2H), 7.81 (d, J=1.7 Hz, 2H), 7.64 (dt, J=6.4, 3.4 Hz, 4H), 7.37-7.30 (m, 4H), 6.75-6.67 (m, 4H), 3.36-3.27 (m, 17H), 2.73 (s, 6H), 2.06-1.95 (m, 8H), 1.23 (d, J=2.0 Hz, 1H)); MS (ES+) m/z=316.40 (M+1, 50%).

Intermediate-21: 1-(4-(3-Fluoro-5-morpholinophenyl)naphthalen-2-yl)ethanone

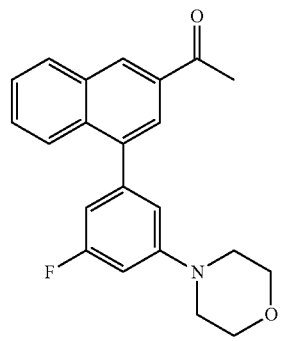 [SMILES: CC(=O)c1cc(-c2cc(F)cc(N3CCOCC3)c2)c2ccccc2c1]

Title compound was prepared by following the similar procedure as described in Intermediate-9 by taking ketone Intermediate-4 and 4-(3-fluoro-5-(4,4,5,5-tetramethyl-1,3,2-dioxaborolan-2-yl)phenyl)morpholine. $^1$H NMR (400 MHz, DMSO-d$_6$) δ 8.75-8.69 (m, 2H), 8.28-8.18 (m, 2H), 7.92-7.83 (m, 4H), 7.73-7.62 (m, 4H), 6.96-6.82 (m, 4H), 6.71 (ddd, J=9.1, 2.3, 1.2 Hz, 2H), 5.76 (s, 1H), 4.03 (q, J=7.1 Hz, 2H), 3.78-3.65 (m, 9H), 3.25-3.18 (m, 8H), 3.09-3.01 (m, 1H), 2.74 (s, 6H), 2.51-2.42 (m, 24H), 1.99 (s, 3H), 1.26-1.04 (m, 7H), 0.89-0.79 (m, 1H). LCMS m/z=391.04.

Intermediate-22: 1-(7-Fluoro-4-(4-(trifluoromethyl)phenyl)naphthalen-2-yl)ethanone

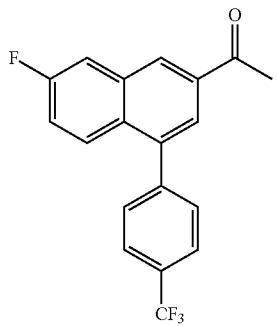

Title compound was prepared by following the similar procedure as described in Intermediate-9 by taking ketone Intermediate-4 and 4-(trifluoromethyl)phenyl)boronic acid. MS (ES+) m/z=333.30 (M+1).

Intermediate-23: 1-(4-(4-(3-Fluorooxetan-3-yl)phenyl)naphthalen-2-yl)ethanone

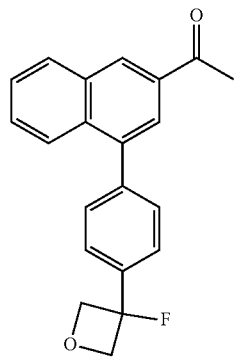 [SMILES: CC(=O)c1cc(-c2ccc(C3(F)COC3)cc2)c2ccccc2c1]

Title compound was prepared by following the similar procedure as described in Intermediate-9 by taking ketone Intermediate-4 and 2-(4-(3-fluorooxetan-3-yl)phenyl)-4,4,5,5-tetramethyl-1,3,2-dioxaborolane. $^1$H NMR (400 MHz, DMSO-$d_6$) δ 8.75 (s, 1H), 8.29-8.22 (m, 1H), 7.91-7.81 (m, 2H), 7.75 (d, J=7.9 Hz, 2H), 7.71-7.60 (m, 4H), 5.04 (dd, J=22.4, 2.2 Hz, 4H), 2.75 (s, 3H), MS (ES+) m/z=321.11.

Intermediate-24: 1-(4-(4-Fluorophenyl)naphthalen-2-yl)ethanone

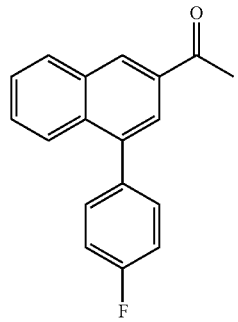 [SMILES: CC(=O)c1cc(-c2ccc(F)cc2)c2ccccc2c1]

Title compound was prepared by following the similar procedure as described in Intermediate-9 by taking ketone Intermediate-4 and 4-fluorophenylboronic acid. $^1$H NMR (400 MHz, DMSO-$d_6$) δ 8.76-8.70 (m, 5H), 8.29-8.20 (m, 5H), 7.88-7.76 (m, 10H), 7.72-7.63 (m, 10H), 7.61-7.51 (m, 10H), 7.45-7.34 (m, 10H), 2.74 (s, 14H); MS (ES+) m/z=265.39 (M+1, 100%).

Intermediate-25: 1-(4-(4-(Trifluoromethyl)phenyl)naphthalen-2-yl)propan-1-one

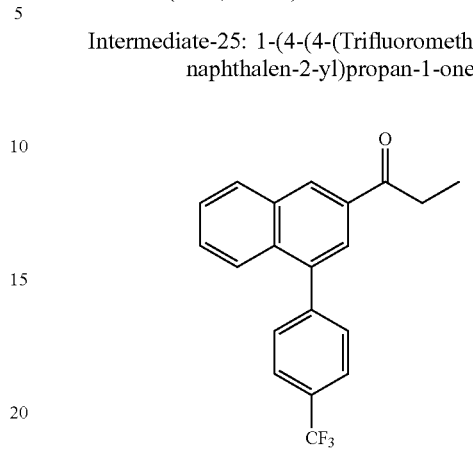

The title compound was prepared by following the similar procedure as described in Intermediate-9 by taking ketone Intermediate-8 and (4-(trifluoromethyl)phenyl)boronic acid. $^1$H NMR (400 MHz, DMSO-$d_6$) δ 8.80-8.75 (m, 1H), 8.29-8.23 (m, 1H), 7.96-7.90 (m, 3H), 7.82-7.74 (m, 3H), 7.72-7.64 (m, 2H), 3.25 (q, J=7.2 Hz, 2H), 1.17 (td, J=7.1, 5.8 Hz, 3H). MS (ES+) m/z=329.

Intermediate-26: 5-(3-Formylnaphthalen-1-yl)-2-methylbenzoate

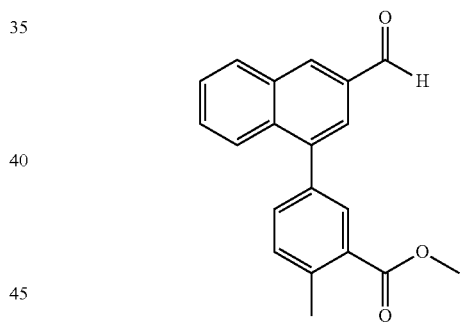

To an oven-dried round-bottomed flask was added Intermediate-2 (100 mg, 0.329 mmol), [3-(methoxycarbonyl)-4-methylphenyl]boronic acid (63.8 mg, 0.329 mmol) in anhydrous dioxane (10 ml) under $N_2$ atmosphere. A degassed aqueous solution of sodium carbonate (105 mg, 0.986 mmol) was then added via syringe to the vigorously stirred reaction mixture, followed by tetrakis(triphenylphosphine)palladium (0) (18.99 mg, 0.016 mmol). The reaction mixture was stirred at 90° C. for 4 h. TLC showed completion of reaction. The reaction mixture was diluted with water (25 ml) and ethyl acetate (25 ml). The phases were separated and the aqueous phase was extracted with ethyl acetate (2×15 ml). The combined organic extract was washed with water (2×25 ml), brine (50 ml) and dried over anhydrous sodium sulphate, filtered and concentrated in vacuo to get 0.2 g of the crude residue. The crude compound was purified by column chromatography over silica gel (100-200 mesh) with isocratic elution of 20% ethyl acetate in hexane to afford title compound (mg, 65%) as a off white solid. $^1$H NMR (400

MHz, CDCl3-d$_6$) δ 10.22 (s, 1H), 8.39 (s, 1H), 8.11-8.07 (m, 2H), 7.93-7.90 (m, 2H), 7.64-7.62 (m, 2H), 7.56-7.54 (m, 1H), 7.42 (d, J=7.6 Hz, 1H), 3.91 (s, 3H), 2.72 (s, 3H); MS (ES+) m/z=304.54.

The below Intermediates-27 to 38 given in Table-1 were prepared by following the similar procedure as described in Intermediate-26 by taking Intermediate-2 and appropriate boronic acid or ester.

TABLE 1

| Intermediate No | Structure | Boronic acid/ester | Mass (m/z) (ES+) |
|---|---|---|---|
| 27 | 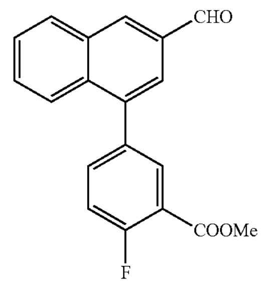 [SMILES: COC(=O)c1cc(-c2cc(C=O)cc3ccccc23)ccc1F] | Methyl-2-fluoro-5-(4,4,5,5-tetramethyl-1,3,2-dioxaborolan-2-yl)benzoate (US2008/81803 A1) | 309.0 |
| 28 | 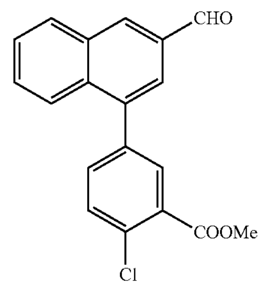 [SMILES: COC(=O)c1cc(-c2cc(C=O)cc3ccccc23)ccc1Cl] | Methyl-2-chloro-5-(4,4,5,5-tetramethyl-1,3,2-dioxaborolan-2-yl)benzoate (WO2004/99146 A1) | 325.0 |
| 29 | 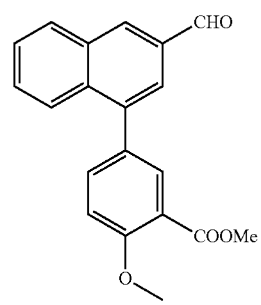 [SMILES: COC(=O)c1cc(-c2cc(C=O)cc3ccccc23)ccc1OC] | Methyl-2-methoxy-5-(4,4,5,5-tetramethyl-1,3,2-dioxaborolan-2-yl)benzoate (WO2008/23161) | 320.9 |
| 30 | 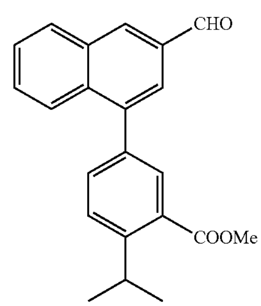 [SMILES: COC(=O)c1cc(-c2cc(C=O)cc3ccccc23)ccc1C(C)C] | Methyl-2-isopropyl-5-(4,4,5,5-tetramethyl-1,3,2-dioxaborolan-2-yl)benzoate | 332.39 |
| 31 | 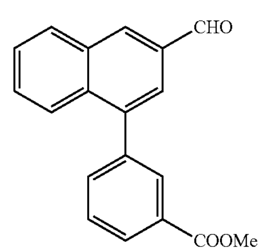 [SMILES: COC(=O)c1cccc(-c2cc(C=O)cc3ccccc23)c1] | (3-Methoxycarbonyl)phenyl boronic acid | 332.34 (M$^+$ + 41) |

TABLE 1-continued

| Intermediate No | Structure | Boronic acid/ester | Mass (m/z) (ES+) |
|---|---|---|---|
| 32 | naphthalene-CHO with 2-F-3-COOMe phenyl | Methyl-2-fluoro-3-(4,4,5,5-tetramethyl-1,3,2-dioxaborolan-2-yl)benzoate. | 350.28 (M$^+$ + 41) |
| 33 | naphthalene-CHO with 2-methyl-3-COOMe phenyl | Methyl-2-methyl-3-(4,4,5,5-tetramethyl-1,3,2-dioxaborolan-2-yl)benzoate (EP2011788) | 346.28 (M$^+$ + 41) |
| 34 | naphthalene-CHO with 4-COOC$_2$H$_5$ phenyl | (4-(Methoxycarbonyl)phenyl) boronic acid | 304.31 |
| 35 | naphthalene-CHO with 4-(C(CH$_3$)$_2$COOMe) phenyl | Methyl-2-methyl-2-(4-(4,4,5,5-tetramethyl-1,3,2-dioxaborolan-2-yl)phenyl)propanoate (WO2006/63167 A1) | 333.0 |
| 36 | naphthalene-CHO with 3-(C(CH$_3$)$_2$COOH) phenyl | 2-Methyl-2-(3-(4,4,5,5-tetramethyl-1,3,2-dioxaborolan-2-yl)phenyl)propanoic acid | 319.37 |

TABLE 1-continued

| Intermediate No | Structure | Boronic acid/ester | Mass (m/z) (ES+) |
|---|---|---|---|
| 37 | ![structure with naphthalene, CHO, fluorophenyl, COOMe] | Methyl-3-(2-fluoro-5-(4,4,5,5-tetramethyl-1,3,2-dioxaborolan-2-yl)phenyl)propanoate | 337.1 |
| 38 | ![structure with naphthalene, CHO, dimethylbenzoate, benzyl ester] | Benzyl 3-(3-formylnaphthalen-1-yl)-2,6-dimethylbenzoate | 395.0 |

Intermediate-39: Methyl 5-(3-acetylnaphthalen-1-yl)-2-methylbenzoate

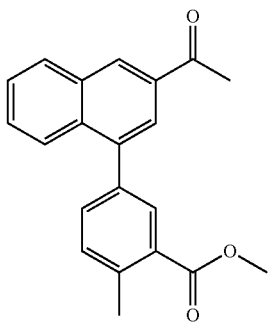 [SMILES: COC(=O)c1cc(-c2cc(C(C)=O)cc3ccccc23)ccc1C]

A suspension of Intermediate-4 (627 mg, 1.970 mmol), methyl-2-methyl-5-(4,4,5,5-tetramethyl-1,3,2-dioxaborolan-2-yl)benzoate (598 mg, 2.167 mmol) and sodium carbonate (626 mg, 5.91 mmol) in EtOH:toluene:water (10 ml, 2:2:1) was degassed by purging nitrogen for 30 minutes. Tetrakis(triphenylphosphine)palladium (0) (114 mg, 0.099 mmol) was added to the reaction mixture and again the reaction mixture was degassed by purging nitrogen for 10 minutes. The resulting suspension was then heated at 65° C. for 2 hrs. After completion of reaction, the reaction mixture was diluted with ethyl acetate (20 ml). Resulting solid was removed by filtration through Celite. Layers were separated and organic layer was washed with brine (25 ml). Organic layer was dried over anhydrous sodium sulfate, filtered and the solvent was evaporated in vacuo to get a crude compound. The crude compound was purified by column chromatography over silica gel (100-200 mesh) with isocratic elution of 20% ethyl acetate in hexane to afford the title compound (600 mg, 1.885 mmol, 96% yield) as off white solid.

$^1$H NMR (400 MHz, Chloroform-d) δ 8.51 (s, 1H), 8.09-8.03 (m, 2H), 7.99 (d, J=1.8 Hz, 1H), 7.91-7.86 (m, 1H), 7.63-7.53 (m, 3H), 7.41 (d, J=7.7 Hz, 1H), 3.91 (s, 3H), 2.78 (s, 3H), 2.73 (s, 3H). MS (ES+), m/z=318.40

The below Intermediates-40 to 67 given in Table-2 were prepared by following the similar procedure as described in Intermediate-39 by taking Intermediate-4, 5 or 8 and appropriate boronic acid or ester.

TABLE 2

| Intermediate No | Structure | Boronic acid/ester | Mass (m/z) (ES+) |
|---|---|---|---|
| 40 | ![structure with naphthalene, acetyl, fluorophenyl, COOMe] | Methyl-2-fluoro-5-(4,4,5,5-tetramethyl-1,3,2-dioxaborolan-2-yl)benzoate (US2008/81803 A1) | 323.28 |

TABLE 2-continued

| Intermediate No | Structure | Boronic acid/ester | Mass (m/z) (ES+) |
|---|---|---|---|
| 41 | naphthalene with acetyl group and 4-chloro-3-(methoxycarbonyl)phenyl substituent | Methyl-2-chloro-5-(4,4,5,5-tetramethyl-1,3,2-dioxaborolan-2-yl)benzoate (WO2004/99146 A1) | 339.9 |
| 42 | naphthalene with acetyl group and 4-(trifluoromethyl)-3-(methoxycarbonyl)phenyl substituent | Methyl-5-(4,4,5,5-tetramethyl-1,3,2-dioxaborolan-2-yl)-2-(trifluoromethyl)benzoate, | 373.07 |
| 43 | naphthalene with acetyl group and 2-methyl-3-(methoxycarbonyl)phenyl substituent | Methyl-2-methyl-3-(4,4,5,5-tetramethyl-1,3,2-dioxaborolan-2-yl)benzoate | 318.34 |
| 44 | naphthalene with acetyl group and 3-methyl-5-(methoxycarbonyl)phenyl substituent | Methyl-3-methyl-5-(4,4,5,5-tetramethyl-1,3,2-dioxaborolan-2-yl)benzoate | 319.11 |
| 45 | naphthalene with acetyl group and 3-methoxy-5-(methoxycarbonyl)phenyl substituent | Methyl 3-methoxy-5-(4,4,5,5-tetramethyl-1,3,2-dioxaborolan-2-yl)benzoate | 335.34 |

TABLE 2-continued

| Intermediate No | Structure | Boronic acid/ester | Mass (m/z) (ES+) |
|---|---|---|---|
| 46 | 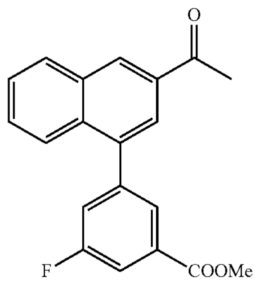 [SMILES: COC(=O)c1cc(C)cc(-c2cc(C(C)=O)cc3ccccc23)c1] | Methyl-3-fluoro-5-(4,4,5,5-tetramethyl-1,3,2-dioxaborolan-2-yl)benzoate | 364.35 |
| 47 | 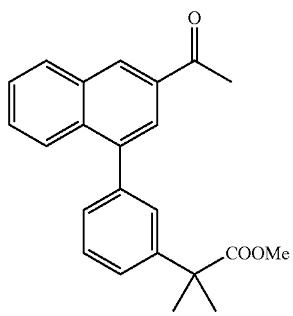 [SMILES: COC(=O)C(C)(C)c1cccc(-c2cc(C(C)=O)cc3ccccc23)c1] | Methyl-2-methyl-2-(3-(4,4,5,5-tetramethyl-1,3,2-dioxaborolan-2-yl)phenyl)propanoate | 347.12 |
| 48 | 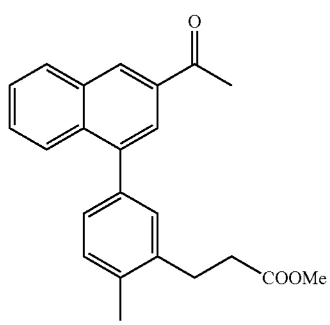 [SMILES: COC(=O)CCc1cc(-c2cc(C(C)=O)cc3ccccc23)ccc1C] | Methyl-3-(2-methyl-5-(4,4,5,5-tetramethyl-1,3,2-dioxaborolan-2-yl)phenyl)propanoate | 347.18 |
| 49 | 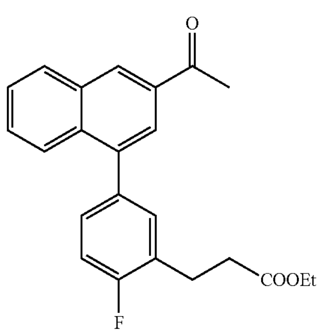 [SMILES: CCOC(=O)CCc1cc(-c2cc(C(C)=O)cc3ccccc23)ccc1F] | Ethyl 3-(2-fluoro-5-(4,4,5,5-tetramethyl-1,3,2-dioxaborolan-2-yl)phenyl)propanoate | 365.18 |
| 50 | 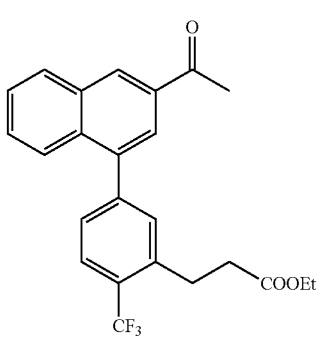 [SMILES: CCOC(=O)CCc1cc(-c2cc(C(C)=O)cc3ccccc23)ccc1C(F)(F)F] | Ethyl-3-(5-(4,4,5,5-tetramethyl-1,3,2-dioxaborolan-2-yl)-2-(trifluoromethyl)phenyl)propanoate | 415.10 |

TABLE 2-continued

| Intermediate No | Structure | Boronic acid/ester | Mass (m/z) (ES+) |
|---|---|---|---|
| 51 | 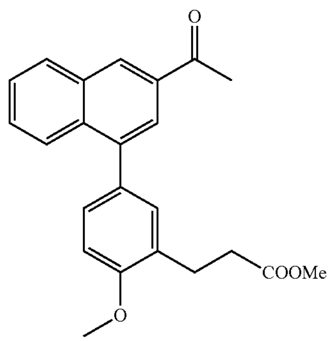 [SMILES: COC(=O)CCc1cc(-c2cc(C(C)=O)cc3ccccc23)ccc1OC] | Methyl-3-(2-methoxy-5-(4,4,5,5-tetramethyl-1,3,2-dioxaborolan-2-yl)phenyl)propanoate | 363.12 |
| 52 | 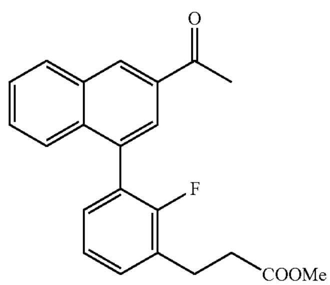 [SMILES: COC(=O)CCc1cccc(-c2cc(C(C)=O)cc3ccccc23)c1F] | Methyl-3-(2-fluoro-3-(4,4,5,5-tetramethyl-1,3,2-dioxaborolan-2-yl)phenyl)propanoate | 351.18 |
| 53 | 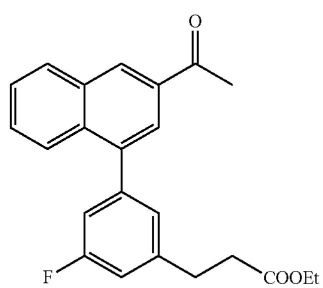 [SMILES: CCOC(=O)CCc1cc(F)cc(-c2cc(C(C)=O)cc3ccccc23)c1] | Ethyl-3-(3-fluoro-5-(4,4,5,5-tetramethyl-1,3,2-dioxaborolan-2-yl)phenyl)propanoate | 365.22 |
| 54 | 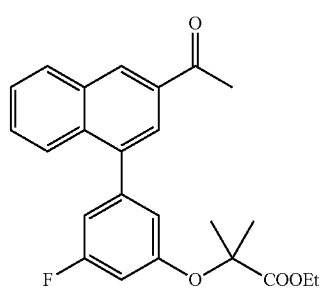 [SMILES: CCOC(=O)C(C)(C)Oc1cc(F)cc(-c2cc(C(C)=O)cc3ccccc23)c1] | Ethyl-2-(3-fluoro-5-(4,4,5,5-tetramethyl-1,3,2-dioxaborolan-2-yl)phenoxy)-2-methylpropanoate | 395.11 |
| 55 | 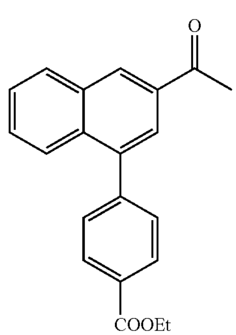 [SMILES: CCOC(=O)c1ccc(-c2cc(C(C)=O)cc3ccccc23)cc1] | (4-(Methoxycarbonyl)phenyl)boronic acid | 318.9 |

TABLE 2-continued

| Intermediate No | Structure | Boronic acid/ester | Mass (m/z) (ES+) |
|---|---|---|---|
| 56 | 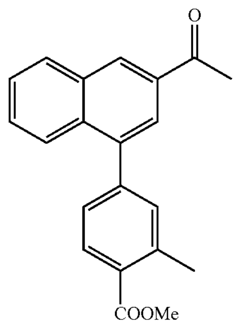 [SMILES: COC(=O)c1ccc(-c2cc(C(C)=O)cc3ccccc23)cc1C] | Methyl-2-methyl-4-(4,4,5,5-tetramethyl-1,3,2-dioxaborolan-2-yl)benzoate [*J. Med. Chem*, 2008, 51(6), 1925-1944] | 319.40 |
| 57 | 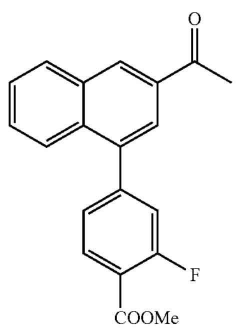 [SMILES: COC(=O)c1ccc(-c2cc(C(C)=O)cc3ccccc23)cc1F] | Methyl-2-fluoro-4-(4,4,5,5-tetramethyl-1,3,2-dioxaborolan-2-yl)benzoate | 323.08 |
| 58 | 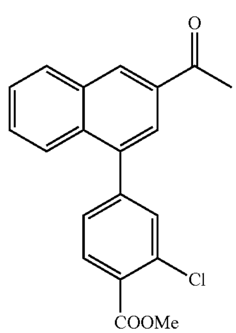 [SMILES: COC(=O)c1ccc(-c2cc(C(C)=O)cc3ccccc23)cc1Cl] | Methyl-2-chloro-4-(4,4,5,5-tetramethyl-1,3,2-dioxaborolan-2-yl)benzoate | 339.18 |
| 59 | 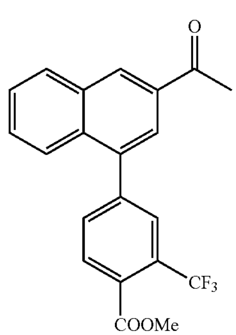 [SMILES: COC(=O)c1ccc(-c2cc(C(C)=O)cc3ccccc23)cc1C(F)(F)F] | Methyl-4-(4,4,5,5-tetramethyl-1,3,2-dioxaborolan-2-yl)-2-(trifluoromethyl)benzoate | 373.09 |

TABLE 2-continued

| Intermediate No | Structure | Boronic acid/ester | Mass (m/z) (ES+) |
|---|---|---|---|
| 60 | (naphthalene with acetyl group and 2-fluoro-4-COOMe phenyl substituent) | Methyl-3-fluoro-4-(4,4,5,5-tetramethyl-1,3,2-dioxaborolan-2-yl)benzoate | 323.20 |
| 61 | (naphthalene with acetyl group and 4-(C(CH3)2COOMe)phenyl substituent) | Methyl-2-methyl-2-(4-(4,4,5,5-tetramethyl-1,3,2-dioxaborolan-2-yl)phenyl)propanoate | 347 |
| 62 | (naphthalene with acetyl group and 4-(CF2COOMe)phenyl substituent) | Methyl-2,2-difluoro-2-(4-(4,4,5,5-tetramethyl-1,3,2-dioxaborolan-2-yl)phenyl)acetate | 355.22 |
| 63 | (naphthalene with acetyl group and 3-fluoro-4-(CH2CH2COOEt)phenyl substituent) | Methyl-3-(2-fluoro-4-(4,4,5,5-tetramethyl-1,3,2-dioxaborolan-2-yl)phenyl)propanoate | 406.16 |

TABLE 2-continued

| Intermediate No | Structure | Boronic acid/ester | Mass (m/z) (ES+) |
|---|---|---|---|
| 64 | 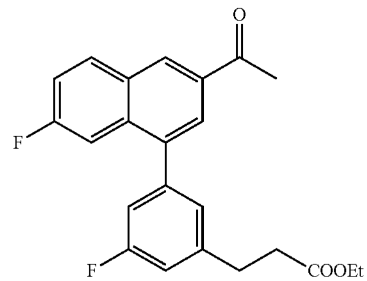 [SMILES: CCOC(=O)CCc1cc(F)cc(-c2cc(C(C)=O)cc3ccc(F)cc23)c1] | Ethyl-3-(3-fluoro-5-(4,4,5,5-tetramethyl-1,3,2-dioxaborolan-2-yl)phenyl)propanoate | 383.16 |
| 65 | 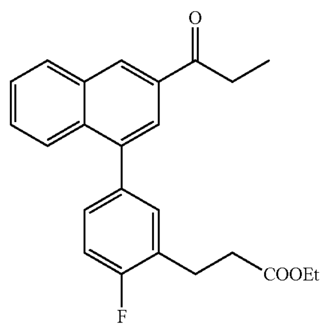 [SMILES: CCOC(=O)CCc1cc(-c2cc(C(=O)CC)cc3ccccc23)ccc1F] | Ethyl-3-(2-fluoro-5-(4,4,5,5-tetramethyl-1,3,2-dioxaborolan-2-yl)phenyl)propanoate | 379.35 |
| 66 | 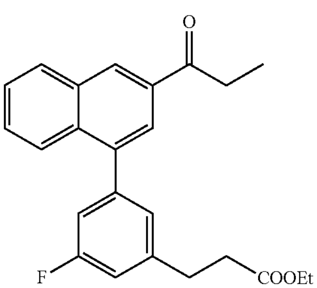 [SMILES: CCOC(=O)CCc1cc(F)cc(-c2cc(C(=O)CC)cc3ccccc23)c1] | Ethyl-3-(3-fluoro-5-(4,4,5,5-tetramethyl-1,3,2-dioxaborolan-2-yl)phenyl)propanoate | 379.22 |
| 67 | 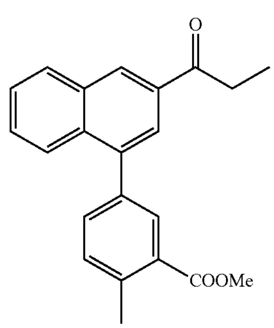 [SMILES: CCC(=O)c1cc(-c2ccc(C)c(C(=O)OC)c2)c2ccccc2c1] | Methyl-2-methyl-5-(4,4,5,5-tetramethyl-1,3,2-dioxaborolan-2-yl)benzoate | 333.4 |

Intermediate-68: (R)-Benzyl 3-(3-(((tert-butoxycarbonyl)(1-(3-methoxyphenyl)ethyl)amino) methyl) naphthalen-1-yl)-2,6-dimethylbenzoate

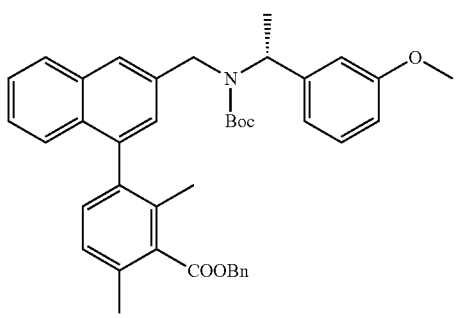

Step-1: (R)-Benzyl 3-(3-(((1-(3-methoxyphenyl) ethyl)amino)methyl)naphthalen-1-yl)-2,6-dimethylbenzoate To stirred a solution of Intermediate-38 (150 mg, 0.380 mmol) and acetic acid (0.022 ml, 0.380 mmol) were added to a solution of (R)-1-(3-methoxyphenyl)ethanamine (57.5 mg, 0.380 mmol) in MeOH (5 ml, ratio: 1.000), THF (5.00 ml, ratio: 1.000) and the resulting mixture was stirred at room temperature for 30 minutes. Then, acetic acid (0.044 ml, 0.761 mmol) and NaCNBH4 (28.7 mg, 0.456 mmol) were added thereto at 0° C. and stirred at room temperature for 16 hours. The reaction mixture was concentrated, poured into a 1N-aqueous sodium hydroxide solution and then extracted with ethyl acetate. The organic layer was washed with a saturated aqueous sodium chloride solution, dried over anhydrous sodium sulfate and then filtered. The filtrate was concentrated under reduced pressure and the resulting residue was purified by a silica gel column chromatography (eluent: hexane/ethyl acetate) to give 0.17 g (95%) of pure product as off white solid.

Step-2: (R)-Benzyl 3-(3-(((tert-butoxycarbonyl)(1-(3-methoxyphenyl)ethyl)amino) methyl) naphthalen-1-yl)-2,6-dimethylbenzoate To a stirred solution step-1 Intermediate (170 mg, 0.321 mmol) in Acetonitrile (6 mL), BOC$_2$O (0.089 mL, 0.385 mmol) was added at 25° C. and stirred the reaction for 16 hour. The progress of reaction was monitored by TLC. After completion of reaction solvent was evaporated under reduced pressure, The residue was subjected to flash column chromatography (silica gel), eluting with Ethyl Acetate: Hexane, to get desired compound 0.19 g (94%) as a off white solid; m/z: 360.0.

Intermediate-69: 1-(4-(3',5-difluoro-[1,1'-biphenyl]-3-yl)naphthalen-2-yl)ethanone

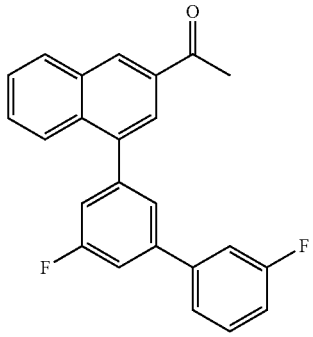 [SMILES: CC(=O)c1cc(-c2cc(F)cc(-c3cccc(F)c3)c2)c2ccccc2c1]

The title compound was prepared by following the similar procedure as described in Intermediate-9 by taking ketone Intermediate-4 and 2-(3',5-difluoro-[1,1'-biphenyl]-3-yl)-4,4,5,5-tetramethyl-1,3,2-dioxaborolane. $^1$H NMR (400 MHz, DMSO-d$_6$) δ 8.77 (d, J=3.0 Hz, 1H), 8.32-8.23 (m, 1H), 8.05-7.95 (m, 1H), 7.95-7.86 (m, 1H), 7.85-7.61 (m, 5H), 7.60-7.48 (m, 1H), 7.47-7.32 (m, 1H), 7.26 (dd, J=9.9, 7.1 Hz, 1H), 6.60 (d, J=9.3 Hz, 1H), 2.88-2.69 (m, 3H); MS (ES+) m/z=265.39 (M+1, 100%).

Intermediate-70: 1-(4-(3-Fluoro-5-(1-methyl-1H-pyrazol-4-yl)phenyl)naphthalen-2-yl) ethanone

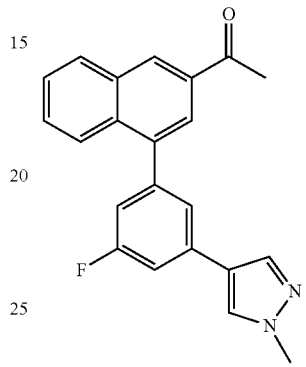

The title compound was prepared by following the similar procedure as described in Intermediate-9 by taking ketone Intermediate-4 and 4-(3-fluoro-5-(4,4,5,5-tetramethyl-1,3,2-dioxaborolan-2-yl)phenyl)-1-methyl-1H-pyrazole. $^1$H NMR (400 MHz, DMSO-d$_6$) δ 8.82-8.70 (m, 1H), 8.36-8.21 (m, 2H), 8.01 (d, J=0.8 Hz, 1H), 7.92 (d, J=1.8 Hz, 1H), 7.89-7.82 (m, 1H), 7.75-7.64 (m, 2H), 7.63-7.51 (m, 2H), 7.16 (ddd, J=9.5, 2.4, 1.4 Hz, 1H), 3.86 (s, 3H), 2.74 (d, J=11.5 Hz, 3H); MS (ES+) m/z=345.22 (M+1, 10%).

EXAMPLES

Example-1

(R)-1-(Naphthalen-1-yl)-N-((4-(4-(trifluoromethyl) phenyl)naphthalen-2-yl) methyl)ethanamine hydrochloride

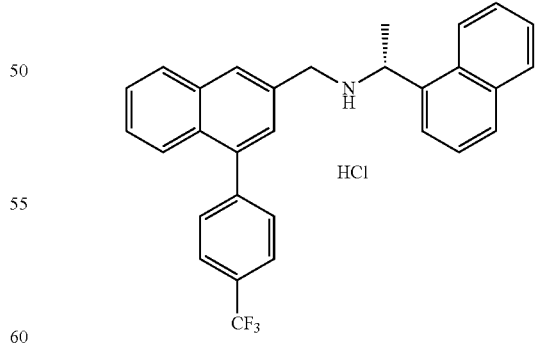

To a stirred solution of Intermediate-9 (150 mg, 0.500 mmol) and (R)-1-(naphthalen-1-yl) ethanamine (86 mg, 0.500 mmol) in methanol (5 ml) and tetrahydrofuran (10 ml) was added acetic acid (0.029 ml, 0.500 mmol). Reaction mixture was stirred at 25° C. for 4 h. Then acetic acid (0.057 ml, 0.999 mmol) was added followed by addition of NaBH₃CN (37.7 mg, 0.599 mmol). Reaction mixture was stirred at 25° C. for 16 hrs. TLC showed completion of reaction. Reaction mixture was quenched with saturated aqueous NaHCO₃ (15 ml) and extracted with ethyl acetate (15 ml). Organic layer was dried over sodium sulfate, concentrated to get 0.3 g of crude compound. This compound was purified by column chromatography using 30% ethyl acetate in hexane as a eluent to give 0.2 g of free amine compound as an off white solid.

This amine was dissolved in dichloromethane (3 ml) and 2M ethereal HCl (2 ml) was added at 0° C. The resulting suspension was stirred for 1 h at 0° C. and the solvent was evaporated in vacuo at 30° C. Resulting salt was triturated with n-pentane (2 ml×2) to give 0.2 g (88%) hydrochloride salt of (R)-1-(Naphthalen-1-yl)-N-((4-(4-(trifluoromethyl)phenyl)naphthalen-2-yl)methyl) ethanamine as a white solid. ¹H NMR (400 MHz, DMSO-d₆) δ 10.32 (bs, 1H), 9.81 (bs, 1H), 8.09-8.06 (m, 3H), 8.03-7.96 (m, 3H), 7.92-7.90 (m, 2H), 7.79 (d, J=8 Hz, 1H), 7.70-7.67 (m, 2H), 7.65-7.52 (m, 6H), 5.37 (q, J=6 Hz, 1H), 4.45-4.41 (m, 1H), 4.29-4.25 (m, 1H), 1.77 (d, J=6.8 Hz, 3H), MS (ES+) m/z=456.04 (M+1, 50%).

The Examples 2 to 5 given in Table-3 were prepared by following the similar procedure as described in Example-1 by taking appropriate aldehyde Intermediate and appropriate amine Intermediate.

TABLE 3

| Ex. No | Structure/Name | Intermediate | ¹H NMR/Mass (m/z) |
|---|---|---|---|
| 2 | 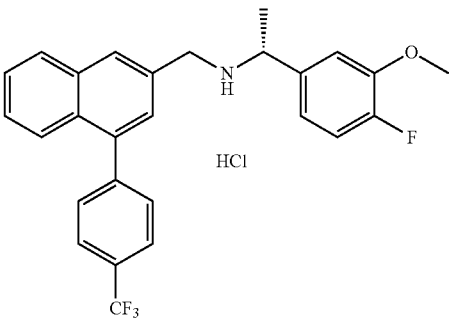<br>(R)-1-(4-Fluoro-3-methoxyphenyl)-N-((4-(4-(trifluoromethyl)phenyl)naphthalen-2-yl)methyl)ethanamine hydrochloride | 9 | ¹H NMR (400 MHz, DMSO-d₆) δ 9.79 (bs, 1H), 9.68 (bs, 1H), 8.06-8.02 (m, 2H), 7.95-7.93 (m, 2H), 7.80 (d, 1H), 7.81-7.74 (m, 2H), 7.65-7.56 (m, 3H), 7.52 (dd, J = 1.6 & 8.4 Hz, 1H), 7.33-7.28 (m, 1H), 7.15-7.12 (m, 1H), 4.47-4.45 (m, 1H), 4.29-4.26 (m, 1H), 4.06-4.03 (m, 1H), 3.85 (s, 3H), 1.64 (d, J = 6.8 Hz, 3H), LCMS: m/z = 454.04 (M + 1, 100%). |
| 3 | 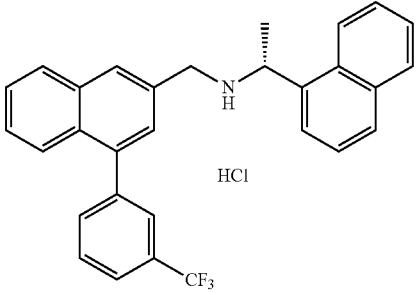 [SMILES: C[C@@H](NCc1cc(-c2cccc(C(F)(F)F)c2)c2ccccc2c1)c1cccc2ccccc12 ; Cl]<br>(R)-1-(Naphthalen-1-yl)-N-((4-(3-(trifluoromethyl)phenyl)naphthalen-2-yl)methyl)ethanamine hydrochloride | 13 | ¹H NMR (400 MHz, DMSO-d₆) δ 10.35 (bs, 1H), 9.79 (bs, 1H), 8.09-8.01 (m, 3H), 8.00-7.96 (m, 3H), 7.87-7.86 (m, 1H), 7.82-7.74 (m, 4H), 7.66-7.53 (m, 6H), 5.39-5.34 (m, 1H), 4.44-4.41 (m, 1H), 4.29-4.255 (m, 1H), 1.77 (d, J = 6.8 Hz, 3H), LCMS: m/z = 456.11 (M + 1, 100%). |
| 4 | 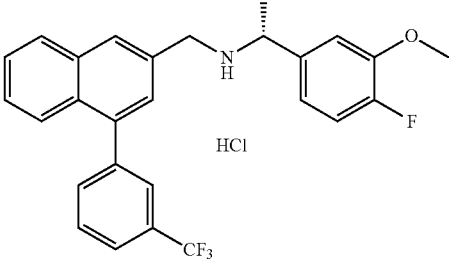<br>(R)-1-(4-Fluoro-3-methoxyphenyl)-N-((4-(3-(trifluoromethyl)phenyl)naphthalen-2-yl)methyl)ethanamine hydrochloride | 13 | ¹H NMR (400 MHz, DMSO-d₆) δ 10.00 (bs, 1H), 9.78 (bs, 1H), 8.07-8.02 (m, 2H), 7.89-7.75 (m, 5H), 7.66-7.56 (m, 4H), 7.30-7.26 (m, 1H), 7.15-7.13 (m, 1H), 4.44 (d, J = 4.8 Hz, 1H), 4.29-4.24 (m, 1H), 4.06 (dd, J = 4 & 7.6 Hz, 1H), 3.84 (s, 3H), 1.65 (d, J = 6.4 Hz, 3H); LCMS: m/z = 454.04 (M + 1, 100%). |

TABLE 3-continued

| Ex. No | Structure/Name | Intermediate | ¹H NMR/Mass (m/z) |
|---|---|---|---|
| 5 | 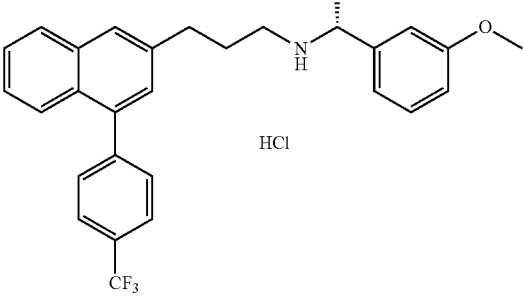<br>(R)-N-(1-(3-Methoxyphenyl)ethyl)-3-(4-(4-(trifluoromethyl)phenyl)naphthalen-2-yl)propan-1-amine hydrochloride | 12 | ¹H NMR (400 MHz, DMSO-d$_6$) δ 9.58 (s, 1H), 9.16 (d, J = 12.5 Hz, 1H), 7.97-7.89 (m, 3H), 7.77 (d, J = 1.9 Hz, 1H), 7.70 (dd, J = 8.2, 5.4 Hz, 3H), 7.56 (ddd, J = 8.2, 6.8, 1.3 Hz, 1H), 7.48 (ddd, J = 8.3, 6.8, 1.4 Hz, 1H), 7.35-7.27 (m, 2H), 7.23-7.19 (m, 1H), 7.11-7.07 (m, 1H), 6.92 (dd, J = 8.1, 2.5 Hz, 1H), 4.33 (dt, J = 12.6, 6.7 Hz, 1H), 3.74 (s, 3H), 2.83 (tt, J = 9.9, 5.0 Hz, 3H), 2.72-2.59 (m, 1H), 2.13-1.98 (m, 2H), 1.57 (d, J = 6.7 Hz, 3H); LCMS: m/z = 464 (M + 1, 100%). |

Example-6

(R)-1-(3-Methoxyphenyl)-N-(1-(4-(4-(trifluoromethyl)phenyl)naphthalen-2-yl) ethyl)ethanamine hydrochloride

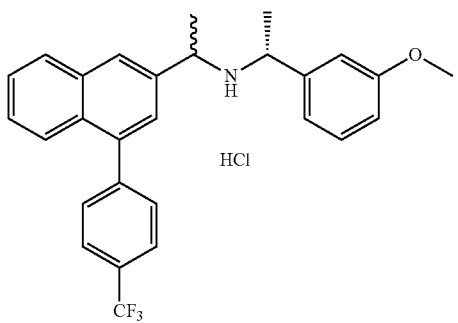 [SMILES: COc1cccc([C@@H](C)NC(C)c2cc(-c3ccc(C(F)(F)F)cc3)c3ccccc3c2)c1 ; Cl]

Intermediate-16 (0.56 g, 1.782 mmol) was added to a solution of (R)-1-(3-methoxyphenyl)ethanamine (0.808 g, 5.35 mmol) in titanium(IV) isopropoxide (6.26 ml, 21.38 mmol) at 25° C. and resulting suspension was stirred at 90° C. for 16 hrs. Reaction mixture was diluted with methanol (3 ml) and cooled to 0° C. Sodium borohydride (0.202 g, 5.35 mmol) was added lot-wise and reaction mixture was stirred at 0° C. for 10 min. TLC showed completion of reaction. Brine (10 ml) and ethyl acetate (20 ml) were added and precipitated solid was filtered through celite, washed with ethyl acetate (10 ml). The phases were separated and the aqueous phase was extracted with ethyl acetate (5 ml). The combined organic extract was dried over anhydrous sodium sulphate, filtered and concentrated in vacuo to get 0.8 g of the crude residue. This residue was purified by column chromatography over silica gel (100-200 mesh) with an isocratic elution of 10% ethyl acetate in petroleum ether to afford a pure compound (0.635 g) as a sticky solid. This mixture of diastereomers was separated by reverse phase preparative HPLC to afford major diastereomers mixed fraction 1 (0.23 g) and mixed fraction 2 (0.264 g) as a sticky solids. This mixture of diastereomers mixed fraction 1 (0.23 g) were separated by chiral preparative HPLC to give major diastereomer mixed fraction 1 (0.2 g) and other mixture of diastereomers mixed fraction 2 (0.264 g) was separated by chiral preparative HPLC to afford major diastereomer mixed fraction 1 (0.17 g) as a sticky solids. To a stirred solution of major diastereomer (0.2 g+0.17 g) in dichloromethane (2 ml), ethereal HCl (3 ml) was then added to this compound at 0° C. and stirred for 1 h. Solvent was evaporated on rotary evaporator at 35° C. and resulting solid was triturated twice with n-pentane to give pure HCl salt of major diastereomer (0.35 g, 0.779 mmol, 43.7% yield) as an off white solid.

It is to be understood by the skilled person in the art that one of the major or minor diastereomers is (R)-1-(3-methoxyphenyl)-N—((R)-1-(4-(4-(trifluoromethyl)phenyl)naphthalen-2-yl) ethyl) ethanamine and the other is (R)-1-(3-methoxyphenyl)-N—((S)-1-(4-(4-(trifluoromethyl)phenyl)naphthalen-2-yl)ethyl)ethanamine.

Method for Reverse Phase Preparative HPLC

Column: YMC TRIART_C18, 50×2.1 mm, 1.9µ; Mobile phase: A: water:CH$_3$CN (90:10 V/V %)+0.1% Ammonium Hydroxide, B: CH$_3$CN:water (90:10 V/V %)+0.1% Ammonium Hydroxide)

Method for Chiral Preparative HPLC Column: CHIRAL CEL OJH 250×4.6 MM, 5µ; Mobile Phase: A=0.1% DEA in methanol This diastereomer (either major or minor) was dissolved in dichloromethane (3 ml) and 2M ethereal HCl (2 ml) was added at 0° C. The resulting suspension was stirred for 1 h at 0° C. and the solvent was evaporated in vacuo at 30° C. Resulting salt was triturated with n-pentane (2 ml×2) to give either major and minor diastereomer's HCl salt.

Major diastereomer's HCl salt (0.35 g, RT=2.36 min (retention time)): ¹H NMR (400 MHz, DMSO-d6) δ 10.01 (d, J=7.3 Hz, 2H), 8.01-7.91 (m, 4H), 7.79 (dd, J=19.2, 8.1 Hz, 3H), 7.68-7.56 (m, 3H), 7.35 (t, J=7.9 Hz, 1H), 7.08-7.05 (m, 1H), 6.98 (dd, J=8.4, 2.5 Hz, 2H), 4.21 (dt, J=10.6, 6.7 Hz, 1H), 4.04 (dq, J=10.6, 7.1, 6.5 Hz, 1H), 3.71 (s, 3H), 1.70 (d, J=6.7 Hz, 3H), 1.57 (d, J=6.6 Hz, 3H)

Minor diastereomer's HCl salt (0.08 g, RT=2.32 min): ¹H NMR (400 MHz, DMSO-d6) δ 10.35 (d, J=11.9 Hz, 1H), 9.37-9.23 (m, 1H), 8.10 (s, 1H), 8.03 (d, J=7.7 Hz, 1H), 7.94 (d, J=7.8 Hz, 2H), 7.83-7.70 (m, 4H), 7.61 (dt, J=20.3, 7.1 Hz, 2H), 7.32 (t, J=7.7 Hz, 1H), 7.20 (s, 1H), 7.10 (d, J=7.4 Hz, 1H), 6.92 (d, J=8.0 Hz, 1H), 4.40 (t, J=7.9 Hz, 1H), 4.28 (q, J=6.3, 5.4 Hz, 1H), 3.72 (s, 3H), 1.71 (d, J=6.4 Hz, 3H), 1.61 (d, J=6.2 Hz, 3H) as a white solids.

The Examples 7 to 23 given in Table-4 were prepared by following the similar procedure as described in Example-6 by taking appropriate ketone Intermediate and appropriate amine Intermediate.

TABLE 4

| Ex. No. | Structure/Name | Intermediate | $^1$H NMR; Mass (m/z) |
|---|---|---|---|
| 7 | 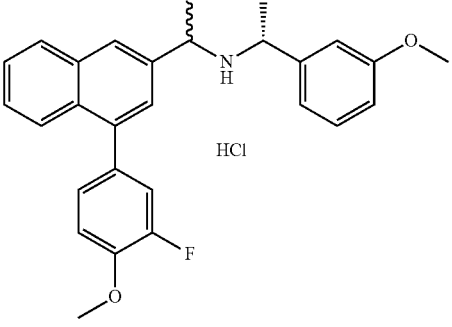 [SMILES: COc1cccc([C@@H](C)NC(C)c2cc(-c3ccc(OC)c(F)c3)c3ccccc3c2)c1 ; Cl]<br>1-(4-(3-Fluoro-4-methoxyphenyl)naphthalen-2-yl)-N-((R)-1-(3-methoxyphenyl)ethyl)ethanamine hydrochloride | 14 | Analysis of major (RT = 2.11 min) isomer: $^1$H NMR (400 MHz, DMSO-d$_6$) δ 9.86 (d, J = 10.0 Hz, 2H), 7.98-7.87 (m, 3H), 7.65-7.56 (m, 2H), 7.50 (d, J = 1.7 Hz, 1H), 7.43-7.29 (m, 4H), 7.09-7.02 (m, 1H), 7.02-6.93 (m, 2H), 4.21 (q, J = 6.5 Hz, 1H), 4.06 (q, J = 6.4 Hz, 1H), 3.95 (s, 3H), 3.73 (s, 3H), 1.68 (d, J = 6.7 Hz, 3H), 1.57 (d, J = 6.7 Hz, 3H); LCMS: m/z = 430.2 (M + 1, 100%). |
| 8 | 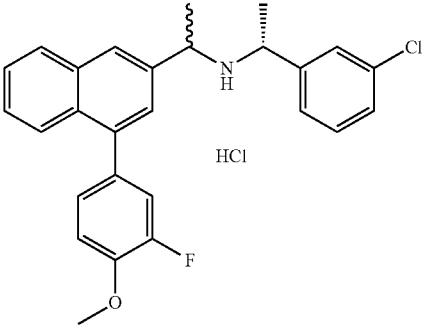 [SMILES: COc1ccc(-c2cc(C(C)N[C@H](C)c3cccc(Cl)c3)cc3ccccc23)cc1F ; Cl]<br>(1R)-1-(3-Chlorophenyl)-N-(1-(4-(3-fluoro-4-methoxyphenyl)naphthalen-2-yl)ethyl)ethanamine hydrochloride | | Analysis of major (RT = 1.84 min) isomer: $^1$H NMR (400 MHz, DMSO-d$_6$) δ 9.83 (s, 2H), 7.97 (dd, J = 8.0, 1.7 Hz, 1H), 7.93-7.87 (m, 2H), 7.66-7.56 (m, 2H), 7.54-7.46 (m, 4H), 7.46-7.26 (m, 4H), 4.29 (q, J = 6.4 Hz, 1H), 4.20 (q, J = 6.4 Hz, 1H), 3.94 (s, 3H), 1.69 (d, J = 6.7 Hz, 3H), 1.57 (d, J = 6.7 Hz, 3H); LCMS: m/z = 434.1 (M$^+$, 100%). |
| 9a, 9b | 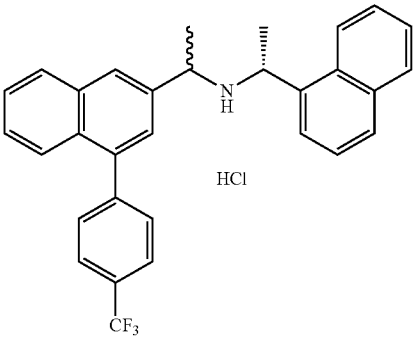 [SMILES: CC(N[C@H](C)c1cccc2ccccc12)c1cc(-c2ccc(C(F)(F)F)cc2)c2ccccc2c1 ; Cl]<br>(1R)-1-(Naphthalen-1-yl)-N-(1-(4-(4-(trifluoromethyl)phenyl)naphthalen-2-yl)ethyl)ethanamine hydrochloride | 16 | Analysis of major 9b (RT = 2.75-min) isomer: $^1$H NMR (400 MHz, DMSO-d$_6$) δ 10.36 (t, J = 9.7 Hz, 1H), 10.23 (d, J = 13.5 Hz, 1H), 8.16 (d, J = 6.9 Hz, 1H), 7.99 (t, J = 8.6 Hz, 2H), 7.83 (d, J = 7.9 Hz, 2H), 7.77 (s, 1H), 7.76-7.70 (m, 2H), 7.67 (t, J = 7.7 Hz, 1H), 7.57 (dq, J = 6.2, 3.8, 2.3 Hz, 2H), 7.43 (q, J = 6.8, 6.1 Hz, 4H), 7.20-7.07 (m, 2H), 4.95 (d, J = 8.7 Hz, 1H), 4.35 (t, J = 9.0 Hz, 1H), 1.78 (d, J = 6.5 Hz, 3H), 1.68 (d, J = 6.4 Hz, 3H); LCMS: m/z = 470.1 (M$^+$, 100%). Analysis of minor isomer 9a: 1H NMR (400 MHz, DMSO-d6) d 10.50 (d, J = 12.1 Hz, 1H), 9.26 (d, J = 11.1 Hz, 1H), 8.21 (s, 1H), 7.99 (dt, J = 33.5, 7.0 Hz, 6H), 7.83 (d, J = 7.9 Hz, 1H), 7.75 (d, J = 7.6 Hz, 1H), 7.47 (m, 2H), 7.37-7.25 (m, 1H), 5.02 (d, J = 7.8 Hz, 1H), 4.73 (s, 1H), 1.79 (d, J = 6.3 Hz, 3H), 1.73 (d, J = 6.2 Hz, 3H)); LCMS: m/z = 470.1 (M$^+$, 100%). |

TABLE 4-continued

| Ex. No. | Structure/Name | Intermediate | $^1$H NMR; Mass (m/z) |
|---|---|---|---|
| 10 | (1R)-1-(3-Chlorophenyl)-N-(1-(4-(4-(trifluoromethyl)phenyl)naphthalen-2-yl)ethyl)ethanamine hydrochloride | 16 | Analysis of major (RT = 2.73 min) isomer: $^1$H NMR (400 MHz, DMSO-d6) δ 10.21 (s, 2H), 7.96 (ddd, J = 12.7, 8.2, 1.8 Hz, 4H), 7.84-7.75 (m, 3H), 7.67-7.58 (m, 2H), 7.57 (t, J = 2.2 Hz, 1H), 7.52 (s, 1H), 7.47 (d, J = 2.5 Hz, 3H), 4.23 (q, J = 6.3 Hz, 1H), 4.12 (q, J = 6.6 Hz, 1H), 1.75-1.67 (m, 3H), 1.62-1.52 (m, 3H); LCMS: m/z = 454.1 (M$^+$, 100%). |
| 11 | (1R)-1-(4-Fluoro-3-methoxyphenyl)-N-(1-(4-(4-(trifluoromethyl)phenyl)naphthalen-2-yl)ethyl)ethanamine hydrochloride | 16 | Analysis of major (RT = 2.33 min) isomer: $^1$H NMR (400 MHz, DMSO-d6) δ 10.07 (d, J = 10.3 Hz, 1H), 9.92 (s, 1H), 8.00 (dd, J = 8.2, 1.4 Hz, 1H), 7.97-7.93 (m, 3H), 7.85-7.80 (m, 1H), 7.78 (d, J = 8.0 Hz, 2H), 7.68-7.56 (m, 3H), 7.37 (dd, J = 8.4, 2.1 Hz, 1H), 7.28 (dd, J = 11.4, 8.3 Hz, 1H), 6.95 (ddd, J = 8.4, 4.2, 2.0 Hz, 1H), 4.28-4.18 (m, 1H), 4.14-4.03 (m, 1H), 3.75 (s, 3H), 1.69 (d, J = 6.7 Hz, 3H), 1.58 (d, J = 6.7 Hz, 3H); LCMS: m/z = 468 (M$^+$, 100%). |
| 12 | (1R)-1-(3-Ethoxyphenyl)-N-(1-(4-(4-(trifluoromethyl)phenyl)naphthalen-2-yl)ethyl)ethanamine hydrochloride | 16 | Analysis of major (RT = 2.53 min) isomer: $^1$H NMR (400 MHz, DMSO-d6) δ 10.00 (s, 2H), 8.08-7.88 (m, 4H), 7.87-7.70 (m, 3H), 7.70-7.45 (m, 3H), 7.33 (t, J = 7.9 Hz, 1H), 7.02 (t, J = 2.0 Hz, 1H), 6.99-6.76 (m, 2H), 4.20 (q, J = 6.6 Hz, 1H), 4.07-3.84 (m, 3H), 1.70 (d, J = 6.7 Hz, 3H), 1.57 (d, J = 6.7 Hz, 3H), 1.29 (t, J = 6.9 Hz, 3H); LCMS: m/z = 464.12 (M + 1, 100%). |
| 13 | (1R)-1-(3-Fluorophenyl)-N-(1-(4-(4-(trifluoromethyl)phenyl)naphthalen-2-yl)ethyl)ethanamine hydrochloride | 16 | Analysis of major (RT = 2.33 min) isomer: $^1$H NMR (400 MHz, DMSO-d6) δ 10.02 (s, 2H), 8.07-7.90 (m, 4H), 7.79 (dd, J = 17.6, 8.3 Hz, 3H), 7.70-7.54 (m, 3H), 7.53-7.33 (m, 2H), 7.31-7.19 (m, 2H), 4.29 (q, J = 6.5 Hz, 1H), 4.18 (q, J = 6.5 Hz, 1H), 1.70 (d, J = 6.7 Hz, 3H), 1.58 (d, J = 6.6 Hz, 3H), LCMS: m/z = 438.09 (M + 1, 100%). |

TABLE 4-continued

| Ex. No. | Structure/Name | Intermediate | ¹H NMR; Mass (m/z) |
|---|---|---|---|
| 14 | 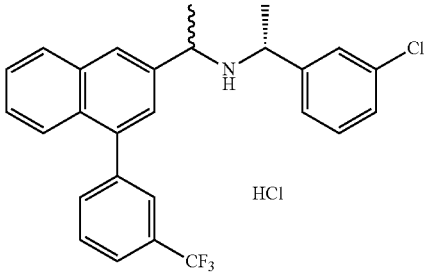 [SMILES: CC(N[C@H](C)c1cccc(Cl)c1)c1cc(-c2cccc(C(F)(F)F)c2)c2ccccc2c1 ; Cl]<br>(1R)-1-(3-Chlorophenyl)-N-(1-(4-(3-(trifluoromethyl)phenyl)naphthalen-2-yl)ethyl)ethanamine hydrochloride | 18 | Analysis of major (RT = 2.63 min) isomer: ¹H NMR (400 MHz, DMSO-d6) δ 9.90 (s, 2H), 8.10-7.93 (m, 2H), 7.95-7.69 (m, 5H), 7.73-7.57 (m, 2H), 7.48 (ddd, J = 16.8, 11.5, 2.0 Hz, 5H), 4.25 (dd, J = 37.5, 6.7 Hz, 2H), 1.69 (d, J = 6.7 Hz, 3H), 1.57 (d, J = 6.7 Hz, 3H), LCMS: m/z = 454.04 (M + 1, 100%). |
| 15 | 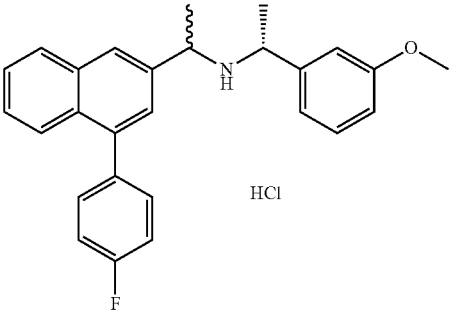 [SMILES: COc1cccc([C@@H](C)NC(C)c2cc(-c3ccc(F)cc3)c3ccccc3c2)c1 ; Cl]<br>1-(4-(4-Fluorophenyl)naphthalen-2-yl)-N-((R)-1-(3-methoxyphenyl)ethyl)ethanamine hydrochloride | 24 | Analysis of major diastereomer: ¹H NMR (400 MHz, DMSO-d6) d 9.95 (d, J = 10.4 Hz, 2H), 8.01-7.93 (m, 1H), 7.93-7.89 (m, 1H), 7.86-7.79 (m, 1H), 7.67-7.53 (m, 4H), 7.50 (d, J = 1.8 Hz, 1H), 7.45-7.31 (m, 3H), 7.06 (t, J = 2.0 Hz, 1H), 7.01-6.94 (m, 2H), 4.21 (q, J = 6.5 Hz, 1H), 4.11-3.98 (m, 1H), 3.72 (s, 3H), 1.69 (d, J = 6.7 Hz, 3H), 1.57 (d, J = 6.7 Hz, 3H); LCMS: m/z = 400.10 (M + 1, 50%). |
| 16 | 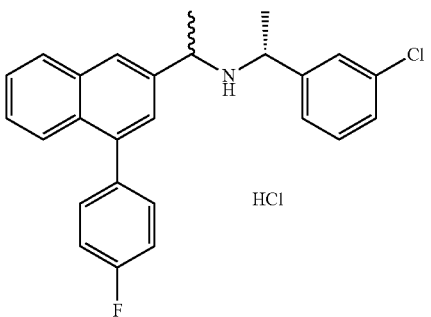 [SMILES: CC(N[C@H](C)c1cccc(Cl)c1)c1cc(-c2ccc(F)cc2)c2ccccc2c1 ; Cl]<br>(1R)-1-(3-Chlorophenyl)-N-(1-(4-(4-fluorophenyl)naphthalen-2-yl)ethyl)ethanamine hydrochloride | 24 | Analysis of major diastereomer ¹H NMR (400 MHz, DMSO-d₆) δ 10.10 (q, J = 13.0, 12.2 Hz, 2H), 8.00-7.87 (m, 2H), 7.82 (d, J = 8.2 Hz, 1H), 7.67-7.54 (m, 4H), 7.54-7.35 (m, 7H), 4.23 (d, J = 9.3 Hz, 1H), 4.15 (q, J = 6.6 Hz, 1H), 1.70 (d, J = 6.6 Hz, 3H), 1.58 (d, J = 6.6 Hz, 3H); LCMS: m/z = 404.04 (M + 1, 10%). |
| 17 | 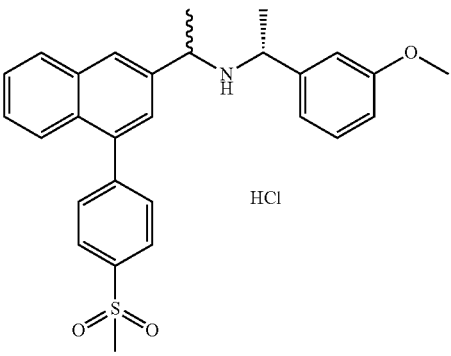<br>(1R)-1-(3-Methoxyphenyl)-N-(1-(4-(4-(methylsulfonyl)phenyl)naphthalen-2-yl)ethyl)ethanamine hydrochloride | 19 | ¹H NMR (400 MHz, DMSO-d6) d 9.98 (s, 2H), 8.17-8.09 (m, 3H), 8.02-7.94 (m, 2H), 7.82 (dq, J = 9.3, 2.8, 2.1 Hz, 4H), 7.73-7.56 (m, 4H), 7.40-7.33 (m, 1H), 4.24 (dt, J = 13.0, 6.9 Hz, 1H), 4.06 (dt, J = 14.2, 7.0 Hz, 1H), 3.72 (d, J = 1.5 Hz, 3H), 3.34 (d, J = 2.2 Hz, 3H), 1.70 (d, J = 6.9 Hz, 3H), 1.57 (d, J = 6.7 Hz, 3H)); LCMS: m/z = 464.05 (M + 1, 10%). |

TABLE 4-continued

| Ex. No. | Structure/Name | Intermediate | ¹H NMR; Mass (m/z) |
|---|---|---|---|
| 18a 18b | 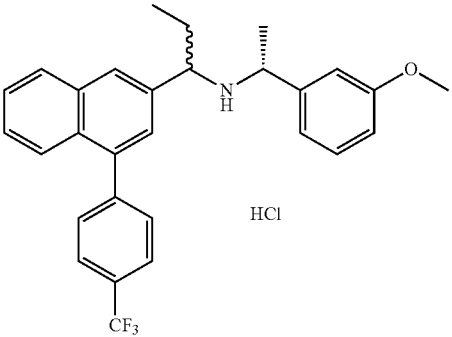 [SMILES: CCC(N[C@H](C)c1cccc(OC)c1)c1cc(-c2ccc(C(F)(F)F)cc2)c2ccccc2c1 ; Cl]<br>N-((R)-1-(3-Methoxyphenyl)ethyl)-1-(4-(4-(trifluoromethyl)phenyl)naphthalen-2-yl)propan-1-amine hydrochloride | 25 | Analysis of major (18a; RT = 2.50 min) isomer: ¹H NMR (400 MHz, DMSO-d6) δ 10.15 (q, J = 13.4, 12.1 Hz, 2H), 8.01-7.91 (m, 3H), 7.90 (s, 1H), 7.86-7.80 (m, 1H), 7.78 (d, J = 8.0 Hz, 2H), 7.60-7.62 (m, 3H), 7.34 (t, J = 7.9 Hz, 1H), 7.05 (t, J = 2.1 Hz, 1H), 6.94-6.96 (m, 2H), 4.03-3.93 (m, 1H), 3.91-3.80 (m, 1H), 3.70 (s, 3H), 2.37-2.25 (m, 1H), 2.06-2.08 (m, 1H), 1.58 (d, J = 6.7 Hz, 3H), 0.63 (t, J = 7.3 Hz, 3H); LCMS: m/z = 464.13 (M + 1, 100%).<br>Analysis of minor (18b; RT = 2.44 min) isomer: ¹H NMR (400 MHz, DMSO-d6) δ 10.34-10.16 (m, 1H), 9.35-9.19 (m, 1H), 8.10 (d, J = 1.7 Hz, 1H), 8.04 (dd, J = 8.0, 1.4 Hz, 1H), 7.94 (d, J = 8.1 Hz, 2H), 7.78 (dd, J = 18.2, 7.8 Hz, 3H), 7.71 (d, J = 1.7 Hz, 1H), 7.62 (dddd, J = 19.5, 8.2, 6.8, 1.4 Hz, 2H), 7.29 (t, J = 7.9 Hz, 1H), 7.17-7.13 (m, 1H), 7.06-7.02 (m, 1H), 6.90 (dd, J = 8.2, 2.5 Hz, 1H), 4.32-4.22 (m, 1H), 4.17 (q, J = 6.3 Hz, 1H), 3.70 (s, 3H), 2.42-2.30 (m, 1H), 2.10-1.96 (m, 1H), 1.61 (d, J = 6.6 Hz, 3H), 0.68 (t, J = 7.3 Hz, 3H); LCMS: m/z = 464.13 (M + 1, 100%). |
| 19 | 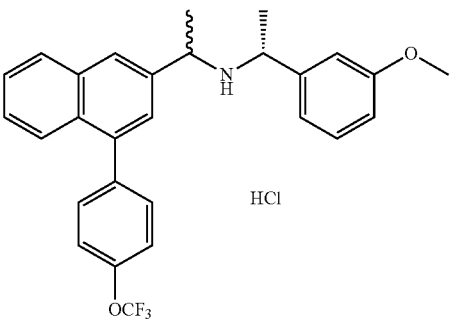 [SMILES: COc1cccc([C@@H](C)NC(C)c2cc(-c3ccc(OC(F)(F)F)cc3)c3ccccc3c2)c1 ; Cl]<br>(1R)-1-(3-Methoxyphenyl)-N-(1-(4-(4-(trifluoromethoxy)phenyl)naphthalen-2-yl)ethyl)ethanamine hydrochloride | 15 | Analysis of major (RT = 2.35 min) isomer: ¹H NMR (400 MHz, DMSO-d6) δ 10.03 (d, J = 8.6 Hz, 2H), 8.01-7.89 (m, 2H), 7.82 (dd, J = 8.0, 1.6 Hz, 1H), 7.73-7.49 (m, 7H), 7.35 (t, J = 7.9 Hz, 1H), 7.15-7.03 (m, 1H), 6.97 (dd, J = 8.1, 2.1 Hz, 2H), 4.19 (q, J = 6.5 Hz, 1H), 4.03 (dp, J = 11.1, 6.6 Hz, 1H), 3.71 (s, 3H), 1.69 (d, J = 6.6 Hz, 3H), 1.57 (d, J = 6.6 Hz, 3H); LCMS: m/z = 466.17 (M + 1, 100%). |
| 20 | 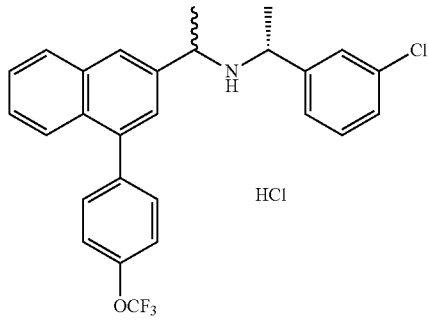 [SMILES: CC(N[C@H](C)c1cccc(Cl)c1)c1cc(-c2ccc(OC(F)(F)F)cc2)c2ccccc2c1 ; Cl]<br>(1R)-1-(3-Chlorophenyl)-N-(1-(4-(4-(trifluoromethoxy)phenyl)naphthalen-2-yl)ethyl)ethanamine hydrochloride | 15 | Analysis of major (RT = 2.63 min) isomer: ¹H NMR (400 MHz, DMSO-d6) δ 9.82 (s, 3H), 8.01-7.95 (m, 1H), 7.92 (d, J = 1.8 Hz, 1H), 7.87-7.81 (m, 1H), 7.67-7.63 (m, 1H), 7.63-7.55 (m, 4H), 7.54-7.49 (m, 3H), 7.48-7.42 (m, 1H), 7.41-7.34 (m, 2H), 4.32 (q, J = 6.5 Hz, 1H), 4.22 (q, J = 6.5 Hz, 1H), 1.69 (d, J = 6.7 Hz, 3H), 1.57 (d, J = 6.7 Hz, 3H); ); LCMS: m/z = 470.11 (M + 1, 100%). |

TABLE 4-continued

| Ex. No. | Structure/Name | Intermediate | ¹H NMR; Mass (m/z) |
|---|---|---|---|
| 21 | 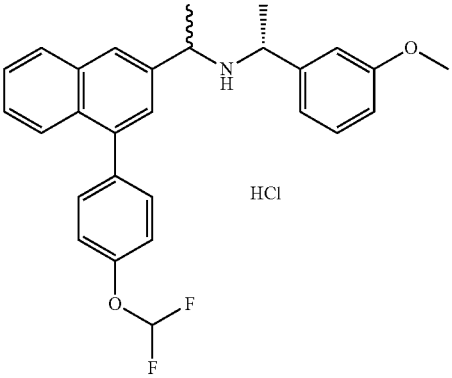 [SMILES: COc1cccc([C@@H](C)NC(C)c2cc(-c3ccc(OC(F)F)cc3)c3ccccc3c2)c1 ; Cl]<br>1-(4-(4-(Difluoromethoxy)phenyl)naphthalen-2-yl)-N-((R)-1-(3-methoxyphenyl)ethyl)ethanamine hydrochloride | 17 | Analysis of major (RT = 2.16 min) isomer: ¹H NMR (400 MHz, DMSO-d6) δ 9.70 (d, J = 13.1 Hz, 1H), 9.45 (s, 1H), 7.93 (dd, J = 8.0, 1.6 Hz, 1H), 7.86-7.82 (m, 1H), 7.72 (d, J = 1.7 Hz, 1H), 7.56 (dddd, J = 21.2, 15.6, 7.7, 1.7 Hz, 6H), 7.40 (ddt, J = 12.3, 10.2, 4.8 Hz, 4H), 7.09-6.99 (m, 2H), 4.41 (q, J = 6.5 Hz, 1H), 4.26 (d, J = 10.5 Hz, 1H), 3.44 (s, 3H), 1.70 (d, J = 6.7 Hz, 3H), 1.51 (d, J = 6.7 Hz, 3H); LCMS: m/z = 448.2 (M + 1, 100%). |
| 22 | 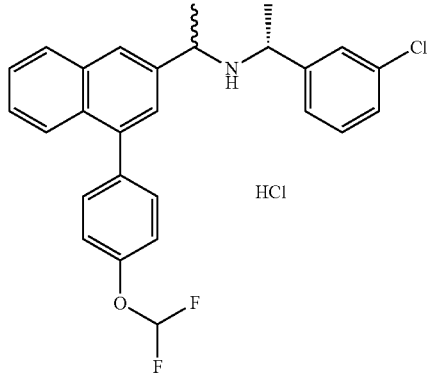 [SMILES: CC(N[C@H](C)c1cccc(Cl)c1)c1cc(-c2ccc(OC(F)F)cc2)c2ccccc2c1 ; Cl]<br>(1R)-1-(3-Chlorophenyl)-N-1-(4-(4-(difluoromethoxy)phenyl)naphthalen-2-yl)ethyl)ethanamine hydrochloride | 17 | Analysis of major (RT = 2.39 min) isomer: ¹H NMR (400 MHz, DMSO-d6) δ 9.82 (s, 3H), 8.01-7.95 (m, 1H), 7.92 (d, J = 1.8 Hz, 1H), 7.87-7.81 (m, 1H), 7.67-7.63 (m, 1H), 7.63-7.55 (m, 4H), 7.54-7.49 (m, 3H), 7.48-7.42 (m, 1H), 7.41-7.34 (m, 2H), 4.32 (q, J = 6.5 Hz, 1H), 4.22 (q, J = 6.5 Hz, 1H), 1.69 (d, J = 6.7 Hz, 3H), 1.57 (d, J = 6.7 Hz, 3H); LCMS: m/z = 452.1 (M + 1, 100%). |
| 23 | 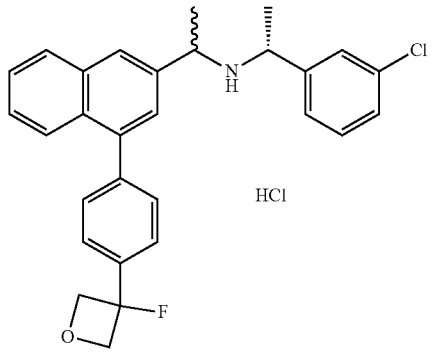 [SMILES: CC(N[C@H](C)c1cccc(Cl)c1)c1cc(-c2ccc(C3(F)COC3)cc2)c2ccccc2c1 ; Cl]<br>(1R)-1-(3-chlorophenyl)-N-(1-(4-(4-(3-fluorooxetan-3-yl)phenyl)naphthalen-2-yl)ethyl)ethanamine hydrochloride | 23 | Analysis of major isomer: ¹H NMR (400 MHz, DMSO-d6) δ 10.08 (d, J = 6.0 Hz, 2H), 8.00-7.91 (m, 2H), 7.89-7.83 (m, 1H), 7.76 (d, J = 8.2 Hz, 2H), 7.68-7.56 (m, 4H), 7.53 (d, J = 1.8 Hz, 2H), 7.51-7.42 (m, 3H), 5.14-4.93 (m, 4H), 4.26 (p, J = 6.8, 6.3 Hz, 1H), 4.16 (q, J = 6.5 Hz, 1H), 1.71 (d, J = 6.6 Hz, 3H), 1.58 (d, J = 6.7 Hz, 3H)); LCMS: m/z = 460.11 (M + 1, 100%). |

Example-24

(R)-Methyl-2-methyl-5-(3-(((1-(naphthalen-1-yl)ethyl)amino)methyl)naphthalen-1-yl)benzoate

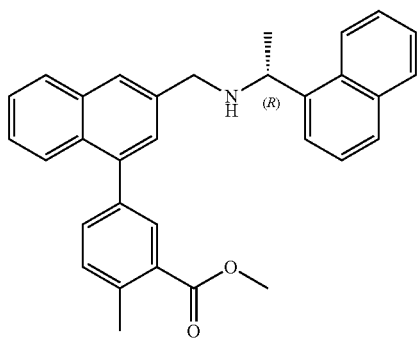

To a stirred solution of Intermediate-26 (100 mg, 0.329 mmol) in methanol (4 mL), and THF (4 mL), was added acetic acid (0.019 ml, 0.329 mmol) and (R)-1-(naphthalen-1-yl)ethanamine (56.3 mg, 0.329 mmol). The resulting mixture was stirred at room temperature for 30 minutes. Then, acetic acid (0.038 ml, 0.657 mmol) and $NaBH_3CN$ (24.78 mg, 0.394 mmol) was added at 0° C. and the reaction mixture was stirred at room temperature for 16 hours. After completion of reaction, the reaction mixture was concentrated. The residue was partitioned between aq.$NaHCO_3$ (10 ml) and ethyl acetate (15 mL×2). The organic layer was washed with brine (15 mL), dried over anhydrous $Na_2SO_4$ and then filtered. The filtrate was concentrated under reduced pressure and resulting residue was purified by column chromatography over silica gel (100-200 mesh) with isocratic elution of 20% ethyl acetate in hexane to afford (R)-methyl-2-methyl-5(3-(((1-(naphthalen-1-yl)ethyl)amino)methyl)naphthalen-1-yl)benzoate (130 mg, 86%) as off white solid.

$^1$H NMR (400 MHz, DMSO-$d_6$) δ 8.20-8.18 (m, 1H), 7.94-7.92 (m, 2H), 7.89 (d, J=2 Hz, 1H), 7.83-7.80 (m, 3H), 7.70 (d, J=8.4 Hz, 1H), 7.58-7.45 (m, 7H), 7.44-7.41 (m, 1H), 4.67-4.63 (m, 1H), 3.83 (s, 3H), 3.82-3.79 (m, 2H), 2.61 (s, 3H), 1.44 (d, J=6.0 Hz, 3H); MS (ES+) m/z=460.11.

The Example-25 to 48 given in Table-5 were prepared by following the similar procedure as described in Example-24 by taking appropriate aldehyde Intermediate and appropriate amine Intermediate.

TABLE 5

| Ex. No | Structure/Name | Amine | Intermediate used | Mass (m/z) (ES+) |
|---|---|---|---|---|
| 25 | ![structure] (R)-Methyl 5-(3-(((1-(3-methoxyphenyl)ethyl)amino)methyl)naphthalen-1-yl)-2-methylbenzoate | (R)-1-(3-Methoxyphenyl)ethanamine | 26 | 440.11 |
| 26 | ![structure] (R)-Methyl 5-(3-(((1-(3-ethoxyphenyl)ethyl)amino)methyl)naphthalen-1-yl)-2-methylbenzoate | (R)-1-(3-Ethoxyphenyl)ethanamine | 26 | 454.12 |

TABLE 5-continued

| Ex. No | Structure/Name | Amine | Intermediate used | Mass (m/z) (ES+) |
|---|---|---|---|---|
| 27 | 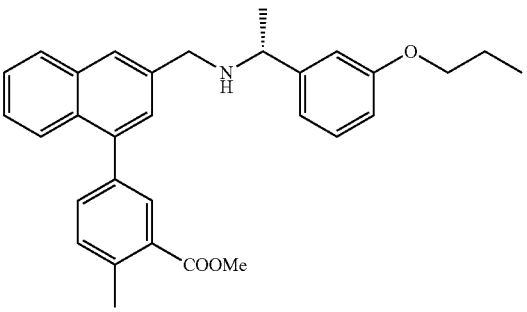 [SMILES: CCCOc1cccc([C@@H](C)NCc2cc(-c3ccc(C)c(C(=O)OC)c3)c3ccccc3c2)c1]<br>(R)-Methyl 2-methyl-5-(3-(((1-(3-propoxyphenyl)eth-yl)amino)methyl)naphthalen-1-yl)benzoate | (R)-1-(3-Propoxy-phenyl)ethanamine | 26 | 468.1 |
| 28 | 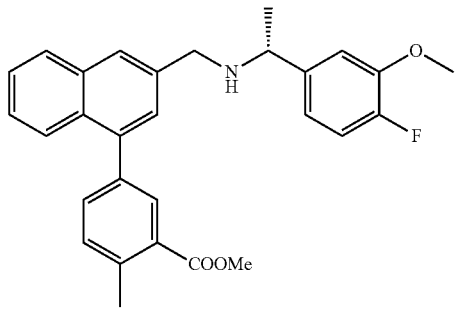 [SMILES: COC(=O)c1cc(-c2cc(CN[C@H](C)c3ccc(F)c(OC)c3)cc3ccccc23)ccc1C]<br>(R)-Methyl 5-(3-(((1-(4-fluoro-3-methoxyphenyl)eth-yl)amino)methyl)naphthalen-1-yl)-2-methylbenzoate | (R)-1-(4-Fluoro-3-methoxy-phenyl)ethanamine | 26 | 458.1 |
| 29 | 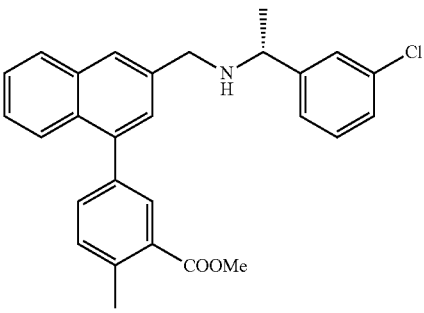 [SMILES: COC(=O)c1cc(-c2cc(CN[C@H](C)c3cccc(Cl)c3)cc3ccccc23)ccc1C]<br>(R)-methyl 5-(3-(((1-(3-chlorophenyl)eth-yl)amino)methyl)naphthalen-1-yl)-2-methylbenzoate | (R)-1-(3-Chloro-phenyl)ethanamine | 26 | 443.96 |
| 30 | 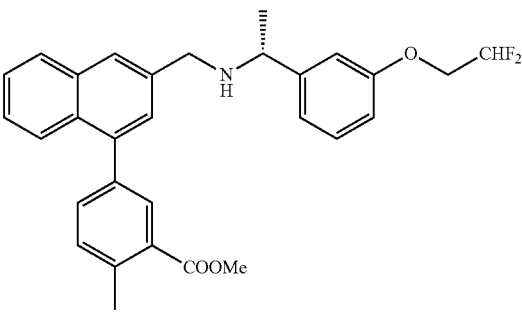 [SMILES: COC(=O)c1cc(-c2cc(CN[C@H](C)c3cccc(OCC(F)F)c3)cc3ccccc23)ccc1C]<br>(R)-Methyl 5-(3-(((1-(3-(2,2-difluoroethoxy)phenyl)eth-yl)amino)methyl)naphthalen-1-yl)-2-methylbenzoate | (R)-1-(3-(2,2-Difluoro-ethoxy)phen-yl)ethanamine | 26 | 490.17 |

TABLE 5-continued

| Ex. No | Structure/Name | Amine | Intermediate used | Mass (m/z) (ES+) |
|---|---|---|---|---|
| 31 | 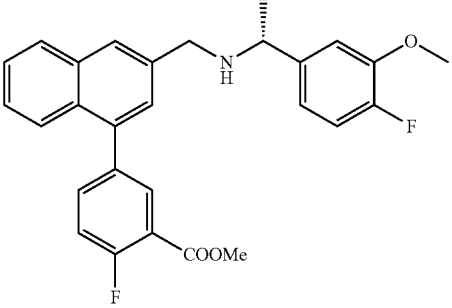<br>(R)-Methyl 2-fluoro-5-(3-(((1-(4-fluoro-3-methoxy-phenyl)ethyl)amino)methyl)naphthalen-1-yl)benzoate | (R)-1-(4-Fluoro-3-methoxy-phenyl)ethanamine | 27 | 462.1 |
| 32 | 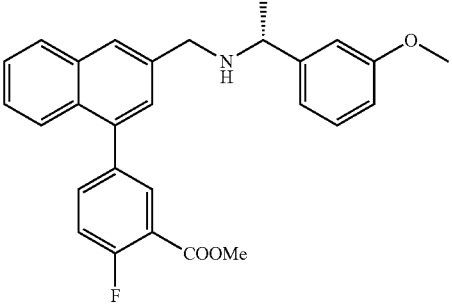<br>(R)-Methyl 2-fluoro-5-(3-(((1-(3-methoxyphenyl)eth-yl)amino)methyl)naphthalen-1-yl)benzoate | (R)-1-(3-Methoxy-phenyl)ethanamine | 27 | 444.1 |
| 33 | 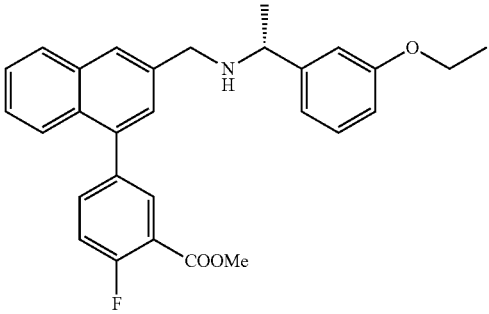 [SMILES: CCOc1cccc([C@@H](C)NCc2cc(-c3ccc(F)c(C(=O)OC)c3)c3ccccc3c2)c1]<br>(R)-Methyl 5-(3-(((1-(3-ethoxyphenyl)eth-yl)amino)methyl)naphthalen-1-yl)-2-fluorobenzoate | (R)-1-(3-Ethoxy-phenyl)ethanamine | 27 | 458.04 |
| 34 | 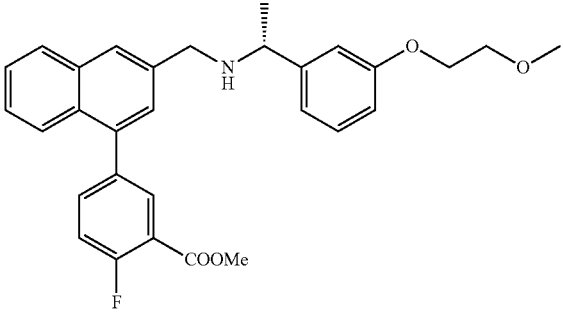 [SMILES: COCCOc1cccc([C@@H](C)NCc2cc(-c3ccc(F)c(C(=O)OC)c3)c3ccccc3c2)c1]<br>(R)-Methyl 2-fluoro-5-(3-(((1-(3-(2-methoxyethoxy)phenyl)eth-yl)amino)methyl)naphthalen-1-yl)benzoate | (R)-1-(3-(2-Methoxyeth-oxy)phenyl)ethana-mine | 27 | 488.11 |

TABLE 5-continued

| Ex. No | Structure/Name | Amine | Intermediate used | Mass (m/z) (ES+) |
|---|---|---|---|---|
| 35 | 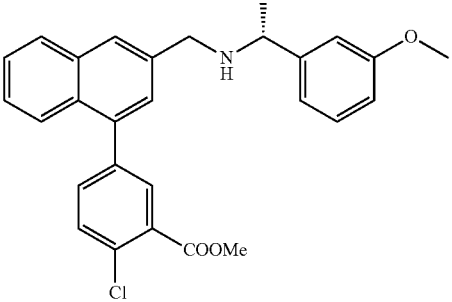<br>(R)-Methyl 2-chloro-5-(3-(((1-(3-methoxyphenyl)eth-yl)amino)methyl)naphthalen-1-yl)benzoate | (R)-1-(3-Methoxy-phenyl)ethanamine | 28 | 460.1 |
| 36 | 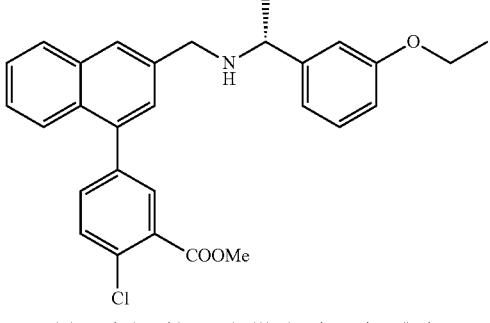<br>(R)-Methyl 2-chloro-5-(3-(((1-(3-ethoxyphenyl)eth-yl)amino)methyl)naphthalen-1-yl)benzoate | (R)-1-(3-Ethoxy-phenyl)ethanamine | 28 | 474.07 |
| 37 | 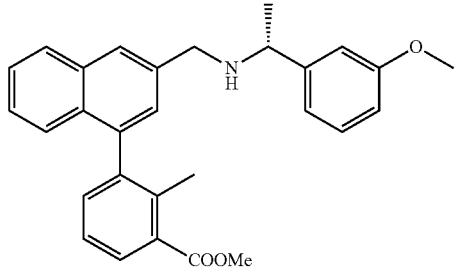 [SMILES: COC(=O)c1cccc(-c2cc(CN[C@H](C)c3cccc(OC)c3)cc3ccccc23)c1F]<br>(R)-Methyl 3-(3-(((1-(3-methoxyphenyl)eth-yl)amino)methyl)naphthalen-1-yl)-2-methylbenzoate | (R)-1-(3-Methoxy-phenyl)ethanamine | 33 | 440.11 |
| 38 | 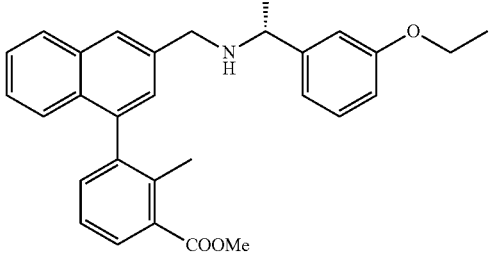<br>(R)-Methyl 3-(3-(((1-(3-ethoxyphenyl)ethyl)amino)meth-yl)naphthalen-1-yl)-2-methylbenzoate | (R)-1-(3-Ethoxy-phenyl)ethanamine | 33 | 454.04 |

TABLE 5-continued

| Ex. No | Structure/Name | Amine | Intermediate used | Mass (m/z) (ES+) |
|---|---|---|---|---|
| 39 | (R)-Methyl 2-fluoro-3-(3-(((1-(3-methoxyphenyl)ethyl)amino)methyl)naphthalen-1-yl)benzoate | (R)-1-(3-Methoxyphenyl)ethanamine | 32 | 444.17 |
| 40 | (R)-Methyl 2-methoxy-5-(3-(((1-(3-methoxyphenyl)ethyl)amino)methyl)naphthalen-1-yl)benzoate | (R)-1-(3-Methoxyphenyl)ethanamine | 29 | 456.04 |
| 41 | (R)-Methyl 2-isopropyl-5-(3-(((1-(3-methoxyphenyl)ethyl)amino)methyl)naphthalen-1-yl)benzoate | (R)-1-(3-Methoxyphenyl)ethanamine | 30 | 468.1 |
| 42 | (R)-Ethyl 4-(3-(((1-(naphthalen-1-yl)ethyl)amino)methyl)naphthalen-1-yl)benzoate | (R)-1-(Naphthalen-1-yl)ethanamine | 34 | 460.1 |

TABLE 5-continued

| Ex. No | Structure/Name | Amine | Intermediate used | Mass (m/z) (ES+) |
|---|---|---|---|---|
| 43 | 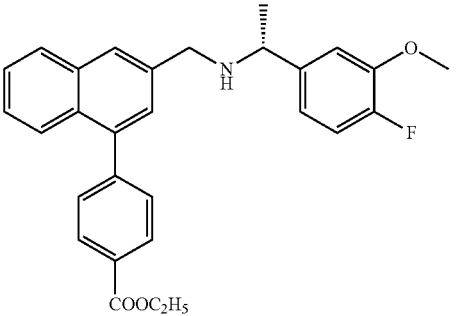<br>(R)-Ethyl 4-(3-(((1-(4-fluoro-3-methoxy-phenyl)ethyl)amino)methyl)naphthalen-1-yl)benzoate | (R)-1-(3-Fluoro-4-methoxy-phenyl)ethanamine | 34 | 458.0 |
| 44 | 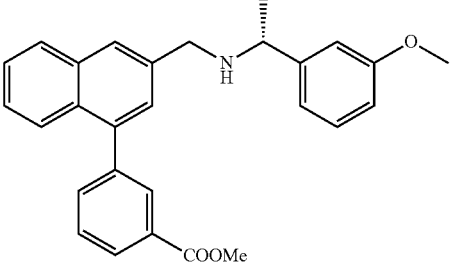<br>(R)-Methyl 3-(3-(((1-(3-methoxyphenyl)eth-yl)amino)methyl)naphthalen-1-yl)benzoate | (R)-1-(3-Methoxy-phenyl)ethanamine | 31 | 426.10 |
| 45 | 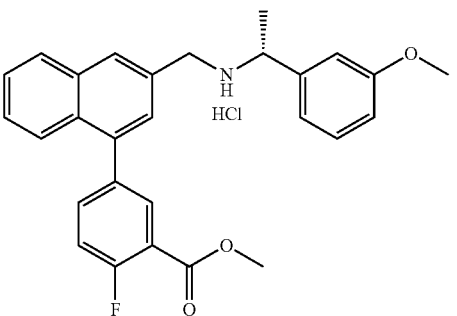 [SMILES: COC(=O)c1cc(-c2cc(CN[C@H](C)c3cccc(OC)c3)cc3ccccc23)ccc1F ; Cl]<br>(R)-methyl 2-fluoro-5-(3-(((1-(3-methoxyphenyl)eth-yl)amino)methyl)naphthalen-1-yl)benzoate hydrochloride | (R)-1-(3-Methoxy-phenyl)ethanamine | 27 | 444.11 |
| 46 | 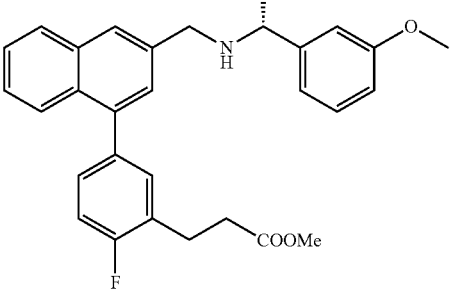<br>(R)-Methyl 3-(2-fluoro-5-(3-(((1-(3-methoxyphenyl)eth-yl)amino)methyl)naphthalen-1-yl)phenyl)propanoate | (R)-1-(3-Methoxy-phenyl)ethanamine | 37 | 471.96 |

TABLE 5-continued

| Ex. No | Structure/Name | Amine | Intermediate used | Mass (m/z) (ES+) |
|---|---|---|---|---|
| 47 | 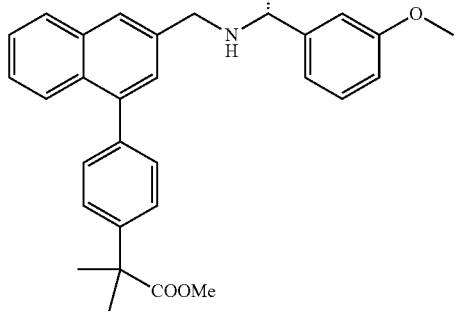<br>(R)-Methyl 2-(4-(3-(((1-(3-methoxyphenyl)eth-yl)amino)methyl)naphthalen-1-yl)phenyl)-2-methylpropanoate | (R)-1-(3-Methoxy-phenyl)ethanamine | 35 | 468.11 |
| 48 | 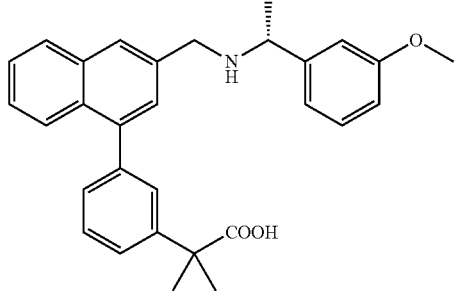<br>(R)-2-(3-(3-(((1-(3-Methoxyphenyl)ethyl)amino)meth-yl)naphthalen-1-yl)phenyl)-2-methylpropanoic acid | (R)-1-(3-Methoxy-phenyl)ethanamine | 36 | 468.11 |

Example-49a, 49b

Isopropyl-5-(3-(1-(((R)-1-(3-methoxyphenyl)ethyl)amino)ethyl)naphthalen-1-yl)-2-methyl benzoate

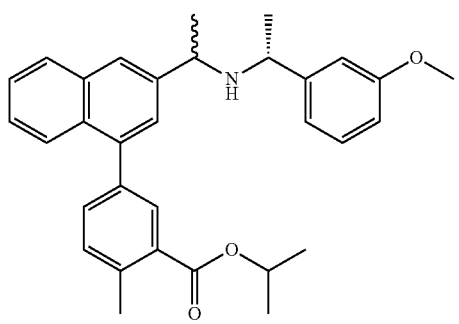 [SMILES: COc1cccc([C@@H](C)NC(C)c2cc(-c3ccc(C)c(C(=O)OC(C)C)c3)c3ccccc3c2)c1]

Intermediate-39 (0.05 g, 0.157 mmol) was added to a solution of (R)-1-(3-methoxyphenyl)ethanamine (0.052 g, 0.346 mmol) in titanium(IV) isopropoxide (0.552 ml, 1.885 mmol) at 25° C. and resulting suspension was stirred at 90° C. for 16 hrs. TLC showed completion of reaction. Reaction mixture was diluted with Methanol (3 ml) and cooled to −78° C. Sodium borohydride (0.089 g, 2.356 mmol) was added lot wise and the reaction mixture was allowed to warm to 0° C. gradually. TLC showed completion of reaction. Methanol (2 ml) and water (5 ml) were added and precipitated inorganic solid was filtered through celite. This filtrate was extracted with ethyl acetate (5 ml). Organic layer was washed with brine (5 ml), filtered and concentrated in vacuo to get crude compound. This residue was purified by column chromatography over silica gel (100-200 mesh) with an isocratic elution of 10% ethyl acetate in petroleum ether to get the title compound (0.028 g, 0.062 mmol, 39.3% yield) as a pale yellow liquid.

The mixture of two diastereomers were separated by reverse phase preparative chromatography (Column: YMC-Triart C18, 50×2.0 mm, 1.9 μm, Mobile phase: A: WATER: $CH_3CN$ (90:10) V/V %+0.1% $NH_4OH$; B: $CH_3CN$:WATER: (90:10) V/V %+0.1% $NH_4OH$; Inj vol: 0.2 ml) with RT=2.52 min (minor: Example-49a) and RT=2.58 min (major: Example-49b).

Example-49 a (Minor): MS (ES+)=m/z: 482.1 (M+1)

Example-49b (Major): $^1$H NMR (400 MHz, DMSO-$d_6$): δ 7.94 (d, J=8.1 Hz, 1H), 7.86 (d, J=2.0 Hz, 1H), 7.74 (d, J=8.2 Hz, 1H), 7.68 (s, 1H), 7.61 (dd, J=7.8, 2.0 Hz, 1H), 7.55-7.43 (m, 4H), 7.21 (d, J=8.4 Hz, 1H), 6.83-6.78 (m, 3H), 5.18-5.11 (m, 1H), 3.72 (s, 3H), 3.60-3.58 (m, 1H), 3.41-3.39 (m, 1H), 2.61 (s, 3H), 1.33-1.16 (m, 12H); MS (ES+)=m/z: 482.1 (M+1)

The isopropyl ester formation of corresponding methyl ester can be explained on the basis of transesterification of methyl ester with titanium tetraisopropoxide.

The Example-50 to 88 given in Table-6 were prepared by following the similar procedure as described in Example-49 by taking appropriate ketone Intermediate and appropriate amine Intermediate.

TABLE 6

| Ex. No. | Structure/Name | Amine | Intermediate used | Mass (m/z) (ES+) |
|---|---|---|---|---|
| 50 | 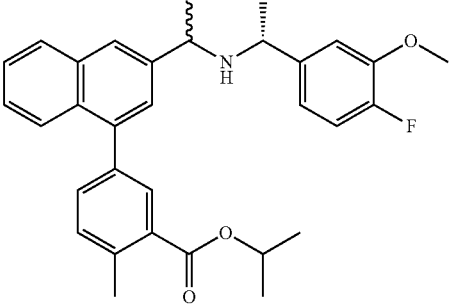<br>Isopropyl 5-(3-(1-(((R)-1-(4-fluoro-3-methoxyphenyl)ethyl)amino)ethyl)naphthalen-1-yl)-2-methylbenzoate | (R)-1-(3-Fluoro-4-methoxy-phenyl)ethanamine | 39 | 500.12 |
| 51 | 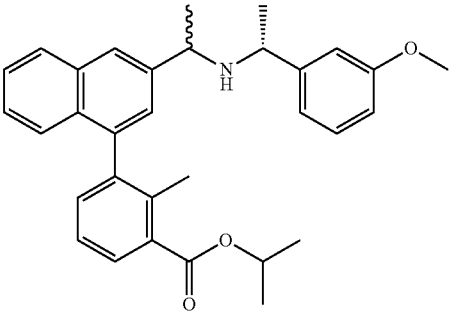 [SMILES: COc1cccc([C@@H](C)NC(C)c2cc(-c3cccc(C(=O)OC(C)C)c3C)c3ccccc3c2)c1]<br>Isopropyl 3-(3-(1-(((R)-1-(3-methoxyphenyl)eth-yl)amino)ethyl)naphthalen-1-yl)-2-methylbenzoate | (R)-1-(3-Methoxy-phenyl)ethanamine | 43 | 482.0 |
| 52 | 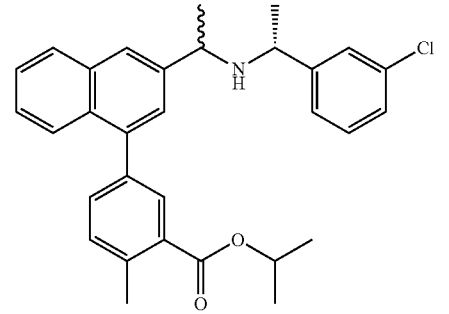<br>Isopropyl 5-(3-(1-(((R)-1-(3-chlorophenyl)eth-yl)amino)ethyl)naphthalen-1-yl)-2-methylbenzoate | (R)-1-(3-Chloro-phenyl)ethanamine | 39 | 487.04 |
| 53 | 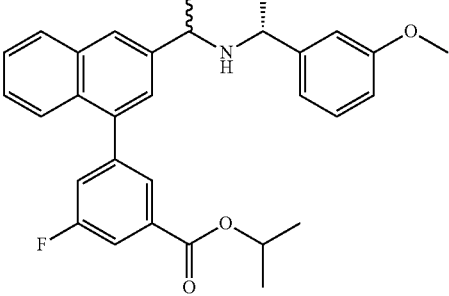<br>Isopropyl 3-fluoro-5-(3-(1-(((R)-1-(3-methoxyphenyl)eth-yl)amino)ethyl)naphthalen-1-yl)benzoate | (R)-1-(3-Methoxy-phenyl)ethanamine | 46 | 486.15 |

TABLE 6-continued

| Ex. No. | Structure/Name | Amine | Intermediate used | Mass (m/z) (ES+) |
|---|---|---|---|---|
| 54 | 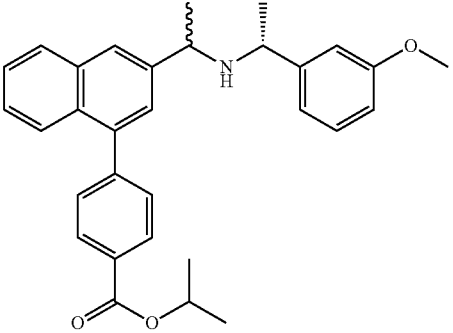 [SMILES: COc1cccc([C@@H](C)NC(C)c2cc(-c3ccc(C(=O)OC(C)C)cc3)c3ccccc3c2)c1]<br>Isopropyl 4-(3-(1-(((R)-1-(3-methoxyphenyl)eth-yl)amino)ethyl)naphthalen-1-yl)benzoate | (R)-1-(3-Methoxy-phenyl)ethanamine | 55 | 468.17 |
| 55 | 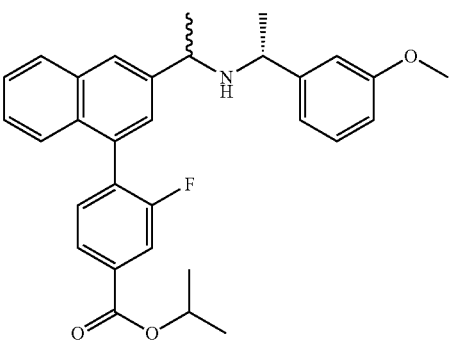 [SMILES: COc1cccc([C@@H](C)NC(C)c2cc(-c3ccc(C(=O)OC(C)C)cc3F)c3ccccc3c2)c1]<br>Isopropyl 3-fluoro-4-(3-(1-(((R)-1-(3-methoxyphenyl)eth-yl)amino)ethyl)naphthalen-1-yl)benzoate | (R)-1-(3-Methoxy-phenyl)ethanamine | 60 | 486.17 |
| 56 | 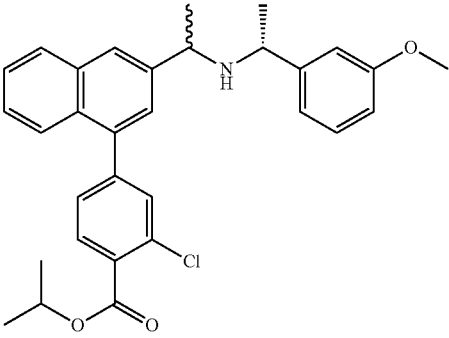<br>Isopropyl 2-chloro-4-(3-(1-(((R)-1-(3-methoxyphenyl)eth-yl)amino)ethyl)naphthalen-1-yl)benzoate | (R)-1-(3-Methoxy-phenyl)ethanamine | 58 | 503.18 |
| 57 | 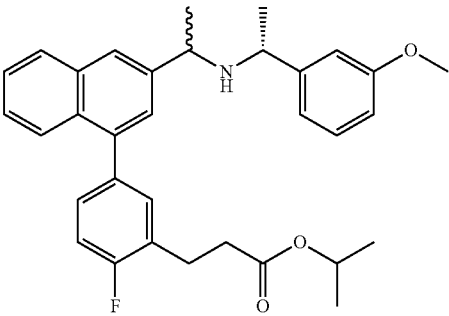<br>Isopropyl 3-(2-fluoro-5-(3-(1-(((R)-1-(3-methoxyphenyl)eth-yl)amino)ethyl)naphthalen-1-yl)phenyl)propanoate | (R)-1-(3-Methoxy-phenyl)ethanamine | 49 | 514.28 |

TABLE 6-continued

| Ex. No. | Structure/Name | Amine | Intermediate used | Mass (m/z) (ES+) |
|---|---|---|---|---|
| 58 | 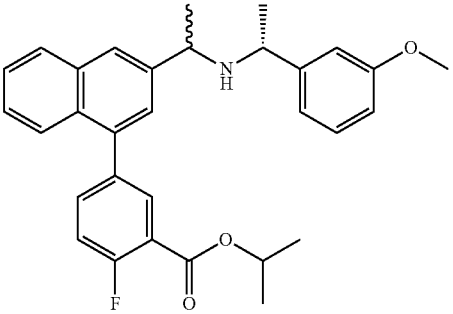<br>Isopropyl 2-fluoro-5-(3-(1-(((R)-1-(3-methoxyphenyl)eth-yl)amino)ethyl)naphthalen-1-yl)benzoate | (R)-1-(3-Methoxy-phenyl)ethanamine | 40 | 486.62 |
| 59 | 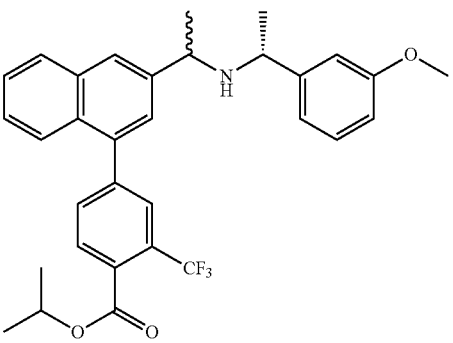<br>Isopropyl 4-(3-(1-(((R)-1-(3-methoxyphenyl)eth-yl)amino)ethyl)naphthalen-1-yl)-2-(trifluoromethyl)benzoate | (R)-1-(3-Methoxy-phenyl)ethanamine | 59 | 536.12 |
| 60 | 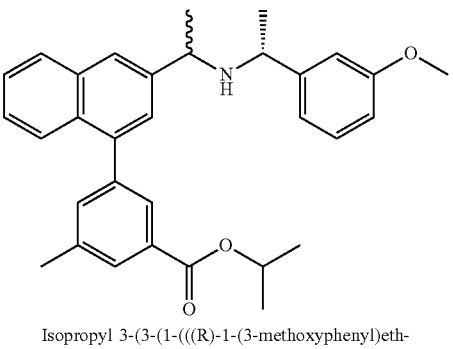<br>Isopropyl 3-(3-(1-(((R)-1-(3-methoxyphenyl)eth-yl)amino)ethyl)naphthalen-1-yl)-5-methylbenzoate | (R)-1-(3-Methoxy-phenyl)ethanamine | 44 | 482.62 |
| 61 | 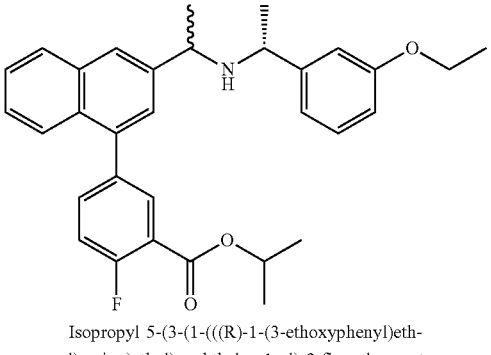<br>Isopropyl 5-(3-(1-(((R)-1-(3-ethoxyphenyl)eth-yl)amino)ethyl)naphthalen-1-yl)-2-fluorobenzoate | (R)-1-(3-Ethoxy-phenyl)ethanamine | 40 | 500.29 |

TABLE 6-continued

| Ex. No. | Structure/Name | Amine | Intermediate used | Mass (m/z) (ES+) |
|---|---|---|---|---|
| 62 | 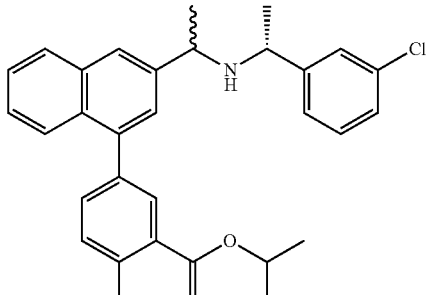Isopropyl 5-(3-(1-(((R)-1-(3-chlorophenyl)eth-yl)amino)ethyl)naphthalen-1-yl)-2-fluorobenzoate | (R)-1-(3-Chloro-phenyl)ethanamine | 40 | 491.25 |
| 63 | 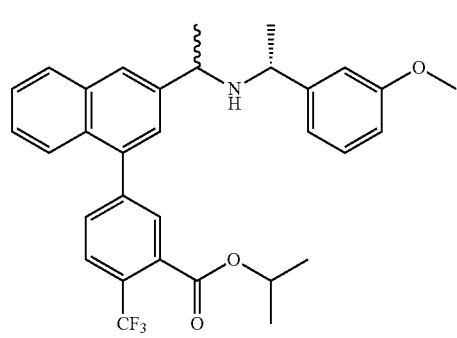 [SMILES: COc1cccc([C@@H](C)NC(C)c2cc(-c3ccc(C(F)(F)F)c(C(=O)OC(C)C)c3)c3ccccc3c2)c1]Isopropyl 5-(3-(1-(((R)-1-(3-methoxyphenyl)eth-yl)amino)ethyl)naphthalen-1-yl)-2-(trifluoromethyl)benzoate | (R)-1-(3-Methoxy-phenyl)ethanamine | 42 | 536.8 |
| 64 | 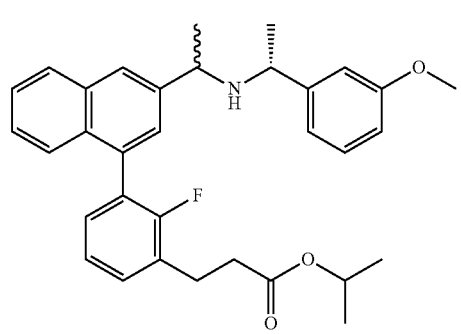 [SMILES: COc1cccc([C@@H](C)NC(C)c2cc(-c3cccc(CCC(=O)OC(C)C)c3F)c3ccccc3c2)c1]Isopropyl 3-(2-fluoro-3-(3-(1-(((R)-1-(3-methoxyphenyl)eth-yl)amino)ethyl)naphthalen-1-yl)phenyl)propanoate | (R)-1-(3-Methoxy-phenyl)ethanamine | 52 | 514.64 |
| 65 | 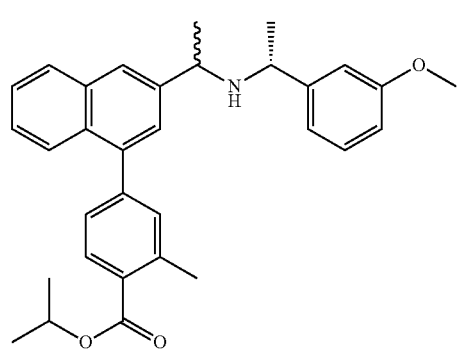 [SMILES: COc1cccc([C@@H](C)NC(C)c2cc(-c3ccc(C(=O)OC(C)C)c(C)c3)c3ccccc3c2)c1]Isopropyl 4-(3-(1-(((R)-1-(3-methoxyphenyl)eth-yl)amino)ethyl)naphthalen-1-yl)-2-methylbenzoate | (R)-1-(3-Methoxy-phenyl)ethanamine | 56 | 482.83 |

TABLE 6-continued

| Ex. No. | Structure/Name | Amine | Intermediate used | Mass (m/z) (ES+) |
|---|---|---|---|---|
| 66 | 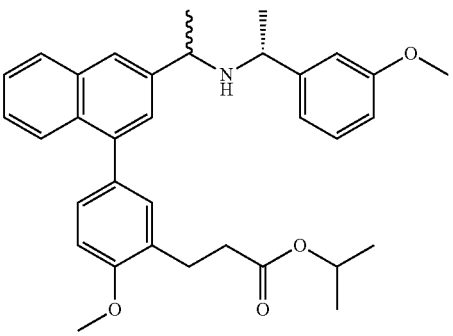 [SMILES: COc1cccc([C@@H](C)NC(C)c2cc(-c3ccc(OC)c(CCC(=O)OC(C)C)c3)c3ccccc3c2)c1]<br>Isopropyl 3-(2-methoxy-5-(3-(1-(((R)-1-(3-methoxyphenyl)ethyl)amino)ethyl)naphthalen-1-yl)phenyl)propanoate | (R)-1-(3-Methoxyphenyl)ethanamine | 51 | 526.18 |
| 67 | 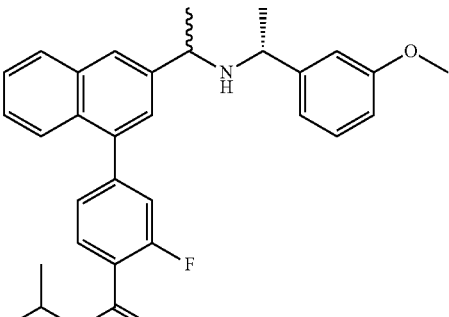<br>Isopropyl 2-fluoro-4-(3-(1-(((R)-1-(3-methoxyphenyl)ethyl)amino)ethyl)naphthalen-1-yl)benzoate | (R)-1-(3-Methoxyphenyl)ethanamine | 57 | 486.05 |
| 68 | 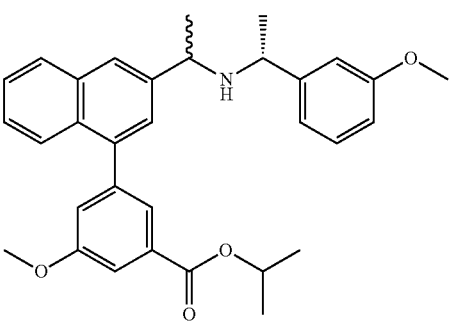 [SMILES: COc1cc(C(=O)OC(C)C)cc(-c2cc(C(C)N[C@H](C)c3cccc(OC)c3)cc3ccccc23)c1]<br>Isopropyl 3-methoxy-5-(3-(1-(((R)-1-(3-methoxyphenyl)ethyl)amino)ethyl)naphthalen-1-yl)benzoate | (R)-1-(3-Methoxyphenyl)ethanamine | 45 | 404.23 |
| 69 | 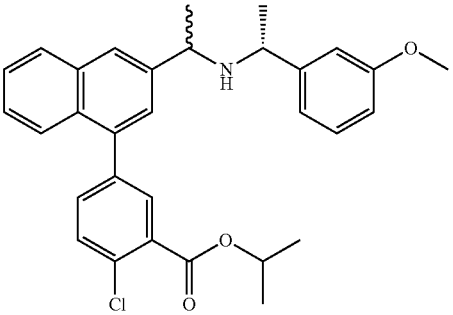 [SMILES: COc1cccc([C@@H](C)NC(C)c2cc(-c3ccc(Cl)c(C(=O)OC(C)C)c3)c3ccccc3c2)c1]<br>Isopropyl 2-chloro-5-(3-(1-(((R)-1-(3-methoxyphenyl)ethyl)amino)ethyl)naphthalen-1-yl)benzoate | (R)-1-(3-Methoxyphenyl)ethanamine | 41 | 503.04 |

TABLE 6-continued

| Ex. No. | Structure/Name | Amine | Intermediate used | Mass (m/z) (ES+) |
|---|---|---|---|---|
| 70 | 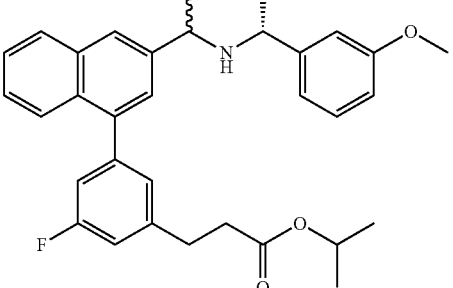
Isopropyl 3-(3-fluoro-5-(3-(1-(((R)-1-(3-methoxyphenyl)eth-yl)amino)ethyl)naphthalen-1-yl)phenyl)propanoate | (R)-1-(3-Methoxy-phenyl)ethanamine | 53 | 513.94 |
| 71 | 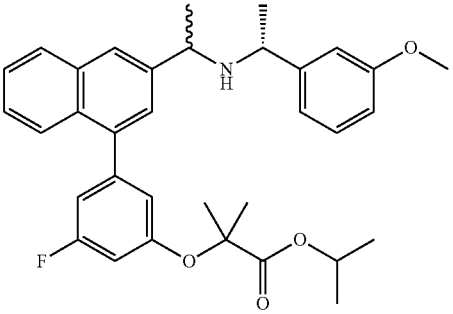 [SMILES: COc1cccc([C@@H](C)NC(C)c2cc(-c3cc(F)cc(OC(C)(C)C(=O)OC(C)C)c3)c3ccccc3c2)c1]
Isopropyl 2-(3-fluoro-5-(3-(1-(((R)-1-(3-methoxyphenyl)eth-yl)amino)ethyl)naphthalen-1-yl)phenoxy)-2-methylpropanoate | (R)-1-(3-Methoxy-phenyl)ethanamine | 54 | 544.34 |
| 72 | 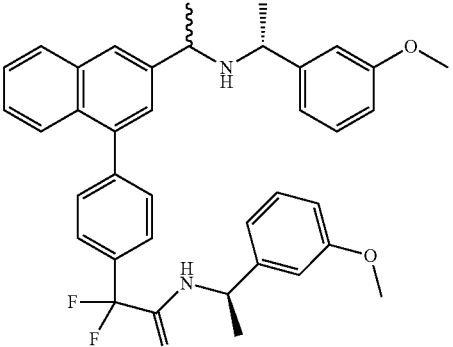
2,2-Difluoro-N-((R)-1-(3-methoxyphenyl)ethyl)-2-(4-(3-(1-(((R)-1-(3-methoxyphenyl)ethyl)amino)ethyl)naphthalen-1-yl)phenyl)acetamide | (R)-1-(3-Methoxy-phenyl)ethanamine | 62 | 609.18 |
| 73 | 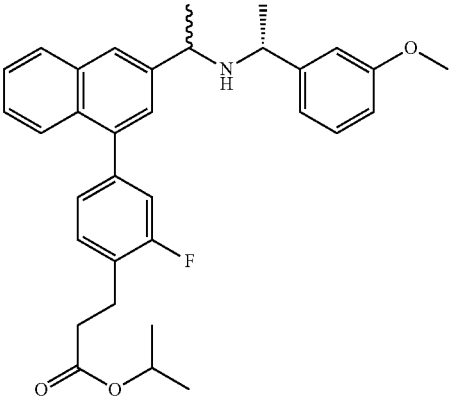 [SMILES: COc1cccc([C@@H](C)NC(C)c2cc(-c3ccc(CCC(=O)OC(C)C)c(F)c3)c3ccccc3c2)c1]
Isopropyl 3-(2-fluoro-4-(3-(1-(((R)-1-(3-methoxyphenyl)eth-yl)amino)ethyl)naphthalen-1-yl)phenyl)propanoate | (R)-1-(3-Methoxy-phenyl)ethanamine | 63 | 514.22 |

TABLE 6-continued

| Ex. No. | Structure/Name | Amine | Intermediate used | Mass (m/z) (ES+) |
|---|---|---|---|---|
| 74 | 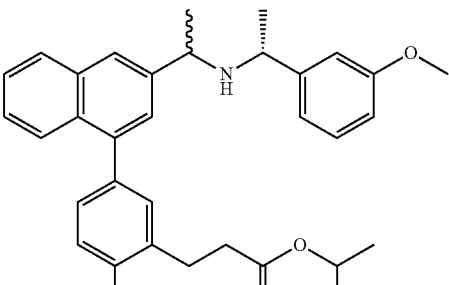<br>Isopropyl 3-(5-(3-(1-(((R)-1-(3-methoxyphenyl)eth-yl)amino)ethyl)naphthalen-1-yl)-2-methylphenyl)propanoate | (R)-1-(3-Methoxy-phenyl)ethanamine | 48 | 510.28 |
| 75 | 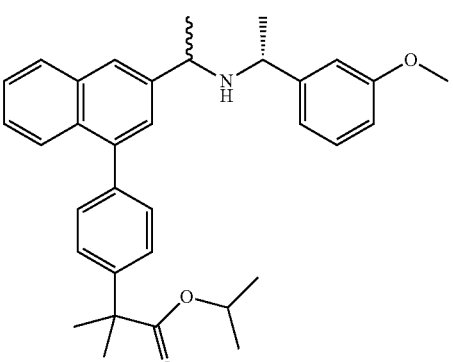<br>Isopropyl 2-(4-(3-(1-(((R)-1-(3-methoxyphenyl)eth-yl)amino)ethyl)naphthalen-1-yl)phenyl)-2-methylpropanoate | (R)-1-(3-Methoxy-phenyl)ethanamine | 61 | 510.06 |
| 76 | 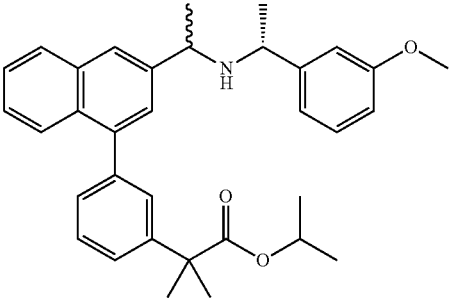 [SMILES: COc1cccc([C@@H](C)NC(C)c2cc(-c3cccc(C(C)(C)C(=O)OC(C)C)c3)c3ccccc3c2)c1]<br>Isopropyl 2-(3-(3-(1-(((R)-1-(3-methoxyphenyl)eth-yl)amino)ethyl)naphthalen-1-yl)phenyl)-2-methylpropanoate | (R)-1-(3-Methoxy-phenyl)ethanamine | 47 | 510.08 |
| 77 | 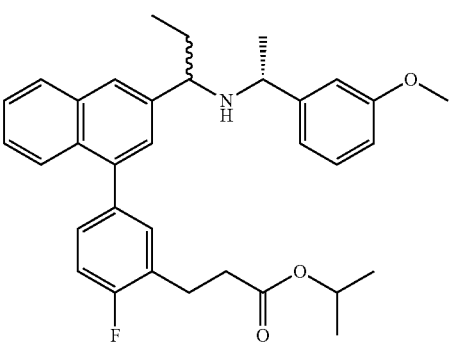 [SMILES: CCC(N[C@H](C)c1cccc(OC)c1)c1cc(-c2ccc(F)c(CCC(=O)OC(C)C)c2)c2ccccc2c1]<br>Isopropyl 3-(2-fluoro-5-(3-(1-(((R)-1-(3-methoxyphenyl)eth-yl)amino)propyl)naphthalen-1-yl)phenyl)propanoate | (R)-1-(3-Methoxy-phenyl)ethanamine | 65 | 528.07 |

TABLE 6-continued

| Ex. No. | Structure/Name | Amine | Intermediate used | Mass (m/z) (ES+) |
|---|---|---|---|---|
| 78 | 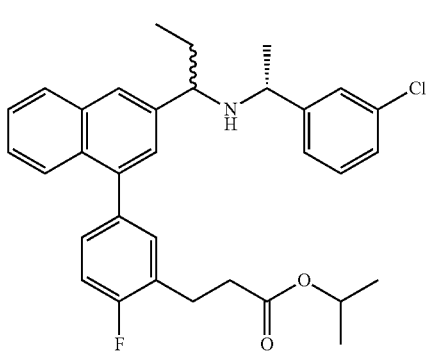 [SMILES: CCC(N[C@H](C)c1cccc(Cl)c1)c1cc(-c2ccc(F)c(CCC(=O)OC(C)C)c2)c2ccccc2c1] Isopropyl 3-(5-(3-(1-(((R)-1-(3-chlorophenyl)eth-yl)amino)propyl)naphthalen-1-yl)-2-fluorophenyl)propanoate | (R)-1-(3-Chloro-phenyl)ethanamine | 65 | 533.94 |
| 79 | 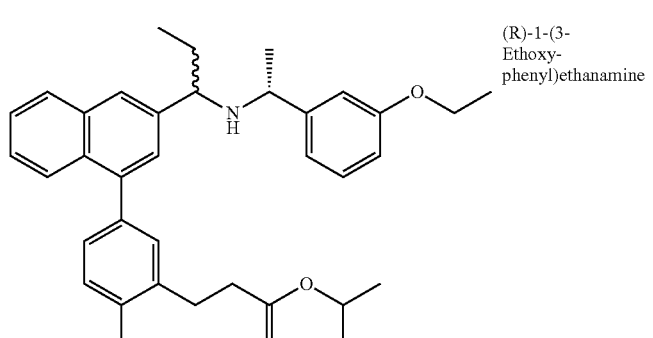 Isopropyl 3-(5-(3-(1-(((R)-1-(3-ethoxyphenyl)eth-yl)amino)propyl)naphthalen-1-yl)-2-fluoro-phenyl)propanoate | (R)-1-(3-Ethoxy-phenyl)ethanamine | 65 | 542.30 |
| 80 | 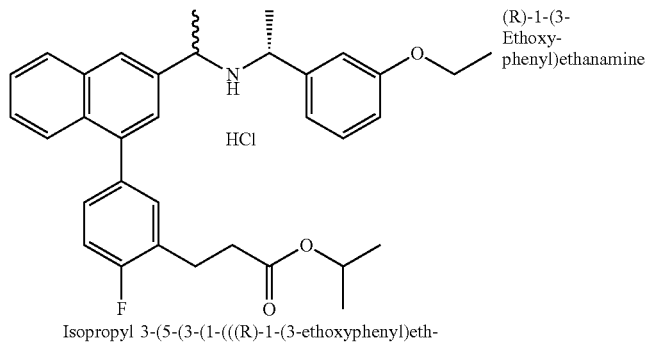 Isopropyl 3-(5-(3-(1-(((R)-1-(3-ethoxyphenyl)eth-yl)amino)ethyl)naphthalen-1-yl)-2-fluoro-phenyl)propanoate | (R)-1-(3-Ethoxy-phenyl)ethanamine | 49 | 528.15 |
| 81 | 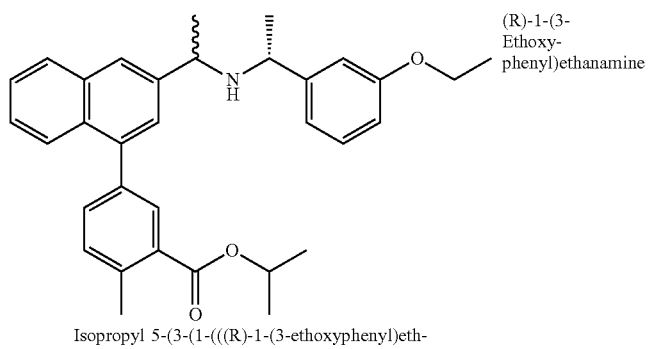 Isopropyl 5-(3-(1-(((R)-1-(3-ethoxyphenyl)eth-yl)amino)ethyl)naphthalen-1-yl)-2-methylbenzoate | (R)-1-(3-Ethoxy-phenyl)ethanamine | 39 | 496.28 |

TABLE 6-continued

| Ex. No. | Structure/Name | Amine | Intermediate used | Mass (m/z) (ES+) |
|---|---|---|---|---|
| 82 | 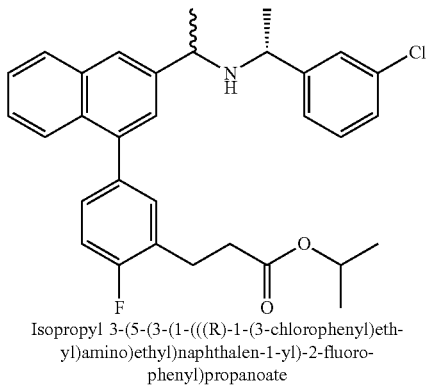<br>Isopropyl 3-(5-(3-(1-(((R)-1-(3-chlorophenyl)eth-yl)amino)ethyl)naphthalen-1-yl)-2-fluoro-phenyl)propanoate | (R)-1-(3-Chloro-phenyl)ethanamine | 49 | 519.06 |
| 83 | 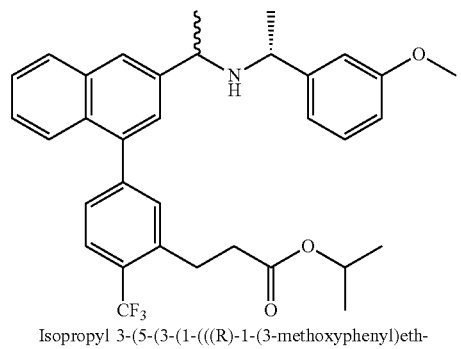<br>Isopropyl 3-(5-(3-(1-(((R)-1-(3-methoxyphenyl)eth-yl)amino)ethyl)naphthalen-1-yl)-2-(tri-fluoromethyl)phenyl)propanoate | (R)-1-(3-Methoxy-phenyl)ethanamine | 50 | 564.26 |
| 84 | 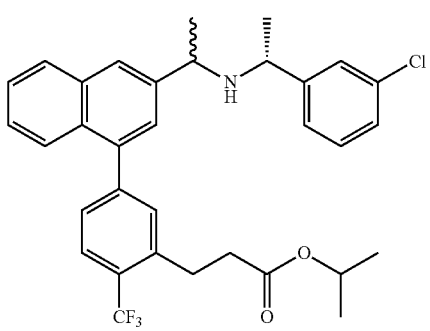 [SMILES: CC(C)OC(=O)CCc1cc(-c2cc(C(C)N[C@H](C)c3cccc(Cl)c3)cc3ccccc23)ccc1C(F)(F)F]<br>Isopropyl 3-(5-(3-(1-(((R)-1-(3-chlorophenyl)eth-yl)amino)ethyl)naphthalen-1-yl)-2-(trifluoro-methyl)phenyl)propanoate | (R)-1-(3-Chloro-phenyl)ethanamine | 50 | 554.1 |
| 85 | 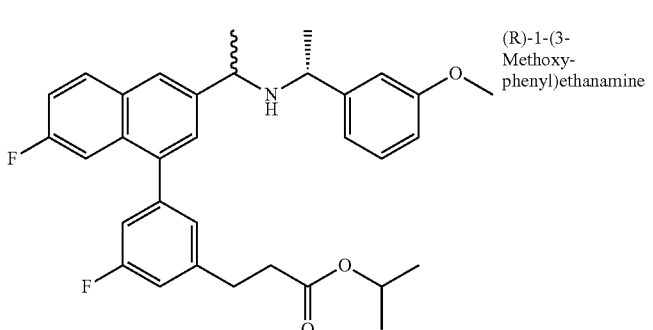<br>Isopropyl 3-(3-fluoro-5-(7-fluoro-3-(1-(((R)-1-(3-methoxy-phenyl)ethyl)amino)ethyl)naphthalen-1-yl)phenyl)propanoate | (R)-1-(3-Methoxy-phenyl)ethanamine | 64 | 532.0 |

TABLE 6-continued

| Ex. No. | Structure/Name | Amine | Intermediate used | Mass (m/z) (ES+) |
|---|---|---|---|---|
| 86 | 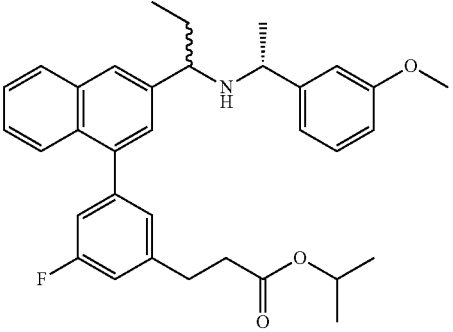 [SMILES: CCC(N[C@H](C)c1cccc(OC)c1)c1cc(-c2cc(F)cc(CCC(=O)OC(C)C)c2)c2ccccc2c1]<br>Isopropyl 3-(3-fluoro-5-(3-(1-(((R)-1-(3-methoxy-phenyl)ethyl)amino)propyl)naphthalen-1-yl)phenyl)propanoate | (R)-1-(3-Methoxy-phenyl)ethanamine | 66 | 528.3 |
| 87 | 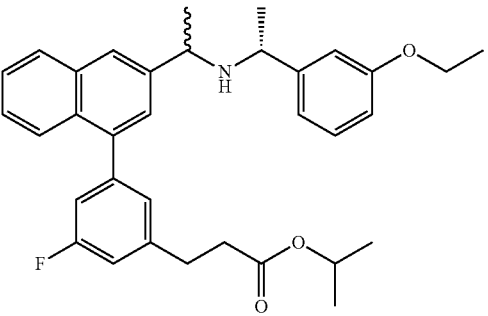 [SMILES: CCOc1cccc([C@@H](C)NC(C)c2cc(-c3cc(F)cc(CCC(=O)OC(C)C)c3)c3ccccc3c2)c1]<br>Isopropyl 3-(3-(3-(1-(((R)-1-(3-ethoxyphenyl)eth-yl)amino)ethyl)naphthalen-1-yl)-5-fluorophenyl)propanoate | (R)-1-(3-Ethoxy-phenyl)ethanamine | 53 | 527.94 |
| 88 | 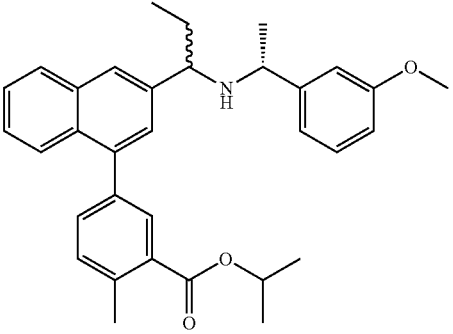 [SMILES: CCC(N[C@H](C)c1cccc(OC)c1)c1cc(-c2ccc(C)c(C(=O)OC(C)C)c2)c2ccccc2c1]<br>Isopropyl 5-(3-(1-(((R)-1-(3-methoxyphenyl)eth-yl)amino)propyl)naphthalen-1-yl)-2-methylbenzoate | (R)-1-(3-Methoxy-phenyl)ethanamine | 67 | 496.65 |

Example-89

(R)-2-Methyl-5-(3-(((1-(naphthalen-1-yl)ethyl)amino)methyl)naphthalen-1-yl) benzoic acid

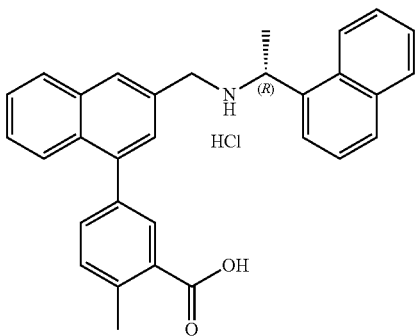

To a solution of Example-24 (130 mg, 0.283 mmol) in MeOH:THF:water (10 ml, 4:4:2) was added NaOH (56.6 mg, 1.414 mmol) at 25° C. The reaction mixture was then refluxed for 2 hrs at 80° C. TLC showed completion of reaction. After completion of reaction, the solvent was evaporated under reduced pressure. The reaction mixture was acidified with 1N HCl to pH 6 at 0° C. Precipitated solid was stirred for 10 minutes & filtered to get a pure title compound. This residue was washed with n-pentane and dried using a rotary evaporator (0 mbar, 50° C.). This carboxylic acid was dissolved in methylene chloride (3 ml) and 2M ethereal HCl (2 ml) was added at 0° C. The resulting suspension was stirred for 1 h at 0° C. and the solvent was evaporated in vacuo at 30° C. Resulting salt was triturated with n-pentane (2 ml×2) to give pure HCl salt of title compound (80 mg, 63.5%) as a white solid.

$^1$H NMR (400 MHz, DMSO-$d_6$) δ 13.02 (s 1H), 10.29 (s, 1H), 9.78 (s, 1H), 8.08-8.06 (m, 2H), 8.02-7.98 (m, 3H), 7.93-7.92 (m, 1H), 7.91 (d, J=1.6 Hz, 1H), 7.80 (d, J=8.4 Hz, 1H), 7.67-7.61 (m, 1H), 7.59-7.53 (m, 6H), 7.47 (d, J=8 Hz, 1H), 5.37-5.36 (m, 1H), 4.42-4.41 (m, 1H), 4.27-4.26 (m, 1H), 2.62 (s, 3H), 1.77 (d, J=6.8 Hz, 3H); MS (ES+) m/z=446

The below Examples-90 to 113 given in Table-7 were prepared by following the similar ester hydrolysis procedure as described in Example-89

TABLE 7

| Ex. No. | Structure/Name | Ester Example | $^1$H NMR/MS (ES+) |
|---|---|---|---|
| 90 | (R)-5-(3-(((1-(3-Methoxyphenyl)ethyl)amino)methyl)naphthalen-1-yl)-2-methylbenzoic acid hydrochloride | 25 | $^1$H NMR (400 MHz, DMSO-$d_6$) δ 13.02 (s, 1H), 10.08 (s, 1H), 9.74 (s, 1H), 8.05-7.98 (m, 2H), 7.94 (d, J = 2.0 Hz, 1H), 7.85-7.77 (m, 1H), 7.68-7.52 (m, 4H), 7.50 (d, J = 7.8 Hz, 1H), 7.38 (t, J = 7.9 Hz, 1H), 7.28 (t, J = 2.0 Hz, 1H), 7.20-7.14 (m, 1H), 6.98 (dd, J = 8.1, 2.5 Hz, 1H), 4.41 (q, J = 6.5 Hz, 1H), 4.29-4.17 (m, 1H), 4.09-3.93 (m, 1H), 3.77 (s, 3H), 2.63 (s, 3H), 1.65 (d, J = 6.7 Hz, 3H); m/z-426.1 |
| 91 | (R)-5-(3-(((1-(3-Ethoxyphenyl)ethyl)amino)ethyl)naphthalen-1-yl)-2-methylbenzoic acid hydrochloride | 26 | $^1$H NMR (400 MHz, DMSO-$d_6$) δ 13.03 (s, 1H), 10.04 (s, 1H), 9.71 (s, 1H), 8.08-7.91 (m, 3H), 7.87-7.73 (m, 1H), 7.65-7.45 (m, 5H), 7.36 (t, J = 7.9 Hz, 1H), 7.25 (t, J = 2.1 Hz, 1H), 7.17-7.09 (m, 1H), 6.95 (dd, J = 8.2, 2.5 Hz, 1H), 4.48-4.33 (m, 1H), 4.29-4.19 (m, 1H), 4.11-3.95 (m, 3H), 2.63 (s, 3H), 1.64 (d, J = 6.6 Hz, 3H), 1.32 (t, J = 6.9 Hz, 3H); m/z-440.1 |

TABLE 7-continued

| Ex. No. | Structure/Name | Ester Example | ¹H NMR/MS (ES+) |
|---|---|---|---|
| 92 | 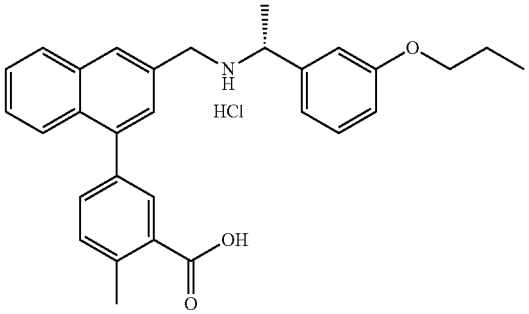 [SMILES: CCCOc1cccc([C@@H](C)NCc2cc(-c3ccc(C)c(C(=O)O)c3)c3ccccc3c2)c1 ; Cl]<br>(R)-2-Methyl-5-(3-(((1-(3-propoxyphenyl)ethyl)amino)methyl)naphthalen-1-yl)benzoic acid hydrochloride | 27 | ¹H NMR (400 MHz, DMSO-$d_6$) δ 13.03 (s, 1H), 9.98 (s, 1H), 9.64 (s, 1H), 8.04-7.97 (m, 2H), 7.94 (d, J = 1.9 Hz, 1H), 7.81 (d, J = 8.1 Hz, 1H), 7.65-7.53 (m, 4H), 7.50 (d, J = 7.8 Hz, 1H), 7.36 (t, J = 7.9 Hz, 1H), 7.25-7.20 (m, 1H), 7.14 (d, J = 7.5 Hz, 1H), 6.96 (dd, J = 8.1, 2.4 Hz, 1H), 4.48-4.34 (m, 1H), 4.34-4.20 (m, 1H), 4.10-3.98 (m, 1H), 3.92 (t, J = 6.5 Hz, 2H), 2.63 (s, 3H), 1.72 (h, J = 7.1 Hz, 2H), 1.63 (d, J = 6.7 Hz, 3H), 0.96 (t, J = 7.4 Hz, 3H); m/z-454.17 |
| 93 | 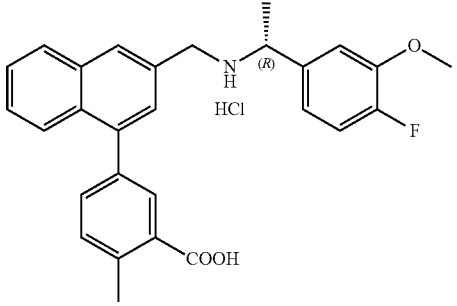<br>(R)-5-(3-(((1-(4-Fluoro-3-methoxyphenyl)ethyl)amino)methyl)naphthalen-1-yl)-2-methylbenzoic acid hydrochloride | 28 | ¹H NMR (400 MHz, DMSO-$d_6$) δ 13.02 (s, 1H), 9.97 (s, 1H), 9.77 (s, 1H), 8.03-7.99 (m, 2H), 7.94 (d, J = 2 Hz, 1H), 7.81 (d, J = 8 Hz, 1H), 7.62-7.55 (m, 5H), 7.49 (d, J = 8, 1H), 7.30-7.27 (m, 1H), 7.16-7.13 (m, 1H), 4.44-4.43 (m, 1H), 4.27-4.24 (m, 1H), 4.07-4.02 (m, 1H), 3.85 (s, 3H), 2.63 (s, 3H), 1.65 (d, J = 6.4 Hz, 3H); m/z-444.11 |
| 94 | 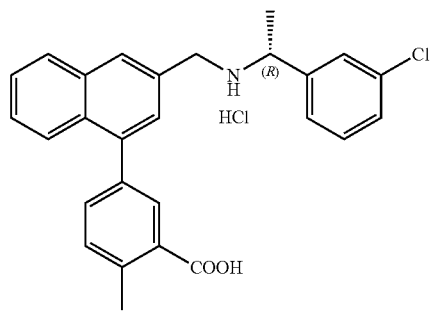<br>(R)-5-(3-(((1-(3-Chlorophenyl)ethyl)amino)methyl)naphthalen-1-yl)-2-methylbenzoic acid hydrochloride | 29 | ¹H NMR (400 MHz, DMSO-$d_6$) δ 13.02 (s, 1H), 10.08 (d, J = 12.4 Hz, 1H), 9.76 (s, 1H), 8.03-8.01 (m, 2H), 7.94 (d, J = 1.4 Hz, 1H), 7.81 (d, J = 8, 1H) 7.39 (s, 1H), 7.62-7.59 (m, 5H), 7.50-7.48 (m, 3H), 4.52-4.48 (m, 1H), 4.33-4.29 (m, 1H), 4.10-4.06 (m, 1H), 2.63 (s, 3H), 1.65 (d, J = 6.7 Hz, 3H); m/z-430.04 |

TABLE 7-continued

| Ex. No. | Structure/Name | Ester Example | ¹H NMR/MS (ES+) |
|---|---|---|---|
| 95 | 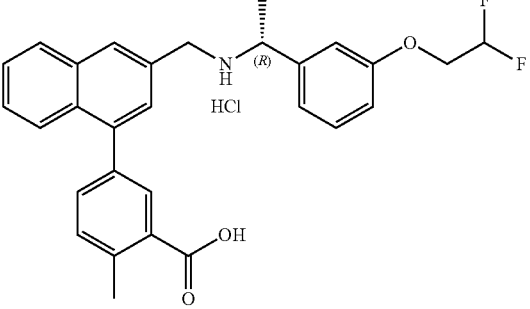<br>(R)-5-(3-(((1-(3-(2,2-Difluoroethoxy)phenyl)ethyl)amino)methyl)naphthalen-1-yl)-2-methylbenzoic acid hydrochloride | 30 | ¹H NMR (400 MHz, DMSO-$d_6$) δ 13.02 (s, 1H), 9.97 (s, 1H), 9.69 (s, 1H), 8.07-7.98 (m, 2H), 7.93 (d, J = 1.9 Hz, 1H), 7.80 (d, J = 8.1 Hz, 1H), 7.68-7.47 (m, 5H), 7.42 (t, J = 8.0 Hz, 1H), 7.30-7.24 (m, 1H), 7.19 (d, J = 7.5 Hz, 1H), 7.06 (dd, J = 8.3, 2.5 Hz, 1H), 6.38 (t, J = 3.4 Hz, 1H), 4.51-4.40 (m, 1H), 4.29-4.23 (m, 3H), 4.06 (d, J = 13.2 Hz, 1H), 2.62 (s, 3H), 1.63 (d, J = 6.7 Hz, 3H); m/z-476.0 |
| 96 | 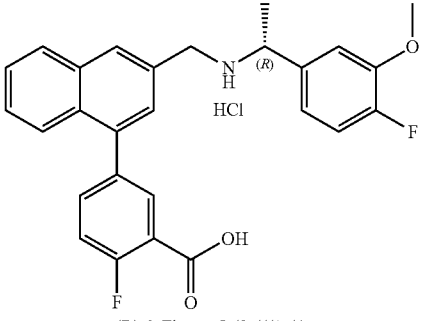<br>(R)-2-Fluoro-5-(3-(((1-(4-fluoro-3-methoxyphenyl)ethyl)amino)methyl)naphthalen-1-yl)benzoic acid hydrochloride | 31 | ¹H NMR (400 MHz, DMSO-$d_6$) δ 13.5 (s, 1H), 10.06 (s, 1H), 9.84 (s, 1H), 8.05 (s, 1H), 8.02-7.95 (m, 2H), 7.80-7.76 (m, 2H), 7.64-7.58 (m, 4H), 7.55 (d, J = 7.8 Hz, 1H), 7.28 (t, J = 7.9 Hz, 1H), 7.16-7.13 (m, 1H), 4.42 (d, J = 4.4 Hz, 1H), 4.29-4.20 (m, 1H), 4.09-3.93 (m, 1H), 3.85 (s, 3H), 1.64 (d, J = 6.7 Hz, 3H); m/z-448 |
| 97 | 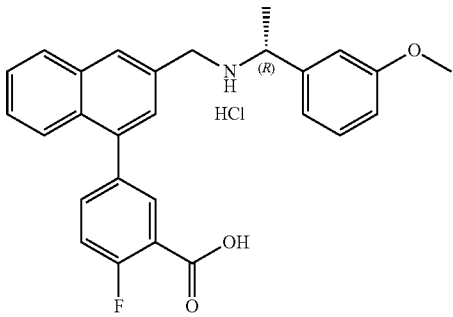<br>(R)-2-Fluoro-5-(3-(((1-(3-methoxyphenyl)ethyl)amino)methyl)naphthalen-1-yl)benzoic acid hydrochloride | 32 | ¹H NMR (400 MHz, DMSO-$d_6$) δ 13.47 (s, 1H), 10.08 (s, 1H), 9.75 (s, 1H), 8.05-8.00 (m, 2H), 7.94 (dd, J = 2.4 & 7.2 Hz, 1H), 7.79-7.77 (m, 2H), 7.63-7.57 (m, 3H), 7.54-7.49 (m, 1H), 7.37 (t, J = 8 Hz, 1H), 7.28 (s, 1H), 7.16 (d, J = 7.6 Hz, 1H), 6.97 (dd, J = 8.4, 2.4 Hz, 1H), 4.47-4.38 (m, 1H), 4.27-4.24 (m, 1H), 4.05-4.02 (m, 1H), 3.76 (s, 3H), 1.64 (d, J = 6.7 Hz, 3H); m/z-430.0 |

TABLE 7-continued

| Ex. No. | Structure/Name | Ester Example | $^1$H NMR/MS (ES+) |
|---|---|---|---|
| 98 | 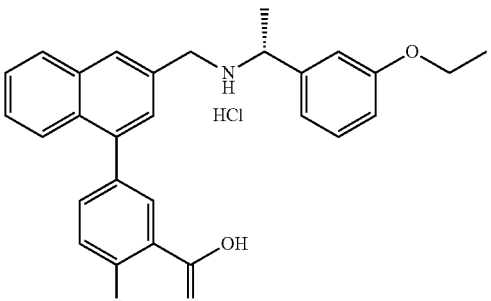<br>(R)-5-(3-(((1-(3-Ethoxyphenyl)ethyl)amino)ethyl)naphthalen-1-yl)-2-fluorobenzoic acid hydrochloride | 33 | $^1$H NMR (400 MHz, DMSO-d$_6$) δ 13.48 (s, 1H), 10.11 (s, 1H), 9.74 (s, 1H), 8.06-7.99 (m, 2H), 7.96 (dd, J = 7.1, 2.4 Hz, 1H), 7.78 (dq, J = 7.1, 2.8 Hz, 2H), 7.67-7.48 (m, 4H), 7.36 (t, J = 7.9 Hz, 1H), 7.28-7.22 (m, 1H), 7.15 (d, J = 7.5 Hz, 1H), 6.95 (dd, J = 8.2, 2.4 Hz, 1H), 4.47-4.34 (m, 1H), 4.33-4.17 (m, 1H), 4.02 (q, J = 6.9 Hz, 3H), 1.64 (d, J = 6.6 Hz, 3H), 1.32 (t, J = 6.9 Hz, 3H); m/z-444.0 |
| 99 | 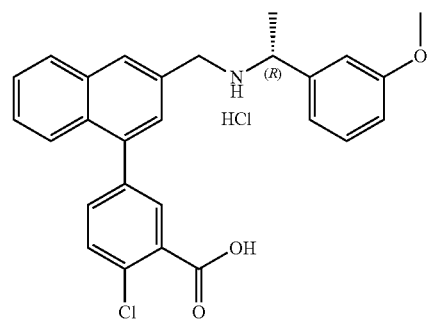<br>(R)-2-Chloro-5-(3-(((1-(3-methoxyphenyl)ethyl)amino)methyl)naphthalen-1-yl)benzoic acid hydrochloride | 35 | $^1$H NMR (400 MHz, DMSO-d$_6$) δ 13.61 (s, 1H), 10.13 (s, 1H), 9.78 (s, 1H), 8.09-7.98 (m, 2H), 7.89 (d, J = 2.2 Hz, 1H), 7.83-7.66 (m, 3H), 7.66-7.54 (m, 3H), 7.37 (t, J = 7.9 Hz, 1H), 7.29 (t, J = 2.1 Hz, 1H), 7.21-7.12 (m, 1H), 6.97 (dd, J = 8.2, 2.5 Hz, 1H), 4.47-4.31 (m, 1H), 4.33-4.17 (m, 1H), 4.09-3.93 (m, 1H), 3.77 (s, 3H), 1.65 (d, J = 6.7 Hz, 3H); m/z-446.04 |
| 100 | 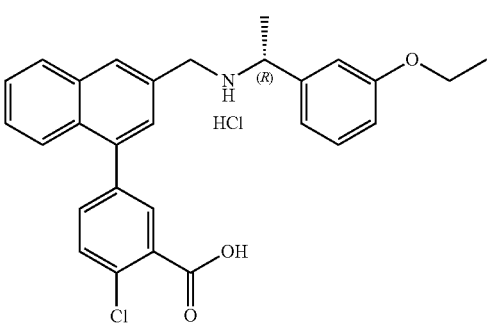<br>(R)-2-Chloro-5-(3-(((1-(3-ethoxyphenyl)ethyl)amino)methyl)naphthalen-1-yl)benzoic acid hydrochloride | 36 | $^1$H NMR (400 MHz, DMSO-d$_6$) δ 13.62 (s, 1H), 10.11 (s, 1H), 9.75 (s, 1H), 8.11-7.97 (m, 2H), 7.89 (d, J = 2.1 Hz, 1H), 7.85-7.55 (m, 6H), 7.36 (t, J = 7.9 Hz, 1H), 7.25 (t, J = 2.1 Hz, 1H), 7.15 (d, J = 7.5 Hz, 1H), 6.95 (dd, J = 8.3, 2.4 Hz, 1H), 4.40 (d, J = 7.3 Hz, 1H), 4.25 (d, J = 13.1 Hz, 1H), 4.02 (q, J = 8.2, 7.1 Hz, 3H), 1.64 (d, J = 6.6 Hz, 3H), 1.32 (t, J = 6.9 Hz, 3H); m/z-460.0 |

TABLE 7-continued

| Ex. No. | Structure/Name | Ester Example | ¹H NMR/MS (ES+) |
|---|---|---|---|
| 101 | 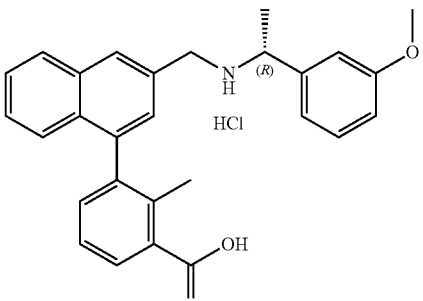<br>(R)-3-(3-(((1-(3-Methoxyphenyl)ethyl)amino)methyl)naphthalen-1-yl)-2-methylbenzoic acid hydrochloride | 37 | ¹H NMR (400 MHz, DMSO-$d_6$) δ 13.05 (s, 1H), 10.11 (d, J = 10.9 Hz, 1H), 9.73 (s, 1H), 8.06 (d, J = 1.9 Hz, 1H), 8.00 (d, J = 8.1 Hz, 1H), 7.88 (dd, J = 7.7, 1.7 Hz, 1H), 7.59 (ddd, J = 8.3, 6.7, 1.3 Hz, 1H), 7.51 (dddd, J = 8.4, 6.0, 1.5 Hz, 2H), 7.47-7.34 (m, 3H), 7.32-7.24 (m, 2H), 7.15 (d, J = 7.3 Hz, 1H), 6.98 (dd, J = 8.4, 2.5 Hz, 1H), 4.39 (q, J = 6.3 Hz, 1H), 4.27 (d, J = 13.4 Hz, 1H), 4.04 (dd, J = 11.5, 6.9 Hz, 1H), 3.77 (d, J = 1.2 Hz, 3H), 2.12 (d, J = 1.9 Hz, 3H), 1.65 (d, J = 6.7 Hz, 3H); m/z-426.1 |
| 102 | 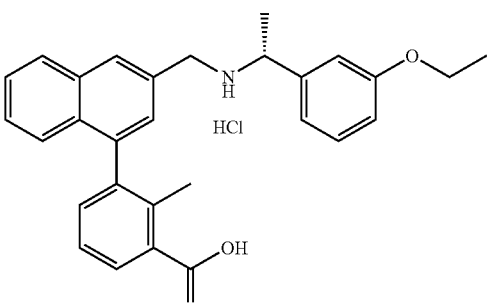<br>(R)-3-(3-(((1-(3-Ethoxyphenyl)ethyl)amino)methyl)naphthalen-1-yl)-2-methylbenzoic acid hydrochloride | 38 | ¹H NMR (400 MHz, DMSO-$d_6$) δ 13.04 (s, 1H), 10.10 (s, 1H), 9.71 (s, 1H), 8.05 (s, 1H), 8.00 (d, J = 8.1 Hz, 1H), 7.88 (dd, J = 7.7, 1.6 Hz, 1H), 7.63-7.56 (m, 1H), 7.56-7.32 (m, 5H), 7.29 (d, J = 8.4 Hz, 1H), 7.23 (dt, J = 5.7, 2.0 Hz, 1H), 7.13 (d, J = 7.5 Hz, 1H), 6.98-6.92 (m, 1H), 4.44-4.33 (m, 1H), 4.32-4.19 (m, 1H), 4.03 (m, 3H), 2.12 (d, J = 2.4 Hz, 3H), 1.64 (d, J = 6.6 Hz, 3H), 1.32 (t, J = 7.0, 1.2 Hz, 3H); m/z-440.04 |
| 103 | 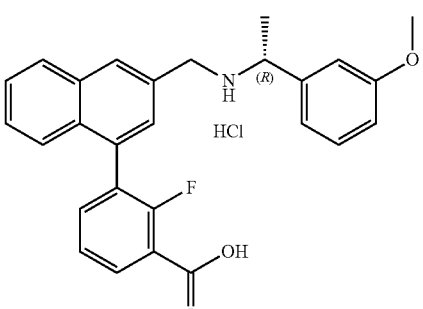<br>(R)-2-Fluoro-3-(3-(((1-(3-methoxyphenyl)ethyl)amino)methyl)naphthalen-1-yl)benzoic acid hydrochloride | 39 | ¹H NMR (400 MHz, DMSO-$d_6$) δ 10.06 (d, J = 35.4 Hz, 1H), 9.83-9.63 (m, 1H), 8.13-8.06 (m, 1H), 8.01 (td, J = 6.9, 1.7 Hz, 2H), 7.73-7.54 (m, 4H), 7.51 (dt, J = 11.3, 5.0 Hz, 2H), 7.38 (t, J = 7.9 Hz, 1H), 7.27 (q, J = 2.4 Hz, 1H), 7.17 (d, J = 7.8 Hz, 1H), 6.98 (dt, J = 8.3, 2.8 Hz, 1H), 4.47-4.35 (m, 1H), 4.32-4.21 (m, 1H), 4.09-3.96 (m, 1H), 3.78 (s, 3H), 1.65 (d, J = 6.7 Hz, 3H); m/z-430.0 |

TABLE 7-continued

| Ex. No. | Structure/Name | Ester Example | ¹H NMR/MS (ES+) |
|---|---|---|---|
| 104 | 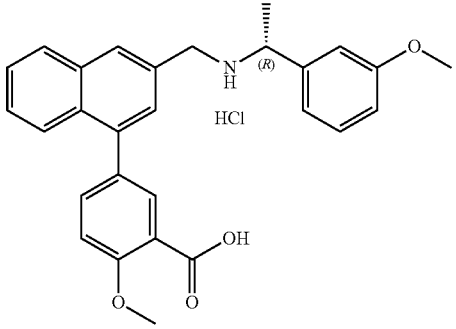<br>(R)-2-Methoxy-5-(3-(((1-(3-methoxyphenyl)ethyl)amino)methyl)naphthalen-1-yl)benzoic acid hydrochloride | 40 | ¹H NMR (400 MHz, DMSO-$d_6$) δ 12.82 (s, 1H), 9.99 (s, 1H), 9.67 (d, J = 11.7 Hz, 1H), 8.07-7.92 (m, 2H), 7.87-7.71 (m, 2H), 7.68-7.49 (m, 4H), 7.45-7.27 (m, 2H), 7.22-7.07 (m, 2H), 6.99 (dd, J = 8.2, 2.5 Hz, 1H), 4.49-4.36 (m, 1H), 4.30 (d, J = 13.1 Hz, 1H), 4.05 (d, J = 13.2 Hz, 1H), 3.91 (s, 3H), 3.76 (s, 3H), 1.62 (d, J = 6.7 Hz, 3H); m/z-442 |
| 105 | 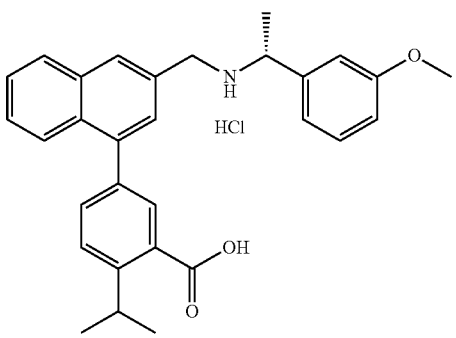 [SMILES: COc1cccc([C@@H](C)NCc2cc(-c3ccc(C(C)C)c(C(=O)O)c3)c3ccccc3c2)c1 ; Cl]<br>(R)-2-Isopropyl-5-(3-(((1-(3-methoxyphenyl)ethyl)amino)methyl)naphthalen-1-yl)benzoic acid hydrochloride | 41 | ¹H NMR (400 MHz, DMSO-$d_6$) δ 13.12 (s, 1H), 10.08 (s, 1H), 9.74 (s, 1H), 8.05-7.97 (m, 2H), 7.88-7.81 (m, 1H), 7.77 (d, J = 1.5 Hz, 1H), 7.69-7.55 (m, 5H), 7.38 (t, J = 7.9 Hz, 1H), 7.31-7.25 (m, 1H), 7.17 (d, J = 7.6 Hz, 1H), 6.98 (dd, J = 8.3, 2.5 Hz, 1H), 4.41 (m, 1H), 4.30-4.20 (m, 1H), 4.02 (m, 1H), 3.81 (m, 1H), 3.77 (s, 3H), 1.64 (d, J = 6.7 Hz, 3H), 1.29 (d, J = 6.8 Hz, 6H); m/z-454.17 |
| 106 | 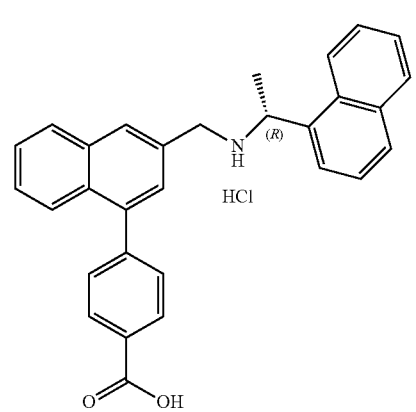<br>(R)-4-(3-(((1-(Naphthalen-1-yl)ethyl)amino)methyl)naphthalen-1-yl)benzoic acid hydrochloride | 42 | ¹H NMR (400 MHz, DMSO-$d_6$) δ 13.12 (s, 1H), 10.26 (s, 1H), 9.78 (s, 1H), 8.11-7.96 (m, 8H), 7.82 (d, J = 8.0 Hz, 1H), 7.67-7.53 (m, 8H), 5.38-5.36 (m, 1H), 4.45-4.43 (m, 1H), 4.29-4.25 (m, 1H), 1.77 (d, J = 6.4 Hz, 3H); m/z-432.04 |

TABLE 7-continued

| Ex. No. | Structure/Name | Ester Example | $^1$H NMR/MS (ES+) |
|---|---|---|---|
| 107 | 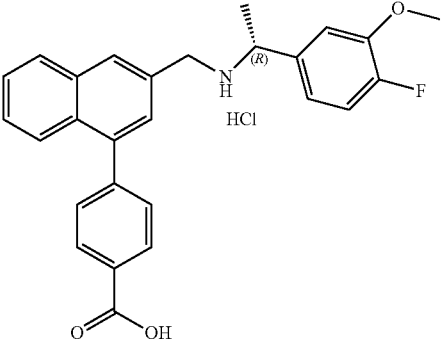<br>(R)-4-(3-(((1-(4-Fluoro-3-methoxyphenyl)ethyl)amino)methyl)naphthalen-1-yl)benzoic acid hydrochloride | 43 | $^1$H NMR (400 MHz, DMSO-d$_6$) δ 13.12 (s, 1H), 9.96 (s, 1H), 9.75 (s, 1H), 8.13 (d, J = 8.0 Hz, 2H), 8.05 (s, 1H), 8.02 (d, J = 7.2 Hz, 1H), 7.83 (d, J = 8.4 Hz, 1H), 7.66-7.56 (m, 6H), 7.30 (dd, J = 11.0, 8.0 Hz, 1H), 7.16-7.13 (m, 1H), 4.48-4.43 (m, 1H), 4.29-4.25 (m, 1H), 4.07-4.03 (m, 1H), 3.85 (s, 3H), 1.65 (d, J = 6.8 Hz, 3H); m/z-430.04 |
| 108 | 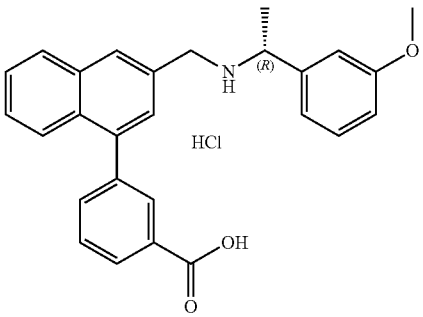<br>(R)-3-(3-(((1-(3-Methoxyphenyl)ethyl)amino)methyl)naphthalen-1-yl)benzoic acid hydrochloride | 44 | $^1$H NMR (400 MHz, DMSO-d$_6$) δ 13.22 (s, 1H), 10.07 (d, J = 11.6 Hz, 1H), 9.73 (d, J = 10.7 Hz, 1H), 8.11-7.98 (m, 4H), 7.88-7.53 (m, 6H), 7.38 (t, J = 7.9 Hz, 1H), 7.31-7.25 (m, 1H), 7.20-7.13 (m, 1H), 6.98 (dd, J = 8.3, 2.5 Hz, 1H), 4.47-4.35 (m, 1H), 4.33-4.21 (m, 1H), 4.10-3.99 (m, 1H), 3.77 (s, 3H), 1.65 (d, J = 6.6 Hz, 3H); m/z-412.16 |
| 109 | 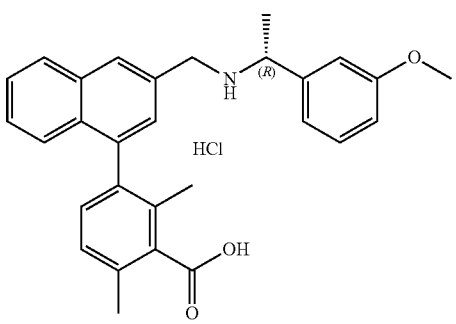<br>(R)-3-(3-(((1-(3-Methoxyphenyl)ethyl)amino)methyl)naphthalen-1-yl)-2,6-dimethylbenzoic acid hydrochloride | Intermediate-68 (debenzylation) | $^1$H NMR (400 MHz, DMSO-d$_6$) δ 13.33 (s, 1H), 10.06 (s, 1H), 9.67 (s, 1H), 8.15-7.94 (m, 2H), 7.69-7.45 (m, 3H), 7.36 (dt, J = 14.0, 8.1 Hz, 2H), 7.25 (d, J = 6.4 Hz, 2H), 7.20-7.12 (m, 2H), 6.98 (dd, J = 8.4, 2.5 Hz, 1H), 4.39 (q, J = 6.2 Hz, 1H), 4.31-4.19 (m, 1H), 4.02 (d, J = 13.9 Hz, 1H), 3.77 (d, J = 2.0 Hz, 3H), 2.37 (s, 3H), 1.90 (s, 3H), 1.64 (d, J = 6.6 Hz, 3H); m/z-440.11 |

TABLE 7-continued

| Ex. No. | Structure/Name | Ester Example | ¹H NMR/MS (ES+) |
|---|---|---|---|
| 110 | 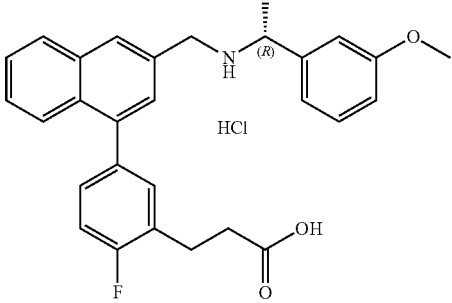<br>(R)-3-(2-Fluoro-5-(3-(((1-(3-methylphenyl)ethyl)amino)methyl)naphthalen-1-yl)phenyl)propanoic acid hydrochloride | 46 | ¹H NMR (400 MHz, DMSO-$d_6$) δ 12.25 (s, 1H), 9.88 (s, 1H), 9.62 (S, 1H), 8.06-7.95 (m, 2H), 7.84 (d, J = 8.1 Hz, 1H), 7.69-7.52 (m, 3H), 7.50-7.30 (m, 4H), 7.29-7.20 (m, 1H), 7.15 (d, J = 7.6 Hz, 1H), 6.99 (dd, J = 8.2, 2.5 Hz, 1H), 4.50-4.36 (m, 1H), 4.32-4.17 (m, 1H), 4.07-3.95 (m, 1H), 3.78 (s, 3H), 2.95 (t, J = 7.6 Hz, 2H), 2.62 (t, J = 7.5 Hz, 2H), 1.64 (d, J = 6.6 Hz, 3H); m/z-458.04 |
| 111 | 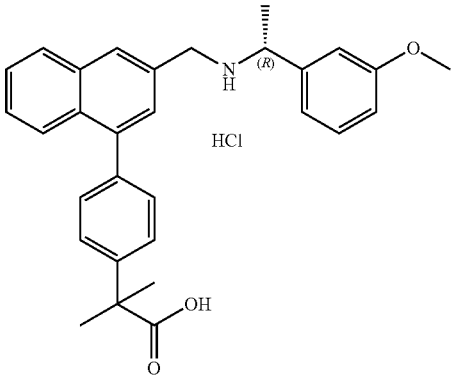<br>(R)-2-(4-(3-(((1-(3-Methoxyphenyl)ethyl)amino)methyl)naphthalen-1-yl)phenyl)-2-methylpropanoic acid hydrochloride | 47 | ¹H NMR (400 MHz, DMSO-$d_6$) δ 12.47 (s, 1H), 10.16 (s, 1H), 9.77 (s, 1H), 7.99 (dt, J = 6.6, 1.3 Hz, 2H), 7.87 (dd, J = 8.0, 1.6 Hz, 1H), 7.68-7.48 (m, 7H), 7.38 (t, J = 7.9 Hz, 1H), 7.33-7.26 (m, 1H), 7.23-7.13 (m, 1H), 6.98 (dd, J = 8.1, 2.6 Hz, 1H), 4.49-4.34 (m, 1H), 4.27-4.14 (m, 1H), 4.09-3.94 (m, 1H), 3.77 (s, 3H), 1.65 (d, J = 6.7 Hz, 3H), 1.56 (s, 6H); m/z-454.1 |
| 112 | 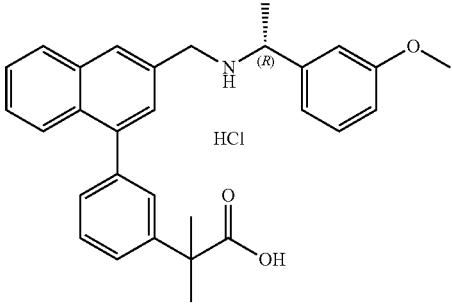<br>(R)-2-(3-(3-(((1-(3-Methoxyphenyl)ethyl)amino)methyl)naphthalen-1-yl)phenyl)-2-methylpropanoic acid hydrochloride | 48 | ¹H NMR (400 MHz, DMSO-$d_6$) δ 12.46 (s, 1H), 10.07 (s, 1H), 9.73 (s, 1H), 8.05-7.96 (m, 2H), 7.82 (d, J = 8.2 Hz, 1H), 7.65-7.50 (m, 4H), 7.51-7.43 (m, 2H), 7.43-7.26 (m, 3H), 7.17 (d, J = 7.6 Hz, 1H), 6.98 (dd, J = 8.2, 2.5 Hz, 1H), 4.51-4.17 (m, 2H), 4.02 (d, J = 15.9 Hz, 2H), 3.77 (s, 3H), 1.64 (d, J = 6.7 Hz, 3H), 1.54 (s, 6H); m/z-454.04. |

TABLE 7-continued

| Ex. No. | Structure/Name | Ester Example | $^1$H NMR/MS (ES+) |
|---|---|---|---|
| 113 | 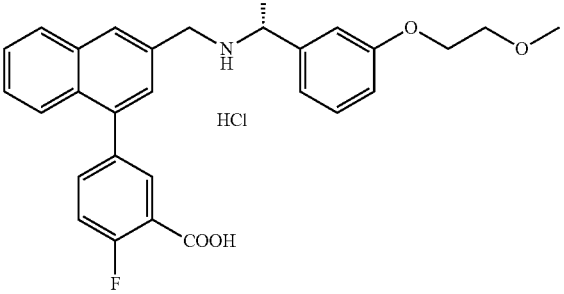  (R)-2-Fluoro-5-(3-(((1-(3-(2-methoxyethoxy)phenyl)ethyl)amino)methyl)naphthalen-1-yl) benzoic acid hydrochloride | 34 | $^1$H NMR (400 MHz, DMSO-d6) d 13.48 (s, 1H), 10.06 (s, 1H), 9.73 (s, 1H), 8.07-7.99 (m, 2H), 7.96 (dd, J = 7.1, 2.4 Hz, 1H), 7.82-7.75 (m, 2H), 7.66-7.48 (m, 4H), 7.37 (t, J = 7.9 Hz, 1H), 7.31-7.26 (m, 1H), 7.16 (d, J = 7.5 Hz, 1H), 6.98 (dd, J = 8.1, 2.5 Hz, 1H), 4.48-4.35 (m, 1H), 4.26 (s, 1H), 4.14-3.98 (m, 3H), 3.70-3.61 (m, 2H), 3.30 (s, 3H), 1.65 (d, J = 6.7 Hz, 3H), 1.09 (t, J = 7.0 Hz, 3H); m/z-474.54. |

Example-114

5-(3-(1-(((R)-1-(3-methoxyphenyl)ethyl)amino)ethyl)naphthalen-1-yl)-2-methylbenzoic acid hydrochloride

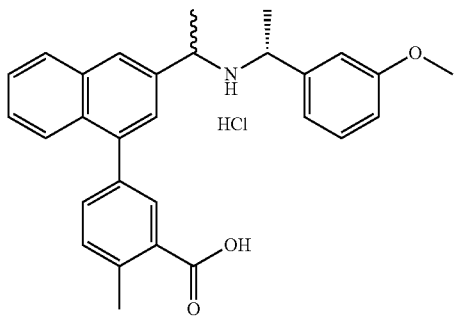 [SMILES: COc1cccc([C@@H](C)NC(C)c2cc(-c3ccc(C)c(C(=O)O)c3)c3ccccc3c2)c1 ; Cl]

Example 114 was obtained by following similar ester hydrolysis procedure as described in Example-89 using Example-49a (Minor diastereomer) and 49b (Major diastereomer) to give 114a (Minor diastereomer) and 114 b (Major diastereomer) respectively.

Minor diastereomer 114a: $^1$H NMR (400 MHz, DMSO-d$_6$) δ 13.03 (s, 1H), 10.09 (brs, 1H), 10.25 (brs, 1H), 7.99-7.91 (m, 3H), 7.83-7.81 (m, 1H), 7.61-7.59 (m, 3H), 7.51-7.49 (m, 2H), 7.34-7.32 (m, 1H), 7.15-7.13 (m, 1H), 7.00-6.93 (m, 2H), 4.20-4.18 (m, 1H), 4.04-4.02 (m, 1H), 3.71 (s, 3H), 2.63 (s, 3H), 1.70 (d, J=6.6 Hz, 3H), 1.57 (d, J=6.6 Hz, 3H); m/z: 440 (M+1).

Major diastereomer: 114b: $^1$H NMR (400 MHz, DMSO-d$_6$) δ 13.03 (s, 1H), 10.24 (brs, 1H), 9.25 (brs, 1H), 8.06 (s, 1H), 8.01 (d, J=7.6 Hz, 1H), 7.93 (d, J=1.7 Hz, 1H), 7.81 (d, J=7.9 Hz, 1H), 7.72-7.53 (m, 4H), 7.50 (d, J=7.7 Hz, 1H), 7.32 (t, J=7.8 Hz, 1H), 7.18 (s, 1H), 7.08 (d, J=7.3 Hz, 1H), 6.96-6.87 (m, 1H), 4.46-4.37 (m, 1H), 4.30-4.20 (m, 1H), 3.71 (s, 3H), 2.63 (s, 3H), 1.70 (d, J=6.4 Hz, 3H), 1.60 (d, J=6.3 Hz, 3H); m/z: 440 (M+1).

The below Examples 115 to 152 given in Table 8 were prepared by following the similar ester hydrolysis procedure as described in Example-89 by taking ester examples.

TABLE 8

| Ex. No. | Structure/Name | Ester Example | $^1$H NMR/MS (ES+) |
|---|---|---|---|
| 115 | 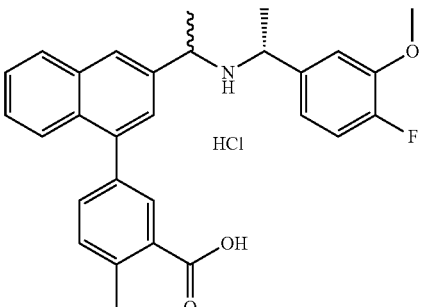  5-(3-(1-(((R)-1-(4-Fluoro-3-methoxyphenyl)ethyl)amino)ethyl)naphthalen-1-yl)-2-methylbenzoic acid hydrochloride | 50 | Analysis of major diastereomer: $^1$H NMR (400 MHz, DMSO-d$_6$) δ 13.14-12.94 (m, 1H), 10.31 (t, J = 10.6 Hz, 1H), 9.98 (d, J = 11.7 Hz, 1H), 8.00-7.90 (m, 3H), 7.83 (dd, J = 7.9, 1.5 Hz, 1H), 7.65-7.54 (m, 4H), 7.50 (d, J = 7.9 Hz, 1H), 7.44 (dd, J = 8.5, 2.1 Hz, 1H), 7.25 (dd, J = 11.4, 8.3 Hz, 1H), 6.94 (ddd, J = 8.3, 4.2, 2.1 Hz, 1H), 4.15-4.17 (m, J = 7.5 Hz, 1H), 4.07-3.96 (m, 1H), 3.75 (s, 3H), 2.64 (s, 3H), 1.70 (d, J = 6.7 Hz, 3H), 1.58 (d, J = 6.7 Hz, 3H); MS (ES+) = m/z: 458.04 (M + 1). |

| Ex. No. | Structure/Name | Ester Example | $^1$H NMR/MS (ES+) |
|---|---|---|---|
| 116 | 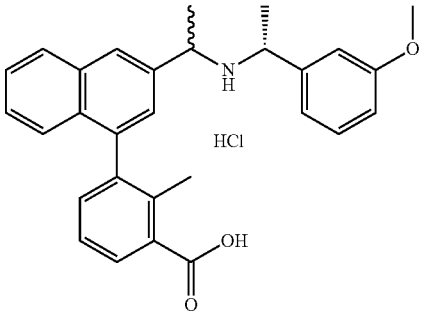 [SMILES: COc1cccc([C@@H](C)NC(C)c2cc(-c3cccc(C(=O)O)c3C)c3ccccc3c2)c1 ; Cl]<br>3-(3-(1-(((R)-1-(3-Methoxyphenyl)ethyl)amino)ethyl)naphthalen-1-yl)-2-methylbenzoic acid hydrochloride | 51 | Analysis of major diastereomer: $^1$H NMR (400 MHz, DMSO-d$_6$) δ 13.04 (s, 1H), 10.05 (s, 2H), 8.02-7.93 (m, 2H), 7.91-7.84 (m, 1H), 7.60 (ddd, J = 8.2, 6.8, 1.3 Hz, 1H), 7.53 (ddd, J = 8.2, 6.8, 1.3 Hz, 1H), 7.47-7.39 (m, 2H), 7.37 (dd, J = 3.4, 1.8 Hz, 1H), 7.35-7.26 (m, 2H), 7.08 (dt, J = 7.7, 2.1 Hz, 1H), 6.99-6.88 (m, 2H), 4.19 (d, J = 10.3 Hz, 1H), 4.08 (q, J = 7.0, 6.4 Hz, 1H), 3.71 (d, J = 8.5 Hz, 3H), 2.13 (d, J = 4.6 Hz, 3H), 1.69 (t, J = 6.4 Hz, 3H), 1.57 (dd, J = 6.8, 4.4 Hz, 3H); MS (ES+) = m/z: 440.2 (M + 1). |
| 117 | 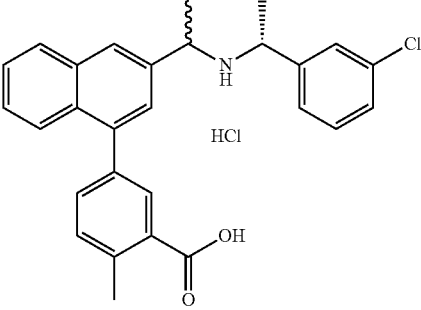 [SMILES: Cc1ccc(-c2cc(C(C)N[C@H](C)c3cccc(Cl)c3)cc3ccccc23)cc1C(=O)O ; Cl]<br>5-(3-(1-(((R)-1-(3-Chlorophenyl)ethyl)amino)ethyl)naphthalen-1-yl)-2-methylbenzoic acid hydrochloride | 52 | Analysis of major diastereomer: $^1$H NMR (400 MHz, DMSO-d$_6$) δ 13.03 (s, 1H), 10.12 (s, 1H), 10.01 (s, 1H), 7.99-7.90 (m, 3H), 7.82 (d, J = 8.2 Hz, 1H), 7.66-7.57 (m, 3H), 7.57-7.40 (m, 6H), 4.25 (q, J = 6.2 Hz, 1H), 4.16 (q, J = 6.6 Hz, 1H), 2.64 (s, 3H), 1.70 (d, J = 6.7 Hz, H), 1.58 (d, J = 6.7 Hz, 3H); MS (ES+) = m/z: 444.04 (M + 1). |
| 118 | 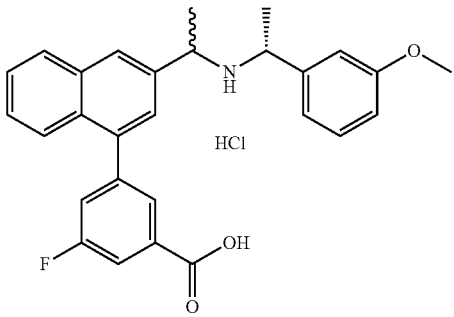 [SMILES: COc1cccc([C@@H](C)NC(C)c2cc(-c3cc(F)cc(C(=O)O)c3)c3ccccc3c2)c1 ; Cl]<br>3-Fluoro-5-(3-(1-(((R)-1-(3-methoxyphenyl)ethyl)amino)ethyl)naphthalen-1-yl)benzoic acid hydrochloride | 53 | Analysis of major diastereomer: $^1$H NMR (400 MHz, DMSO-d$_6$) δ 13.53 (s, 1H), 10.28-9.90 (m, 2H), 8.01-7.95 (m, 2H), 7.90 (t, J = 1.5 Hz, 1H), 7.86-7.77 (m, 2H), 7.72-7.58 (m, 3H), 7.56 (d, J = 1.7 Hz, 1H), 7.34 (t, J = 7.9 Hz, 1H), 7.13-7.07 (m, 1H), 6.97 (dd, J = 8.2, 2.2 Hz, 2H), 4.19 (t, J = 8.3 Hz, 1H), 4.02 (t, J = 9.8 Hz, 1H), 3.71 (s, 3H), 1.71 (d, J = 6.7 Hz, 3H), 1.58 (d, J = 6.7 Hz, 3H); MS (ES+) = m/z: 444 (M + 1). |

TABLE 8-continued

| Ex. No. | Structure/Name | Ester Example | $^1$H NMR/MS (ES+) |
|---|---|---|---|
| 119 | 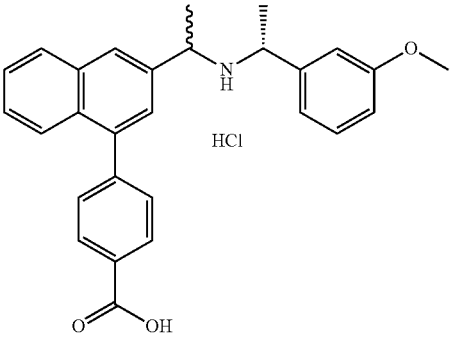 [SMILES: COc1cccc([C@@H](C)NC(C)c2cc(-c3ccc(C(=O)O)cc3)c3ccccc3c2)c1 ; Cl]<br>4-(3-(1-(((R)-1-(3-Methoxyphenyl)ethyl)amino)ethyl)naphthalen-1-yl)benzoic acid hydrochloride | 54 | Analysis of major diastereomer: $^1$H NMR (400 MHz, DMSO-d$_6$) δ 13.12 (s, 1H), 10.10 (d, J = 10.6 Hz, 2H), 8.15-8.10 (m,. 2H), 7.99-7.93 (m, 2H), 7.84 (dd, J = 8.3, 1.5 Hz, 1H), 7.70-7.55 (m, 5H), 7.35 (t, J = 7.9 Hz, 1H), 7.09 (t, J = 2.1 Hz, 1H), 6.97 (dd, J = 8.2, 2.1 Hz, 2H), 4.18 (dt, J = 13.2, 7.0 Hz, 1H), 4.02 (h, J = 6.8 Hz, 1H), 3.72 (s, 3H), 1.70 (d, J = 6.7 Hz, 3H), 1.58 (d, J = 6.6 Hz, 3H); MS (ES+) = m/z: 426.10 (M + 1). |
| 120 | 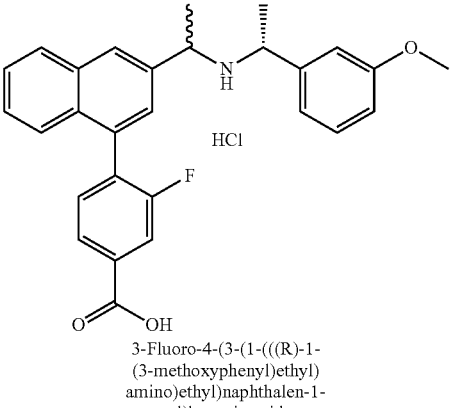<br>3-Fluoro-4-(3-(1-(((R)-1-(3-methoxyphenyl)ethyl)amino)ethyl)naphthalen-1-yl)benzoic acid hydrochloride | 55 | Analysis of major diastereomer: $^1$H NMR (400 MHz, DMSO-d$_6$) δ 13.46 (s, 1H), 9.99 (s, 2H), 8.18-7.81 (m, 4H), 7.77-7.42 (m, 5H), 7.34 (dt, J = 15.9, 7.9 Hz, 1H), 7.09 (s, 1H), 6.96 (dt, J = 16.2, 7.4 Hz, 2H), 4.25 (s, 1H), 4.16-3.98 (m, 1H), 3.73 (d, J = 11.8 Hz, 3H), 1.69 (t, J = 6.4 Hz, 3H), 1.58 (d, J = 6.5 Hz, 3H); MS (ES+) = m/z: 443 (M + 1). |
| 121 | 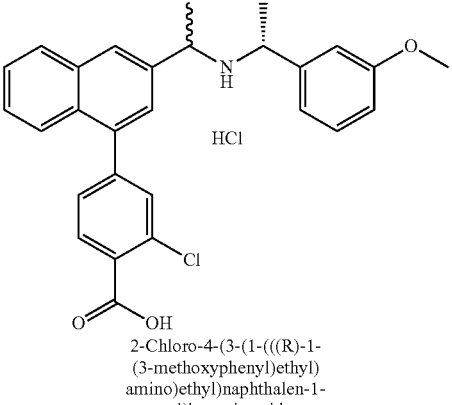<br>2-Chloro-4-(3-(1-(((R)-1-(3-methoxyphenyl)ethyl)amino)ethyl)naphthalen-1-yl)benzoic acid hydrochloride | 56 | Analysis of major diastereomer: $^1$H NMR (400 MHz, DMSO-d$_6$) δ 8.08-7.90 (m, 2H), 7.92-7.77 (m, 2H), 7.71-7.50 (m, 5H), 7.31 (t, J = 7.9 Hz, 1H), 7.05-6.84 (m, 3H), 4.00 (s, 1H), 3.72 (s, 3H), 3.40 (d, J = 7.0 Hz, 1H), 1.55 (d, J = 6.6 Hz, 3H), 1.43 (d, J = 6. Hz, 3H); MS (ES+) = m/z: 423.9 (M + 1). |

TABLE 8-continued

| Ex. No. | Structure/Name | Ester Example | $^1$H NMR/MS (ES+) |
|---|---|---|---|
| 122 | 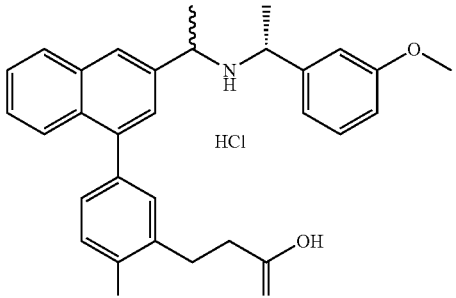<br>3-(2-Fluoro-5-(3-(1-(((R)-1-(3-methoxyphenyl)ethyl)amino)ethyl)naphthalen-1-yl)phenyl)propanoic acid hydrochloride | 57 | Analysis of major diastereomer: $^1$H NMR (400 MHz, DMSO-$d_6$) δ 12.28 (d, J = 14.0 Hz, 1H), 10.01 (t, J = 13.5 Hz, 2H), 7.95 (dd, J = 8.1, 1.5 Hz, 1H), 7.93-7.89 (m, 1H), 7.86 (d, J = 8.1 Hz, 1H), 7.65-7.54 (m, 2H), 7.51-7.44 (m, 2H), 7.43-7.31 (m, 3H), 7.11-7.06 (m, 1H), 6.97 (ddd, J = 6.8, 4.6, 2.0 Hz, 2H), 4.18 (q, J = 6.4 Hz, 1H), 4.03 (q, J = 7.1 Hz, 1H), 3.72 (s, 3H), 2.95 (t, J = 7.6 Hz, 2H), 2.63 (t, J = 7.6 Hz, 2H), 1.69 (d, J = 6.7 Hz, 3H), 1.57 (d, J = 6.6 Hz, 3H); MS (ES+) = m/z: 472 (M + 1). |
| 123 | 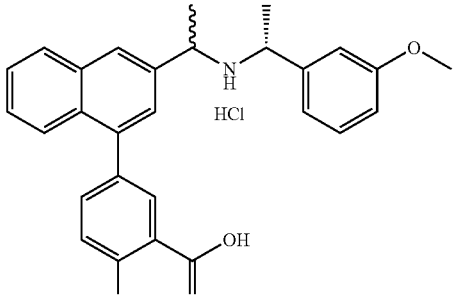<br>2-Fluoro-5-(3-(1-(((R)-1-(3-methoxyphenyl)ethyl)amino)ethyl)naphthalen-1-yl)benzoic acid hydrochloride | 58 | Analysis of major diastereomer: $^1$H NMR (400 MHz, DMSO-$d_6$) δ 13.47 (s, 1H), 9.95 (s, 2H), 7.96 (d, J = 9.4, 4.9, 1.5 Hz, 3H), 7.84-7.75 (m, 2H), 7.70-7.47 (m, 4H), 7.35 (t, J = 7.9 Hz, 1H), 7.13-7.04 (m, 1H), 6.96 (td, J = 6.3, 5.8, 2.8 Hz, 2H), 4.21 (d, J = 7.1 Hz, 1H), 4.5 (d, J = 6.6 Hz, 1H), 3.71 (s, 3H), 1.69 (d, J = 6.7 Hz, 3H), 1.56 (d, J = 6.7 Hz, 3H); MS (ES+) = m/z: 453.9 (M + 1). |
| 124 | 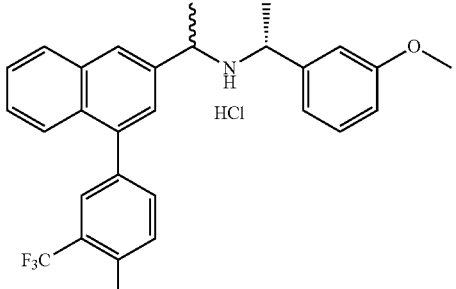<br>4-(3-(1-(((R)-1-(3-Methoxyphenyl)ethyl)amino)ethyl)naphthalen-1-yl)-2-(trifluoromethyl)benzoic acid hydrochloride | 59 | Analysis of major diastereomer: $^1$H NMR (400 MHz, DMSO-$d_6$) δ 13.77 (s, 1H), 10.16 (s, 2H), 8.05-7.96 (m, 3H), 7.92 (d, J = 8.2 Hz, 2H), 7.78 (dd, J = 7.8, 1.7 Hz, 1H), 7.69-7.53 (m, 3H), 7.32 (t, J = 7.9 Hz, 1H), 7.15-7.03 (m, 1H), 6.96 (dt, J = 8.4, 2.0 Hz, 2H), 4.18 (d, J = 7.1 Hz, 1H), 4.08-3.94 (m, 1H), 3.69 (s, 3H), 1.71 (d, J = 6.7 Hz, 3H), 1.58 (d, J = 6.6 Hz, 3H); MS (ES+) = m/z: 494.10 (M + 1). |

TABLE 8-continued

| Ex. No. | Structure/Name | Ester Example | ¹H NMR/MS (ES+) |
|---|---|---|---|
| 125 | 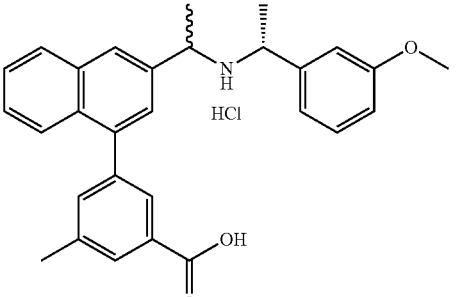<br>3-(3-(1-(((R)-1-(3-Methoxyphenyl)ethyl)amino)ethyl)naphthalen-1-yl)-5-methylbenzoic acid hydrochloride | 60 | Analysis of major diastereomer: ¹H NMR (400 MHz, DMSO-d₆) δ 13.10 (s, 1H), 10.15 (t, J = 9.8 Hz, 1H), 10.01 (t, J = 10.3 Hz, 1H), 7.96 (dd, J = 7.4, 1.6 Hz, 2H), 7.87 (dt, J = 14.6, 1.7 Hz, 2H), 7.80 (dd, J = 8.0, 1.5 Hz, 1H), 7.65-7.55 (m, 3H), 7.49 (d, J = 1.8 Hz, 1H), 7.34 (t, J 7.9 Hz, 1H), 7.14-7.07 (m, 1H), 6.97 (dd, J = 8.3, 2.3 Hz, 2H), 4.19 (dq, J = 10.6, 5.6, 4.1 Hz, 1H), 4.08-3.95 (m, 1H), 3.71 (s, 3H), 1.70 (d, J = 6.7 Hz, 3H), 1.58 (d, J = 6.6 Hz, 3H); MS (ES+) = m/z: 440.04 (M + 1). |
| 126 | 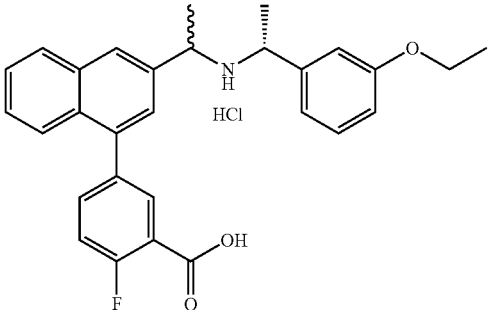 [SMILES: CCOc1cccc([C@@H](C)NC(C)c2cc(-c3ccc(F)c(C(=O)O)c3)c3ccccc3c2)c1 ; Cl]<br>5-(3-(1-(((R)-1-(3-Ethoxyphenyl)ethyl)amino)ethyl)naphthalen-1-yl)-2-fluorobenzoic acid hydrochloride | 61 | Analysis of major diastereomer: ¹H NMR (400 MHz, DMSO-d₆) δ 13.5 (s, 1H), 10.07 (s, 2H), 7.97 (dt, J = 7.5, 2.3 Hz, 3H), 7.79 (ddd, J = 8.4, 5.8, 2.3 Hz, 2H), 7.70-7.39 (m, 4H), 7.32 (t, J = 7.9 Hz, 1H), 7.12-6.99 (m, 1H), 6.94 (dd, J = 8.1, 2.1 Hz, 2H), 4.18 (d, J = 7.0 Hz, 1H) 3.94 (ddq, J = 32.6, 9.6, 7.2 Hz, 3H), 1.70 (d, J = 6.7 Hz, 3H), 1.57 (d, J = 6.6 Hz, 3H), 1.29 (t, J = 6.9 Hz, 3H); MS (ES+) = m/z: 456 (M + 1). |
| 127 | 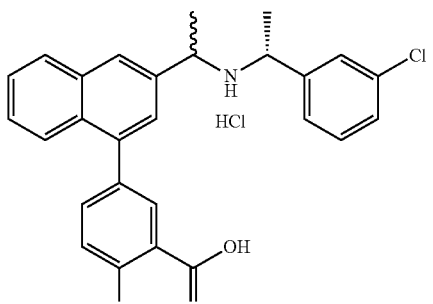<br>5-(3-(1-(((R)-1-(3-Chlorophenyl)ethyl)amino)ethyl)naphthalen-1-yl)-2-fluorobenzoic acid hydrochloride | 62 | Analysis of major diastereomer: ¹H NMR (400 MHz, DMSO-d₆) δ 13.47 (s, 1H), 10.10 (d, J = 38.8 Hz, 2H), 8.07-7.86 (m, 3H), 7.78 (ddd, J = 8.3, 4.7, 2.2 Hz, 2H), 7.70-7.16 (m, 8H), 4.19 (d, J = 37.7 Hz, 2H), 1.70 (d, J = 6.6 Hz, 3H), 1.57 (d, J = 6.6 Hz, 3H); MS (ES+) = m/z: 448 (M + 1). |

TABLE 8-continued

| Ex. No. | Structure/Name | Ester Example | $^1$H NMR/MS (ES+) |
|---|---|---|---|
| 128 | 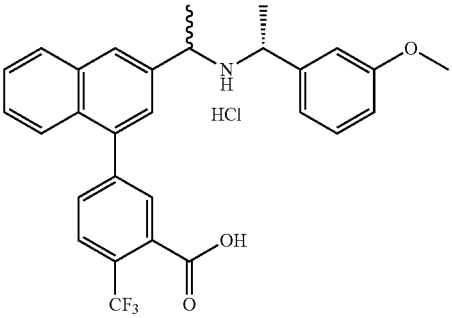 [SMILES: COc1cccc([C@@H](C)NC(C)c2cc(-c3ccc(C(F)(F)F)c(C(=O)O)c3)c3ccccc3c2)c1 ; Cl]<br>5-(3-(1-(((R)-1-(3-Methoxyphenyl)ethyl)amino)ethyl)naphthalen-1-yl)-2-(trifluoromethyl)benzoic acid hydrochloride | 63 | Analysis of major diastereomer: $^1$H NMR (400 MHz, DMSO-$d_6$) δ 13.82 (s, 1H), 10.08 (s, 2H), 8.04 (d, J = 8.1 Hz, 1H), 7.99 (td, J = 4.0, 3.2, 1.9 Hz, 2H), 7.93 (d, J = 1.8 Hz, 1H), 7.91-7.85 (m, 1H), 7.83-7.78 (m, 1H), 7.69-7.56 (m, 3H), 7.34 (t, J = 7.9 Hz, 1H), 7.11-7.07 (m, 1H), 6.96 (dd, J = 8.0, 2.1 Hz, 2H), 4.20 (d, J = 7.1 Hz, 1H), 4.09-3.97 (m, 1H), 3.70 (s, 3H), 1.70 (d, J = 6.7 Hz, 3H), 1.57 (d, J = 6.7 Hz, 3H); MS (ES+) = m/z: 494.06 (M + 1). |
| 129 | 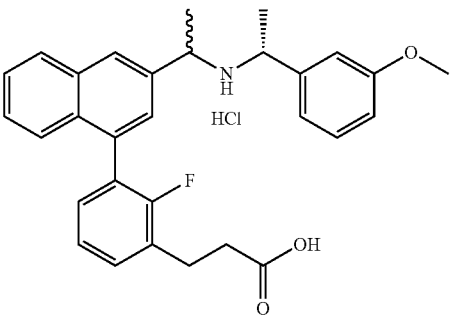 [SMILES: COc1cccc([C@@H](C)NC(C)c2cc(-c3cccc(CCC(=O)O)c3F)c3ccccc3c2)c1 ; Cl]<br>3-(2-Fluoro-3-(3-(1-(((R)-1-(3-methoxyphenyl)ethyl)amino)ethyl)naphthalen-1-yl)phenyl)propanoic acid hydrochloride | 64 | Analysis of major diastereomer: $^1$H NMR (400 MHz, DMSO-$d_6$) δ 12.28 (s, 1H), 9.97 (d, J = 30.4 Hz, 2H), 8.13-7.90 (m, 2H), 7.74-7.42 (m, 5H), 7.41-7.24 (m, 3H), 7.16-7.03 (m, 1H), 7.03-6.90 (m, 2H), 4.21 (d, J = 9.4 Hz, 1H), 4.03 (m, 1H), 3.73 (d, J = 12.1 Hz, 3H), 2.9 (q, J = 9.1, 8.5 Hz, 2H), 2.63 (td, J = 8.4, 7.7, 5.8 Hz, 2H), 1.69 (dd, J = 6.8, 4.2 Hz, 3H), 1.58 (d, J = 6.6 Hz, 3H); MS (ES+) = m/z: 472 (M + 1). |
| 130 | 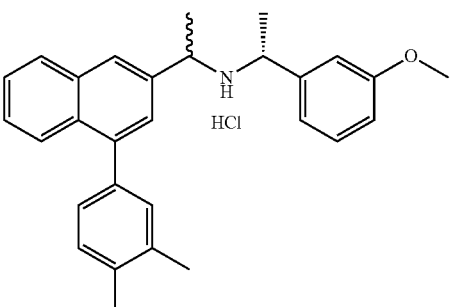<br>4-(3-(1-(((R)-1-(3-Methoxyphenyl)ethyl)amino)ethyl)naphthalen-1-yl)-2-methylbenzoic acid hydrochloride | 65 | Analysis of major diastereomer: $^1$H NMR (400 MHz, DMSO-$d_6$) δ 12.97 (s, 1H), 9.95 (d, J = 11.5 Hz, 2H), 8.11-7.89 (m, 3H), 7.85 (d, J = 8.1 Hz, 1H), 7.68-7.55 (m, 2H), 7.52 (d, J = 1.8 Hz, 1H), 7.49-7.40 (m, 2H), 7.35 (t, J = 7.9 Hz, 1H), 7.07 (t, J = 2.0 Hz, 1H), 6.98 (dt, J 8.2, 2.4 Hz, 2H), 4.22 (q, J = 6.6 Hz, 1H), 4.09-3.93 (m, 1H), 3.72 (s, 3H), 2.64 (s, 3H), 1.69 (d, J = 6.6 Hz, 3H), 1.57 (d, J = 6.6 Hz, 3H); MS (ES+) = m/z: 440 (M + 1). |

TABLE 8-continued

| Ex. No. | Structure/Name | Ester Example | $^1$H NMR/MS (ES+) |
|---|---|---|---|
| 131 | 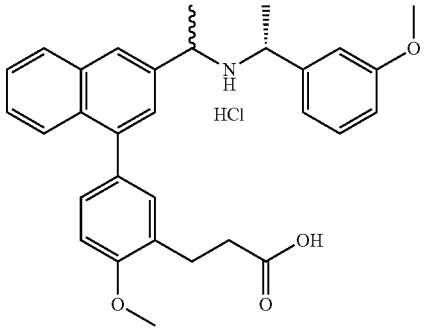 [SMILES: COc1cccc([C@@H](C)NC(C)c2cc(-c3ccc(OC)c(CCC(=O)O)c3)c3ccccc3c2)c1 ; Cl]

3-(2-Methoxy-5-(3-(1-
(((R)-1-(3-methoxyphenyl)
ethyl)amino)ethyl)
naphthalen-1-yl)phenyl)
propanoic acid
hydrochloride | 66 | Analysis of major diastereomer: $^1$H NMR (400 MHz, DMSO-d$_6$) δ 12.16 (s, 1H), 9.99 (d, J = 24.8 Hz, 2H), 7.93 (dt, J = 8.3, 1.5 Hz, 2H), 7.87 (d, J = 1.8 Hz, 1H), 7.56-7.58 (m, 2H), 7.47 (d, J = 1.8 Hz, 1H), 7.39-7.30 (m, 3H), 7.15 (d, J = 8.4 Hz, 1H), 7.09 (t, J = 2.0 Hz, 1H), 6.98 (t, J = 5.9, 2.8 Hz, 2H), 4.18 (t, J = 8.9 Hz, 1H), 4.08-3.97 (m, 1H), 3.90 (s, 3H), 3.72 (s, 3H), 2.88 (t, J = 7.7 Hz, 2H), 2.56 (t, J = 7.7 Hz, 2H), 1.69 (d, J = 6.7 Hz, 3H), 1.57 (d, J = 6.6 Hz, 3H); MS (ES+) = m/z: 483.86 (M + 1). |
| 132 | 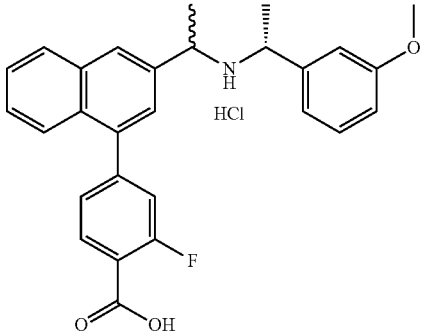 [SMILES: COc1cccc([C@@H](C)NC(C)c2cc(-c3ccc(C(=O)O)c(F)c3)c3ccccc3c2)c1 ; Cl]

2-Fluoro-4-(3-(1-(((R)-1-
(3-methoxyphenyl)ethyl)
amino)ethyl)naphthalen-1-
yl)benzoic acid
hydrochloride | 67 | Analysis of major diastereomer: $^1$H NMR (400 MHz, DMSO-d$_6$) δ 13.41 (s, 1H), 10.07 (s, 2H), 8.05 (t, J = 7.9 Hz, 1H), 8.00-7.93 (m, 2H), 7.87 (dd, J = 7.8, 1.7 Hz, 1H), 7.68-7.57 (m, 3H), 7.54-7.45 (m, 2H), 7.35 (t, J = 7.9 Hz, 1H), 7.06 (t, J = 2.0 Hz, 1H), 6.98 (dd, J = 8.0, 2.1 Hz, 2H), 4.20 (q, J = 6.4 Hz, 1H), 4.08-3.96 (m, 1H), 3.72 (s, 3H), 1.70 (d, J = 6.7 Hz, 3H), 1.58 (d, J = 6.6 Hz, 3H); MS (ES+) = m/z: 444.04 (M + 1). |
| 133 | 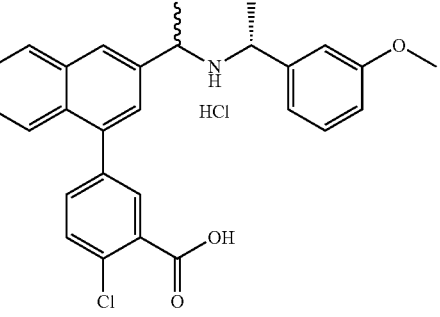

2-Chloro-5-(3-(1-(((R)-1-
(3-methoxyphenyl)ethyl)
amino)ethyl)naphthalen-1-
yl)benzoic acid
hydrochloride | 69 | Analysis of major diastereomer: $^1$H NMR (400 MHz, DMSO-d$_6$) δ 13.62 (s, 1H), 10.21 (s, 2H), 8.02-7.92 (m, 2H), 7.89 (d, J = 2.1 Hz, 1H), 7.84-7.77 (m, 1H), 7.75 (d, J = 8.2 Hz, 1H), 7.72-7.55 (m, 3H), 7.53 (d, J = 1.7 Hz, 1H), 7.33 (t, J = 7.9 Hz, 1H), 7.15-7.07 (m, 1H), 696 (dd, J = 8.4, 2.4 Hz, 2H), 4.15 (q, J = 6.7 Hz, 1H), 3.98 (q, J = 6.4 Hz, 1H), 3.71 (s, 3H), 1.70 (d, J = 6.7 Hz, 3H), 1.58 (d, J = 6.6 Hz, 3H); MS (ES+) = m/z: 460 (M + 1). |

TABLE 8-continued

| Ex. No. | Structure/Name | Ester Example | $^1$H NMR/MS (ES+) |
|---|---|---|---|
| 134 | 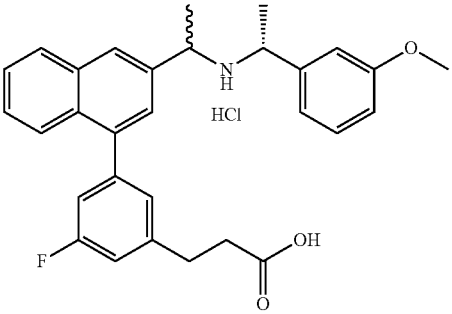 [SMILES: COc1cccc([C@@H](C)NC(C)c2cc(-c3cc(F)cc(CCC(=O)O)c3)c3ccccc3c2)c1 ; Cl]<br>3-(3-Fluoro-5-(3-(1-(((R)-1-(3-methoxyphenyl)ethyl)amino)ethyl)naphthalen-1-yl)phenyl)propanoic acid hydrochloride | 70 | Analysis of major diastereomer: $^1$H NMR (400 MHz, DMSO-d$_6$) δ 12.23 (s, 1H), 9.97 (d, J = 11.6 Hz, 2H), 8.00-7.91 (m, 2H), 7.91-7.84 (m, 1H), 7.67-7.55 (m, 2H), 7.51 (d, J = 1.8 Hz, 1H), 7.35 (t, J = 7.9 Hz, 1H), 7.29-7.14 (m, 3H), 7.09-7.03 (m, 1H), 6.98 (dd, J = 8.2, 2.2 Hz, 2H), 4.21 (p, J = 6.5, 6.0 Hz, 1H), 4.03 (qd, J = 7.2, 4.2 Hz, 1H), 3.72 (s, 3H), 2.95 (t, J = 7.6 Hz, 2H), 2.65 (t, J = 7.6 Hz, 2H), 1.69 (d, J = 6.7 Hz, 3H), 1.57 (d, J = 6.6 Hz, 3H); MS (ES+) = m/z: 472.16 (M + 1). |
| 135 | 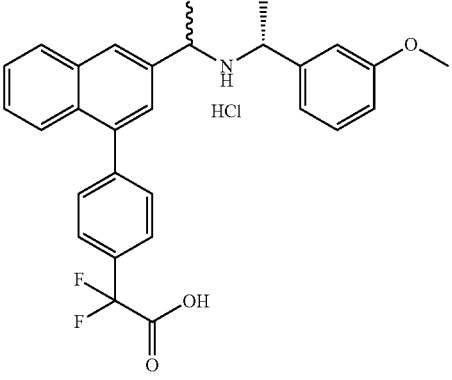 [SMILES: COc1cccc([C@@H](C)NC(C)c2cc(-c3ccc(C(F)(F)C(=O)O)cc3)c3ccccc3c2)c1 ; Cl]<br>2,2-Difluoro-2-(4-(3-(1-(((R)-1-(3-methoxyphenyl)ethyl)amino)ethyl)naphthalen-1-yl)phenyl)acetic acid hydrochloride | 72 | Analysis of major diastereomer: $^1$H NMR (400 MHz, DMSO-d$_6$) δ 10.06 (s, 2H), 8.09-7.90 (m, 2H), 7.90-7.43 (m, 8H), 7.35 (t, J = 7.9 Hz, 1H), 7.08 (s, 1H), 6.98 (d, J = 7.9 Hz, 2H), 4.19 (s, 1H), 4.03 (s, 1H), 3.71 (s, 3H), 1.70 (d, J = 6.6 Hz, 3H), 1.58 (d, J = 6.6 Hz, 3H); MS (ES+) = m/z: 476 (M + 1). |
| 136 | 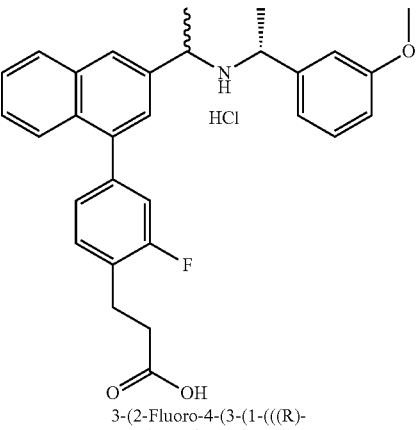<br>3-(2-Fluoro-4-(3-(1-(((R)-1-(3-methoxyphenyl)ethyl)amino)ethyl)naphthalen-1-yl)phenyl)propanoic acid hydrochloride | 73 | Analysis of major diastereomer: $^1$H NMR (400 MHz, DMSO-d$_6$) δ 12.30 (s, 1H), 10.02 (d, J = 11.8 Hz, 2H), 7.96 (dd, J = 7.6, 1.8 Hz, 1H), 7.91 (d, J = 2.0 Hz, 1H), 7.88 (dd, J = 7.8, 1.7 Hz, 1H), 7.66-7.55 (m, 2H), 7.54-7.47 (m, 2H), 7.38-7.27 (m, 3H), 7.08-7.03 (m, 1H), 6.8 (dd, J = 8.3, 2.7 Hz, 2H), 4.18 (t, J = 9.1 Hz, 1H), 4.07-3.98 (m, 1H), 3.72 (s, 3H), 2.96 (t, J = 7.6 Hz, 2H), 2.64 (t, J = 7.6 Hz, 2H), 1.69 (d, J = 6.7 Hz, 3H), 1.57 (d, J = 6.7 Hz, 3H); MS (ES+) = m/z: 472.05 (M + 1). |

TABLE 8-continued

| Ex. No. | Structure/Name | Ester Example | $^1$H NMR/MS (ES+) |
|---|---|---|---|
| 137 | 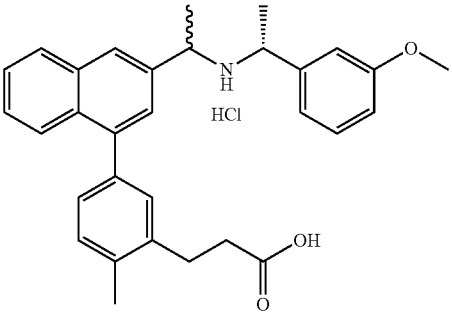 [SMILES: COc1cccc([C@@H](C)NC(C)c2cc(-c3ccc(C)c(CCC(=O)O)c3)c3ccccc3c2)c1 ; Cl]<br>3-(5-(3-(1-(((R)-1-(3-Methoxyphenyl)ethyl)amino)ethyl)naphthalen-1-yl)-2-methylphenyl)propanoic acid hydrochloride | 74 | Analysis of major diastereomer: $^1$H NMR (400 MHz, DMSO-d$_6$) δ 12.21 (s, 1H), 10.01 (dd, J = 25.4, 12.8 Hz, 2H), 8.09-7.82 (m, 3H), 7.65-7.42 (m, 3H), 7.41-7.29 (m, 3H), 7.26 (dd, J = 7.6, 1.9 Hz, 1H), 7.12-7.05 (m, 1H), 7.03-6.92 (m, 2H), 4.18 (d, J = 7.8 Hz, 1H), 4.11-3.96 (m, 1H), 3.72 (s, 3H), 2.92 (t, J = 7.7 Hz, 2H), 2.58 (t, J = 7.8 Hz, 2H), 2.39 (s, 3H), 1.69 (d, J = 6.7 Hz, 3H), 1.57 (d, J = 6.6 Hz, 3H); MS (ES+) = m/z: 468 (M + 1). |
| 138 | 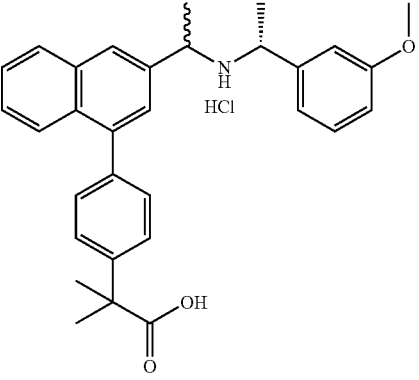 [SMILES: COc1cccc([C@@H](C)NC(C)c2cc(-c3ccc(C(C)(C)C(=O)O)cc3)c3ccccc3c2)c1 ; Cl]<br>2-(4-(3-(1-(((R)-1-(3-Methoxyphenyl)ethyl)amino)ethyl)naphthalen-1-yl)phenyl)-2-methylpropanoic acid hydrochloride | 75 | Analysis of major diastereomer: $^1$H NMR (400 MHz, DMSO-d$_6$) δ 12.45 (s, 1H), 10.09-9.88 (m, 2H), 7.95 (d, J = 7.8 Hz, 1H), 7.89 (d, J = 7.6 Hz, 2H), 7.65-7.47 (m, 7H), 7.35 (t, J = 7.9 Hz, 1H), 7.09-7.05 (m, 1H), 6.98 (dd, J = 8.2, 2.2 Hz, 2H), 4.18 (t, J = 8.6 Hz, 1H), 3.71 (, 3H), 1.69 (d, J = 6.6 Hz, 3H), 1.57 (s, 9H); MS (ES+) = m/z: 468.21 (M + 1). |
| 139 | 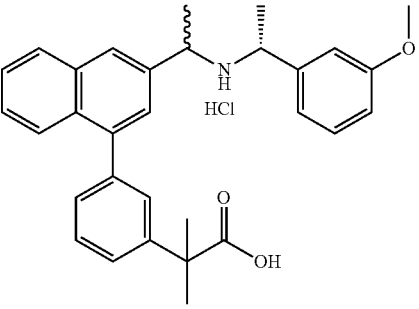 [SMILES: COc1cccc([C@@H](C)NC(C)c2cc(-c3cccc(C(C)(C)C(=O)O)c3)c3ccccc3c2)c1 ; Cl]<br>2-(3-(3-(1-(((R)-1-(3-Methoxyphenyl)ethyl)amino)ethyl)naphthalen-1-yl)phenyl)-2-methylpropanoic acid hydrochloride | 76 | Analysis of major diastereomer: $^1$H NMR (400 MHz, DMSO-d$_6$) δ 12.48 (s, 1H), 9.72 (s, 2H), 7.98 (dd, J = 8.1, 1.5 Hz, 1H), 7.93 (d, J = 1.9 Hz, 1H), 7.84 (d, J = 8.2 Hz, 1H), 7.66-7.43 (m, 6H), 7.43-7.33 (m, 2H), 7.06 (t, J = 2.1 Hz, 1H), 7.02-6.95 (m, 2H), 4.27 (s, 1H), 4.12 s, 1H), 3.72 (m, 3H), 1.68 (d, J = 6.7 Hz, 3H), 1.56 (d, J = 6.2 Hz, 9H); MS (ES+) = m/z: 468.23 (M + 1). |

TABLE 8-continued

| Ex. No. | Structure/Name | Ester Example | ¹H NMR/MS (ES+) |
|---|---|---|---|
| 140 | 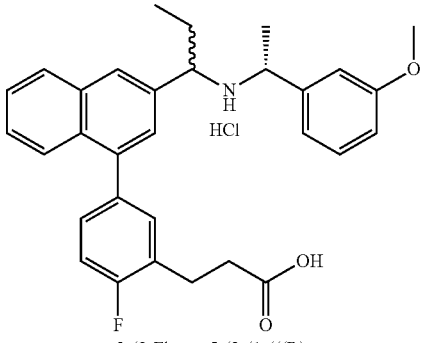<br>3-(2-Fluoro-5-(3-(1-(((R)-1-(3-methoxyphenyl)ethyl)amino)propyl)naphthalen-1-yl)phenyl)propanoic acid hydrochloride | 77 | Analysis of major diastereomer: ¹H NMR (400 MHz, DMSO-$d_6$) δ 12.27 (s, 1H), 10.05 (d, J = 7.3 Hz, 2H), 7.95 (dd, J = 8.0, 1.6 Hz, 1H), 7.90-7.82 (m, 2H), 7.65-7.55 (m, 2H), 7.48 (dd, J = 7.4, 2.2 Hz, 2H), 7.42 (ddd, J = 7.5, 5.0, 2.2 Hz, 1H), 7.38-7.32 (m, 2H), 7.07-7.04 m, 1H), 7.00-6.92 (m, 2H), 3.96 (p, J = 6.7 Hz, 1H), 3.86 (dq, J = 11.0, 5.3 Hz, 1H), 3.71 (s, 3H), 2.96 (t, J = 7.6 Hz, 2H), 2.63 (t, J = 7.6 Hz, 2H), 2.29 (td, J = 7.7, 3.7 Hz, 1H), 2.09 (s, 1H), 1.57 (d, J = 6.7 Hz, 3H), 0.63 (t, J = 7.3 Hz, 3H); MS (ES+) = m/z: 486.19 (M + 1). |
| 141 | 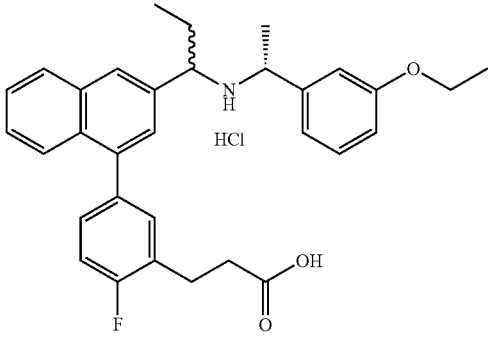 [SMILES: CCOc1cccc([C@@H](C)NC(CC)c2cc(-c3ccc(F)c(CCC(=O)O)c3)c3ccccc3c2)c1 ; Cl]<br>3-(5-(3-(1-(((R)-1-(3-Ethoxyphenyl)ethyl)amino)propyl)naphthalen-1-yl)-2-fluorophenyl)propanoic acid hydrochloride | 79 | Analysis of major diastereomer: ¹H NMR (400 MHz, DMSO-$d_6$) δ 12.25 (s, 1H), 10.25-10.02 (m, 2H), 7.96-7.91 (m, 1H), 7.90-7.86 (m, 1H), 7.84 (s, 1H), 7.65-7.55 (m, 2H), 7.54-7.46 (m, 2H), 7.41 (ddd, J = 7.6, 5.1, 2.2 Hz, 1H), 7.38-7.28 (m, 2H), 7.06-7.02 (m, 1H), 6.97-6.89 (m, 2H), 4.04-3.88 (m, 3H), 3.83 (td, J = 11.1, 5.3 Hz, 1H), 2.95 (t, J = 7.7 Hz, 2H), 2.64 (t, J = 7.6 Hz, 2H), 2.32 (dq, J = 11.6, 6.6, 5.4 Hz, 1H), 2.07 (dd,d, J = 13.5, 11.3, 7.2 Hz, 1H), 1.58 (d, J = 6.6 Hz, 3H), 1.29 (t, J = 6.9 H, 3H), 0.63 (t, J = 7.3 Hz, 3H); MS (ES+) = m/z: 500.18 (M + 1). |
| 142 | 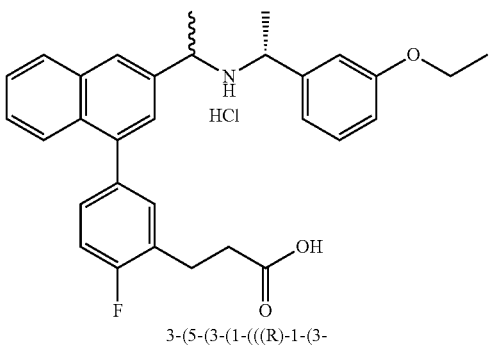<br>3-(5-(3-(1-(((R)-1-(3-Ethoxyphenyl)ethyl)amino)ethyl)naphthalen-1-yl)-2-fluorophenyl)propanoic acid hydrochloride | 80 | Analysis of major diastereomer: ¹H NMR (400 MHz, DMSO-$d_6$) δ 12.29 (s, 1H), 9.99 (d, J = 10.1 Hz, 2H), 7.94 (dd, J = 8.2, 1.5 Hz, 1H), 7.90 (d, J = 1.9 Hz, 1H), 7.86 (dd, J = 8.0, 1.5 Hz, 1H), 7.59 (dddd, J = 16.9, 8.2, 6.8, 1.4 Hz, 2H), 7.51-7.44 (m, 2H), 7.40 (ddd, J = 7.6, 5.1, 2. Hz, 1H), 7.38-7.30 (m, 2H), 7.06-7.03 (m, 1H), 6.94 (ddd, J = 7.8, 6.0, 2.0 Hz, 2H), 4.18 (q, J = 6.5 Hz, 1H), 4.06-3.86 (m, 3H), 2.95 (t, J = 7.6 Hz, 2H), 2.63 (t, J = 7.6 Hz, 2H), 1.69 (d, J = 6.7 Hz, 3H), 1.57 (d, J = 6.6 Hz, 3H), 1.29 (t, J = 6.9 Hz, 3H); MS (ES+) = m/z: 486.11 (M + 1). |

TABLE 8-continued

| Ex. No. | Structure/Name | Ester Example | ¹H NMR/MS (ES+) |
|---|---|---|---|
| 143 | 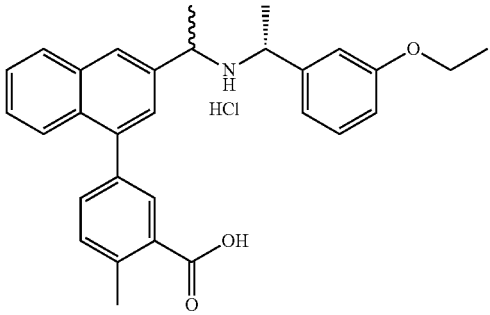 [SMILES: CCOc1cccc([C@@H](C)NC(C)c2cc(-c3ccc(C)c(C(=O)O)c3)c3ccccc3c2)c1 ; Cl]<br>5-(3-(1-(((R)-1-(3-Ethoxyphenyl)ethyl)amino)ethyl)naphthalen-1-yl)-2-methylbenzoic acid hydrochloride | 81 | Analysis of major diastereomer: ¹H NMR (400 MHz, DMSO-$d_6$) δ 9.68 (s, 2H), 7.96 (qd, J = 8.2, 1.9 Hz, 3H), 7.88-7.79 (m, 1H), 7.74-7.55 (m, 4H), 7.55-7.44 (m, 2H), 7.35 (t, J = 7.9 Hz, 1H), 7.08-6.89 (m, 4H), 4.27 (s, 1H), 4.11 (s, 1H), 3.99-3.86 (m, 2H), 2.64 (s, 3H), 1.67 (d, J = 6.7 Hz, 3H), 1.55 (d, J = 6.6 Hz, 3H), 1.29 (t, J = 7.0 Hz, 3H); MS (ES+) = m/z: 454.17 (M + 1). |
| 144 | 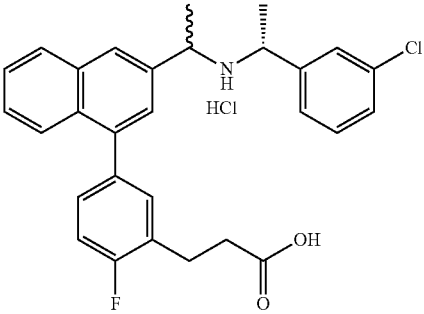 [SMILES: CC(N[C@H](C)c1cccc(Cl)c1)c1cc(-c2ccc(F)c(CCC(=O)O)c2)c2ccccc2c1 ; Cl]<br>3-(5-(3-(1-(((R)-1-(3-Chlorophenyl)ethyl)amino)ethyl)naphthalen-1-yl)-2-fluorophenyl)propanoic acid hydrochloride | 82 | Analysis of major diastereomer: ¹H NMR (400 MHz, DMSO-$d_6$) δ 12.27 (s, 1H), 10.19 (dd, J = 25.6, 14.2 Hz, 2H), 7.97-7.92 (m, 1H), 7.91 (d, J = 2.1 Hz, 1H), 7.89-7.82 (m, 1H), 7.60 (dddd, J = 17.6, 8.2, 6.8, 1.4 Hz, 2H), 7.53 (d, J = 2.6 Hz, 1H), 7.51-7.44 (m, 5H), 7.44-7.0 (m, 2H), 4.22 (p, J = 6.4 Hz, 1H), 4.12 (q, J = 6.5, 5.9 Hz, 1H), 2.96 (t, J = 7.6 Hz, 2H), 2.63 (t, J = 7.6 Hz, 2H), 1.71 (d, J = 6.6 Hz, 3H), 1.58 (d, J = 6.7 Hz, 3H); MS (ES+) = m/z: 476.11 (M + 1). |
| 145 | 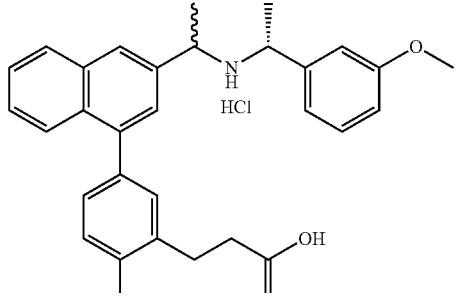<br>3-(5-(3-(1-(((R)-1-(3-Methoxyphenyl)ethyl)amino)ethyl)naphthalen-1-yl)-2-(trifluoromethyl)phenyl)propanoic acid hydrochloride | 83 | Analysis of major diastereomer: ¹H NMR (400 MHz, DMSO-$d_6$) δ 12.35 (s, 1H), 10.01 (t, J = 10.4 Hz, 1H), 9.65 (t, J = 10.6 Hz, 1H), 7.95-7.83 (m, 3H), 7.75 (d, J = 1.8 Hz, 1H), 7.69-7.55 (m, 6H), 7.45-7.37 (m, 1H), 7.06 (t, J = 7.5 Hz, 1H), 7.00 (d, J = 8.3 Hz, 1H), 4.37 (dd, = 12.7, 6.5 Hz, 1H), 4.22 (d, J = 9.2 Hz, 1H), 3.37 (d, J = 4.1 Hz, 4H), 3.11 (t, J = 7.9 Hz, 2H), 2.66 (dd, J = 8.9, 6.4 Hz, 2H), 1.72 (d, J = 6.7 Hz, 3H), 1.52 (d, J = 6.7 Hz, 3H); MS (ES+) = m/z: 522.2 (M + 1). |

TABLE 8-continued

| Ex. No. | Structure/Name | Ester Example | $^1$H NMR/MS (ES+) |
|---|---|---|---|
| 146 | 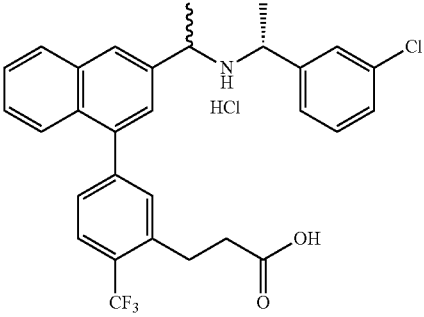 [SMILES: CC(N[C@H](C)c1cccc(Cl)c1)c1cc(-c2ccc(C(F)(F)F)c(CCC(=O)O)c2)c2ccccc2c1 ; Cl]<br>3-(5-(3-(1-(((R)-1-(3-Chlorophenyl)ethyl)amino)ethyl)naphthalen-1-yl)-2-(trifluoromethyl)phenyl)propanoic acid hydrochloride | 84 | Analysis of major diastereomer: $^1$H NMR (400 MHz, DMSO-d$_6$) δ 12.35 (s, 1H), 10.07 (s, 2H), 8.02-7.94 (m, 2H), 7.87 (dd, J = 15.5, 8.2 Hz, 2H), 7.70-7.55 (m, 5H), 7.54-7.41 (m, 4H), 4.27 (q, J = 6.4 Hz, 1H), 4.16 (q, J = 6.5 Hz, 1H), 3.11 (t, J = 7.9 Hz, 2H), 2.65 (dd, J = 9.1 6.8 Hz, 2H), 1.71 (d, J = 6.6 Hz, 3H), 1.58 (d, J = 6.7 Hz, 3H); MS (ES+) = m/z: 525.94 (M + 1). |
| 147 | 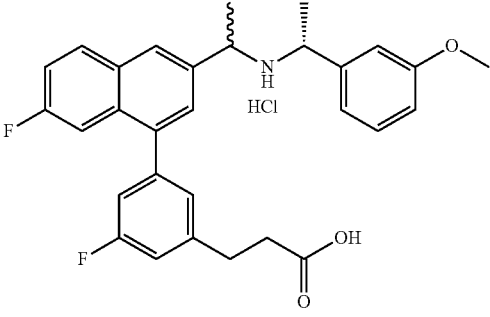 [SMILES: COc1cccc([C@@H](C)NC(C)c2cc(-c3cc(F)cc(CCC(=O)O)c3)c3cc(F)ccc3c2)c1 ; Cl]<br>3-(3-Fluoro-5-(7-fluoro-3-(1-(((R)-1-(3-methoxyphenyl)ethyl)amino)ethyl)naphthalen-1-yl)phenyl)propanoic acid hydrochloride | 85 | Analysis of major diastereomer: $^1$H NMR (400 MHz, DMSO-d$_6$) δ 12.22 (s, 1H), 10.07-9.92 (m, 2H), 8.07 (dd, J = 9.1, 5.9 Hz, 1H), 7.98 (d, J = 1.9 Hz, 1H), 7.61-7.47 (m, 3H), 7.35 (t, J = 7.9 Hz, 1H), 7.30-7.18 (m, 3H), 7.07 (t, J = 2.0 Hz, 1H), 6.98 (dd, J = 8.0, 2.1 Hz, 2H), .21 (p, J = 6.4 Hz, 1H), 4.03 (q, J = 6.6 Hz, 1H), 3.72 (s, 3H), 2.95 (t, J = 7.6 Hz, 2H), 2.66 (t, J = 7.6 Hz, 2H), 1.69 (d, J = 6.6 Hz, 3H), 1.57 (d, J = 6.6 Hz, 3H); MS (ES+) = m/z: 490.12 (M + 1). |
| 148 | 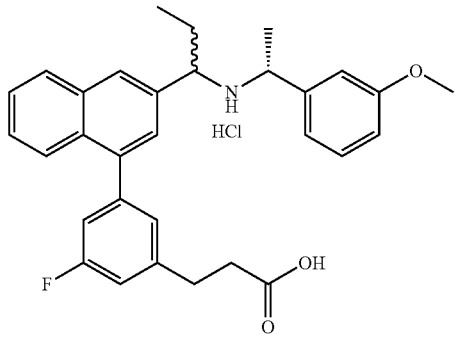 [SMILES: CCC(N[C@H](C)c1cccc(OC)c1)c1cc(-c2cc(F)cc(CCC(=O)O)c2)c2ccccc2c1 ; Cl]<br>3-(3-Fluoro-5-(3-(1-(((R)-1-(3-methoxyphenyl)ethyl)amino)propyl)naphthalen-1-yl)phenyl)propanoic acid hydrochloride | 86 | Analysis of major diastereomer: $^1$H NMR (400 MHz, DMSO-d$_6$) δ 12.24 (s, 1H), 9.96 (s, 2H), 7.99-7.93 (m, 1H), 7.89 (dd, J = 8.9, 7.2 Hz, 2H), 7.68-7.56 (m, 2H), 7.50 (s, 1H), 7.40-7.31 (m, 1H), 7.28-7.16 (m, 3H), 7.05-6.94 (m, 3H), 4.00 (p, J = 7.3, 6.4 Hz, 1H), 3.93 " 3.82 (m, 1H), 3.71 (s, 3H), 2.95 (t, J = 7.6 Hz, 2H), 2.66 (t, J = 7.6 Hz, 2H), 2.28 (ddd, J = 12.0, 7.5, 4.5 Hz, 1H), 2.13-2.02 (m, 1H), 1.57 (d, J = 6.6 Hz, 3H), 0.64 (t, J = 7.3 Hz, 3H); MS (ES+) = m/z: 486.15 (M + 1). |

TABLE 8-continued

| Ex. No. | Structure/Name | Ester Example | ¹H NMR/MS (ES+) |
|---|---|---|---|
| 149 | 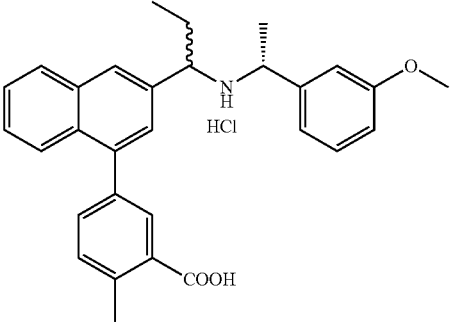 [SMILES: CCC(N[C@H](C)c1cccc(OC)c1)c1cc(-c2ccc(C)c(C(=O)O)c2)c2ccccc2c1 ; Cl]<br>5-(3-(1-(((R)-1-(3-Methoxyphenyl)ethyl)amino)propyl)naphthalen-1-yl)-2-methylbenzoic acid hydrochloride | 88 | Analysis of major diastereomer: ¹H NMR (400 MHz, DMSO-$d_6$) d 13.04 (s, 1H), 10.02 (dt, J = 32.6, 11.2 Hz, 2H), 7.96 (dd, J = 7.0, 1.8 Hz, 2H), 7.89-7.82 (m, 2H), 7.61 (dqd, J = 8.3, 6.9, 1.5 Hz, 3H), 7.53-7.46 (m, 2H), 7.34 (t, J = 7.9 Hz, 1H), 7.09-7.05 (m, 1H), 6.95 (ddd, J = 12.0, 7.5, 2.0 Hz, 2H), 3.99 (t, J = 9.2 Hz, 1H), 3.92-3.82 (m, 1H), 3.70 (s, 3H), 2.64 (s, 3H), 2.29 (ddd, J = 11.8, 7.8, 4.2 Hz, 1H), 2.13-2.00 (m, 1H), 1.57 (d, J = 6.7 Hz, 3H), 0.63 (t, J = 7.3 Hz, 3H) ); MS (ES+) = m/z: 454.58 (M + 1). |
| 150 | 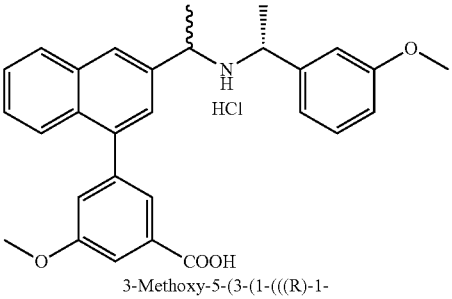<br>3-Methoxy-5-(3-(1-(((R)-1-(3-methoxyphenyl)ethyl)amino)ethyl)naphthalen-1-yl)benzoic acid hydrochloride | 68 | Analysis of major diastereomer: 1H NMR (400 MHz, DMSO-$d_6$) d 12.65 (s, 1H), 9.83 (s, 2H), 8.00-7.91 (m, 2H), 7.88-7.81 (m, 1H), 7.69-7.52 (m, 5H), 7.40-7.30 (m, 2H), 7.10-7.04 (m, 1H), 7.00-6.93 (m, 2H), 4.30-4.17 (m, 1H), 4.09 (dt, J = 12.2, 6.1 Hz, 1H), 3.90 (s, 3H), 3.71 (s, 3H), 1.68 (d, J = 6.7 Hz, 3H), 1.56 (d, J = 6.6 Hz, 3H) MS (ES+) = m/z: 456.54 (M + 1). |
| 151 | 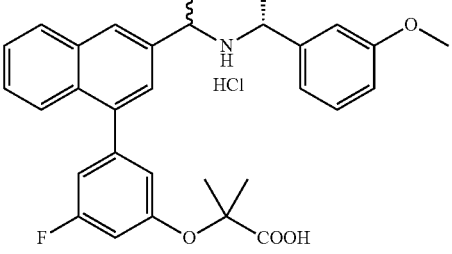<br>2-(3-Fluoro-5-(3-(1-(((R)-1-(3-methoxyphenyl)ethyl)amino)ethyl)naphthalen-1-yl)phenoxy)-2-methylpropanoic acid hydrochloride | 71 | Analysis of major diastereomer: 1H NMR (400 MHz, DMSO-$d_6$) d 13.25 (s, 1H), 9.91 (d, J = 34.6 Hz, 2H), 7.99-7.91 (m, 2H), 7.89-7.83 (m, 1H), 7.67-7.59 (m, 2H), 7.53 (d, J = 1.8 Hz, 1H), 7.35 (t, J = 7.9 Hz, 1H), 7.08-7.03 (m, 1H), 7.03-6.95 (m, 3H), 6.82-6.74 (m, 2H), 4.23 (d, J = 8.9 Hz, 1H), 4.10-4.01 (m, 1H), 3.72 (s, 3H), 1.68 (d, J = 6.7 Hz, 3H), 1.62-1.54 (m, 9H) ); MS (ES+) = m/z: 502.60 (M + 1). |

TABLE 8-continued

| Ex. No. | Structure/Name | Ester Example | $^1$H NMR/MS (ES+) |
|---|---|---|---|
| 152 | 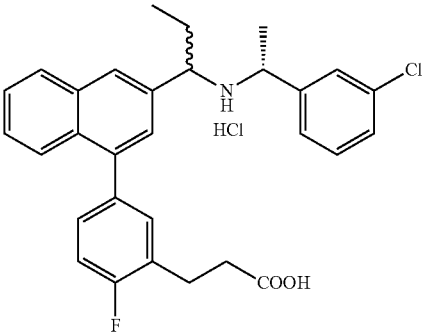 [SMILES: CCC(N[C@H](C)c1cccc(Cl)c1)c1cc(-c2ccc(F)c(CCC(=O)O)c2)c2ccccc2c1 ; Cl]<br>3-(5-(3-(1-(((R)-1-(3-Chlorophenyl)ethyl)amino)propyl)naphthalen-1-yl)-2-fluorophenyl)propanoic acid hydrochloride | 78 | Analysis of major diastereomer: 1H NMR (400 MHz, DMSO-$d_6$) d 12.27 (s, 1H), 10.12 (dd, J = 13.4, 6.6 Hz, 2H), 7.95 (dd, J = 8.0, 1.6 Hz, 1H), 7.89-7.82 (m, 2H), 7.66-7.56 (m, 2H), 7.48 (p, J = 2.3, 1.9 Hz, 5H), 7.42 (ddt, J = 12.1, 5.0, 2.3 Hz, 2H), 7.35 (dd, J = 9.9, 8.4 Hz, 1H), 4.08 (q, J = 6.5 Hz, 1H), 3.91 (tt, J = 10.5, 4.4 Hz, 1H), 2.96 (t, J = 7.7 Hz, 2H), 2.63 (t, J = 7.6 Hz, 2H), 2.29 (dt, J = 8.4, 5.6 Hz, 1H), 2.12-2.02 (m, 1H), 1.57 (d, J = 6.6 Hz, 3H), 0.64 (t, J = 7.3 Hz, 3H) ); MS (ES+) = m/z: 491.02 (M + 1). |

The Example-153 to 155 given in Table-9 were prepared by following the similar procedure as described in Example-24 or 49 by taking appropriate aldehyde and ketone Intermediate and appropriate amine Intermediate.

TABLE 9

| Ex. No. | Structure/Name | Intermediate | $^1$H NMR; Mass (m/z) |
|---|---|---|---|
| 153 | 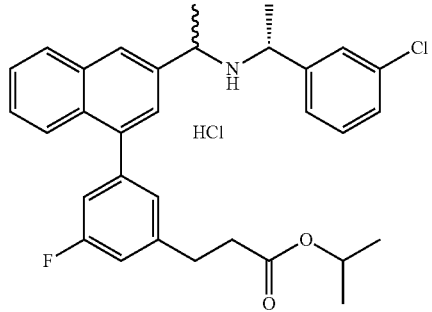 [SMILES: CC(C)OC(=O)CCc1cc(F)cc(-c2cc(C(C)N[C@H](C)c3cccc(Cl)c3)cc3ccccc23)c1 ; Cl]<br>Isopropyl 3-(3-(3-(1-(((R)-1-(3-chlorophenyl)ethyl)amino)ethyl) naphthalen-1-yl)-5-fluorophenyl) propanoate hydrochloride | 53 | Analysis of major diastereomer: $^1$H NMR (400 MHz, DMSO-$d_6$) d 10.12-9.91 (m, 2H), 7.99-7.91 (m, 2H), 7.85 (d, J = 8.1 Hz, 1H), 7.61 (dddd, J = 18.7, 8.2, 6.8, 1.4 Hz, 2H), 7.53-7.42 (m, 5H), 7.28-7.16 (m, 3H), 4.89 (hept, J = 6.3 Hz, 1H), 4.25 (q, J = 6.4 Hz, 1H), 4.15 (q, J = 6.5 Hz, 1H), 2.97 (t, J = 7.5 Hz, 2H), 2.69 (t, J = 7.5 Hz, 2H), 1.70 (d, J = 6.6 Hz, 3H), 1.58 (d, J = 6.6 Hz, 3H), 1.14 (d, J = 6.2 Hz, 6H); MS (ES+) = m/z: 518.16 (M + 1, 100%). |
| 154 | 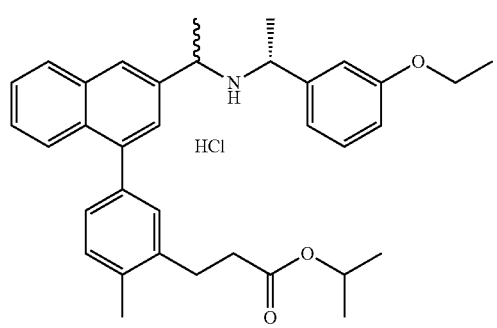 [SMILES: CCOc1cccc([C@@H](C)NC(C)c2cc(-c3ccc(C)c(CCC(=O)OC(C)C)c3)c3ccccc3c2)c1 ; Cl]<br>Isopropyl 3-(5-(3-(1-(((R)-1-(3-ethoxyphenyl)ethyl) amino) ethyl)naphthalen-1-yl)-2-methylphenyl) propanoate hydrochloride | 48 | $^1$H NMR (400 MHz, DMSO-$d_6$) δ 10.10-9.84 (m, 2H), 7.96-7.85 (m, 3H), 7.65-7.51 (m, 2H), 7.45 (d, J = 1.7 Hz, 1H), 7.33 (dt, J = 7.9, 4.1 Hz, 2H), 7.29-7.23 (m, 2H), 7.07-7.01 (m, 1H), 6.95 (td, J = 6.5, 3.2 Hz, 2H), 4.87 (hept, J = 6.3 Hz, 1H), 4.23-4.12 (m, 1H), 4.06-3.86 (m, 3H), 2.94 (t, J = 7.6 Hz, 2H), 2.62 (t, J = 7.6 Hz, 2H), 2.39 (s, 3H), 1.68 (d, J = 6.7 Hz, 3H), 1.57 (d, J = 6.6 Hz, 3H), 1.29 (t, J = 6.9 Hz, 3H), 1.10 (d, J = 6.2 Hz, 6H); MS (ES+) = m/z: 524.26 (M + 1, 100%). |

TABLE 9-continued

| Ex. No. | Structure/Name | Intermediate | $^1$H NMR; Mass (m/z) |
|---|---|---|---|
| 155 | 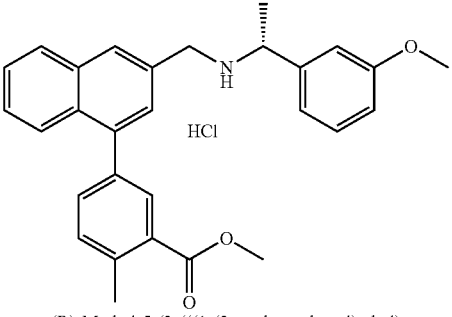<br>(R)-Methyl 5-(3-(((1-(3-methoxyphenyl)ethyl)amino)methyl) naphthalen-1-yl)-2-methylbenzoate hydrochloride | 26 | $^1$H NMR (400 MHz, DMSO-d$_6$) d 10.02 (d, J = 11.1 Hz, 1H), 9.71 (s, 1H), 8.06-7.99 (m, 2H), 7.93 (d, J = 2.0 Hz, 1H), 7.78 (d, J = 8.2 Hz, 1H), 7.67-7.51 (m, 5H), 7.38 (t, J = 7.9 Hz, 1H), 7.30-7.25 (m, 1H), 7.16 (d, J = 7.5 Hz, 1H), 6.98 (dd, J = 8.2, 2.5 Hz, 1H), 4.42 (t, J = 9.4 Hz, 1H), 4.33-4.21 (m, 1H), 4.03 (s, 1H), 3.84 (s, 3H), 3.77 (s, 3H), 2.63 (s, 3H), 1.64 (d, J = 6.6 Hz, 3H); MS (ES+) = m/z: 524.26 (M + 1, 100%). |

The below Examples-156 to 158 given in Table-10 were prepared by following the similar ester hydrolysis procedure as described in Example-89

TABLE 10

| Ex. No. | Structure/Name | Ester Example | $^1$H NMR; Mass (m/z) |
|---|---|---|---|
| 156 | 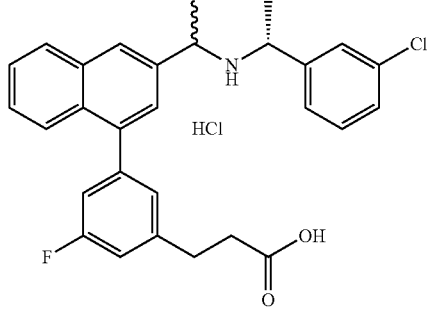 [SMILES: CC(N[C@H](C)c1cccc(Cl)c1)c1cc(-c2cc(F)cc(CCC(=O)O)c2)c2ccccc2c1 ; Cl]<br>3-(3-(3-(1-(((R)-1-(3-Chlorophenyl)ethyl)amino)ethyl)naphthalen-1-yl)-5-fluorophenyl)propanoic acid hydrochloride | 153 | Analysis of major diastereomer: $^1$H NMR (400 MHz, DMSO-d$_6$) d 12.24 (s, 1H), 10.15-9.94 (m, 2H), 7.99-7.94 (m, 1H), 7.94-7.91 (m, 1H), 7.90-7.85 (m, 1H), 7.61 (dddd, J = 14.8, 8.3, 6.8, 1.5 Hz, 2H), 7.52 (d, J = 1.8 Hz, 2H), 7.50-7.43 (m, 3H), 7.25 (td, J = 4.6, 2.7 Hz, 2H), 7.20 (dt, J = 9.5, 2.0 Hz, 1H), 4.25 (q, J = 6.5 Hz, 1H), 4.15 (q, J = 6.7 Hz, 1H), 2.95 (t, J = 7.6 Hz, 2H), 2.65 (t, J = 7.6 Hz, 2H), 1.70 (d, J = 6.7 Hz, 3H), 1.58 (d, J = 6.7 Hz, 3H); MS (ES+) = m/z: 476.12 (M + 1, 100%). |
| 157 | 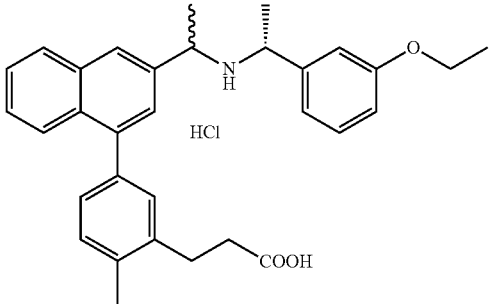 [SMILES: CCOc1cccc([C@@H](C)NC(C)c2cc(-c3ccc(C)c(CCC(=O)O)c3)c3ccccc3c2)c1 ; Cl]<br>3-(5-(3-(1-(((R)-1-(3-Ethoxyphenyl)ethyl)amino)ethyl)naphthalen-1-yl)-2-methylphenyl) propanoic acid hydrochloride | 154 | $^1$H NMR (400 MHz, DMSO-d$_6$) d 12.22 (s, 1H), 10.01 (d, J = 11.6 Hz, 2H), 7.98-7.88 (m, 3H), 7.58 (dddd, J = 18.7, 8.2, 6.9, 1.4 Hz, 2H), 7.47 (d, J = 1.7 Hz, 1H), 7.39-7.30 (m, 3H), 7.27 (dd, J = 7.6, 1.9 Hz, 1H), 7.08-7.03 (m, 1H), 6.99-6.92 (m, 2H), 4.18 (q, J = 6.5 Hz, 1H), 4.07-3.87 (m, 3H), 2.92 (t, J = 7.7 Hz, 2H), 2.58 (dd, J = 8.5, 7.1 Hz, 2H), 1.69 (d, J = 6.7 Hz, 3H), 1.57 (d, J = 6.7 Hz, 3H), 1.30 (t, J = 7.0 Hz, 3H) ); MS (ES+) = m/z: 482.18 (M + 1). |

TABLE 10-continued

| Ex. No. | Structure/Name | Ester Example | $^1$H NMR; Mass (m/z) |
|---|---|---|---|
| 158 | 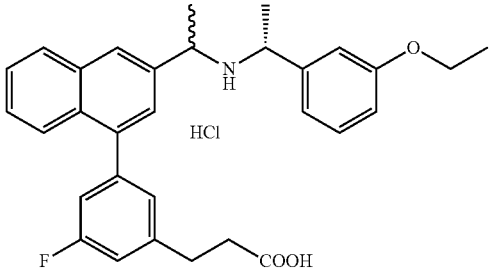 [SMILES: CCOc1cccc([C@@H](C)NC(C)c2cc(-c3cc(F)cc(CCC(=O)O)c3)c3ccccc3c2)c1 ; Cl]

3-(3-(3-(1-(((R)-1-(3-Ethoxyphenyl)ethyl)amino)ethyl)naphthalen-1-yl)-5-fluorophenyl)propanoic acid hydrochloride | 87 | 1H NMR (400 MHz, DMSO-$d_6$) d 12.23 (s, 1H), 9.89 (s, 2H), 8.00-7.92 (m, 2H), 7.91-7.85 (m, 1H), 7.68-7.57 (m, 2H), 7.51 (d, J = 1.7 Hz, 1H), 7.34 (t, J = 7.9 Hz, 1H), 7.29-7.23 (m, 2H), 7.20 (dt, J = 9.6, 1.9 Hz, 1H), 7.05-7.00 (m, 1H), 6.96 (dd, J = 8.3, 2.8 Hz, 2H), 4.22 (q, J = 6.6 Hz, 1H), 4.10-3.90 (m, 3H), 2.95 (t, J = 7.6 Hz, 2H), 2.66 (t, J = 7.6 Hz, 2H), 1.69 (d, J = 6.7 Hz, 3H), 1.57 (d, J = 6.7 Hz, 3H), 1.30 (t, J = 6.9 Hz, 4H) ); MS (ES+) = m/z: 486.18 (M + 1). |

The Examples 159 to 165 given in Table-11 were prepared by following the similar procedure as described in Example-6 by taking appropriate ketone Intermediate and appropriate amine Intermediate.

TABLE 11

| Ex. No. | Structure | Intermediate | $^1$H NMR/MS(ES+) |
|---|---|---|---|
| 159 | 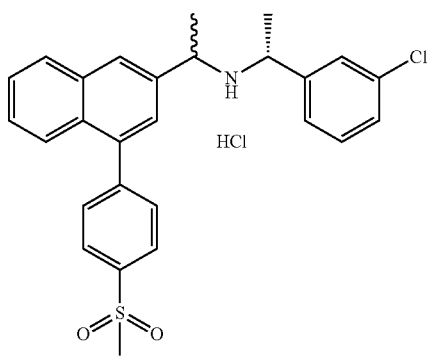 [SMILES: CC(N[C@H](C)c1cccc(Cl)c1)c1cc(-c2ccc(S(C)(=O)=O)cc2)c2ccccc2c1 ; Cl]

(1R)-1-(3-Chlorophenyl)-N-(1-(4-(4-(methylsulfonyl)phenyl)naphthalen-2-yl)ethyl)ethanamine hydrochloride | 19 | 1H NMR (400 MHz, DMSO-$d_6$) d 10.10 (d, J = 7.3 Hz, 2H), 8.18-8.08 (m, 2H), 8.04-7.93 (m, 2H), 7.82 (dt, J = 8.5, 2.1 Hz, 3H), 7.70-7.41 (m, 7H), 4.27 (q, J = 6.5 Hz, 1H), 4.16 (p, J = 6.6 Hz, 1H), 3.34 (s, 3H), 1.71 (d, J = 6.6 Hz, 3H), 1.58 (d, J = 6.7 Hz, 3H); LCMS: m/z = 464.05 (M + 1, 100%). |
| 160 | 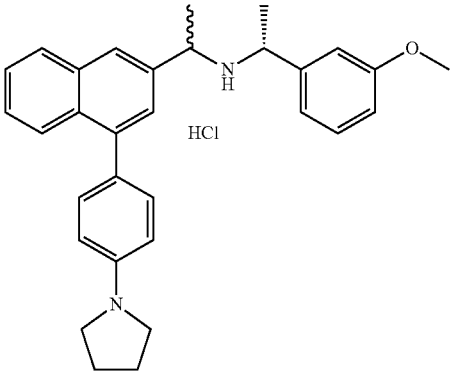 [SMILES: COc1cccc([C@@H](C)NC(C)c2cc(-c3ccc(N4CCCC4)cc3)c3ccccc3c2)c1 ; Cl]

(1R)-1-(3-Chlorophenyl)-N-(1-(4-(4-(pyrrolidin-1-yl) phenyl)naphthalen-2-yl)ethyl)ethanamine hydrochloride | 20 | $^1$H NMR (400 MHz, DMSO-$d_6$) δ 10.25-9.92 (m, 2H), 8.01-7.95 (m, 1H), 7.91 (dd, J = 8.0, 1.6 Hz, 1H), 7.82 (d, J = 1.9 Hz, 1H), 7.65-7.50 (m, 3H), 7.45 (d, J = 1.7 Hz, 1H), 7.35 (dd, J = 12.0, 8.1 Hz, 3H), 7.13-7.08 (m, 1H), 6.98 (dd, J = 8.4, 2.5 Hz, 2H), 6.77 (d, J = 8.8 Hz, 2H), 4.15 (d, J = 8.6 Hz, 1H), 4.01 (dt, J = 12.5, 7.5 Hz, 1H), 3.73 (s, 3H), 3.34 (t, J = 6.8 Hz, 4H), 2.02 (td, J = 7.8, 7.0, 3.7 Hz, 5H), 1.70 (d, J = 6.8 Hz, 3H), 1.58 (d, J = 6.6 Hz, 3H) ); LCMS: m/z = 450.54 (M + 1, 100%). |

TABLE 11-continued

| Ex. No. | Structure | Intermediate | ¹H NMR/MS(ES+) |
|---|---|---|---|
| 161 | 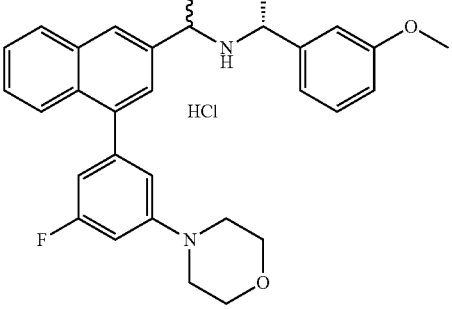<br>1-(4-(3-Fluoro-5-morpholinophenyl)naphthalen-2-yl)-N-((R)-1-(3-methoxyphenyl)ethyl)ethanamine hydrochloride | 21 | 1H NMR (400 MHz, DMSO-$d_6$) d 10.13 (s, 2H), 7.92 (tt, J = 10.2, 3.1 Hz, 3H), 7.64-7.55 (m, 2H), 7.54 (d, J = 1.7 Hz, 1H), 7.33 (t, J = 7.8 Hz, 1H), 7.11-7.07 (m, 1H), 6.99-6.86 (m, 4H), 6.74 (dt, J = 9.2, 1.6 Hz, 1H), 4.15 (q, J = 6.4 Hz, 1H), 3.80-3.72 (m, 5H), 3.71 (s, 3H), 3.23 (dd, J = 6.3, 3.7 Hz, 4H), 1.70 (d, J = 6.7 Hz, 3H), 1.58 (d, J = 6.7 Hz, 3H) ); LCMS: m/z = 484.19 (M + 1, 100%). |
| 162 | 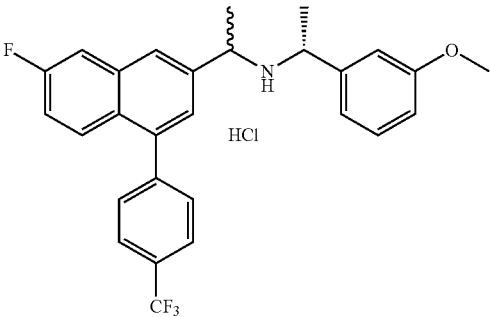 [SMILES: COc1cccc([C@@H](C)NC(C)c2cc(-c3ccc(C(F)(F)F)cc3)c3ccc(F)cc3c2)c1 ; Cl]<br>(1R)-1-(3-methoxyphenyl)-N-(1-(7-fluoro-4-(4-(trifluoromethyl)phenyl)naphthalen-2-yl)ethyl)ethanamine hydrochloride | 22 | 1H NMR (400 MHz, DMSO-$d_6$) d 10.00 (s, 2H), 8.06-7.91 (m, 4H), 7.87 (dd, J = 9.4, 5.5 Hz, 1H), 7.78 (t, J = 9.6 Hz, 3H), 7.64-7.47 (m, 3H), 7.42-7.28 (m, 1H), 7.25-7.04 (m, 2H), 7.02-6.88 (m, 3H), 4.23 (q, J = 6.5 Hz, 1H), 4.08 (q, J = 6.6 Hz, 1H), 3.72 (s, 3H), 1.69 (d, J = 6.8 Hz, 3H), 1.58 (d, J = 6.6 Hz, 3H) ); LCMS: m/z = 468.11 (M + 1, 100%). |
| 163a, 163b | 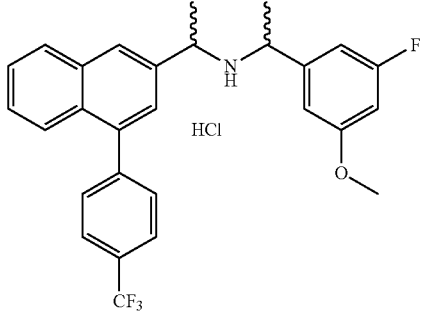<br>1-(3-Fluoro-5-methoxyphenyl)-N-(1-(4-(4-(trifluoromethyl)phenyl) naphthalen-2-yl)ethyl)ethanamine hydrochloride | 16 | Analysis of minor isomer (a):¹H NMR (400 MHz, DMSO-$d_6$) d 10.07 (s, 2H), 8.03-7.97 (m, 2H), 7.94 (d, J = 8.0 Hz, 2H), 7.84-7.79 (m, 1H), 7.79-7.71 (m, 3H), 7.67-7.56 (m, 3H), 7.09-6.92 (m, 2H), 6.88 (tt, J = 4.7, 2.2 Hz, 2H), 4.27 (dt, J = 13.2, 7.0 Hz, 1H), 4.14-4.03 (m, 1H), 3.72 (d, J = 3.7 Hz, 4H), 1.72 (t, J = 6.3 Hz, 3H), 1.59 (dd, J = 18.7, 6.7 Hz, 4H) ); LCMS: m/z = 468.10 (M + 1, 100%).<br>Analysis of major isomer (b): ¹H NMR (400 MHz, DMSO-$d_6$) d 10.09 (d, J = 10.6 Hz, 2H), 7.99 (dt, J = 4.4, 1.9 Hz, 2H), 7.95 (d, J = 8.0 Hz, 2H), 7.82 (d, J = 8.3 Hz, 1H), 7.77 (d, J = 8.0 Hz, 2H), 7.70-7.55 (m, 3H), 6.95 (dt, J = 9.5, 1.9 Hz, 1H), 6.92-6.85 (m, 2H), 4.34-4.22 (m, 1H), 4.08 (p, J = 6.8 Hz, 1H), 3.73 (s, 3H), 1.71 (d, J = 6.7 Hz, 3H), 1.56 (d, J = 6.6 Hz, 3H) ); LCMS: m/z = 468.10 (M + 1, 100%) |

TABLE 11-continued

| Ex. No. | Structure | Intermediate | ¹H NMR/MS(ES+) |
|---|---|---|---|
| 164 | 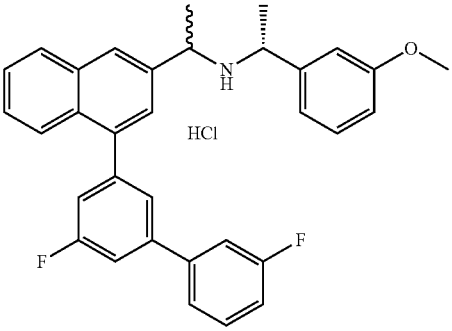 [SMILES: COc1cccc([C@@H](C)NC(C)c2cc(-c3cc(F)cc(-c4cccc(F)c4)c3)c3ccccc3c2)c1 ; Cl]<br>1-(4-(3',5-Difluoro-[1,1'-biphenyl]-3-yl)naphthalen-2-yl)-N-((R)-1-(3-methoxy phenyl)ethyl) ethanamine hydrochloride | 69 | m/z: 494.11 (M + 1, 100%). |
| 165 | 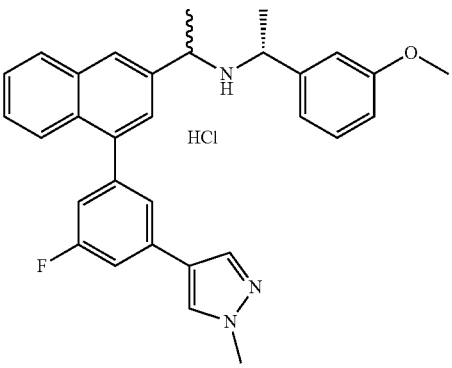 [SMILES: COc1cccc([C@@H](C)NC(C)c2cc(-c3cc(F)cc(-c4cnn(C)c4)c3)c3ccccc3c2)c1 ; Cl]<br>1-(4-(3-Fluoro-5-(1-methyl-1H-pyrazol-4-yl)phenyl)naphthalen-2-yl)-N-((R)-1-(3-methoxy phenyl)ethyl)ethanamine hydrochloride | 70 | m/z: 480.78 (M + 1, 100%). |

The below Example-166 and 167 ester compounds were prepared by following the similar procedure as described in Example-49 by using corresponding intermediates.

Example-166

Isopropyl 5-(3-(1-(((R)-1-(3-fluoro-5-methoxyphenyl)ethyl) naphthalen-1-yl)-2-methylbenzoate

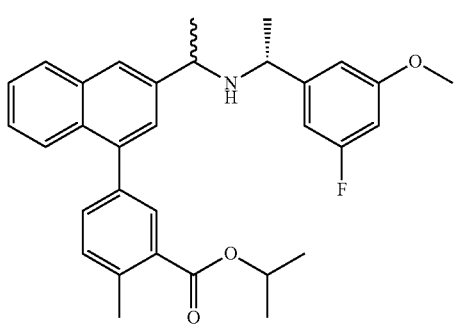 [SMILES: COc1cc(F)cc([C@@H](C)NC(C)c2cc(-c3ccc(C)c(C(=O)OC(C)C)c3)c3ccccc3c2)c1]

¹H NMR (400 MHz, DMSO-d₆) δ 7.99-7.92 (m, 1H), 7.86 (d, J=2.0 Hz, 1H), 7.81 (s, 1H), 7.76-7.69 (m, 2H), 7.61 (dd, J=7.8, 2.0 Hz, 1H), 7.57-7.39 (m, 4H), 6.78-6.59 (m, 3H), 5.15 (p, J=6.3 Hz, 2H), 3.77-3.68 (m, 3H), 2.66-2.54 (m, 4H), 1.37-1.26 (m, 9H), 1.26-1.20 (m, 3H); MS (ES+) m/z=500.18 (M+1, 100%).

Example-167

Isopropyl 3-(3-fluoro-5-(3-(1-(((R)-1-(3-fluoro-5-methoxyphenyl)ethyl)amino)ethyl)naphthalen-1-yl) phenyl)propanoate

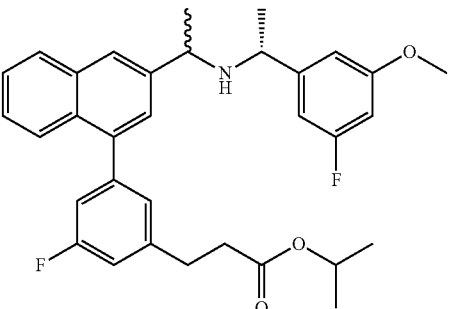

¹H NMR (400 MHz, DMSO-d₆) δ 7.99-7.89 (m, 1H), 7.85-7.75 (m, 1H), 7.71 (d, J=1.7 Hz, 1H), 7.60-7.38 (m, 3H), 7.26-7.11 (m, 3H), 6.79-6.61 (m, 3H), 4.93-4.83 (m, 1H), 3.73 (s, 3H), 3.58 (d, J=6.9 Hz, 1H), 3.40 (t, J=6.2 Hz, 1H), 2.96 (t, J=7.3 Hz, 2H), 2.69 (t, J=7.3 Hz, 2H), 1.35-1.26 (m, 3H), 1.19 (dd, J=7.0, 1.4 Hz, 3H), 1.12 (d, J=6.3 Hz, 6H); MS (ES+) m/z=532.17 (M+1, 100%).

The below Example-168 and 169 compounds were prepared by following the similar hydrolysis procedure as described in Example-89 by using Example-166 and 167 respectively.

Example-168

5-(3-(1-(((R)-1-(3-Fluoro-5-methoxyphenyl)ethyl)amino)ethyl)naphthalen-1-yl)-2-methyl benzoic acid hydrochloride

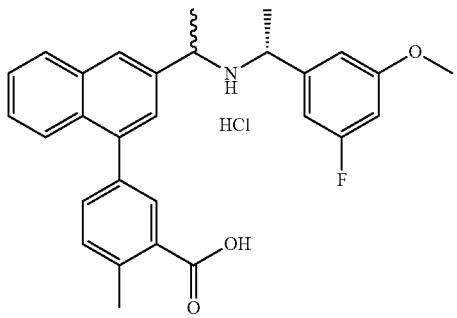 [SMILES: COc1cc(F)cc([C@@H](C)NC(C)c2cc(-c3ccc(C)c(C(=O)O)c3)c3ccccc3c2)c1 ; Cl]

MS (ES+) m/z=458.54 (M+1, 100%).

Example-169

3-(3-Fluoro-5-(3-(1-(((R)-1-(3-fluoro-5-methoxyphenyl)ethyl)amino)ethyl)naphthalen-1-yl) phenyl) propanoic acid hydrochloride

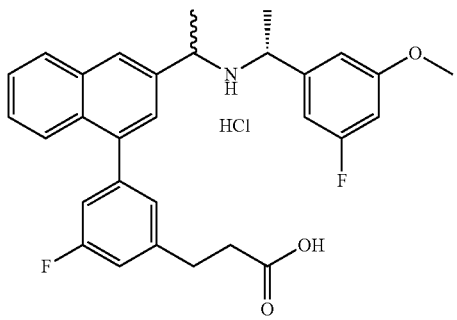 [SMILES: COc1cc(F)cc([C@@H](C)NC(C)c2cc(-c3cc(F)cc(CCC(=O)O)c3)c3ccccc3c2)c1 ; Cl]

MS (ES+) m/z=490.55 (M+1, 100%).

In-Vitro Pharmacological Activity

Certain illustrative compounds within the scope of the invention are screened for CaSR activity according to the procedure given below. The screening of the compounds may also be carried by other methods and procedures known to skilled in the art.

In-Vitro Assay Method of Calcimimetics Through Modulation of Calcium Sensing Receptor (CaSR):

The ability of the compounds to modulate Calcium sensing receptor is determined by measuring an increase in intracellular calcium $[Ca^{2+}]i$. Stably transfected HEK293 cells expressing hCaSR_pTriEx-3 hygro vector are developed. Cells are grown overnight on a 96-well plate to 80% confluency in Ham's F12 containing 20% FBS at 37° C., 5% $CO_2$. Subsequently, cells are washed extensively with 20 mM HEPES buffer containing 126 mM $NaCl_2$, 1 mM $MgCl_2$ and 4 mM KCl to remove serum components that might interfere with the assay. Cells are loaded with calcium sensing Fluo4NW dye in HEPES base buffer containing 0.1% BSA and 1 mg/ml glucose for 30 minutes to measure changes in intracellular calcium. The activities of the compounds are measured in FLIPR using 0.3 mM $CaCl_2$ in 20 mM HEPES base buffer. The effectiveness of the compound to modulate receptor activity is determined by calculating the $EC_{50}$ responses for that compound in an 8-point assay and plotted using GraphPad Prism 5.

The compounds prepared were tested using the above assay procedure and the results obtained are given below. The $EC_{50}$ (nM) values of few representative compounds are set forth in Table-12.

The in-vitro activity data has been given in Table-12 for representative compounds.

TABLE-12

| Example number | $EC_{50}$ in range |
|---|---|
| 1, 3, 6, 7, 8, 9b, 10, 11, 12, 13, 14, 15, 16, 18a, 19, 20, 21, 22, 23, 45, 90, 91, 97, 98, 108, 110, 118, 120, 122, 123, 126, 129, 133, 134, 135, 137, 142, 155, 157, 158, 161, 162 | less than 20 nM |
| 2, 4, 5, 9a, 89, 99, 100, 102, 103, 107, 114b, 116, 124, 131, 136, 141, 143, 144, 153, 156, 163b | between 20.01 to 50 nM |
| 17, 92, 93, 94, 95, 96, 101, 102, 104, 105, 106, 109, 111, 112, 113, 115, 117, 119, 121, 125, 127, 128, 130, 132, 138, 139, 140, 145, 146, 147, 148, 149, 150, 151, 152, 154, 159, 163a | between 50.01 to 400 nM |

Thus, the above in-vitro assay method shows that the compounds of the invention were found to exhibit agonistic activity for CaSR, thereby showing utility for treating diseases, disorders associated with the modulation of CaSR.

In-Vivo Activity in CKD Wistar Rats:

Animals were fed with 0.75% adenine diet for a period of 28 days for development of chronic kidney disease (CKD). After measurement of plasma PTH on day 28, animals were randomized based on plasma PTH (intact PTH) levels before using them for the study. Overnight fasted animals were bled retro-orbitally to collect basal blood sample (0.5 ml). Rats were dosed orally with vehicle and with test compounds Formulated in PEG 300:PG:Captisol (20:15:65). Six to eight animals were used in each group then compounds of the invention were administered at 1 mg/kg dose. Post 2 h oral dosing animals were fed with feed and water ad libitum. Post treatment blood samples were collected by retro-orbital bleeding under light ether anesthesia at different time points for plasma PTH estimation. Plasma PTH was measured using sandwich ELISA kits (Immunotopics, USA). Percentage suppression of plasma PTH was calculated with respect to individual basal untreated values by using the following Formula $$\text{Percent suppression} = \frac{\text{Pre-treated individual value} - \text{Post-treated individual}}{\text{Pre-treated individual value}} \times 100$$

Thus, the above in-vivo method shows that the compounds of the invention were found to exhibit suppress plasma PTH levels, thereby showing utility for treating diseases, disorders associated with the modulation of CaSR.

In-Vivo Activity in Nephrectomized SD Rats:

"Male, Sprague Dawley rats weighing 200-270 g were used for the study. In 5/6 nephrectomized rat model of CKD, the original renal functional mass was reduced to five sixths (⅚) by two step surgery. In a first surgery, under anesthesia the abdominal cavity was cut opened and the left kidney was decapsulated. The 1/3 region of kidney at both ends was excised and the abdominal incision was closed. One week after the first surgery, the right kidney was removed completely by transecting the vessels and ureter. After the second surgery, all nephrectomized animals were fed with 1.2% phosphorus diet and the Sham control animals with normal control diet till the termination of the study. Post three weeks of second surgery, animals were bled retro-orbitally to collect blood for estimation of ionized Calcium in whole blood and biochemical parameters like Phosphorous, Urea, BUN, Creatinine and intact PTH in plasma. Plasma iPTH was measured using Rat Bioactive intact PTH ELISA kits by sandwich ELISA method. After confirmation of desired iPTH levels, animals were randomized based on iPTH levels into different treatment and vehicle control groups with 8-10 animals in each group and 8 animals were kept on sham control group. Post randomization, treatment was initiated immediately with test and reference article for 27 days with daily record of body weight. During treatment, on day 14 and day 27 post 24 h last dose, all animals were bled retro-orbitally for estimation of biochemical parameters as mentioned above. To evaluate the acute effect, plasma iPTH was measured on day 27 post 2 h last dose.

Percentage suppression of plasma iPTH was calculated by using the following Formula:

$$\text{Percent suppression} = \frac{\text{mean of vehicle} - \text{post-treated individual value}}{\text{mean of vehicle}} \times 100$$

Thus, the above in-vivo method shows that the compounds of the invention were found to exhibit suppress plasma iPTH levels, thereby showing utility for treating diseases, disorders associated with the modulation of CaSR.

Although certain embodiments and Examples have been described in detail above, those having ordinary skill in the art will clearly understand that many modifications are possible in the embodiments and Examples without departing from the teachings thereof. All such modifications are intended to be encompassed within the below claims of the invention.

The invention claimed is:
1. A compound having the Formula (I):

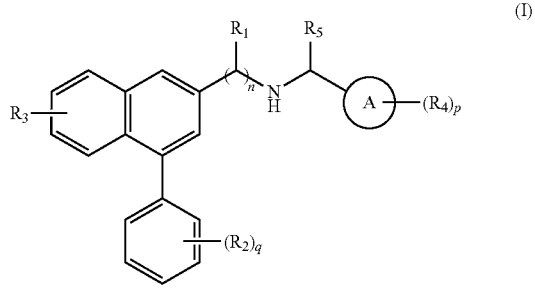

ring A is phenyl or naphthyl;
$R_1$ is hydrogen or substituted or unsubstituted ($C_1$-$C_6$) alkyl;
$R_2$, which may be same or different at each occurrence, is independently selected from halogen, cyano, substituted or unsubstituted ($C_1$-$C_6$)alkyl, substituted or unsubstituted ($C_1$-$C_6$)haloalkyl, substituted or unsubstituted ($C_1$-$C_6$)hydroxyalkyl, —X—C(O)—Z, —$OR_9$, —$NR_7R_8$, —$NR_7C(O)R_6$, —$S(O)_{0-2}R_6$, —$S(O)_2NR_7R_8$, —$NR_7S(O)_2R_6$, substituted or unsubstituted ($C_3$-$C_{12}$)cycloalkyl, substituted or unsubstituted phenyl, substituted or unsubstituted 5- to 6-membered heteroaryl, substituted or unsubstituted 5- to 6-membered heterocyclyl and ring D;
ring D is

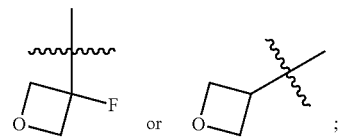 [SMILES: *C1(F)COC1 ; *C1COC1]

X is selected from a bond, —$(CR_aR_b)_m$—, —$NR_2$—, —$O(CR_aR_b)_m$—, —$(CR_aR_b)_mO$—, —$C(O)NR_{12}$—, —$(CR_aR_b)_mO$—$(CR_aR_b)_m$— and —$C(O)NR_{12}(CR_aR_b)_m$—;
$R_a$ and $R_b$ which may be same or different at each occurrence, are independently selected from hydrogen, halogen, hydroxy, substituted or unsubstituted ($C_1$-$C_6$) alkyl, substituted or unsubstituted ($C_1$-$C_6$)haloalkyl and substituted or unsubstituted ($C_3$-$C_6$)cycloalkyl; or $R_a$ and $R_b$, together with the carbon atom to which they are attached, form a substituted or unsubstituted 3 to 6 membered saturated carbocyclic ring;
Z is —$OR_{10}$ or —$NR_7R_8$;
$R_3$ is selected from hydrogen, halogen, substituted or unsubstituted ($C_1$-$C_6$)alkyl, substituted or unsubstituted ($C_1$-$C_6$)haloalkyl, —$OR_9$, and substituted or unsubstituted ($C_3$-$C_{12}$)cycloalkyl;
$R_4$, which may be same or different at each occurrence, is independently selected from halogen, substituted or unsubstituted ($C_1$-$C_6$)alkyl, substituted or unsubstituted ($C_1$-$C_6$)haloalkyl, substituted or unsubstituted ($C_1$-$C_6$) alkoxyalkyl, —$SF_5$ and —$OR_9$;
$R_5$ is substituted or unsubstituted ($C_1$-$C_6$)alkyl;
$R_6$ is selected from substituted or unsubstituted ($C_1$-$C_6$) alkyl, substituted or unsubstituted ($C_3$-$C_{12}$)cycloalkyl and substituted or unsubstituted ($C_6$-$C_{14}$)aryl;
$R_7$ and $R_8$, which may be same or different at each occurrence, are independently selected from hydrogen, substituted or unsubstituted ($C_1$-$C_6$)alkyl, —$(CR_aR_b)_{1-2}R_{11}$, —$(CR_cR_d)_m$—OH and substituted or unsubstituted ($C_3$-$C_{12}$)cycloalkyl;
$R_c$ and $R_d$ which may be same or different at each occurrence, are independently hydrogen or substituted or unsubstituted ($C_1$-$C_6$)alkyl;
$R_9$ is independently selected from hydrogen, substituted or unsubstituted ($C_1$-$C_6$)alkyl, substituted or unsubstituted ($C_1$-$C_6$)haloalkyl, substituted or unsubstituted ($C_1$-$C_6$)alkoxyalkyl and substituted or unsubstituted ($C_3$-$C_{12}$)cycloalkyl;
$R_{10}$ is selected from hydrogen, substituted or unsubstituted ($C_1$-$C_6$)alkyl and —$(CR_aR_b)_{1-2}$phenyl;
$R_{11}$ is substituted or unsubstituted phenyl, wherein the substituents are selected from halogen, ($C_1$-$C_6$)alkyl and —$OR_9$;
$R_{12}$ is hydrogen or substituted or unsubstituted ($C_1$-$C_6$) alkyl;
'm' is an integer ranging from 1 to 3, both inclusive;
'n' is an integer ranging from 1 to 3, both inclusive;
'p' is an integer ranging from 0 to 3, both inclusive; and 'q' is an integer ranging from 1 to 3, both inclusive;
or a pharmaceutically acceptable salt thereof.

2. The compound of claim 1 having the Formula (II):

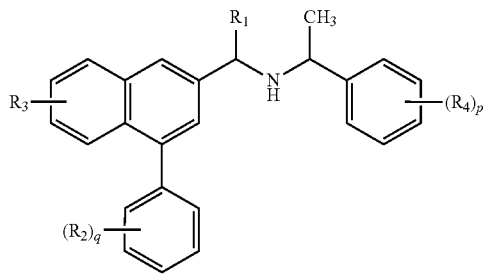

(II)

wherein, $R_1$ is hydrogen or substituted or unsubstituted $(C_1-C_6)$ alkyl;

$R_2$, which may be same or different at each occurrence, is independently selected from halogen, substituted or unsubstituted $(C_1-C_6)$alkyl, substituted or unsubstituted $(C_1-C_6)$haloalkyl, —X—C(O)—Z, —$OR_9$ and —S$(O)_{0-2}R_6$;

X is selected from a bond, —$(CR_aR_b)_m$—, —$O(CR_aR_b)_m$— and —$(CR_aR_b)_mO$—;

$R_a$ and $R_b$ which may be same or different at each occurrence, are independently selected from hydrogen, halogen, hydroxy and substituted or unsubstituted $(C_1-C_6)$alkyl;

Z is —$OR_{10}$ or —$NR_7R_8$;

$R_3$ is selected from hydrogen, halogen and substituted or unsubstituted $(C_1-C_6)$alkyl;

$R_4$, which may be same or different at each occurrence, is independently selected from halogen, substituted or unsubstituted $(C_1-C_6)$alkyl, substituted or unsubstituted $(C_1-C_6)$haloalkyl, substituted or unsubstituted $(C_1-C_6)$alkoxyalkyl and —$OR_9$;

$R_6$ is substituted or unsubstituted $(C_1-C_6)$alkyl or substituted or unsubstituted $(C_3-C_{12})$cycloalkyl;

$R_7$ and $R_8$, which may be same or different at each occurrence, are independently selected from hydrogen, substituted or unsubstituted $(C_1-C_6)$alkyl, —$(CR_aR_b)_{1-2}R_{11}$ and substituted or unsubstituted $(C_3-C_{12})$cycloalkyl;

$R_9$ is selected from hydrogen, substituted or unsubstituted $(C_1-C_6)$alkyl, substituted or unsubstituted $(C_1-C_6)$haloalkyl, substituted or unsubstituted $(C_1-C_6)$alkoxyalkyl and substituted or unsubstituted $(C_3-C_{12})$cycloalkyl;

$R_{10}$ is hydrogen or substituted or unsubstituted $(C_1-C_6)$ alkyl;

$R_{11}$ is substituted or unsubstituted phenyl, wherein the substituents are selected from halogen, $(C_1-C_6)$alkyl and $(C_1-C_6)$alkoxy;

'm' is an integer ranging from 1 to 3, both inclusive;

'p' is an integer ranging from 0 to 2, both inclusive; and

'q' is an integer ranging from 1 to 3, both inclusive;

or a pharmaceutically acceptable salt thereof.

3. The compound of claim 1 having the Formula (III):

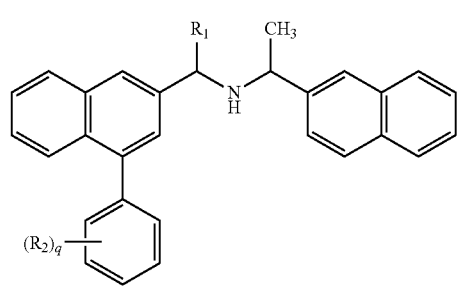

(III)

$R_1$ is hydrogen or substituted or unsubstituted $(C_1-C_6)$ alkyl;

$R_2$, which may be same or different at each occurrence, is independently selected from halogen, substituted or unsubstituted $(C_1-C_6)$alkyl, substituted or unsubstituted $(C_1-C_6)$haloalkyl and —X—C(O)—Z;

X is selected from a bond, —$(CR_aR_b)_m$—, —$O(CR_aR_b)_m$— and —$(CR_aR_b)_mO$—;

$R_a$ and $R_b$ which may be same or different at each occurrence, are independently selected from hydrogen, halogen, hydroxy and substituted or unsubstituted $(C_1-C_6)$alkyl;

Z is —$OR_{10}$ or —$NR_7R_8$;

$R_7$ and $R_8$, which may be same or different at each occurrence, are independently selected from hydrogen, substituted or unsubstituted $(C_1-C_6)$alkyl and substituted or unsubstituted $(C_3-C_{12})$cycloalkyl;

$R_{10}$ is hydrogen or substituted or unsubstituted $(C_1-C_6)$ alkyl;

'm' is an integer ranging from 1 to 3, both inclusive; and

'q' is an integer ranging from 1 to 3, both inclusive;

or a pharmaceutically acceptable salt thereof.

4. The compound of claim 1 having the Formula (IV):

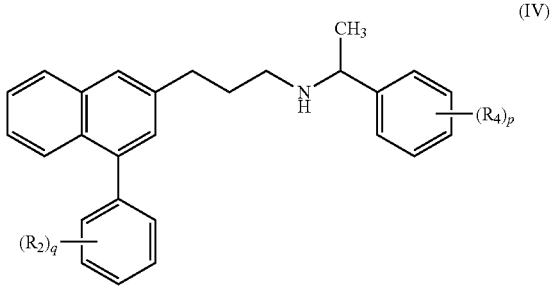

(IV)

$R_2$, which may be same or different at each occurrence, is independently selected from halogen, substituted or unsubstituted $(C_1-C_6)$alkyl and substituted or unsubstituted $(C_1-C_6)$haloalkyl;

$R_4$, which may be same or different at each occurrence, is independently selected from halogen, substituted or unsubstituted $(C_1-C_6)$alkyl, substituted or unsubstituted $(C_1-C_6)$haloalkyl, and —$OR_9$;

$R_9$ is hydrogen or substituted or unsubstituted $(C_1-C_6)$ alkyl;

'p' is an integer ranging from 0 to 2, both inclusive; and

'q' is an integer ranging from 1 to 3, both inclusive;

or a pharmaceutically acceptable salt thereof.

5. The compound of claim 1 having the Formula (V):

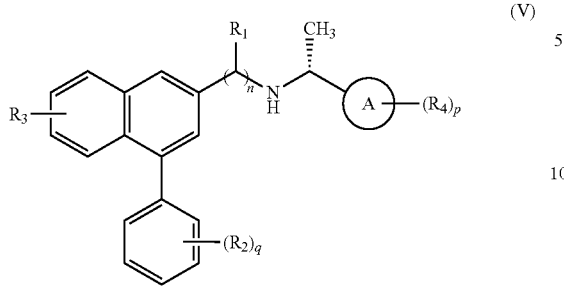

(V)

wherein, ring A is phenyl or naphthyl;

$R_1$ is hydrogen or substituted or unsubstituted $(C_1-C_6)$alkyl;

$R_2$, which may be same or different at each occurrence, is independently selected from halogen, substituted or unsubstituted $(C_1-C_6)$alkyl, substituted or unsubstituted $(C_1-C_6)$haloalkyl, —X—C(O)—Z, —OR$_9$ and —S(O)$_{0-2}$-alkyl;

X is selected from a bond, —(CR$_a$R$_b$)$_m$— and —O(CR$_a$R$_b$)$_m$—;

$R_a$ and $R_b$ which may be same or different at each occurrence, are independently selected from hydrogen, halogen and substituted or unsubstituted $(C_1-C_6)$alkyl;

Z is —OR$_{10}$ or —NR$_7$R$_8$;

$R_3$ is hydrogen or halogen;

$R_4$, which may be same or different at each occurrence, is independently selected from halogen, substituted or unsubstituted $(C_1-C_6)$alkyl, substituted or unsubstituted $(C_1-C_6)$haloalkyl and —OR$_9$;

$R_7$ and $R_8$ are independently selected from hydrogen, substituted or unsubstituted $(C_1-C_6)$alkyl and (CR$_a$R$_b$)$_{1-2}$R$_{11}$;

$R_9$ is selected from hydrogen, substituted or unsubstituted $(C_1-C_6)$alkyl and substituted or unsubstituted $(C_1-C_6)$haloalkyl;

$R_{10}$ is hydrogen or substituted or unsubstituted $(C_1-C_6)$alkyl;

$R_{11}$ is substituted or unsubstituted phenyl, wherein the substituents are selected from halogen, $(C_1-C_6)$alkyl and $(C_1-C_6)$alkoxy;

'm' is an integer ranging from 1 to 3, both inclusive;

'n' is an integer ranging from 1 to 3, both inclusive;

'p' is an integer ranging from 0 to 2, both inclusive; and

'q' is an integer ranging from 1 to 3, both inclusive;

or a pharmaceutically acceptable salt thereof.

6. The compound of claim 1, wherein $R_4$ is independently selected from halogen, substituted or unsubstituted $(C_1-C_6)$alkyl and substituted or unsubstituted $(C_1-C_6)$haloalkyl and —OR$_9$ where $R_9$ is $(C_1-C_6)$alkyl or $(C_1-C_6)$haloalkyl; and 'p' is 0, 1 or 2.

7. The compound of claim 1 wherein $R_1$ is hydrogen or substituted or unsubstituted $(C_1-C_6)$alkyl.

8. The compound of claim 7, wherein $(C_1-C_{64})$alkyl is methyl or ethyl.

9. The compound of claim 1, wherein $R_2$ is independently selected from halogen, substituted or unsubstituted $(C_1-C_6)$alkyl, substituted or unsubstituted $(C_1-C_6)$haloalkyl, substituted or unsubstituted $(C_1-C_6)$hydroxyalkyl, —X—C(O)—Z, —O—$(C_1-C_6)$alkyl, —O—$(C_1-C_6)$haloalkyl, —NHC(O)alkyl, —S(O)$_{0-2}$alkyl, substituted or unsubstituted phenyl, substituted or unsubstituted 5- to 6-membered heteroaryl, substituted or unsubstituted 5- to 6-membered heterocyclyl,

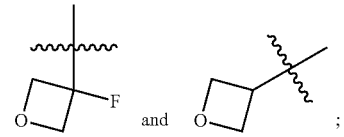 [SMILES: *C1(F)COC1 ; *C1COC1]

and herein X is selected from a bond, —(CR$_a$R$_b$)$_m$— and —O(CR$_a$R$_b$)$_m$— where $R_a$ and $R_b$ are independently hydrogen, halogen or substituted or unsubstituted $(C_1-C_6)$alkyl; Z is —OR$_{10}$ where $R_{10}$ is hydrogen or $(C_1-C_6)$alkyl; 'm' is selected from 1, 2 or 3 and 'q' is selected from 1, 2 or 3.

10. The compound of claim 1, wherein, $R_1$ is $(C_1-C_3)$alkyl;

$R_2$ which may be same or different at each occurrence, is independently selected from halogen, $(C_1-C_4)$alkyl, $(C_1-C_4)$haloalkyl, —X—C(O)—Z, —O—$(C_1-C_4)$alkyl or —O—$(C_1-C_4)$haloalkyl;

X is selected from a bond or —(CR$_a$R$_b$)$_m$ where $R_a$ and $R_b$ are independently hydrogen or substituted or unsubstituted $(C_1-C_6)$alkyl;

Z is —OH;

$R_3$ is hydrogen;

$R_4$, which may be same or different at each occurrence, is independently selected from halogen and —OR$_9$;

$R_9$ is $(C_1-C_4)$alkyl or $(C_1-C_4)$haloalkyl;

$R_5$ is $(C_1-C_3)$alkyl;

'm' is an integer selected from 1 or 2;

'n' is 1;

'p' is 0, 1 or 2; and

'q' is an integer ranging from 1 to 3, both inclusive;

or a pharmaceutically acceptable salt thereof.

11. A compound which is selected from:

(R)-1-(Naphthalen-1-yl)-N-((4-(4-(trifluoromethyl)phenyl)naphthalen-2-yl) methyl)ethanamine hydrochloride;

(R)-1-(4-Fluoro-3-methoxyphenyl)-N-((4-(4-(trifluoromethyl)phenyl)naphthalen-2-yl)methyl) ethanamine hydrochloride;

(R)-1-(Naphthalen-1-yl)-N-((4-(3-(trifluoromethyl) phenyl)naphthalen-2-yl) methyl)ethanamine hydrochloride;

(R)-1-(4-Fluoro-3-methoxyphenyl)-N-((4-(3-(trifluoromethyl)phenyl) naphthalen-2-yl) methyl)ethanamine hydrochloride;

(R)—N-(1-(3-Methoxyphenyl)ethyl)-3-(4-(4-(trifluoromethyl) phenyl) naphthalen-2-yl)propan-1-amine hydrochloride;

(1R)-1-(3-Methoxyphenyl)-N-(1-(4-(4-(trifluoromethyl) phenyl)naphthalen-2-yl) ethyl)ethanamine hydrochloride;

1-(4-(3-Fluoro-4-methoxyphenyl) naphthalen-2-yl)-N—((R)-1-(3-methoxyphenyl) ethyl) ethanamine hydrochloride;

(1R)-1-(3-Chlorophenyl)-N-(1-(4-(3-fluoro-4-methoxyphenyl) naphthalen-2-yl) ethyl) ethanamine hydrochloride;

(1R)-1-(Naphthalen-1-yl)-N-(1-(4-(4-(trifluoromethyl) phenyl) naphthalen-2-yl) ethyl) ethanamine hydrochloride;

(1R)-1-(3-Chlorophenyl)-N-(1-(4-(4-(trifluoromethyl) phenyl) naphthalen-2-yl) ethyl) ethanamine hydrochloride;
(1R)-1-(4-Fluoro-3-methoxyphenyl)-N-(1-(4-(4-(trifluoromethyl)phenyl) naphthalen-2-yl) ethyl) ethanamine hydrochloride;
(1R)-1-(3-Ethoxyphenyl)-N-(1-(4-(4-(trifluoromethyl) phenyl)naphthalen-2-yl)ethyl)ethanamine hydrochloride;
(1R)-1-(3-Fluorophenyl)-N-(1-(4-(4-(trifluoromethyl) phenyl) naphthalen-2-yl)ethyl)ethanamine hydrochloride;
(1R)-1-(3-Chlorophenyl)-N-(1-(4-(3-(trifluoromethyl) phenyl) naphthalen-2-yl) ethyl)ethanamine hydrochloride;
1-(4-(4-Fluorophenyl) naphthalen-2-yl)-N—((R)-1-(3-methoxyphenyl)ethyl) ethanamine hydrochloride;
(1R)-1-(3-Chlorophenyl)-N-(1-(4-(4-fluorophenyl) naphthalen-2-yl)ethyl) ethanamine hydrochloride;
(1R)-1-(3-Methoxyphenyl)-N-(1-(4-(4-(methylsulfonyl) phenyl)naphthalen-2-yl) ethyl)ethanamine hydrochloride;
N—((R)-1-(3-Methoxyphenyl)ethyl)-1-(4-(4-(trifluoromethyl)phenyl) naphthalen-2-yl)propan-1-amine hydrochloride;
(1R)-1-(3-Methoxyphenyl)-N-(1-(4-(4-(trifluoromethoxy)phenyl) naphthalen-2-yl)ethyl) ethanamine hydrochloride;
(1R)-1-(3-Chlorophenyl)-N-(1-(4-(4-(trifluoromethoxy) phenyl) naphthalen-2-yl)ethyl)ethanamine hydrochloride;
1-(4-(4-(Difluoromethoxy) phenyl) naphthalen-2-yl)-N—((R)-1-(3-methoxyphenyl) ethyl) ethanamine hydrochloride;
(1R)-1-(3-Chlorophenyl)-N-(1-(4-(4-(difluoromethoxy) phenyl) naphthalen-2-yl)ethyl)ethanamine hydrochloride;
(1R)-1-(3-chlorophenyl)-N-(1-(4-(4-(3-fluorooxetan-3-yl)phenyl)naphthalen-2-yl)ethyl)ethanamine hydrochloride;
(N)-Methyl-2-methyl-5-(3-(((1-(naphthalen-1-yl)ethyl) amino)methyl)naphthalen-1-yl)benzoate;
(R)-Methyl 5-(3-(((1-(3-methoxyphenyl)ethyl) amino)-methyl) naphthalen-1-yl)-2-methylbenzoate;
(R)-Methyl 5-(3-(((1-(3-ethoxyphenyl)ethyl)amino) methyl)naphthalen-1-yl)-2-methylbenzoate;
(R)-Methyl 2-methyl-5-(3-(((1-(3-propoxyphenyl) ethyl) amino)methyl) naphthalen-1-yl)benzoate;
(R)-Methyl 5-(3-(((1-(4-fluoro-3-methoxyphenyl) ethyl) amino)methyl)naphthalen-1-yl)-2-methylbenzoate;
(R)-methyl 5-(3-(((1-(3-chlorophenyl)ethyl)amino) methyl)naphthalen-1-yl)-2-methylbenzoate;
(R)-Methyl 5-(3-(((1-(3-(2,2-difluoroethoxy)phenyl) ethyl) amino)methyl)naphthalen-1-yl)-2-methylbenzoate;
(R)-Methyl 2-fluoro-5-(3-(((1-(4-fluoro-3-methoxyphenyl) ethyl)amino)methyl)naphthalen-1-yl)benzoate;
(R)-Methyl 2-fluoro-5-(3-(((1-(3-methoxyphenyl)ethyl) amino)methyl)naphthalen-1-yl)benzoate;
(R)-Methyl 5-(3-(((1-(3-ethoxyphenyl)ethyl)amino) methyl)naphthalen-1-yl)-2-fluorobenzoate;
(R)-Methyl 2-fluoro-5-(3-(((1-(3-(2-methoxyethoxy) phenyl)ethyl)amino)methyl) naphthalen-1-yl)benzoate;
(R)-Methyl 2-chloro-5-(3-(((1-(3-methoxyphenyl) ethyl) amino)methyl) naphthalen-1-yl)benzoate;
(R)-Methyl 2-chloro-5-(3-(((1-(3-ethoxyphenyl) ethyl) amino)methyl) naphthalen-1-yl)benzoate;

(R)-Methyl 3-(3-(((1-(3-methoxyphenyl)ethyl)amino) methyl)naphthalen-1-yl)-2-methylbenzoate
(R)-Methyl 3-(3-(((1-(3-ethoxyphenyl)ethyl)amino) methyl)naphthalen-1-yl)-2-methylbenzoate;
(R)-Methyl 2-fluoro-3-(3-(((1-(3-methoxyphenyl) ethyl) amino)methyl) naphthalen-1-yl)benzoate;
(R)-Methyl 2-methoxy-5-(3-(((1-(3-methoxyphenyl) ethyl)amino) methyl) naphthalen-1-yl)benzoate;
(R)-Methyl 2-isopropyl-5-(3-(((1-(3-methoxyphenyl) ethyl) amino)methyl)naphthalen-1-yl)benzoate;
(R)-Ethyl 4-(3-(((1-(naphthalen-1-yl)ethyl)amino) methyl)naphthalen-1-yl)benzoate;
(R)-Ethyl 4-(3-(((1-(4-fluoro-3-methoxyphenyl) ethyl) amino)methyl) naphthalen-1-yl)benzoate;
(R)-Methyl 3-(3-(((1-(3-methoxyphenyl)ethyl)amino) methyl)naphthalen-1-yl) benzoate;
(R)-methyl 2-fluoro-5-(3-(((1-(3-methoxyphenyl) ethyl) amino)methyl) naphthalen-1-yl)benzoate hydrochloride;
(R)-Methyl 3-(2-fluoro-5-(3-(((1-(3-methoxyphenyl) ethyl)amino)methyl) naphthalen-1-yl)phenyl) propanoate;
(R)-Methyl 2-(4-(3-(((1-(3-methoxyphenyl)ethyl)amino) methyl)naphthalen-1-yl) phenyl)-2-methylpropanoate;
(R)-2-(3-(3-(((1-(3-Methoxyphenyl)ethyl)amino)methyl) naphthalen-1-yl)phenyl)-2-methylpropanoic acid;
Isopropyl-5-(3-(1-(((R)-1-(3-methoxyphenyl)ethyl) amino)ethyl)naphthalen-1-yl)-2-methyl benzoate;
Isopropyl 5-(3-(1-(((R)-1-(4-fluoro-3-methoxyphenyl) ethyl)amino)ethyl)naphthalen-1-yl)-2-methylbenzoate;
Isopropyl 3-(3-(1-(((R)-1-(3-methoxyphenyl)ethyl) amino) ethyl)naphthalen-1-yl)-2-methylbenzoate;
Isopropyl 5-(3-(1-(((R)-1-(3-chlorophenyl)ethyl)amino) ethyl)naphthalen-1-yl)-2-methylbenzoate;
Isopropyl 3-fluoro-5-(3-(1-(((R)-1-(3-methoxyphenyl) ethyl) amino)ethyl)naphthalen-1-yl)benzoate;
Isopropyl 4-(3-(1-(((R)-1-(3-methoxyphenyl)ethyl) amino)ethyl)naphthalen-1-yl)benzoate;
Isopropyl 3-fluoro-4-(3-(1-(((R)-1-(3-methoxyphenyl) ethyl) amino)ethyl)naphthalen-1-yl)benzoate;
Isopropyl 2-chloro-4-(3-(1-(((R)-1-(3-methoxyphenyl) ethyl) amino)ethyl)naphthalen-1-yl)benzoate;
Isopropyl 3-(2-fluoro-5-(3-(1-(((R)-1-(3-methoxyphenyl) ethyl) amino)ethyl)naphthalen-1-yl)phenyl)propanoate;
Isopropyl 2-fluoro-5-(3-(1-(((R)-1-(3-methoxyphenyl) ethyl) amino)ethyl)naphthalen-1-yl)benzoate;
Isopropyl 4-(3-(1-(((R)-1-(3-methoxyphenyl)ethyl) amino)ethyl) naphthalen-1-yl)-2-(trifluoromethyl)benzoate;
Isopropyl 3-(3-(1-(((R)-1-(3-methoxyphenyl)ethyl) amino)ethyl) naphthalen-1-yl)-5-methylbenzoate;
Isopropyl 5-(3-(1-(((R)-1-(3-ethoxyphenyl)ethyl)amino) ethyl) naphthalen-1-yl)-2-fluorobenzoate;
Isopropyl 5-(3-(1-(((R)-1-(3-chlorophenyl)ethyl)amino) ethyl) naphthalen-1-yl)-2-fluorobenzoate;
Isopropyl 5-(3-(1-(((R)-1-(3-methoxyphenyl)ethyl) amino) ethyl) naphthalen-1-yl)-2-(trifluoromethyl)benzoate;
Isopropyl 3-(2-fluoro-3-(3-(1-(((R)-1-(3-methoxyphenyl) ethyl) amino)ethyl) naphthalen-1-yl)phenyl)propanoate;
Isopropyl 4-(3-(1-(((R)-1-(3-methoxyphenyl)ethyl) amino) ethyl) naphthalen-1-yl)-2-methylbenzoate;
Isopropyl 3-(2-methoxy-5-(3-(1-(((R)-1-(3-methoxyphenyl)ethyl) amino)ethyl) naphthalen-1-yl)phenyl)propanoate;

Isopropyl 2-fluoro-4-(3-(1-(((R)-1-(3-methoxyphenyl) ethyl) amino)ethyl) naphthalen-1-yl)benzoate;
Isopropyl 3-methoxy-5-(3-(1-(((R)-1-(3-methoxyphenyl) ethyl)amino) ethyl) naphthalen-1-yl)benzoate;
Isopropyl 2-chloro-5-(3-(1-(((R)-1-(3-methoxyphenyl) ethyl) amino)ethyl) naphthalen-1-yl)benzoate;
Isopropyl 3-(3-fluoro-5-(3-(1-(((R)-1-(3-methoxyphenyl) ethyl) amino)ethyl) naphthalen-1-yl)phenyl)propanoate;
Isopropyl 2-(3-fluoro-5-(3-(1-(((R)-1-(3-methoxyphenyl) ethyl) amino)ethyl)naphthalen-1-yl)phenoxy)-2-methylpropanoate;
2,2-Difluoro-N—((R)-1-(3-methoxyphenyl)ethyl)-2-(4-(3-(1-(((R)-1-(3-methoxyphenyl) ethyl)amino)ethyl) naphthalen-1-yl)phenyl)acetamide;
Isopropyl 3-(2-fluoro-4-(3-(1-(((R)-1-(3-methoxyphenyl) ethyl) amino)ethyl) naphthalen-1-yl)phenyl)propanoate;
Isopropyl 3-(5-(3-(1-(((R)-1-(3-methoxyphenyl)ethyl) amino) ethyl) naphthalen-1-yl)-2-methyl phenyl)propanoate;
Isopropyl 2-(4-(3-(1-(((R)-1-(3-methoxyphenyl)ethyl) amino)ethyl) naphthalen-1-yl)phenyl)-2-methyl propanoate;
Isopropyl 2-(3-(3-(1-(((R)-1-(3-methoxyphenyl)ethyl) amino) ethyl) naphthalen-1-yl)phenyl)-2-methyl propanoate;
Isopropyl 3-(2-fluoro-5-(3-(1-(((R)-1-(3-methoxyphenyl) ethyl)amino) propyl) naphthalen-1-yl)phenyl)propanoate;
Isopropyl 3-(5-(3-(1-(((R)-1-(3-chlorophenyl)ethyl) amino)propyl) naphthalen-1-yl)-2-fluorophenyl) propanoate;
Isopropyl 3-(5-(3-(1-(((R)-1-(3-ethoxyphenyl)ethyl) amino)propyl)naphthalen-1-yl)-2-fluorophenyl) propanoate;
Isopropyl 3-(5-(3-(1-(((R)-1-(3-ethoxyphenyl)ethyl) amino)ethyl) naphthalen-1-yl)-2-fluorophenyl) propanoate;
Isopropyl 5-(3-(1-(((R)-1-(3-ethoxyphenyl)ethyl)amino) ethyl) naphthalen-1-yl)-2-methylbenzoate;
Isopropyl 3-(5-(3-(1-(((R)-1-(3-chlorophenyl)ethyl) amino)ethyl) naphthalen-1-yl)-2-fluorophenyl) propanoate;
Isopropyl 3-(5-(3-(1-(((R)-1-(3-methoxyphenyl) ethyl) amino) ethyl)naphthalen-1-yl)-2-(trifluoromethyl)phenyl)propanoate;
Isopropyl 3-(5-(3-(1-(((R)-1-(3-chlorophenyl)ethyl) amino)ethyl) naphthalen-1-yl)-2-(trifluoro methyl)phenyl)propanoate;
Isopropyl 3-(3-fluoro-5-(7-fluoro-3-(1-(((R)-1-(3-methoxyphenyl) ethyl)amino)ethyl)naphthalen-1-yl) phenyl)propanoate;
Isopropyl 3-(3-fluoro-5-(3-(1-(((R)-1-(3-methoxyphenyl) ethyl) amino)propyl) naphthalen-1-yl)phenyl)propanoate;
Isopropyl 3-(3-(3-(1-(((R)-1-(3-ethoxyphenyl)ethyl) amino)ethyl)naphthalen-1-yl)-5-fluorophenyl)propanoate;
Isopropyl 5-(3-(1-(((R)-1-(3-methoxyphenyl)ethyl) amino)propyl)naphthalen-1-yl)-2-methylbenzoate;
(R)-2-Methyl-5-(3-(((1-(naphthalen-1-yl)ethyl)amino) methyl)naphthalen-1-yl)benzoic acid;
(R)-5-(3-(((1-(3-Methoxyphenyl)ethyl)amino)methyl) naphthalen-1-yl)-2-methylbenzoic acid hydrochloride;
(R)-5-(3-(((1-(3-Ethoxyphenyl)ethyl) amino)methyl) naphthalen-1-yl)-2-methylbenzoic acid hydrochloride;
(R)-2-Methyl-5-(3-(((1-(3-propoxyphenyl)ethyl) amino) methyl)naphthalen-1-yl)benzoic acid hydrochloride;
(R)-5-(3-(((1-(4-Fluoro-3-methoxyphenyl)ethyl) amino) methyl)naphthalen-1-yl)-2-methylbenzoic acid hydrochloride;
(R)-5-(3-(((1-(3-Chlorophenyl)ethyl)amino)methyl) naphthalen-1-yl)-2-methylbenzoic acid hydrochloride;
(R)-5-(3-(((1-(3-(2,2-Difluoroethoxy)phenyl)ethyl) amino)methyl)naphthalen-1-yl)-2-methylbenzoic acid hydrochloride;
(R)-2-Fluoro-5-(3-(((1-(4-fluoro-3-methoxyphenyl) ethyl)amino)methyl)naphthalen-1-yl)benzoic acid hydrochloride;
(R)-2-Fluoro-5-(3-(((1-(3-methoxyphenyl)ethyl) amino) methyl)naphthalen-1-yl)benzoic acid hydrochloride;
(R)-5-(3-(((1-(3-Ethoxyphenyl)ethyl) amino) methyl) naphthalen-1-yl)-2-fluorobenzoic acid hydrochloride;
(R)-2-Chloro-5-(3-(((1-(3-methoxyphenyl)ethyl) amino) methyl)naphthalen-1-yl)benzoic acid hydrochloride;
(R)-2-Chloro-5-(3-(((1-(3-ethoxyphenyl)ethyl)amino) methyl)naphthalen-1-yl)benzoic acid hydrochloride;
(R)-3-(3-(((1-(3-Methoxyphenyl)ethyl) amino)methyl) naphthalen-1-yl)-2-methylbenzoic acid hydrochloride;
(R)-3-(3-(((1-(3-Ethoxyphenyl)ethyl) amino)methyl) naphthalen-1-yl)-2-methylbenzoic acid hydrochloride;
(R)-2-Fluoro-3-(3-(((1-(3-methoxyphenyl)ethyl) amino) methyl)naphthalen-1-yl)benzoic acid hydrochloride;
(R)-2-Methoxy-5-(3-(((1-(3-methoxyphenyl)ethyl) amino)methyl)naphthalen-1-yl)benzoic acid hydrochloride;
(R)-2-Isopropyl-5-(3-(((1-(3-methoxyphenyl)ethyl) amino)methyl)naphthalen-1-yl)benzoic acid hydrochloride;
(R)-4-(3-(((1-(Naphthalen-1-yl)ethyl)amino) methyl) naphthalen-1-yl)benzoic acid hydrochloride;
(R)-4-(3-(((1-(4-Fluoro-3-methoxyphenyl)ethyl) amino) methyl)naphthalen-1-yl)benzoic acid hydrochloride;
(R)-3-(3-(((1-(3-Methoxyphenyl)ethyl) amino)methyl) naphthalen-1-yl)benzoic acid hydrochloride;
(R)-3-(3-(((1-(3-Methoxyphenyl)ethyl) amino)methyl) naphthalen-1-yl)-2,6-dimethylbenzoic acid hydrochloride;
(R)-3-(2-Fluoro-5-(3-(((1-(3-methoxyphenyl)ethyl) amino)methyl)naphthalen-1-yl)phenyl)propanoic acid hydrochloride;
(R)-2-(4-(3-(((1-(3-Methoxyphenyl)ethyl) amino)methyl) naphthalen-1-yl)phenyl)-2-methylpropanoic acid hydrochloride;
(R)-2-(3-(3-(((1-(3-Methoxyphenyl)ethyl) amino)methyl) naphthalen-1-yl)phenyl)-2-methylpropanoic acid hydrochloride;
(R)-2-Fluoro-5-(3-(((1-(3-(2-methoxyethoxy)phenyl) ethyl)amino)methyl) naphthalen-1-yl) benzoic acid hydrochloride;
5-(3-(1-(((R)-1-(3-methoxyphenyl)ethyl)amino)ethyl) naphthalen-1-yl)-2-methylbenzoic acid hydrochloride;
5-(3-(1-(((R)-1-(4-Fluoro-3-methoxyphenyl)ethyl) amino)ethyl)naphthalen-1-yl)-2-methylbenzoic acid hydrochloride;
3-(3-(1-(((R)-1-(3-Methoxyphenyl)ethyl) amino)ethyl) naphthalen-1-yl)-2-methylbenzoic acid hydrochloride;
5-(3-(1-(((R)-1-(3-Chlorophenyl)ethyl)amino) ethyl) naphthalen-1-yl)-2-methylbenzoic acid hydrochloride;
3-Fluoro-5-(3-(1-(((R)-1-(3-methoxyphenyl)ethyl) amino)ethyl)naphthalen-1-yl)benzoic acid hydrochloride;

4-(3-(1-(((R)-1-(3-Methoxyphenyl)ethyl) amino)ethyl) naphthalen-1-yl)benzoic acid hydrochloride;

3-Fluoro-4-(3-(1-(((R)-1-(3-methoxyphenyl) amino)ethyl)naphthalen-1-yl)benzoic acid hydrochloride;

2-Chloro-4-(3(1-(((R)-1-(3-methoxyphenyl)ethyl) amino)ethyl)naphthalen-1-yl)benzoic acid hydrochloride;

3-(2-Fluoro-5-(3-(1-(((R)-1-(3-methoxyphenyl) ethyl) amino)ethyl)naphthalen-1-yl)phenyl)propanoic acid hydrochloride;

2-Fluoro-5-(3-(1-(((R)-1-(3-methoxyphenyl)ethyl) amino)ethyl)naphthalen-1-yl)benzoic acid hydrochloride;

4-(3-(1-(((R)-1-(3-Methoxyphenyl)ethyl) amino)ethyl) naphthalen-1-yl)-2-(trifluoromethyl) benzoic acid hydrochloride;

3-(3-(1-(((R)-1-(3-Methoxyphenyl)ethyl) amino)ethyl) naphthalen-1-yl)-5-methylbenzoic acid hydrochloride;

5-(3-(1-(((R)-1-(3-Ethoxyphenyl)ethyl) amino)ethyl) naphthalen-1-yl)-2-fluorobenzoic acid hydrochloride;

5-(3-(1-(((R)-1-(3-Chlorophenyl)ethyl)amino)ethyl) naphthalen-1-yl)-2-fluorobenzoic acid hydrochloride;

5-(3-(1-(((R)-1-(3-Methoxyphenyl)ethyl) amino)ethyl) naphthalen-1-yl)-2-(trifluoromethyl) benzoic acid hydrochloride;

3-(2-Fluoro-3-(3-(1-(((R)-1-(3-methoxyphenyl)ethyl) amino)ethyl)naphthalen-1-yl)phenyl)propanoic acid hydrochloride;

4-(3-(1-(((R)-1-(3-Methoxyphenyl)ethyl) amino)ethyl) naphthalen-1-yl)-2-methylbenzoic acid hydrochloride;

3-(2-Methoxy-5-(3-(1-(((R)-1-(3-methoxyphenyl) ethyl) amino)ethyl) naphthalen-1-yl)phenyl) propanoic acid hydrochloride;

2-Fluoro-4-(3-(1-(((R)-1-(3-methoxyphenyl)ethyl) amino)ethyl)naphthalen-1-yl)benzoic acid hydrochloride;

2-Chloro-5-(3-(1-(((R)-1-(3-methoxyphenyl)ethyl) amino)ethyl)naphthalen-1-yl)benzoic acid hydrochloride;

3-(3-Fluoro-5-(3-(1-(((R)-1-(3-methoxyphenyl)ethyl) amino)ethyl)naphthalen-1-yl)phenyl)propanoic acid hydrochloride;

2,2-Difluoro-2-(4-(3-(1-(((R)-1-(3-methoxyphenyl) ethyl) amino)ethyl) naphthalen-1-yl)phenyl) acetic acid hydrochloride;

3-(2-Fluoro-4-(3-(1-(((R)-1-(3-methoxyphenyl) ethyl) amino)ethyl) naphthalen-1-yl)phenyl) propanoic acid hydrochloride;

3-(5-(3-(1-(((R)-1-(3-Methoxyphenyl)ethyl) amino) ethyl)naphthalen-1-yl)-2-methylphenyl) propanoic acid hydrochloride;

2-(4-(3-(1-(((R)-1-(3-Methoxyphenyl)ethyl) amino) ethyl)naphthalen-1-yl)phenyl)-2-methylpropanoic acid hydrochloride;

2-(3-(3-(1-(((R)-1-(3-Methoxyphenyl)ethyl) amino) ethyl)naphthalen-1-yl)phenyl)-2-methylpropanoic acid hydrochloride;

3-(2-Fluoro-5-(3-(1-(((R)-1-(3-methoxyphenyl)ethyl) amino)propyl)naphthalen-1-yl)phenyl)propanoic acid hydrochloride;

3-(5-(3-(1-(((R)-1-(3-Ethoxyphenyl)ethyl) amino)propyl) naphthalen-1-yl)-2-fluorophenyl) propanoic acid hydrochloride;

3-(5-(3-(1-(((R)-1-(3-Ethoxyphenyl)ethyl) amino) ethyl) naphthalen-1-yl)-2-fluorophenyl) propanoic acid hydrochloride;

5-(3-(1-(((R)-1-(3-Ethoxyphenyl)ethyl) amino) ethyl) naphthalen-1-yl)-2-methylbenzoic acid hydrochloride;

3-(5-(3-(1-(((R)-1-(3-Chlorophenyl)ethyl)amino)ethyl) naphthalen-1-yl)-2-fluorophenyl)propanoic acid hydrochloride;

3-(5-(3-(1-(((R)-1-(3-Methoxyphenyl)ethyl) amino) ethyl)naphthalen-1-yl)-2-(trifluoromethyl) phenyl)propanoic acid hydrochloride;

3-(5-(3-(1-(((R)-1-(3-Chlorophenyl)ethyl) amino)ethyl) naphthalen-1-yl)-2-(trifluoromethyl) phenyl)propanoic acid hydrochloride;

3-(3-Fluoro-5-(7-fluoro-3-(1-(((R)-1-(3-methoxyphenyl) ethyl) amino)ethyl)naphthalen-1-yl)phenyl)propanoic acid hydrochloride;

3-(3-Fluoro-5-(3-(1-(((R)-1-(3-methoxyphenyl) ethyl) amino)propyl)naphthalen-1-yl)phenyl)propanoic acid hydrochloride;

5-(3-(1-(((R)-1-(3-Methoxyphenyl)ethyl) amino)propyl) naphthalen-1-yl)-2-methylbenzoic acid hydrochloride;

3-Methoxy-5-(3-(1-(((R)-1-(3-methoxyphenyl)ethyl) amino)ethyl)naphthalen-1-yl)benzoic acid hydrochloride;

2-(3-Fluoro-5-(3-(1-(((R)-1-(3-methoxyphenyl)ethyl) amino)ethyl)naphthalen-1-yl)phenoxy)-2-methylpropanoic acid hydrochloride;

3-(5-(3-(1-(((R)-1-(3-Chlorophenyl)ethyl)amino)propyl) naphthalen-1-yl)-2-fluorophenyl)propanoic acid hydrochloride;

Isopropyl 3-(3-(3-(1-(((R)-1-(3-chlorophenyl) ethyl) amino)ethyl) naphthalen-1-yl)-5-fluorophenyl) propanoate hydrochloride;

Isopropyl 3-(5-(3-(1-(((R)-1-(3-ethoxyphenyl)ethyl) amino) ethyl)naphthalen-1-yl)-2-methylphenyl) propanoate hydrochloride (R)-Methyl 5-(3-(((1-(3-methoxyphenyl)ethyl) amino)methyl) naphthalen-1-yl)-2-methylbenzoate hydrochloride;

3-(3-(3-(1-(((R)-1-(3-Chlorophenyl)ethyl)amino)ethyl) naphthalen-1-yl)-5-fluorophenyl)propanoic acid hydrochloride;

3-(5-(3-(1-(((R)-1-(3-Ethoxyphenyl)ethyl) amino)ethyl) naphthalen-1-yl)-2-methylphenyl) propanoic acid hydrochloride;

3-(3-(3-(1-(((R)-1-(3-Ethoxyphenyl)ethyl) amino)ethyl) naphthalen-1-yl)-5-fluorophenyl) propanoic acid hydrochloride;

(1R)-1-(3-Chlorophenyl)-N-(1-(4-(4-(methylsulfonyl) phenyl)naphthalen-2-yl)ethyl)ethanamine hydrochloride;

(1R)-1-(3-Chlorophenyl)-N-(1-(4-(4-(pyrrolidin-1-yl) phenyl)naphthalen-2-yl)ethyl)ethanamine hydrochloride;

1-(4-(3-Fluoro-5-morpholinophenyl)naphthalen-2-yl)-N—((R)-1-(3-methoxyphenyl) ethyl)ethanamine hydrochloride;

(1R)-1-(3-methoxy phenyl)-N-(1-(7-fluoro-4-(4-(trifluoromethyl) phenyl)naphthalen-2-yl) ethyl)ethanamine 1-(3-Fluoro-5-methoxyphenyl)-N-(1-(4-(4-(trifluoromethyl) phenyl) naphthalen-2-yl)ethyl)ethanamine hydrochloride;

1-(4-(3',5-Difluoro-[1,1'-biphenyl]-3-yl)naphthalen-2-yl)-N—((R)-1-(3-methoxy phenyl)ethyl) ethanamine hydrochloride;

1-(4-(3-Fluoro-5-(1-methyl-1H-pyrazol-4-yl)phenyl) naphthalen-2-yl)-N—((R)-1-(3-methoxy phenyl)ethyl) ethanamine hydrochloride;

Isopropyl-5-(3-(1-(((R)-1-(3-fluoro-5-methoxyphenyl) ethyl)amino) ethyl) naphthalen-1-yl)-2-methylbenzoate;

Isopropyl-3-(3-fluoro-5-(3-(1-(((R)-1-(3-fluoro-5-methoxyphenyl)ethyl)amino) ethyl) naphthalen-1-yl) phenyl)propanoate;

5-(3-(1-(((R)-1-(3-Fluoro-5-methoxyphenyl)ethyl)
amino)ethyl)naphthalen-1-yl)-2-methyl benzoic acid
hydrochloride; and 3-(3-Fluoro-5-(3-(1-(((R)-1-(3-fluoro-5-methoxyphenyl)
ethyl)amino) ethyl)naphthalen-1-yl) phenyl)propanoic
acid hydrochloride or a free base thereof or a pharmaceutically acceptable
salt thereof.

12. The compound of claim 1, wherein the pharmaceutically acceptable salt is hydrochloride salt.

13. A pharmaceutical composition comprising one or more compounds according to claim 1, and one or more pharmaceutically acceptable excipients.

14. A method of treating diseases or disorders, syndromes or conditions associated with the modulation of calcium sensing receptor (CaSR) in a subject in need thereof wherein the method comprises administering to the subject a therapeutically effective amount of a compound according to claim 1, or a pharmaceutically acceptable salt thereof.

15. The method of claim 14, wherein the diseases, disorders, syndromes or conditions associated with the modulation of calcium sensing receptor (CaSR) are selected from hyperparathyroidism, chronic renal failure (with or without dialysis), chronic kidney disease (with or without dialysis) and their complications.

16. The method of claim 15, wherein hyperparathyroidism is primary hyperparathyroidism, secondary hyperparathyroidism or tertiary hyperparathyroidism.

17. The method of claim 14, wherein the diseases, disorders, syndromes or conditions associated with the modulation of CaSR receptors are selected from the group consisting of parathyroid adenoma, parathyroid hyperplasia, parathyroid carcinoma, vascular & valvular calcification, abnormal calcium homeostasis, hypercalcemia, abnormal phosphorous homeostasis, hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which (Ca2+)e ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

18. A process for the preparation of compound of Formula (Ic) and Formula (Id):

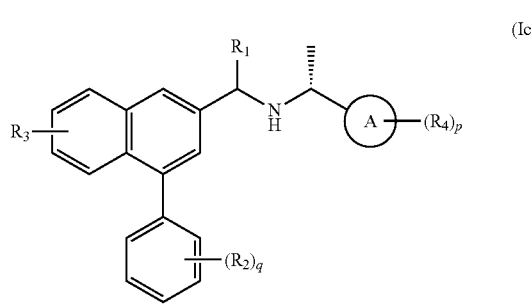

(Ic)

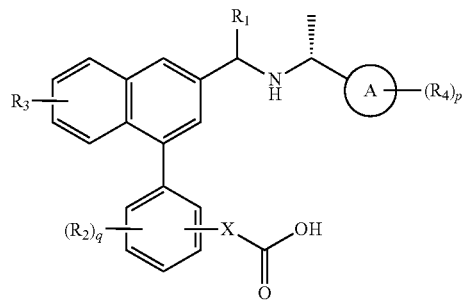

(Id)

wherein ring A, $R_1$, $R_2$, $R_3$, $R_4$, X, 'p' and 'q' are as described in claim 1;

the process comprising the steps of:

(a) reacting compound of Formula (1) with compound of Formula (1a) in presence of base and palladium complex to give compound of Formula (2)

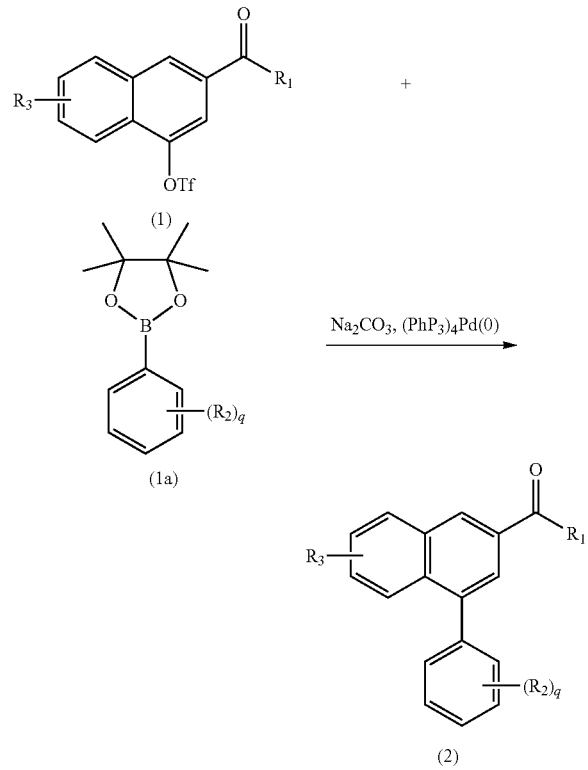

(b) coupling of a compound of Formula (2) with compound of Formula (12) followed by reduction using suitable reducing agent to give compound of Formula (Ic)

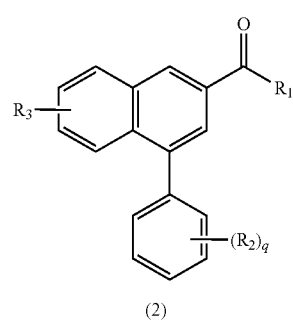

(2)

-continued
(c) hydrolyzing a compound of Formula (Ic) (when any of R₂ is X—(CO)—Z represents to an ester) to give corresponding acid compound of Formula (Id) where 'q' is 0, 1 or 2
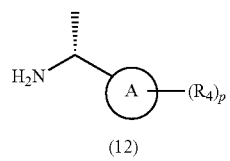
(12)
1. condensation
2. reduction
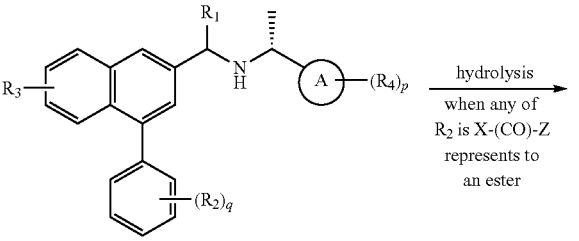
hydrolysis
when any of
R₂ is X-(CO)-Z
represents to
an ester
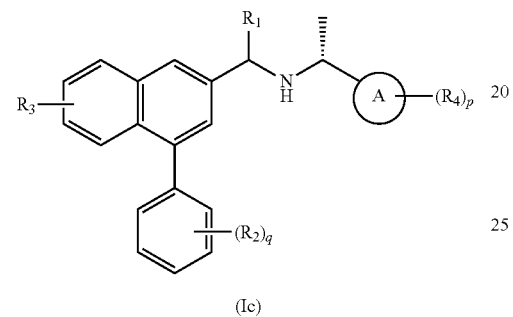
(Ic)
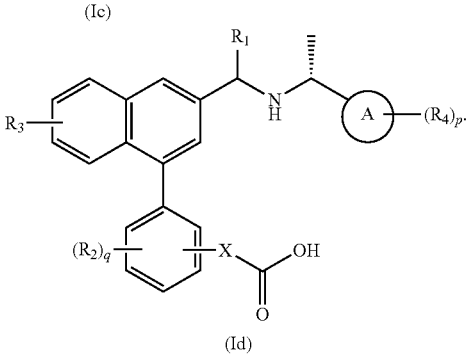
(Id)
* * * * *